(12) United States Patent
Bergheim et al.

(10) Patent No.: US 9,504,536 B2
(45) Date of Patent: Nov. 29, 2016

(54) DENTAL TREATMENT SYSTEM

(71) Applicant: SONENDO, INC., Laguna Hills, CA (US)

(72) Inventors: Bjarne Bergheim, Mission Viejo, CA (US); Mehrzad Khakpour, Laguna Hills, CA (US); Jennifer Chen, Irvine, CA (US); Alexis Dechelette, Del Mar, CA (US)

(73) Assignee: SONENDO, INC., Laguna Hills, CA (US)

( * ) Notice: Subject to any disclaimer, the term of this patent is extended or adjusted under 35 U.S.C. 154(b) by 0 days.

(21) Appl. No.: 14/172,809

(22) Filed: Feb. 4, 2014

(65) Prior Publication Data
US 2015/0010882 A1    Jan. 8, 2015

Related U.S. Application Data

(60) Provisional application No. 61/760,620, filed on Feb. 4, 2013, provisional application No. 61/767,741, filed on Feb. 21, 2013, provisional application No. 61/864,393, filed on Aug. 9, 2013, provisional application No. 61/767,746, filed on Feb. 21, 2013, provisional application No. 61/805,110, filed on Mar. 25, 2013.

(51) Int. Cl.
*A61C 17/02*    (2006.01)
*A61C 5/02*    (2006.01)
(Continued)

(52) U.S. Cl.
CPC .............. *A61C 5/02* (2013.01); *A61C 1/0061* (2013.01); *A61C 1/087* (2013.01); *A61C 17/02* (2013.01); *A61C 17/0202* (2013.01); *A61C 17/028* (2013.01); *A61C 17/0217* (2013.01)

(58) Field of Classification Search
CPC A61C 17/0202; A61C 17/02; A61C 1/0061; A61C 1/087; A61C 17/028; A61C 17/0217
See application file for complete search history.

(56) References Cited

U.S. PATENT DOCUMENTS

| | | |
|---|---|---|
| 1,500,107 A | 7/1924 | Chandler |
| 3,023,306 A | 2/1962 | Kester |

(Continued)

FOREIGN PATENT DOCUMENTS

| | | |
|---|---|---|
| AU | 2012-202315 A1 | 4/2012 |
| AU | 2007140780 | 5/2014 |

(Continued)

OTHER PUBLICATIONS

Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.

(Continued)

*Primary Examiner* — Ralph Lewis
(74) *Attorney, Agent, or Firm* — Knobbe, Martens, Olson & Bear LLP

(57) ABSTRACT

A dental treatment system can include a console, a tooth coupler, and an interface member that provides at least one of fluidic, electrical, mechanical, and data communication between the tooth coupler and the console. The tooth coupler (which may comprise a handpiece or a treatment cap) can act as a working end of the system to administer a suitable treatment procedure, such as a cleaning procedure, an obturation procedure, a restoration procedure, etc. The tooth coupler can removably engage the interface member such that the clinician can easily engage and disengage the tooth coupler and interface member.

50 Claims, 56 Drawing Sheets

(51) Int. Cl.
*A61C 17/028* (2006.01)
*A61C 1/00* (2006.01)
*A61C 1/08* (2006.01)

(56) References Cited

U.S. PATENT DOCUMENTS

| | | |
|---|---|---|
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,624,907 A | 12/1971 | Brass et al. |
| 3,703,170 A | 11/1972 | Ryckman, Jr. |
| 3,756,225 A | 9/1973 | Moret et al. |
| 3,828,770 A | 8/1974 | Kuris et al. |
| 3,921,296 A | 11/1975 | Harris |
| 3,930,505 A | 1/1976 | Wallach |
| 3,962,790 A | 6/1976 | Riitano et al. |
| 4,021,921 A | 5/1977 | Detaille |
| 4,060,600 A | 11/1977 | Vit |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,376,835 A | 3/1983 | Schmitt et al. |
| 4,386,911 A | 6/1983 | Maloney et al. |
| 4,424,036 A | 1/1984 | Lokken |
| 4,474,251 A | 10/1984 | Johnson, Jr. |
| 4,534,542 A | 8/1985 | Russo |
| 4,608,017 A | 8/1986 | Sadohara |
| 4,676,749 A | 6/1987 | Mabille |
| 4,789,335 A | 12/1988 | Geller et al. |
| 4,872,837 A | 10/1989 | Issalene et al. |
| 4,941,459 A | 7/1990 | Mathur |
| 4,957,436 A | 9/1990 | Ryder |
| 4,973,246 A | 11/1990 | Black et al. |
| 4,993,947 A | 2/1991 | Grosrey |
| 5,013,300 A | 5/1991 | Williams |
| 5,029,576 A | 7/1991 | Evans, Sr. |
| 5,037,431 A | 8/1991 | Summers et al. |
| 5,046,950 A | 9/1991 | Favonio |
| 5,195,952 A | 3/1993 | Solnit et al. |
| 5,267,856 A | 12/1993 | Wolbarsht et al. |
| 5,295,828 A | 3/1994 | Grosrey |
| 5,307,839 A | 5/1994 | Loebker et al. |
| 5,322,504 A | 6/1994 | Doherty et al. |
| 5,380,201 A | 1/1995 | Kawata |
| 5,387,376 A | 2/1995 | Gasser |
| D356,866 S | 3/1995 | Meller |
| 5,435,724 A | 7/1995 | Goodman et al. |
| 5,474,451 A | 12/1995 | Dalrymple et al. |
| 5,490,779 A | 2/1996 | Malmin |
| 5,547,376 A | 8/1996 | Harrel |
| 5,554,896 A | 9/1996 | Hogan |
| 5,562,692 A | 10/1996 | Bair |
| 5,564,929 A | 10/1996 | Alpert |
| 5,570,182 A | 10/1996 | Nathel et al. |
| 5,591,184 A | 1/1997 | McDonnell et al. |
| 5,601,430 A | 2/1997 | Kutsch et al. |
| 5,620,414 A | 4/1997 | Campbell, Jr. |
| 5,643,299 A | 7/1997 | Bair |
| 5,674,226 A | 10/1997 | Doherty et al. |
| 5,730,727 A | 3/1998 | Russo |
| 5,735,815 A | 4/1998 | Bair |
| 5,759,159 A | 6/1998 | Masreliez |
| 5,795,153 A | 8/1998 | Rechmann |
| 5,797,745 A | 8/1998 | Ruddle |
| 5,810,037 A | 9/1998 | Sasaki et al. |
| 5,816,807 A | 10/1998 | Matsutani et al. |
| 5,839,896 A | 11/1998 | Hickok et al. |
| 5,842,863 A | 12/1998 | Bruns et al. |
| 5,853,384 A | 12/1998 | Bair |
| 5,865,790 A | 2/1999 | Bair |
| 5,868,570 A | 2/1999 | Hickok et al. |
| 5,874,677 A | 2/1999 | Bab et al. |
| 5,879,160 A | 3/1999 | Ruddle |
| 5,915,965 A | 6/1999 | Ohlsson et al. |
| 5,975,897 A | 11/1999 | Propp et al. |
| 5,989,023 A | 11/1999 | Summer et al. |
| 6,053,735 A | 4/2000 | Buchanan |
| 6,079,979 A | 6/2000 | Riitano |
| 6,122,300 A | 9/2000 | Freiberg et al. |
| 6,143,011 A | 11/2000 | Hood et al. |
| 6,159,006 A | 12/2000 | Cook et al. |
| 6,162,177 A | 12/2000 | Bab et al. |
| 6,162,202 A | 12/2000 | Sicurelli et al. |
| 6,164,966 A | 12/2000 | Turdiu et al. |
| 6,179,617 B1 | 1/2001 | Ruddle |
| 6,190,318 B1 | 2/2001 | Bab et al. |
| 6,221,031 B1 | 4/2001 | Heraud |
| 6,224,378 B1 | 5/2001 | Valdes et al. |
| 6,227,855 B1 | 5/2001 | Hickok et al. |
| 6,245,032 B1 | 6/2001 | Sauer et al. |
| 6,290,502 B1 | 9/2001 | Hugo |
| 6,312,440 B1 | 11/2001 | Hood et al. |
| 6,315,557 B1 | 11/2001 | Messick |
| 6,386,871 B1 | 5/2002 | Rossell |
| 6,390,815 B1 | 5/2002 | Pond |
| 6,440,103 B1 | 8/2002 | Hood et al. |
| 6,454,566 B1 | 9/2002 | Lynch et al. |
| 6,464,498 B1 | 10/2002 | Pond |
| 6,497,572 B2 | 12/2002 | Hood et al. |
| 6,511,493 B1 | 1/2003 | Moutafis et al. |
| 6,514,077 B1 | 2/2003 | Wilk |
| 6,527,766 B1 | 3/2003 | Bair |
| 6,562,050 B1 | 5/2003 | Owen |
| 6,572,709 B1 | 6/2003 | Kaneda et al. |
| 6,638,219 B1 | 10/2003 | Asch et al. |
| 6,641,394 B2 | 11/2003 | Garman |
| 6,817,862 B2 | 11/2004 | Hickok |
| D499,486 S | 12/2004 | Kuhn et al. |
| 6,881,061 B2 | 4/2005 | Fisher |
| 6,910,887 B2 | 6/2005 | Van Den Houdt |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,011,644 B1 | 3/2006 | Andrew et al. |
| 7,044,737 B2 | 5/2006 | Fu |
| 7,163,400 B2 | 1/2007 | Cozean et al. |
| 7,238,342 B2 | 7/2007 | Torabinejad et al. |
| 7,261,561 B2 | 8/2007 | Ruddle et al. |
| 7,270,544 B2 | 9/2007 | Schemmer et al. |
| 7,306,577 B2 | 12/2007 | Lemoine et al. |
| 7,326,054 B2 | 2/2008 | Todd et al. |
| 7,549,861 B2 | 6/2009 | Ruddle et al. |
| 7,845,944 B2 | 12/2010 | DiGasbarro |
| 7,959,441 B2 | 6/2011 | Glover et al. |
| 7,980,854 B2 | 7/2011 | Glover et al. |
| 8,002,544 B2 | 8/2011 | Rizoiu et al. |
| 8,047,841 B2 | 11/2011 | Jefferies |
| 8,128,401 B2 | 3/2012 | Ruddle et al. |
| 8,204,612 B2 * | 6/2012 | Feine .......... A61C 1/0061 433/100 |
| D669,180 S | 10/2012 | Takashi et al. |
| 8,295,025 B2 | 10/2012 | Edel et al. |
| 8,317,514 B2 | 11/2012 | Weill |
| 8,322,910 B2 | 12/2012 | Gansmuller et al. |
| 8,506,293 B2 | 8/2013 | Pond |
| 8,617,090 B2 | 12/2013 | Fougere et al. |
| 8,684,956 B2 | 4/2014 | McDonough et al. |
| 8,747,005 B2 | 6/2014 | Kemp et al. |
| 8,753,121 B2 | 6/2014 | Gharib et al. |
| 8,977,085 B2 | 3/2015 | Walsh et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,101,377 B2 | 8/2015 | Boutoussov et al. |
| D745,966 S | 12/2015 | Piorek et al. |

(56) References Cited

U.S. PATENT DOCUMENTS

| | | | |
|---|---|---|---|
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 2002/0012897 A1 | 1/2002 | Tingley et al. |
| 2002/0072032 A1 | 6/2002 | Senn et al. |
| 2002/0108614 A1 | 8/2002 | Schultz |
| 2003/0096213 A1 | 5/2003 | Hickok et al. |
| 2003/0191429 A1 | 10/2003 | Andrew et al. |
| 2003/0207231 A1 | 11/2003 | Nance |
| 2003/0207232 A1 | 11/2003 | Todd et al. |
| 2004/0048226 A1 | 3/2004 | Garman |
| 2004/0063074 A1 | 4/2004 | Fisher |
| 2004/0072122 A1 | 4/2004 | Hegemann |
| 2004/0073374 A1 | 4/2004 | Lockhart et al. |
| 2004/0101809 A1 | 5/2004 | Weiss et al. |
| 2004/0126732 A1 | 7/2004 | Nusstein |
| 2004/0127892 A1 | 7/2004 | Harris |
| 2005/0096529 A1 | 5/2005 | Cooper et al. |
| 2005/0136375 A1 | 6/2005 | Sicurelli, Jr. et al. |
| 2005/0155622 A1 | 7/2005 | Leis |
| 2005/0170312 A1 | 8/2005 | Pond |
| 2005/0199261 A1 | 9/2005 | Vanhauwermeiren et al. |
| 2005/0271531 A1 | 12/2005 | Brown et al. |
| 2005/0277898 A1 | 12/2005 | Dimalanta et al. |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0246395 A1 | 11/2006 | Pond |
| 2006/0257819 A1 | 11/2006 | Johnson |
| 2006/0264808 A1 | 11/2006 | Staid et al. |
| 2007/0009449 A1 | 1/2007 | Kanca |
| 2007/0020576 A1 | 1/2007 | Osborn et al. |
| 2007/0042316 A1 | 2/2007 | Pichat et al. |
| 2007/0083120 A1 | 4/2007 | Cain et al. |
| 2007/0148615 A1* | 6/2007 | Pond ............... A61C 1/0084 433/80 |
| 2007/0248932 A1* | 10/2007 | Gharib ............... A61C 17/02 433/81 |
| 2007/0287125 A1 | 12/2007 | Weill |
| 2008/0014545 A1 | 1/2008 | Schippers |
| 2008/0032259 A1 | 2/2008 | Schoeffel |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0155770 A1 | 7/2008 | Grez |
| 2008/0160479 A1 | 7/2008 | Ruddle et al. |
| 2008/0160480 A1 | 7/2008 | Ruddle et al. |
| 2008/0188848 A1* | 8/2008 | Deutmeyer ...... A61B 17/32002 606/40 |
| 2008/0199831 A1 | 8/2008 | Teichert et al. |
| 2008/0255498 A1 | 10/2008 | Houle |
| 2008/0311540 A1 | 12/2008 | Gottenbos et al. |
| 2009/0004621 A1 | 1/2009 | Quan et al. |
| 2009/0011380 A1 | 1/2009 | Wang |
| 2009/0047624 A1* | 2/2009 | Tsai ............... A61C 17/20 433/119 |
| 2009/0054881 A1 | 2/2009 | Krespi |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0208898 A1 | 8/2009 | Kaplan |
| 2009/0211042 A1 | 8/2009 | Bock |
| 2009/0220908 A1 | 9/2009 | Divito et al. |
| 2009/0263759 A1 | 10/2009 | Van Herpern |
| 2010/0092922 A1 | 4/2010 | Ruddle |
| 2010/0143861 A1 | 6/2010 | Gharib |
| 2010/0152634 A1 | 6/2010 | Dove |
| 2010/0160838 A1 | 6/2010 | Krespi |
| 2010/0229316 A1 | 9/2010 | Hohlbein et al. |
| 2010/0273125 A1 | 10/2010 | Janssen et al. |
| 2010/0330539 A1 | 12/2010 | Glover et al. |
| 2011/0027746 A1 | 2/2011 | McDonough et al. |
| 2011/0072605 A1 | 3/2011 | Steur |
| 2011/0087605 A1 | 4/2011 | Pond |
| 2011/0111365 A1 | 5/2011 | Gharib et al. |
| 2011/0117517 A1 | 5/2011 | Bergheim et al. |
| 2011/0143310 A1 | 6/2011 | Hunter |
| 2011/0229845 A1 | 9/2011 | Chen |
| 2011/0269099 A1 | 11/2011 | Glover et al. |
| 2011/0281231 A1 | 11/2011 | Rizoiu et al. |
| 2012/0135373 A1 | 5/2012 | Cheng et al. |
| 2012/0141953 A1 | 6/2012 | Mueller |
| 2012/0148979 A1 | 6/2012 | Ruddle |
| 2012/0237893 A1 | 9/2012 | Bergheim |
| 2012/0276497 A1 | 11/2012 | Gharib |
| 2013/0040267 A1 | 2/2013 | Bergheim |
| 2013/0084544 A1 | 4/2013 | Boutoussov et al. |
| 2013/0084545 A1 | 4/2013 | Netchitailo et al. |
| 2013/0143180 A1 | 6/2013 | Glover et al. |
| 2013/0177865 A1 | 7/2013 | Ostler |
| 2013/0216980 A1 | 8/2013 | Boronkay et al. |
| 2013/0236857 A1 | 9/2013 | Boutoussov et al. |
| 2013/0296910 A1* | 11/2013 | Deng ............... A61B 17/32002 606/170 |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0072931 A1 | 3/2014 | Fougere et al. |
| 2014/0080090 A1 | 3/2014 | Laufer |
| 2014/0087333 A1 | 3/2014 | DiVito et al. |
| 2014/0099597 A1 | 4/2014 | Bergheim |
| 2014/0113243 A1 | 4/2014 | Boutoussov et al. |
| 2014/0124969 A1 | 5/2014 | Blaisdell et al. |
| 2014/0170588 A1 | 6/2014 | Miller et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0349246 A1 | 11/2014 | Johnson et al. |
| 2015/0010878 A1 | 1/2015 | Seibel et al. |
| 2015/0044631 A1 | 2/2015 | Lifshitz et al. |
| 2015/0044632 A1 | 2/2015 | Bergheim et al. |
| 2015/0056567 A1 | 2/2015 | Fregoso et al. |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1 | 5/2015 | Breysse |
| 2015/0147718 A1 | 5/2015 | Khakpour |
| 2015/0150650 A1 | 6/2015 | Netchitailo et al. |
| 2015/0173852 A1 | 6/2015 | Khakpour |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0366634 A1 | 12/2015 | Gharib et al. |
| 2015/0374471 A1 | 12/2015 | Stangel et al. |
| 2016/0095679 A1 | 4/2016 | Khakpour et al. |
| 2016/0100921 A1 | 4/2016 | Ungar |
| 2016/0113733 A1 | 4/2016 | Pond et al. |
| 2016/0135581 A1 | 5/2016 | Pai |

FOREIGN PATENT DOCUMENTS

| | | |
|---|---|---|
| AU | 2011316839 | 8/2015 |
| CN | 102724929 | 10/2012 |
| CN | 103347462 | 10/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 1 214 916 | 6/2002 |
| EP | 2 821 027 | 1/2015 |
| EP | 2 836 156 | 2/2015 |
| EP | 2 836 157 | 2/2015 |
| EP | 2 951 019 | 12/2015 |

(56) References Cited

FOREIGN PATENT DOCUMENTS

| | | |
|---|---|---|
| EP | 3 013 277 | 5/2016 |
| FR | 1 225 547 | 7/1960 |
| FR | 2 831 050 | 10/2001 |
| GB | 917 633 | 2/1963 |
| HK | 1 188 108 A | 4/2014 |
| IL | 219169 | 4/2013 |
| JP | 2000-254153 A | 9/2000 |
| JP | 2004-313659 | 11/2003 |
| JP | 2005-095374 | 4/2005 |
| JP | 2009-114953 | 5/2009 |
| JP | 2013-510688 | 3/2013 |
| JP | 2013-544120 | 12/2013 |
| JP | 2015-510829 | 4/2015 |
| JP | 2015-512761 | 4/2015 |
| KR | 10-2012-0084897 A | 7/2012 |
| WO | WO 92/12685 | 8/1992 |
| WO | WO 98/25536 | 6/1995 |
| WO | WO 00/45731 | 8/2000 |
| WO | WO 01/93773 | 12/2001 |
| WO | WO 02/078644 | 10/2002 |
| WO | WO 03/086223 | 10/2003 |
| WO | WO 2004/082501 | 9/2004 |
| WO | WO 2005/007008 | 1/2005 |
| WO | WO 2005/032393 | 4/2005 |
| WO | WO 2006/082101 | 8/2006 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/064947 | 5/2009 |
| WO | WO 2009/137815 | 11/2009 |
| WO | WO 2010/099538 | 9/2010 |
| WO | WO 2011/060327 | 5/2011 |
| WO | WO 2012/054905 | 4/2012 |
| WO | WO 2013/15700 | 1/2013 |
| WO | WO 2013/061251 | 5/2013 |
| WO | WO 2013/142385 | 9/2013 |
| WO | WO 2013/155492 | 10/2013 |
| WO | WO 2014/100751 | 6/2014 |
| WO | WO2014/121293 | 8/2014 |
| WO | WO 2015/168329 | 11/2015 |

OTHER PUBLICATIONS

Al-Jadaa et al; Acoustic Hypochlorite Activation in Simulated Curved Canals; pp. 1408-1411; Journal of Endodontics, vol. 35, No. 10; Oct. 2009.
Anand et al; Prevention of Nozzle Wear in High-Speed Slurry Jets Using Porous Lubricated Nozzles; pp. 1-13; Department of Mechanical Engineering, The Johns Hopkins University, Oct. 2000.
Anantharamaiah et al; A simple expression for predicting the inlet roundness of micro-nozzles; pp. N31-N39; Journal of Micromechanics and Microengineering, vol. 17; Mar. 21, 2007.
Anantharamaiah et al; A study on flow through hydroentangling nozzles and their degradation; pp. 4582-4594; Chemical Engineering Science, vol. 61; May 2006.
Anantharamaiah et al; Numerical Simulation of the Formation of Constricted Waterjets in Hydroentangling Nozzles Effects of Nozzle Geometry; pp. 31-238; Chemical Engineering Research.
Attin et al; Clinical evaluation of the cleansing properties of the nonistrumental technique for cleaning root canals; pp. 929-933; International Endodontic Journal, vol. 35, Issue 11; Nov. 2002.
Batchelor et al; Analysis of the stability of axisymmetric jets; pp. 529-551; Journal of Fluid Mechanics, vol. 14; Dec. 1962.
Begenir et al; Effect of Nozzle Geometry on Hydroentangling Water Jets: Experimental Observations; pp. 178-184; Textile Research Journal, vol. 74; Feb. 2004.
Begenir, Asli; The Role of Orifice Design in Hydroentanglement; Thesis submitted to North Carolina State University; dated Dec. 2002, in 107 pages.
Borkent et al; Is there gas entrapped on submerged silicon wafers? Visualizing nano-scale bubbles with cavitation; pp. 225-228; Solid State Phenomena, vol. 134 (2008); available online Nov. 2007.
Bremond et al; Cavitation on surfaces; pp. S3603-53608; Journal of Physics: Condensed Matter, vol. 17; Oct. 28, 2005.
Brennen, Christopher E.; Fission of collapsing cavitation bubbles; pp. 153-166; Journal of Fluid Mechanics, vol. 472; Dec. 2002.
Chang et al; Effects of Inlet Surface Roughness, Texture, and Nozzle Material on Cavitation; pp. 299-317; Atomization and Sprays, vol. 16 (2006).
Culjat et al., "B-Scan Imaging of Human Teeth Using Ultrasound," Apr. 2003, in 4 pages.
Didenkulov et al; Nonlinear Acoustic Diagnostics of Scatterer Spatial Distribution in a Cavitation Jet; Nov. 19-23, 2001, pp. 276-278, XI Session of the Russion Acoustical Society.
Dumouchel, Christophe; On the experimental investigation on primary atomization of liquid streams; pp. 371-422; Experimental Fluids, vol. 45; Jun. 22, 2008.
Eddingfield et al; Mathematical Modeling of High Velocity Water Jets; pp. 25-39; Proceedings of 1st U.S. Water Jet Conference; 1981.
EMS Electro Medical Systems, "Cleaning", in 2 pages, dated 2005, downloaded from http://www.ems-dent.com/en/endodontics cleaning. htm.
ESI Endo Soft Instruments, EMS Electro Medical Systems, Brochure in 2 pages, downloaded from www.emsdent.com, dated Jan. 2004.
European Extended Search Report re EP Application No. 09743801.4, dated Jun. 4, 2012.
European Extended Search Report, dated Sep. 22, 2011, for EP Application No. 07755777.5., in 7 pages.
Feng et al; Enhancement of ultrasonic cavitation yield by multifrequency sonication; pp. 231-236; Ultrasonics Sonochemistry, vol. 9; Oct. 2002.
Flint, E. B., et al., "The Temperature of Cavitation", Science, vol. 253, Sep. 20, 1991, pp. 1397-1399.
Foldyna et al; Acoustic wave propagation in high-pressure system; pp. e1457-e1460; Ultrasonics vol. 44 (Supplement 1); Jun. 8, 2006.
Fuchs, "Ultrasonic Cleaning: Fundamental Theory and Application," Blackstone-Ney Ultrasonics, Jamestown, NY, May 2002.
G.E. Reisman and C.E. Brennen, "Pressure Pulses Generated by Cloud Cavitation", FED—vol. 236, 1996 Fluids Engineering Division Conference, vol. 1, pp. 319-328, ASME 1996.
G.E. Reisman, Y.-C. Wang and C.E. Brennen, "Observations of shock waves in cloud cavitation", J. Fluid Mech. (1998), vol. 355, pp. 255-283.
Ghassemieh et al; Effect of Nozzle Geometry on the Flow Characteristics of Hydroentangling Jets; pp. 444-450; Textile Research Journal, vol. 73; May 2003.
Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.
Hahn et al; Acoustic resonances in the bubble plume formed by a plunging water jet; pp. 1751-1782; Proceedings of the Royal Society of London A, vol. 459; May 16, 2003.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hungarian Written Opinion and Search Report via/re Singapore Application No. 189554, mailed Oct. 13, 2013.
Hydrocision Products: SpineJet Hydrosurgery; system webpage in 2 pages, copyright 2010, downloaded from http://www.hydrocision.com on Apr. 22, 2010.

(56) References Cited

OTHER PUBLICATIONS

Hydrocision SpineJet XL HydroSurgery System; Brochure in 2 pages, copyright 2004-2006, downloaded from http://www.hydrocision.com on Apr. 22, 2010.
International Preliminary Report and Written Opinion dated Nov. 9, 2010 for International Appl. No. PCT/US09/43386, in 6 pages.
International Preliminary Report on Patentability dated Aug. 6, 2009, for International Appl. No. PCT/US08/52122, in 13 pages.
International Preliminary Report on Patentability dated Oct. 30, 2008, for International Appl. No. PCT/US07/09633, in 5 pages.
International Preliminary Report on Patentability re App. No. PCT/US2010/056620, issued May 15, 2012, in 10 pages.
International Preliminary Report on Patentability, re PCT Application No. PCT/US11/57401, mailed Jan. 25, 2013 in 13 pages.
International Search Report and Written Opinion dated Apr. 11, 2008, for International Appl. No. PCT/US07/09633, in 8 pages.
International Search Report and Written Opinion dated Aug. 8, 2008, for International Appl. No. PCT/US08/52122, in 18 pages.
International Search Report and Written Opinion dated Jul. 29, 2009, for International Appl. No. PCT/US09/43386, in 8 pages.
International Search Report and Written Opinion from International Application No. PCT/US2011/057401, Jan. 30, 2012, in 20 pages.
International Search Report and Written Opinion mailed Jun. 28, 2013, re PCT Application No. PCT/US2013/036493, in 21 pages.
International Search Report and Written Opinion re App. No. PCT/US2010/056620, dated Jan. 12, 2011, in 17 pages.
International Search Report and Written Opinion, re PCT Application No. PCT/US 13/32635, mailed Jun. 17, 2013 in 14 pages.
Jackson et al; Nozzle Design for Coherent Water Jet Production; pp. 53-89; Proceeding of the 2nd US Water Jet Conference; May 1983.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; in CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.
Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.

Maximum Dental Inc., "Canal Clean Max", "Intra Canal Irrigation and Aspiration Device, and "SonicMax, Endo-Perio Sonic Handpiece, in 3 pages, downloaded from www.dentalmaximum.com on May 8, 2008.
Ohrn et al; Geometric Effects on Spray Cone Angle for Plain-Orifice Atomizers; pp. 253-268; Atomization and Sprays, vol. 1 (1991).
Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound a la carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sabeti, "Healing of apical periodontitis after endodontic treatment with and without obturation in dogs," Journal of Endodontics, Jul. 2006, pp. 628-633.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Zuo et al; An Attribution of Cavitation Resonance: Volumetric Oscillations of Cloud; pp. 152-158; Journal of Hydrodynamics, vol. 21; Apr. 2009.
European Extended Search Report re EP Application No. 14187012.1, dated Mar. 3, 2015, in 10 pages.
European Extended Search Report, re EP Application No. 08728345.3, dated Mar. 3, 2014.

(56) References Cited

OTHER PUBLICATIONS

International Preliminary Report on Patentability and Written Opinion, mailed Oct. 14, 2014, re PCT Application No. PCT/US2013/036493, in 14 pages.
International Preliminary Report on Patentability re PCT Application No. PCT/US2014/014732, issued Aug. 4, 2015.
International Preliminary Report on Patentability, re PCT Application No. PCT/US2013/077286, issued Jun. 23, 2015.
International Search Report and Written Opinion re App. No. PCT/US2014/014732, mailed Jul. 18, 2014.
International Search Report and Written Opinion, re PCT Application No. PCT/US2013/077286, mailed May 27, 2014.
International Search Report and Written Opinion, re PCT Application No. PCT/US2014/036451, mailed Jan. 21, 2015, in 20 pages.
International Search Report and Written Opinion, re PCT Application No. PCT/US2014/044186, mailed Jan. 21, 2015, in 19 pages.
International Search Report and Written Opinion, re PCT Application No. PCT/US2015/028360, mailed Sep. 28, 2015, in 24 pages.
European Extended Search Report, re EP Application No. 11835265.7, dated Mar. 30, 2016, in 9 pages.
U.S. Appl. No. 61/701,947, filed Sep. 17, 2012, Laufer.
U.S. Appl. No. 61/894,762, filed Oct. 23, 2013, Lifshitz et al.
U.S. Appl. No. 61/895,316, filed Oct. 24, 2013, Lifshitz et al.
European Extended Search Report, re EP Application No. 10830829.7, dated Oct. 21, 2015.
European Extended Search Report, re EP Application No. 13763534.8, dated Jan. 15, 2016.
European Extended Search Report, re EP Application No. 13775073.3, dated Nov. 3, 2015.
International Preliminary Report on Patentability, re PCT Application No. PCT/US2014/036451, issued Nov. 3, 2015, 2015, in 11 pages.
International Preliminary Report on Patentability, re PCT Application No. PCT/US2014/044186, mailed Dec. 29, 2015, in 19 pages.
Wohlemuth et al.: "Effectiveness of GentleWave System in Removing Separated Instruments," JOE, vol. 41, No. 11, Nov. 2015.

\* cited by examiner

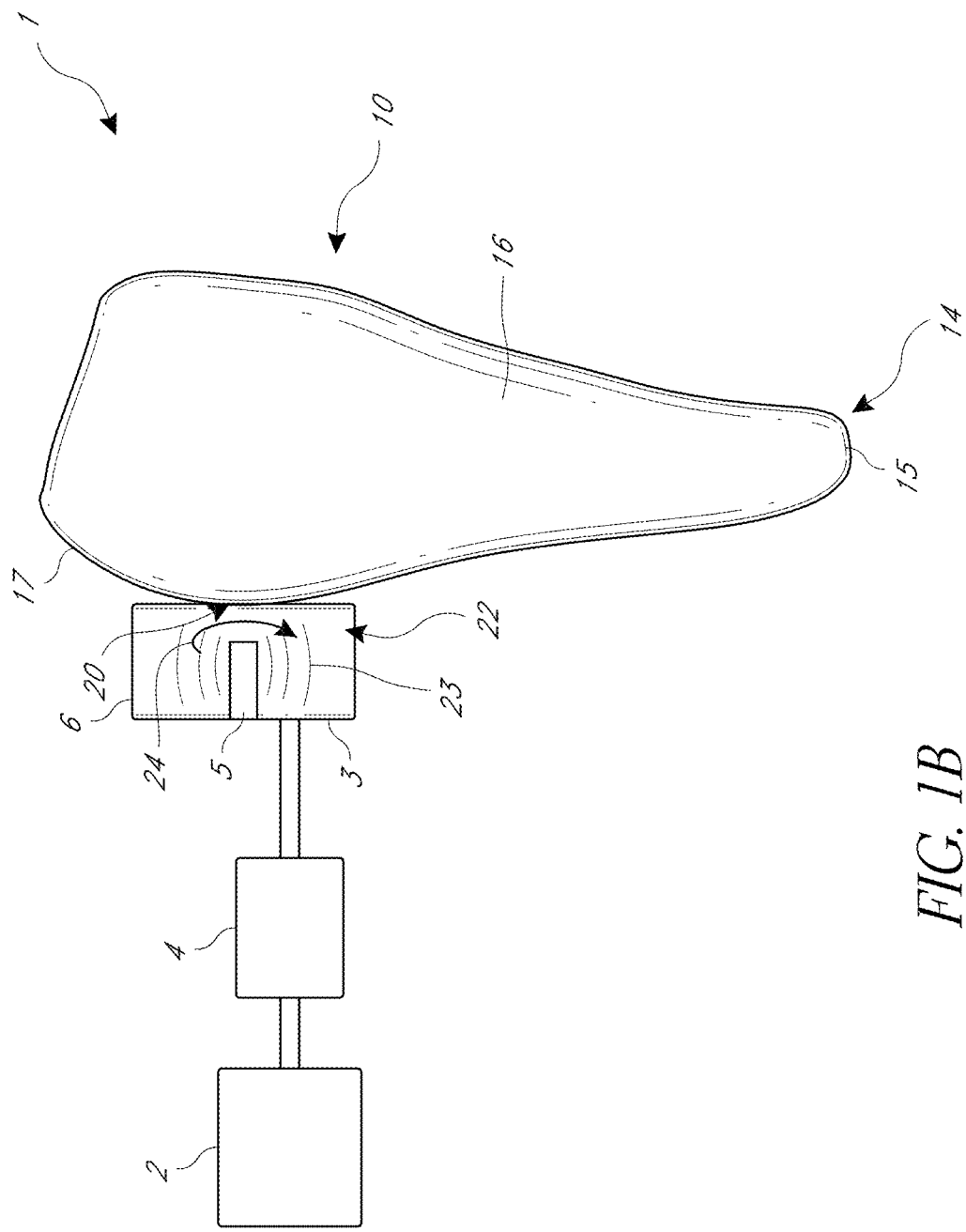

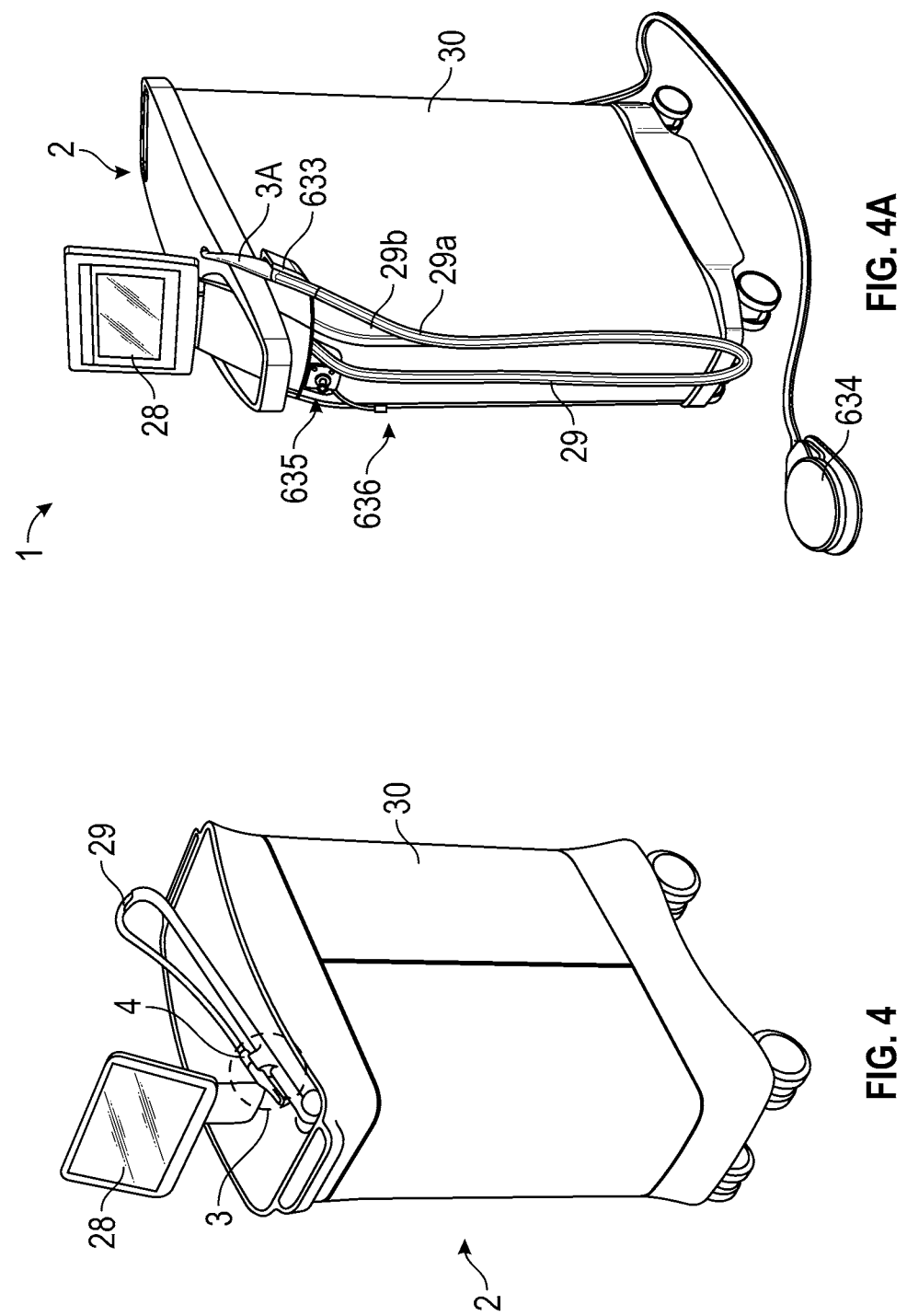

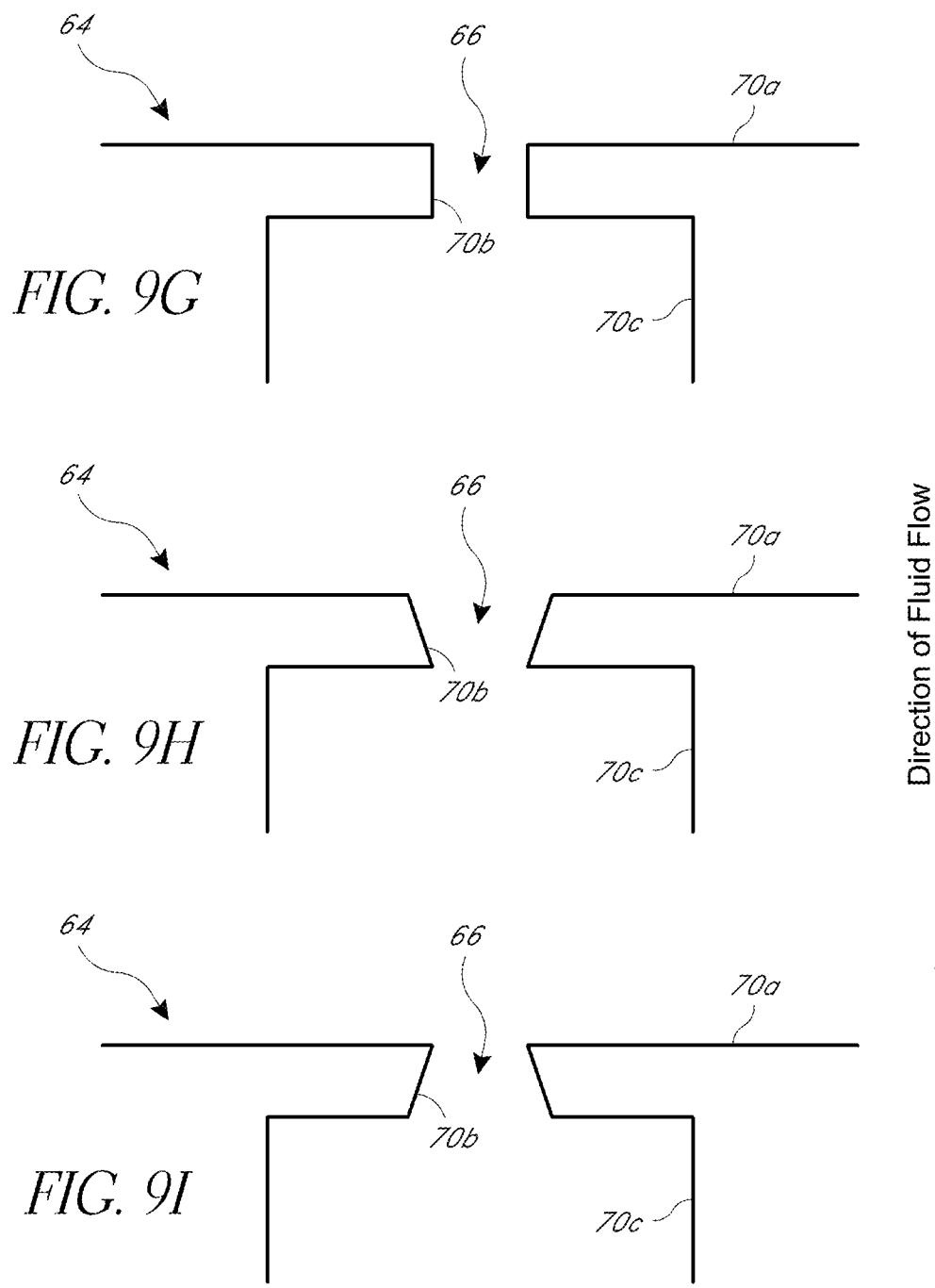

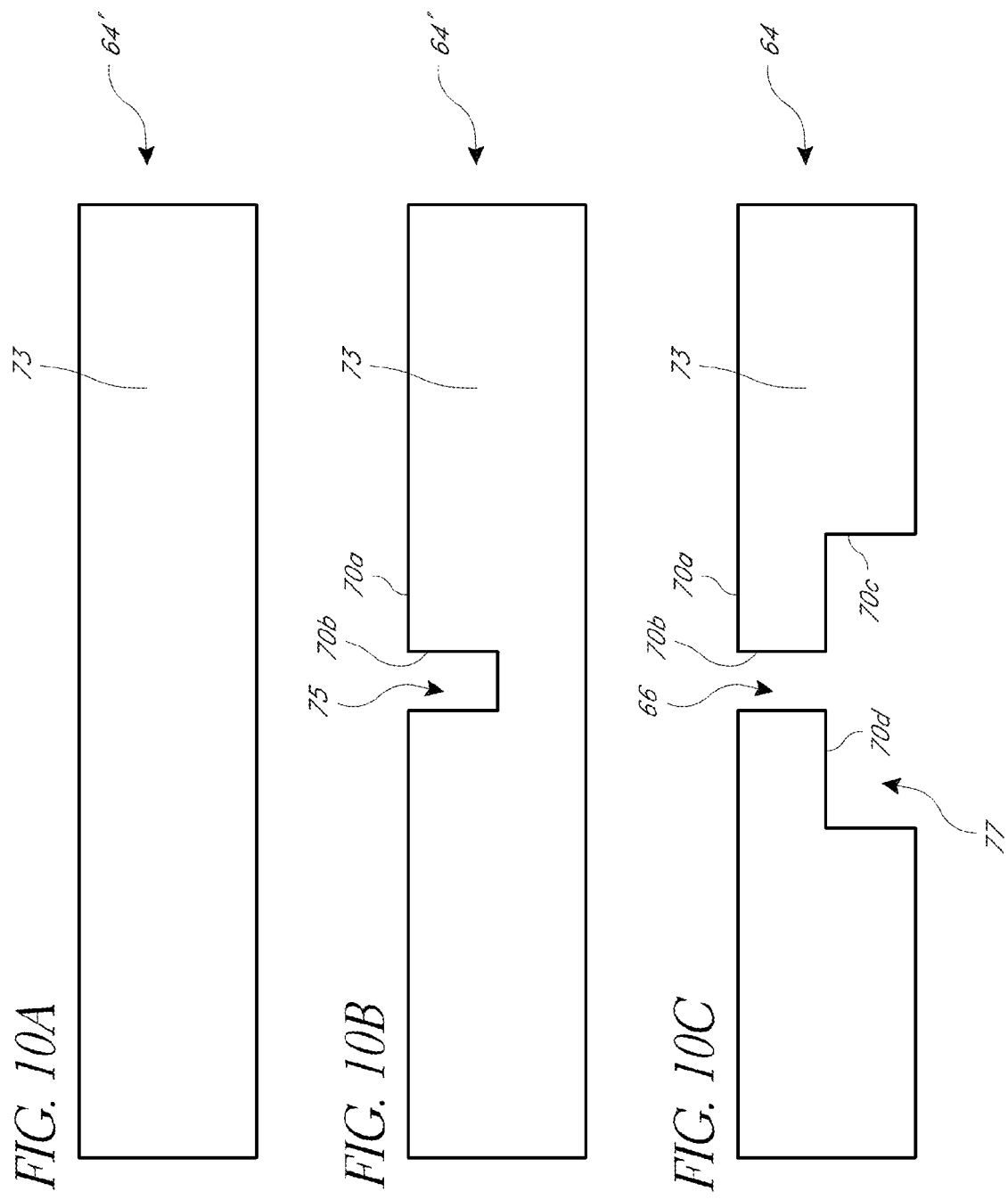

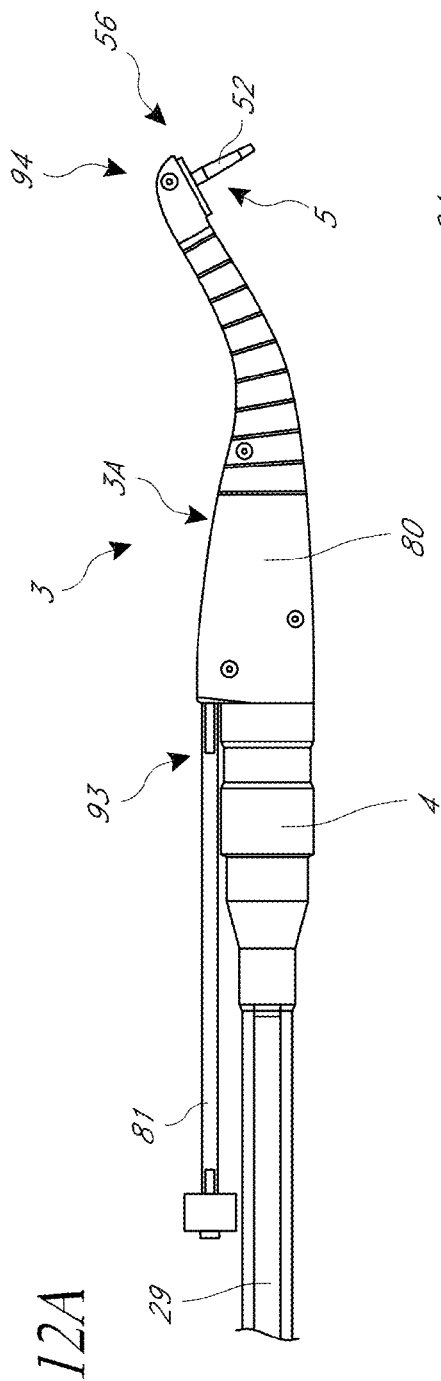
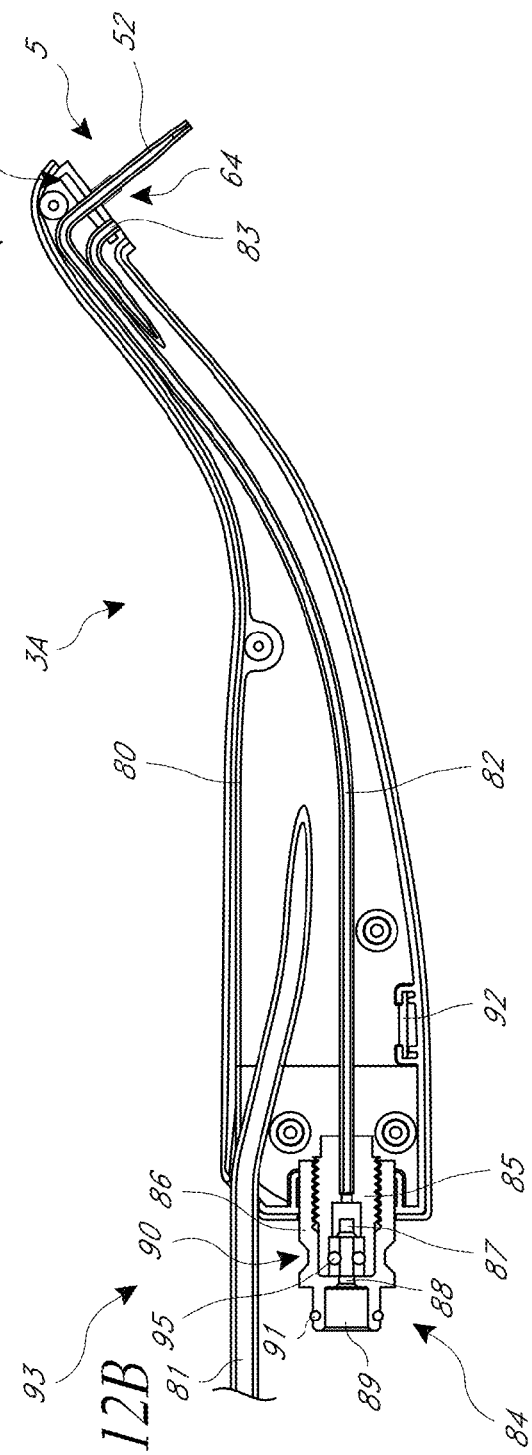
FIG. 12A
FIG. 12B

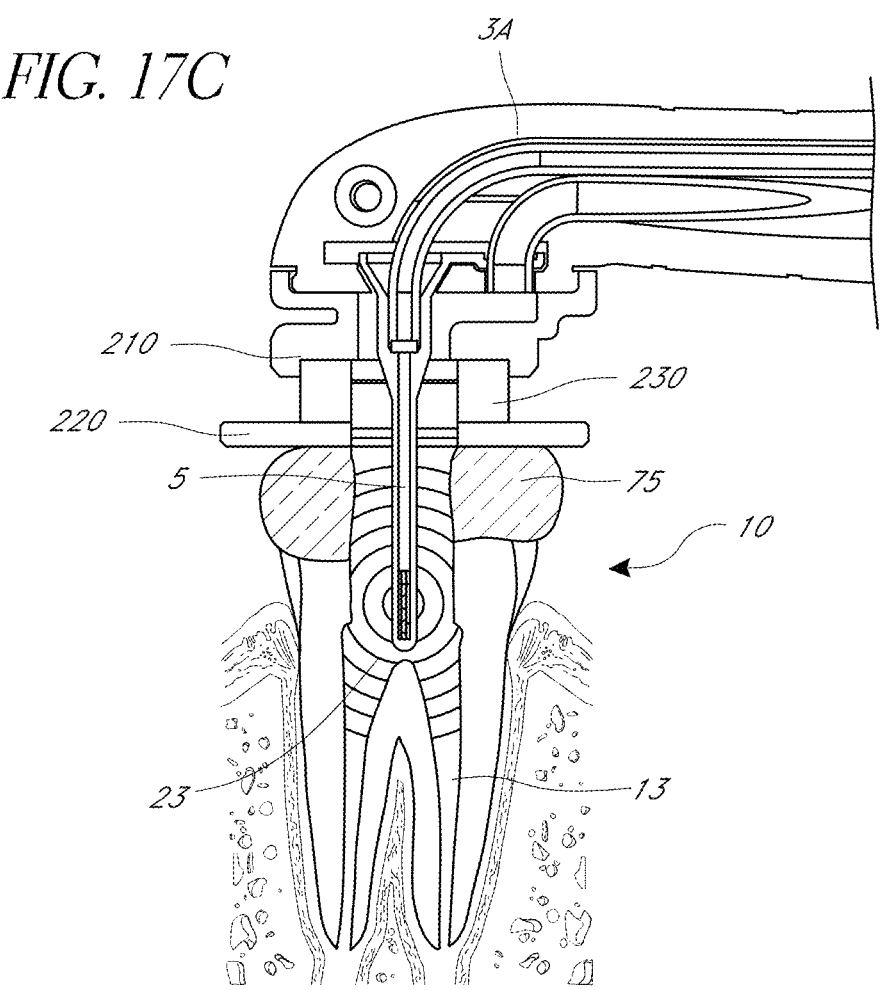

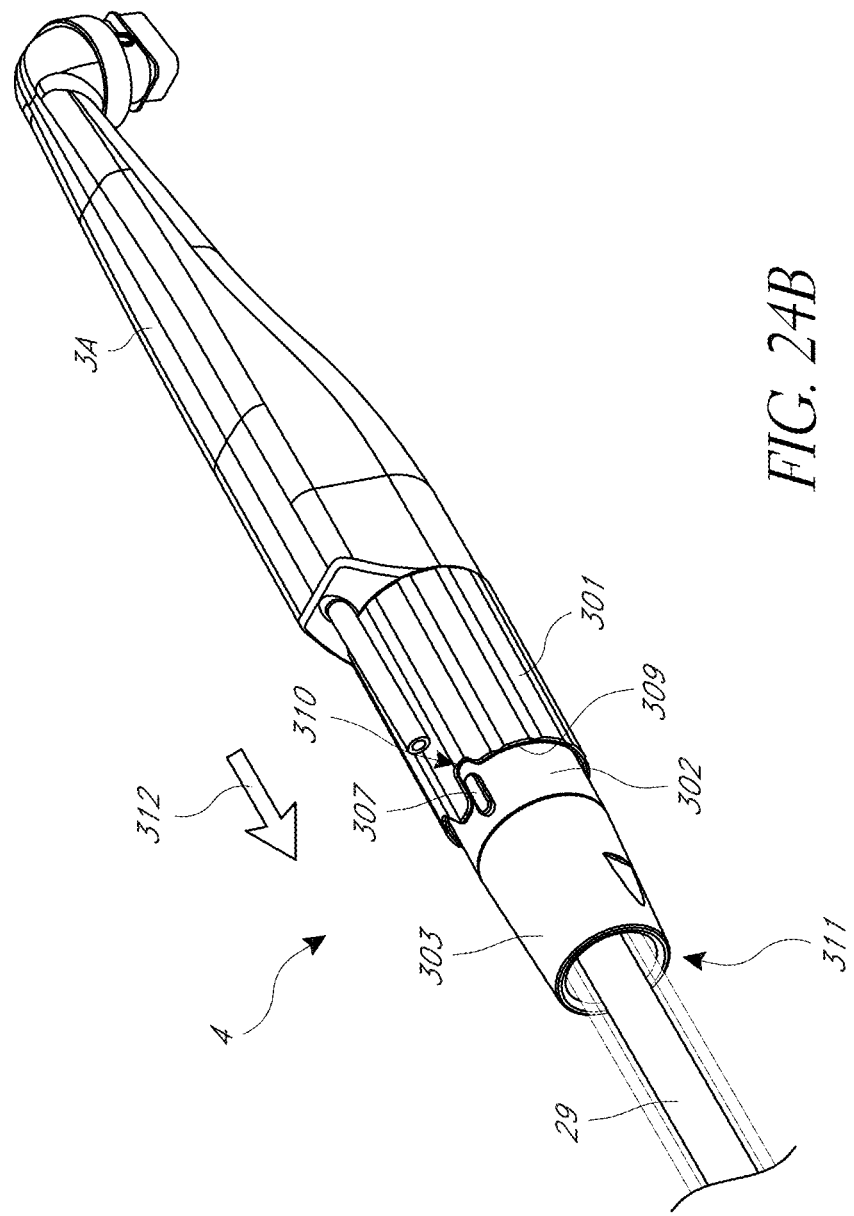

DENTAL TREATMENT SYSTEM

CROSS-REFERENCE TO RELATED APPLICATIONS

This application claims the benefit of U.S. Provisional Patent Application No. 61/760,620, filed Feb. 4, 2013, entitled "METHODS FOR MAKING ORIFICE FOR USE IN DENTISTRY;" U.S. Provisional Patent Application No. 61/767,741, filed Feb. 21, 2013, entitled "APPARATUS AND METHODS FOR TREATING ROOT CANALS OF TEETH;" U.S. Provisional Patent Application No. 61/864,393, filed Aug. 9, 2013, entitled "APPARATUS AND METHODS FOR TREATING ROOT CANALS OF TEETH;" U.S. Provisional Patent Application No. 61/767,746, filed Feb. 21, 2013, entitled "APPARATUS AND METHODS FOR SEALING TEETH;" U.S. Provisional Patent Application No. 61/805,110, filed Mar. 25, 2013, entitled "APPARATUS AND METHODS FOR SEALING TEETH;" each of which is hereby incorporated by reference herein in its entirety and for all purposes

BACKGROUND

1. Field of the Invention

The field relates generally to dental treatment systems, and, in particular, to dental treatment systems having a dental apparatus connected to a console.

2. Description of the Related Art

In conventional dental and endodontic procedures, mechanical instruments such as drills, files, brushes, etc. are used to clean unhealthy material from a tooth. For example, dentists often use drills to mechanically break up carious regions (e.g., cavities) in a surface of the tooth. Such procedures are often painful for the patient and frequently do not remove all the diseased material. Furthermore, in conventional root canal treatments, an opening is drilled through the crown or side of a diseased tooth, and endodontic files are inserted into the root canal system to open the canal spaces and remove organic material therein. The root canal is then filled with solid matter such as gutta percha or a flowable obturation material, and the tooth is restored. However, this procedure typically does not remove all organic material from the canal spaces, which can lead to post-procedure complications such as infection. In addition, motion of the endodontic file and/or other sources of positive pressure may force organic material through an apical opening into periapical tissues. In some cases, an end of the endodontic file itself may pass through the apical opening. Such events may result in trauma to the soft tissue near the apical opening and lead to post-procedure complications. Accordingly, there is a continuing need for improved dental and endodontic treatments.

SUMMARY

Various non-limiting aspects of the present disclosure will now be provided to illustrate features of the disclosed apparatus, methods, and compositions. Examples of apparatus, methods, and compositions for endodontic treatments are provided.

In one embodiment, a dental apparatus configured to treat a tooth is disclosed. The apparatus can include a housing having a proximal portion and a distal portion, the distal portion configured to couple to the tooth. The apparatus can include a fluid jet assembly coupled to the housing and configured to generate a jet of fluid. The apparatus can include a high pressure fluid supply line disposed in the housing and in fluid communication with the fluid jet assembly. The high-pressure fluid line can be adapted to convey pressurized liquid to the liquid jet assembly. A connector can be disposed near the proximal portion of the housing. The connector can be configured to removably couple to an interface member in fluid or electrical communication with the dental treatment system. The connector can include a shank and an interior receiving chamber configured to receive a portion of the interface member. The shank can include an engagement structure disposed on its exterior surface and configured to interact with a corresponding engagement structure on the interface member, the receiving chamber extending distal of at least a portion of the engagement structure on the shank.

The connector can further comprise threaded engagement features configured to threadably couple to the interface member. The threaded engagement features can comprise external threads formed on an outer surface of the connector. The connector can further comprise a first opening proximal to and in fluid communication with the high-pressure fluid line and a second opening disposed proximal the first opening. The second opening can be larger than the first opening and configured to receive the interface member. In some embodiments, a filter can be disposed proximal a proximal end of the fluid supply line. One or more gaskets can be disposed proximal the filter between the filter and a proximal end of the apparatus. The one or more gaskets can comprise at least one of a polyether ether ketone (PEEK) ring and an ethylene propylene diene monomer (EPDM) rubber o-ring. In some embodiments, the apparatus can comprise a handpiece. In other embodiments, the apparatus can comprise a treatment cap configured to attach to the tooth.

In another embodiment, a dental treatment system is disclosed. The system can include an interface member configured to connect a dental treatment apparatus to a console to provide at least one of fluid and electrical communication between the console and the treatment apparatus. The treatment apparatus can be configured to couple the system to a tooth and comprising a connector. The interface member can comprise an engagement structure disposed at a distal portion of the interface member and configured such that, when the engagement structure engages a corresponding engagement structure of the connector, the interface member and the dental treatment apparatus are secured along a longitudinal direction of the system. The interface member can include a swivel member disposed proximal the engagement structure, the swivel member configured to permit relative rotation between the interface member and the dental treatment apparatus.

In some embodiments, the treatment apparatus can comprise a dental handpiece. In some embodiments, high pressure tubing can extend through the distal portion and can be configured to engage the dental treatment apparatus to provide fluid communication between the tubing and a high pressure fluid supply line of the treatment apparatus. The engagement structure of the interface member can comprise an internal thread. The interface member can include an outer shell and an inner shell. The swivel member can comprise a projection extending inwardly from the outer shell into a recess of the inner shell In another embodiment, a dental treatment system is disclosed. The system can include one or more fluid reservoirs configured to supply fluid to the system. A pump can be configured to pressurize the one or more fluids supplied to the system. The system can comprise an interface configured to provide mechanical, fluidic, or electronic communication with a tooth coupler configured to couple to a tooth. The system can further include a processing unit. The processing unit can comprise a controller module configured to control the operation of the pump and a management module configured to manage data related to one or more dental treatment procedures performed by the system.

In some embodiments, the system can include a console, wherein the fluid reservoirs, the pump, the interface, and the processing unit are housed in or on the console. The processing unit can further comprise a communications module configured to communicate over a network with one or more external systems. In some embodiments, the communications module can be configured to send to or receive from the one or more external systems the data related to the one or more treatment procedures. In some embodiments, the communications module can be configured to communicate with at least one of an emergency system, an imaging system, a patient data management system, an office inventory system, and a patient scheduling system. The communications module can be configured to communicate with the office inventory system to indicate when system components or materials should be ordered. In some embodiments, the tooth coupler can include a handpiece. The system can further include a degassing system in fluid communication with the one or more fluid reservoirs, the degassing system configured to remove dissolve gases from the fluid supplied to the system. The system can also include a mixing system in fluid communication with the one or more fluid reservoirs, the mixing system configured to mix a plurality of fluids together.

In another embodiment, a dental treatment apparatus for treating a tooth is disclosed. The apparatus can comprise a housing and a treatment assembly coupled to the housing. The treatment assembly can be configured to perform a treatment procedure on the tooth. The apparatus can include a communications chip coupled to the housing. The communications chip can be configured to communicate information about at least one of the treatment procedure and the dental treatment apparatus to a communications reader.

In some embodiments, the housing can be configured to removably couple to a console. The communications chip can comprise a wireless chip, and the wireless chip can be configured to wirelessly transmit the information to the reader. In various embodiments, the wireless chip can comprise a radio frequency identification (RFID) chip, and the reader can comprise a RFID reader. The communications chip can be configured to communicate information related to a number of treatment procedures performed by the dental treatment apparatus. If the number of treatment procedures performed by the dental treatment apparatus is greater than a predetermined number, one of the communications chip and the reader can be configured to disable the dental treatment apparatus. In some arrangements, the predetermined number can be one. The communications chip can be configured to communicate identifying information regarding the particular dental treatment apparatus. The identifying information can comprise at least one of serial number, lot number, date of manufacture, and name of manufacturer. In some embodiments, if the identifying information indicates that the dental treatment apparatus is an unauthorized apparatus, one of the communications chip and the reader can be configured to disable the dental treatment apparatus.

In some embodiments, the communications chip can be configured to communicate status information relating to a status of a treatment procedure. The communications chip can be configured to communicate information about the treatment procedure relating to at least one of treatment type, treatment duration, patient name, treatment outcome, and degree of completeness of procedure. In some embodiments, the housing can comprise a dental handpiece. The communications chip can be configured to communicate information related to a type of the handpiece. In some embodiments, the treatment assembly can comprise a pressure wave generator, which can be a fluid jet device in some embodiments.

In yet another embodiment, a dental treatment system is disclosed. The system can include a console and one or more conduits coupled to the console. The system can include a reader in data communication with the console. The system can include a dental treatment apparatus configured to removably couple to the one or more conduits, the one or more conduits providing at least one of fluidic, electrical, and data communication between the console and the dental treatment apparatus when coupled to the dental treatment apparatus. The dental treatment apparatus can comprise a memory device coupled thereto. The memory device can be configured to communicate information about at least one of the treatment procedure and the dental treatment apparatus to the reader.

In some embodiments, the memory device can comprise a communications chip. The communications chip can comprise a wireless chip, the wireless chip configured to wirelessly transmit the information to the reader. In some embodiments, the wireless chip comprises a radio frequency identification (RFID) chip, and the reader comprises a RFID reader. The communications chip can be configured to communicate information related to a number of treatment procedures performed by the dental treatment apparatus to the reader. If the number of treatment procedures performed by the dental treatment apparatus is greater than a predetermined number, the reader can be configured to communicate with the console to prevent the dental apparatus from being used in a treatment procedure. The predetermined number can be one in some embodiments. The communications chip can be configured to communicate identifying information regarding the particular dental treatment apparatus to the reader. The identifying information can comprise at least one of serial number, lot number, date of manufacture, and name of manufacturer. If the identifying information indicates that the dental treatment apparatus is an unauthorized apparatus, the reader can be configured to communicate with the console to prevent the dental apparatus from being used in a treatment procedure.

In some embodiments, the communications chip can be configured to communicate status information relating to a status of a treatment procedure. The communications chip can be configured to communicate to the reader information about the treatment procedure relating to at least one of treatment type, treatment duration, patient name, treatment outcome, and degree of completeness of procedure. The reader can be configured to communicate to the console information about the treatment procedure relating to at least one of treatment type, treatment duration, patient name, treatment outcome, and degree of completeness of procedure. The console can be configured to communicate the information about the treatment procedure to a patient data management system.

In another embodiment, an apparatus for treating a tooth is disclosed. The apparatus can include a handpiece and an occlusal magnet configured to be attached to the tooth. The apparatus can include a handpiece magnet coupled to the handpiece, the handpiece magnet configured to magnetically couple to the occlusal magnet to substantially seal or attach the handpiece to the tooth.

In some embodiments, the apparatus can include one or more spacer magnets configured to be disposed between the occlusal magnet and the handpiece magnet, the one or more spacer magnets configured to magnetically couple to the occlusal magnet and the handpiece magnet. The occlusal magnet can have an opening formed therethrough that defines an inner diameter. The one or more spacer magnets each may have an opening formed therethrough that defines an inner diameter. The inner diameter of the occlusal magnet may be substantially the same as the inner diameter(s) of the one or more spacer magnets.

A pressure wave generator can be coupled to a distal portion of the handpiece. The pressure wave generator can be configured to pass through an opening of the handpiece magnet, the opening(s) of the spacer magnet(s), and the opening of the occlusal magnet. In some embodiments, a magnetic strength between the occlusal magnet and a spacer magnet adjacent the occlusal magnet can be less than a magnetic strength between the handpiece magnet and a spacer magnet adjacent the handpiece magnet. A magnetic strength between the occlusal magnet and a spacer magnet adjacent the occlusal magnet can be less than a magnetic strength between two adjacent spacer magnets. The one or more spacer magnets can be configured to align the occlusal magnet with the handpiece magnet. The one or more spacer magnets can be configured to offset the handpiece from a portion of the tooth by a separation distance.

In yet another embodiment, an apparatus for treating a tooth is disclosed. The apparatus can include a handpiece and an attachment member configured to be attached to the tooth. An alignment member can be configured to align a distal end portion of the handpiece with the attachment member when the attachment member is attached to the tooth. The alignment member and the attachment member can be configured to seal the tooth the handpiece.

In some embodiments, the attachment member can comprise an occlusal magnet, and the alignment member can comprise a handpiece magnet coupled to the handpiece. One or more spacer magnets can be configured to couple the handpiece magnet to the occlusal magnet. In various embodiments, the alignment member and the attachment member can be configured to seal the tooth to the handpiece when the user rotates the handpiece relative to the tooth. In other embodiments, the alignment member and the attachment member can be configured to disengage when the user rotates the handpiece. In some embodiments, the user can engage the magnets to couple to the tooth by translating the alignment member towards the attachment member.

In another embodiment, a method of manufacturing a nozzle for a liquid jet device is disclosed. The method can comprise forming a first hole through a first plate. The method can include forming a second hole through a second plate, the second hole larger than the first hole. The method can include attaching the first plate to the second plate such that the first hole is aligned with the second hole, wherein a perimeter of the first hole is completely within a perimeter of the second hole.

In some embodiments, forming the first hole can comprise cutting through a thickness of the first plate such that side walls of the first hole have a first surface roughness, and forming the second hole can comprise cutting through a thickness of the second plate such that side walls of the second hole have a second surface roughness, the second surface roughness being rougher than the first surface roughness. In some embodiments, forming the first hole can comprise cutting the first hole using a laser. In some embodiments, forming the first hole can comprise cutting the first hole using electric discharge machining (EDM). In some embodiments, forming the second hole can comprise cutting the first hole using a mechanical tool.

In another embodiment, a method of manufacturing a nozzle for a liquid jet device is disclosed. The method can comprise forming a top trench partially through a thickness of a plate in a top side of the plate. The method can further comprise forming a bottom trench partially through the thickness of the plate in a bottom side of the plate until the bottom trench meets the top trench to define a through hole between the top and bottom sides of the plate. The top trench can have a width smaller than a width of the bottom trench.

In some embodiments, the top and bottom trenches can comprise substantially circular trenches.

In another embodiment, a dental apparatus configured to treat a tooth is disclosed. The apparatus can include a housing having a proximal portion and a distal portion, the distal portion configured to couple to the tooth. The apparatus can include a liquid jet assembly coupled to the housing and configured to generate a jet of liquid. The apparatus can include a high-pressure fluid line disposed in the housing and in fluid communication with the liquid jet assembly, the high-pressure fluid line adapted to convey pressurized liquid to the liquid jet assembly. The apparatus can include a connector disposed near the proximal portion of the housing, the connector configured to removably couple to an interface member in fluid or electrical communication with the dental treatment system.

In some embodiments, the apparatus comprises a first opening proximal to and in fluid communication with the high-pressure fluid line, and a second opening disposed proximal the first opening, the second opening larger than the first opening and configured to receive the interface member. In some embodiments, the dental apparatus can comprise a dental handpiece. In other embodiments, the apparatus can comprise a treatment cap. The engagement feature can comprise a recess formed in an outer surface of the connector. The recess can be a groove.

In one embodiment, a method for engaging a dental treatment apparatus with an interface member in communication with a dental console is disclosed. The dental apparatus can be configured to treat a tooth and can have a connector. The method can include inserting one of the connector and the interface member into the other of connector and the interface member. The method can further include securing the connector to the interface member by translating the connector and the interface member towards one another until the connector and the interface member are secured together. The method can further include after securing the connector to the interface member, releasing the connector from the interface member by rotating the interface member relative to the connector and translating the connector and interface member towards one another to disengage the connector and interface member.

In another embodiment, a dental treatment system is disclosed. The system can include an interface member configured to connect a tooth coupler or dental treatment apparatus to a console to provide at least one of fluid and electrical communication between the console and the tooth coupler, the tooth coupler configured to couple the system to a tooth and comprising a connector. The interface member can comprise an inner shell and an outer shell rotatably engaged with the inner shell, the outer shell comprising a projection on an inner surface of the outer shell. The interface member can comprise a slider disposed at least in part in the outer shell. When the connector is translated towards the outer shell, the connector can cause the slider to translate relative to the outer shell until the projection of the outer shell engages a recess of the connector to secure the outer shell to the connector. When the inner shell is rotated relative to the outer shell and urged towards the outer shell, the projection of the outer shell can disengage from the recess of the connector to release the interface member from the connector.

For purposes of this summary, certain aspects, advantages, and novel features of certain disclosed inventions are summarized. It is to be understood that not necessarily all such advantages may be achieved in accordance with any particular embodiment of the invention. Thus, for example, those skilled in the art will recognize that the inventions disclosed herein may be embodied or carried out in a manner that achieves one advantage or group of advantages as taught herein without necessarily achieving other advantages as may be taught or suggested herein. Further, the foregoing is intended to summarize certain disclosed inventions and is not intended to limit the scope of the inventions disclosed herein.

BRIEF DESCRIPTION OF THE DRAWINGS

The foregoing and other features, aspects, and advantages of the embodiments of the apparatus and methods of cleaning teeth are described in detail below with reference to the drawings of various embodiments, which are intended to illustrate and not to limit the embodiments of the invention. The drawings comprise the following figures in which:

FIG. 1B is a schematic diagram of a system that includes components capable of removing unhealthy or undesirable material from a treatment region on an exterior surface of the tooth and/or gums.

FIG. 4 is a schematic perspective view of an example console.

FIG. 4A is a schematic perspective view of a console in accordance with another embodiment.

FIGS. 9A-9I are side cross-sectional views of example nozzle profiles, according to various embodiments.

FIGS. 10A-10C are side cross-sectional views of a nozzle at various stages of an example manufacturing process.

FIG. 12A is a schematic side view of a handpiece, in accordance with one embodiment.

FIG. 12B is a side cross-sectional view of the handpiece shown in FIG. 12A.

FIG. 17C is a side cross-sectional view of the magnetic sealing assembly disclosed in FIG. 17B.

FIG. 24B is a three-dimensional perspective view of the handpiece when the latch is substantially aligned with the notch.

Throughout the drawings, reference numbers may be re-used to indicate a general correspondence between referenced elements. The drawings are provided to illustrate example embodiments described herein and are not intended to limit the scope of the disclosure.

DETAILED DESCRIPTION

The present disclosure describes systems, apparatus, methods, and compositions for performing dental and/or endodontic procedures. Various embodiments disclosed herein can effectively and safely remove unhealthy material from a treatment region of a tooth, e.g., from within the tooth and/or from outside surfaces of the tooth. In particular, the embodiments disclosed herein can remove unhealthy materials, such as unhealthy organic matter, inorganic matter, pulp tissue, caries, stains, calculus, plaque, biofilm, bacteria, pus, decayed tooth matter, and food remnants from the treatment region without substantially damaging healthy dentin or enamel. For example, the disclosed systems, apparatus, methods, and compositions advantageously may be used with root canal cleaning treatments, e.g., to efficiently remove unhealthy or undesirable materials such as organic and/or inorganic matter from a root canal system and/or to disinfect the root canal system. In other arrangements, the disclosed systems, apparatus, methods, and compositions advantageously may be used with caries treatments, hygiene treatments, obturation treatments, and/or restoration treatments. Organic material (or organic matter) includes organic substances typically found in healthy or diseased teeth or root canal systems such as, for example, soft tissue, pulp, blood vessels, nerves, connective tissue, cellular matter, pus, and microorganisms, whether living, inflamed, infected, diseased, necrotic, or decomposed. Inorganic matter includes calcified tissue and calcified structures, which are frequently present in the root canal system. In some embodiments, the root canal can be filled with an obturation material (e.g., a flowable obturation material that can be hardened into a solid or semi-solid state, gutta percha or other solid or semi-solid materials) after treatment of the root canal.

Various systems disclosed herein can include a console and a tooth coupler configured to couple to a tooth to perform a treatment procedure. An interface member can connect the tooth coupler to the console to provide mechanical, fluidic, data and/or electrical connection between the tooth coupler and the console. The clinician can interact with the console to initiate and control various treatment procedures.

I. Overview of System and Methods

A. Overview of System Components

Figure 1A:
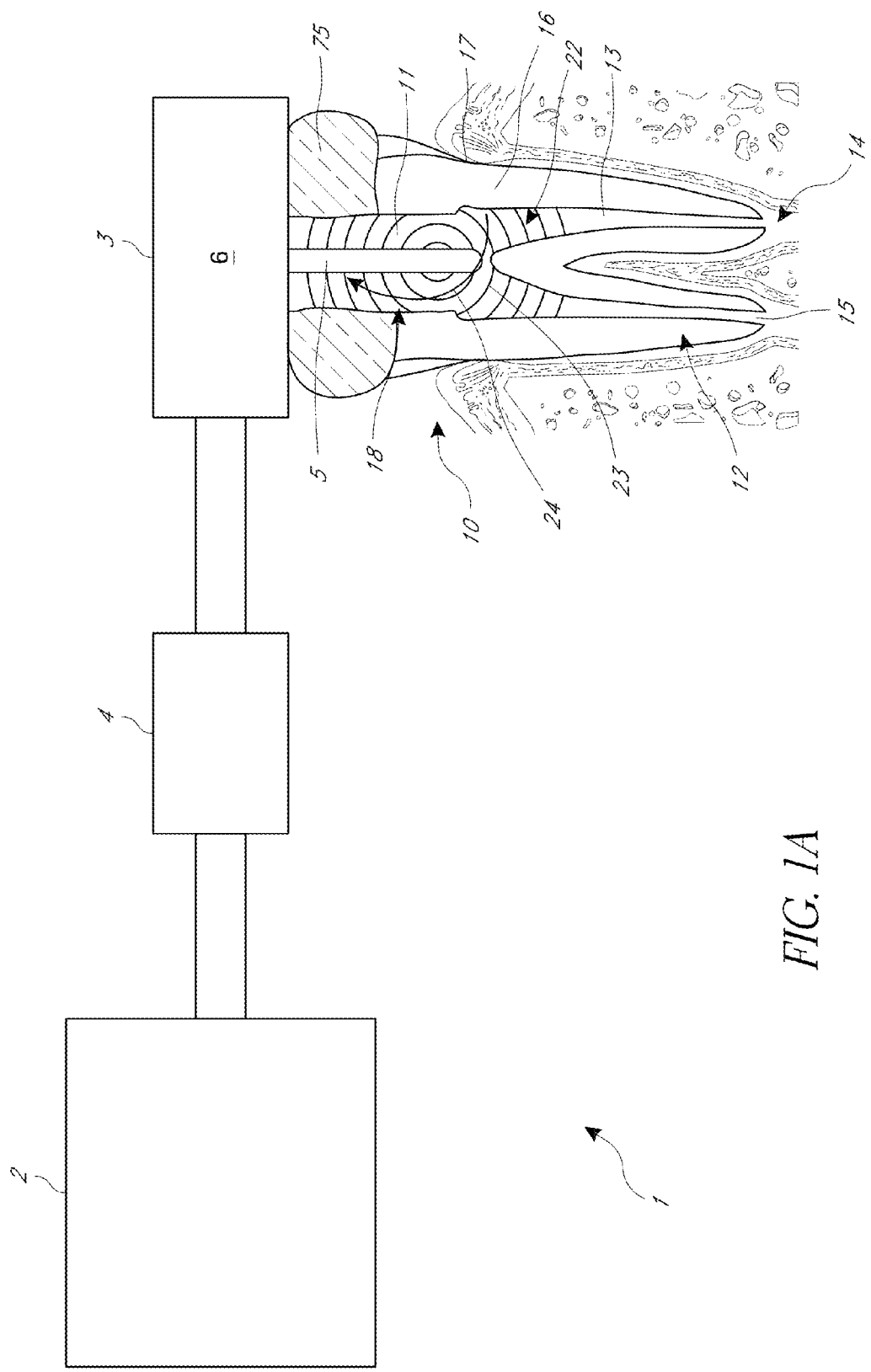
FIG. 1A is a schematic diagram of a system, in accordance various embodiments disclosed herein.

FIG. 1A is a schematic diagram of a system 1, in accordance with the embodiments disclosed herein. The system 1 shown in FIG. 1A may be configured to perform various types of treatment procedures, including, e.g., cleaning treatments, obturation treatments, restoration treatments, etc. In the embodiment shown in FIG. 1A, the system 1 is illustrated as being coupled to a tooth 10 that is a molar tooth of a mammal, such as a human. However, as explained herein, the tooth 10 may be any other suitable type of tooth, such as a pre-molar, bicuspid, incisor, canine, etc. Furthermore, the system 1 shown in FIG. 1A can include components capable of removing unhealthy or undesirable materials from a tooth or surrounding gum tissue, for example, a root canal 13 of the tooth 10.

The tooth 10 includes hard structural and protective layers, including a hard layer of dentin 16 and a very hard outer layer of enamel 17. A pulp cavity 11 is defined within the dentin 16. The pulp cavity 11 comprises one or more root canals 13 extending toward an apex 14 of each root 12. The pulp cavity 11 and root canal 13 contain dental pulp, which is a soft, vascular tissue comprising nerves, blood vessels, connective tissue, odontoblasts, and other tissue and cellular components. Blood vessels and nerves enter/exit the root canal 13 through a tiny opening, the apical foramen or apical opening 15, near a tip of the apex 14 of the root 12. It should be appreciated that, although the tooth 10 illustrated herein is a molar, the embodiments disclosed herein can advantageously be used to treat any suitable type of tooth, including pre-molars, canines, incisors, etc.

As illustrated in FIG. 1A, the system 1 can be used to remove unhealthy materials (such as organic and inorganic matter) from an interior of the tooth 10, e.g., from the root canal 13 of the tooth 10. For example, an endodontic access opening 18 can be formed in the tooth 10, e.g., on an occlusal surface, a buccal surface, or a lingual surface. The access opening 18 provides access to a portion of a pulp cavity 11 of the tooth 10. The system 1 can include a console 2, a pressure wave generator 5, and a tooth coupler 3 adapted to couple to the tooth 10. The tooth coupler 3 can couple to the tooth 10 in any suitable way. In some arrangements, the tooth coupler 3 can attach to the tooth 10 by way of a tooth seal 75. In some embodiments, the tooth coupler 3 can define a chamber 6 configured to retain fluid therein. In some embodiments, the pulp cavity 11 can define a tooth chamber configured to retain fluid therein. In some embodiments, the tooth coupler 3 may not define a chamber, and the tooth chamber defined at least in part by the pulp cavity 11 can retain fluid.

A system interface member 4 can electrically, mechanically, and/or fluidly connect the console 2 with the tooth coupler 3 and pressure wave generator 5. For example, in some embodiments, the system interface member 4 can removably couple the tooth coupler 3 to the console 2. In such embodiments, the clinician may use the tooth coupler 3 one time (or a few times), and may dispose the tooth coupler 3 after each procedure (or after a set number of procedures). The console 2 and interface member 4 may be reused multiple times to removably couple (e.g., to connect and/or disconnect) to multiple tooth couplers 3 using suitable engagement features, as discussed herein. The interface member 4 can include various electrical and/or fluidic pathways to provide electrical, electronic, and/or fluidic communication between the console 2 and the tooth coupler 3. The console 2 can include a control system and various fluid and/or electrical systems configured to operate the pressure wave generator 5 during a treatment procedure. The console 2 can also include a management module configured to manage data regarding the treatment procedure. As explained herein, the console 2 can include a communications module configured to communicate with external entities about the treatment procedures.

The system 1 can be used in cleaning procedures to clean substantially the entire root canal system. In other embodiments, such as obturation procedures, the system 1 can be used to fill substantially the entire root canal system with an obturation or filler material. In still other procedures, the system 1 can be used to restore a tooth 10. For example, in cleaning procedures, the chamber 6 of the tooth coupler 3 and/or the pulp cavity 11 of the tooth 10 can be at least partially (or substantially) filled with a fluid 22. In various embodiments disclosed herein, the pressure wave generator 5 can generate pressure waves 23 that propagate through the fluid 22. The generated pressure waves 23 may be of sufficient power and relatively low frequencies to produce fluid motion 24 in the pulp cavity 11 of the tooth 10, the root canal 13, and/or in the chamber 6 of the tooth coupler 4, and/or the pressure wave generator 5 can generate pressure waves of sufficient power and relatively higher frequencies to produce surface effect cavitation and/or microscale fluid motion created by the impact of the waves on a dental surface, either inside or outside the tooth 10. That is, for example, the pressure wave generators 5 disclosed herein can act as fluid motion generators to generate large-scale or bulk fluid motion 24 in or near the tooth 10, and can also generate smaller-scale fluid motion at higher frequencies. In some arrangements, the fluid motion 24 in the chamber 6 can generate induced fluid motion such as vortices, swirl, etc. in the tooth 10 and root canal 13 that can clean and/or fill the canal 13. In some arrangements, the pressure waves 23 can generate normal stress or shear stress or a combination of both onto the surfaces within the treatment region. Additional systems and methods for cleaning teeth, e.g., using pressure wave generators that can include a liquid jet device, (including molars, pre-molars, etc.) may be found in U.S. Patent Publication US 2007/0248932, in U.S. Patent Publication 2011/0117517, in U.S. Patent Publication US 2012/0237893 and in U.S. patent application Ser. No. 14/137,937, filed Dec. 20, 2013, titled "APPARATUS AND METHODS FOR CLEANING TEETH AND ROOT CANALS," each of which is incorporated by reference herein in its entirety and for all purposes.

FIG. 1B is a schematic diagram of a system 1 that includes components capable of removing unhealthy or undesirable material from a treatment region 20 on an exterior surface of the tooth 10. For example, as in FIG. 1A, the system 1 can include a tooth coupler 3 and a pressure wave generator 5. The tooth coupler 3 can communicate with a console 2 by way a system interface member 4. Unlike the system 1 of FIG. 1A, however, the tooth coupler 3 is coupled to a treatment region 20 on an exterior surface of the tooth 10. For example, the system 1 of FIG. 1B can be activated to clean an exterior surface of the tooth 10, e.g., a carious region of the tooth 10 and/or remove undesirable dental deposits, such as plaque, calculus biofilms, bacteria, etc, from the tooth 10 and/or surround gum tissue. In other embodiments, the system 1 can be activated to fill a treated region on the exterior surface of the tooth 10 with a filling or restoration material. As with the embodiment of FIG. 1A, pressure waves 23 and/or fluid motion 24 can be generated in the tooth coupler 3 and chamber 6, which can act to clean and/or fill the treatment region 20 of the tooth 10. Additional details of systems and methods for treating carious regions of teeth may be found in International Application Publication WO 2013/142385 (PCT/US2013/032635), having an international filing date of Mar. 15, 2013, entitled "APPARATUS AND METHODS FOR CLEANING TEETH," which is incorporated by reference herein in its entirety and for all purposes. Additional details of systems and methods for removing undesirable dental deposits (such as plaque, calculus, etc.) from teeth and/or gums may be found in International Application Publication WO 2013/155492 (Application No. PCT/US2013/036493), having an international filing date of Apr. 12, 2013, entitled "APPARATUS AND METHODS FOR CLEANING TEETH AND GINGIVAL POCKETS," and in U.S. patent application Ser. No. 13/861,211, filed Apr. 11, 2013, entitled "APPARATUS AND METHODS FOR CLEANING TEETH AND GINGIVAL POCKETS," each of which is incorporated by reference herein in its entirety and for all purposes.

Figure 1C:
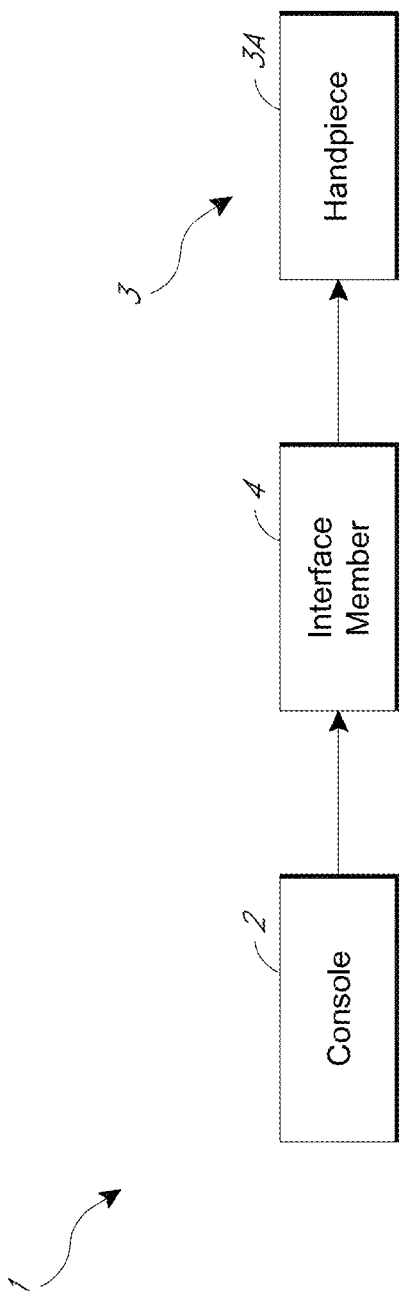
FIG. 1C is a schematic diagram of a system in which the tooth coupler comprises a dental handpiece.

The tooth coupler 3 disclosed herein can be any suitable structure or housing configured to couple to the tooth 10 for a treatment procedure. As used herein, "couple" is meant to include arrangements in which there is a connection with the tooth 10, as well as arrangements in which the coupler 3 is placed against or in the tooth and is held by the clinician in that position. The pressure wave generator 5 can be coupled to and/or disposed in or on the tooth coupler 3. For example, FIG. 1C is a schematic diagram of a system 1 in which the tooth coupler 3 comprises a dental handpiece 3A. As explained in more detail herein, the dental handpiece 3A can include a body or housing shaped to be gripped by the clinician. In some embodiments, the pressure wave generator 5 can be coupled to or formed with a distal portion of the handpiece 3A. Before a treatment procedure (e.g., a cleaning procedure, an obturation procedure, a restorative procedure, etc.), the clinician can connect the handpiece 3A to the interface member 4 of the system 1. The clinician can manipulate the handpiece 3A such that the pressure wave generator 5 is positioned near the treatment region on or in the tooth 10. The clinician can activate the pressure wave generator 5 using controls on the console 2 and/or the handpiece 3A, and can perform the desired treatment procedure. After performing the treatment procedure, the clinician can disconnect the handpiece 3A from the interface member 4 and can remove the handpiece 3A from the system 1.

Figure 1D:
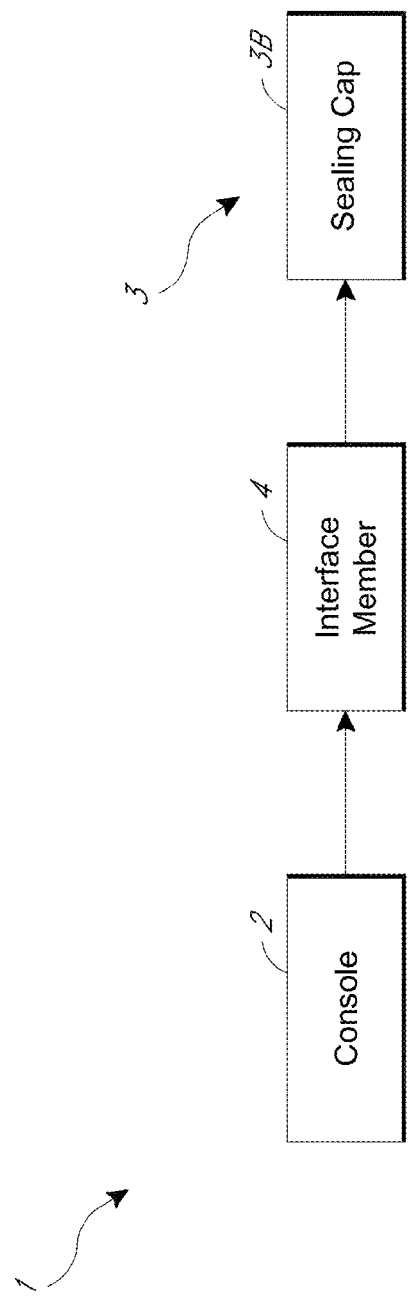
FIG. 1D is a schematic diagram of a system in which the tooth coupler comprises a treatment cap.

In other embodiments, the tooth coupler 3 can comprise a treatment cap 3B, as shown in the schematic system diagram of FIG. 1D. In the embodiment of FIG. 1D, the pressure wave generator 5 may be coupled to or disposed in or on the treatment cap 3B. The clinician can connect the treatment cap 3B to the interface member 4. For example, in some embodiments, a hose or other type of tube can connect the treatment cap 3B to the interface member 4. Before the treatment procedure, the clinician can attach or directly couple the treatment cap 3B to the treatment region of the tooth 10. For example, in some embodiments, the clinician can attach the treatment cap 3B over an access opening 18 of the tooth 10 to place the treatment cap 3B and pressure wave generator 5 in fluid communication with the pulp cavity 11 and root canal 13 of the tooth 10. In other embodiments, the clinician can attach the treatment cap 3B over a treatment region on an exterior surface of the tooth 10, e.g., over a carious region or a region that includes unhealthy deposits, such as plaque, calculus, etc. In some embodiments, the treatment cap 3B may be substantially sealed or attached to the tooth 10 during the treatment procedure. For example, after attaching the treatment cap 3B to the tooth 10, the clinician may not or may only minimally manipulate the treatment cap 3B relative to the tooth 10 during treatment. In other arrangements, the clinician may still desire to move or reposition the treatment cap 3B relative to the tooth 10 during treatment. Once the treatment procedure is finished, the clinician can disconnect the treatment cap 3B from the interface member 4 and can remove the treatment cap 3B from the system 1.

B. Overview of Treatment Procedures

The system 1 disclosed herein can be used with various types of treatment procedures. For example, some embodiments disclosed herein can advantageously remove undesirable or unhealthy materials from a tooth such that substantially all the unhealthy material is removed while inducing minimal or no discomfort and/or pain in the patient. For example, when activated by the clinician, the pressure wave generator 5 can induce various fluidic effects that interact with the unhealthy material to be removed, even when the pressure wave generator 5 is disposed at a position remote from the treatment region of the tooth, e.g., the region of the tooth that includes the unhealthy or undesirable material to be removed. The pressure wave generator 5 can impart energy to a fluid 22 that induces the relatively large-scale or bulk circulation or movement 24 of liquid in the chamber 6 and/or tooth 10, and that also generates pressure waves 23 that propagate through the fluid 22 and tooth 10. The generated fluid motion 24 and pressure waves 23 can magnify or enhance the properties of the fluid 22 to enhance cleaning of the tooth 10. In some embodiments, the pressure wave generator 5 can be used to obturate or fill the root canals and/or other treated regions of the tooth, and can also be used to restore or build up a damaged or diseased tooth.

1. Enhancing the Cleaning of Teeth

The system 1 disclosed herein can be used to clean teeth. For example, the system 1 can be configured to clean organic and inorganic material, including diseased pulp, bacteria, etc., from root canals of the tooth 10. In some embodiments, the system 1 can be configured to remove carious regions of the tooth 10, e.g., regions of the tooth 10 that are decayed. The carious regions can be formed on an exterior surface of the tooth 10 in some arrangements. Moreover, the system 1 can be configured to clean undesirable dental deposits from exterior surfaces of the tooth 10, including plaque, calculus, biofilms, bacteria, and other unhealthy deposits. In some arrangements, the system 1 can utilize, alone or in combination, the chemistry of various treatment fluids, pressure waves generated by the pressure wave generator 5, and fluid motion 24 created in the chamber 6 of the tooth coupler 3 and/or in a chamber within the tooth 10.

a. Chemistry of Various Treatment Fluids

In cleaning procedures, the fluid 22 supplied to the chamber 6 and/or to the pulp cavity 11 of the tooth 10 can comprise a treatment fluid that can be introduced into the tooth 10 and the chamber 6 to assist in removing unhealthy or undesirable materials from the tooth 10. The treatment fluids can be selected based on the chemical properties of the fluids when reacting with the undesirable or unhealthy material to be removed from the tooth 10. The treatment fluids disclosed herein can include any suitable fluid, including, e.g., water, saline, etc. Various chemicals can be added to treatment fluid for various purposes, including, e.g., tissue dissolving agents (e.g., NaOCl or bleach), disinfectants (e.g., chlorhexidine), anesthesia, fluoride therapy agents, ethylenediaminetetraacetic acid (EDTA), citric acid, and any other suitable chemicals. For example, any other antibacterial, decalcifying, disinfecting, mineralizing, or whitening solutions may be used as well. The clinician can supply the various fluids to the tooth in one or more treatment cycles, and can supply different fluids sequentially or simultaneously.

During some treatment cycles, bleach-based solutions (e.g., solutions including NaOCl) can be used to dissociate diseased tissue (e.g., diseased organic matter in the root canal 13) and/or to remove bacteria, biofilm or endotoxins (Lipopolysaccharide or LPS) from the tooth 10. One example of a treatment solution comprises water or saline with 0.3% to 6% bleach (NaOCl). In some methods, tissue dissolution and dental deposit removal in the presence of bleach may not occur when the bleach concentration is less than 1%. In some treatment methods disclosed herein, tissue dissolution and dental deposit removal can occur at smaller (or much smaller) concentrations.

During other treatment cycles, the clinician can supply an EDTA-based solution to remove undesirable or unhealthy calcified material from the tooth 10. For example, if a portion of the tooth 10 and/or root canal 13 is shaped or otherwise instrumented during the procedure, a smear layer may form on the walls of the canal 13. The smear layer can include a semi-crystalline layer of debris, which may include remnants of pulp, bacteria, dentin, and other materials. Treatment fluids that include EDTA may be used to remove part or all of the smear layer, and/or calcified deposits on the tooth 10. EDTA may also be used to remove dentin packed into isthmuses and lateral canals during the instrumentation process. EDTA may also be used to remove a microscopic layer off enamel and cleaning and staining purposes. Other chemicals such as citric acid may also be used for similar purposes.

During yet other cycles, for example, the clinician may supply a treatment fluid that comprises substantially water. The water can be used to assist in irrigating the tooth before, during, and/or after the treatment. For example, the water can be supplied to remove remnants of other treatment fluids (e.g., bleach or EDTA) between treatment cycles. Because bleach has a pH that tends to be a base and because EDTA is an acid, it can be important to purge the tooth 10 and chamber 6 between bleach and EDTA treatments to avoid potentially damaging chemical reactions. Furthermore, the water can be supplied with a sufficient momentum to help remove detached materials that are disrupted during the treatment. For example, the water can be used to convey waste material from the tooth 10.

Various solutions may be used in combination at the same time or sequentially at suitable concentrations. In some embodiments, chemicals and the concentrations of the chemicals can be varied throughout the procedure by the clinician and/or by the system to improve patient outcomes. For example, during an example treatment procedure, the clinician can alternate between the use of water, bleach, and EDTA, in order to achieve the advantages associated with each of these chemicals. In one example, the clinician may begin with a water cycle to clean out any initial debris, then proceed with a bleach cycle to dissociate diseased tissue and bacteria from the tooth. A water cycle may then be used to remove the bleach and any remaining detached materials from the tooth 10. The clinician may then supply EDTA to the tooth to remove calcified deposits and/or portions of a smear layer from the tooth 10. Water can then be supplied to remove the EDTA and any remaining detached material from the tooth 10 before a subsequent bleach cycle. The clinician can continually shift between cycles of treatment fluid throughout the procedure. The above example is for illustrative purposes only. It should be appreciated that the order of the cycling of treatment liquids may vary in any suitable manner and order.

Thus, the treatment fluids used in the embodiments disclosed herein can react chemically with the undesirable or unhealthy materials to dissociate the unhealthy materials from the healthy portions of the tooth 10. The treatment fluids can also be used to irrigate waste fluid and/or detached or delaminated materials out of the tooth 10. In some embodiments, as explained in more detail herein, the treatment solution (including any suitable composition) can be degassed, which may improve cavitation and/or reduce the presence of gas bubbles in some treatments. In some embodiments, the dissolved gas content can be less than about 1% by volume.

b. Enhancement of Cleaning Using Pressure Waves and Examples of Pressure Wave Generators A pressure wave generator 5 can remove unhealthy materials from a tooth by propagating pressure waves 23 through a propagation medium such as the fluid 22 (e.g., the treatment fluid) to the treatment region, which can include one or more teeth and/or gums. Without being limited by theory, a few potential ways that the pressure waves 23 remove undesirable materials are presented herein. Note that these principles, and the principles described above, may be generally applicable for each embodiment disclosed herein.

In some arrangements, cavitation may be induced by the generated pressure waves 23. Upon irradiation of a liquid (e.g., water or other treatment fluid) with high intensity pressure or pressure waves 23, acoustic cavitation may occur. The oscillation or the implosive collapse of small cavitation bubbles can produce localized effects, which may further enhance the cleaning process, e.g., by creating intense, small-scale localized heat, shock waves, and/or microjets and shear flows. Therefore, in some treatment methods, acoustic cavitation may be responsible for or involved in enhancing the chemical reactions, sonochemistry, sonoporation, soft tissue/cell/bacteria dissociation, delamination and breakup of biofilms.

For example, if the treatment liquid contains chemical(s) that act on a particular target material (e.g., diseased organic or inorganic matter, stains, caries, dental calculus, plaque, bacteria, biofilms, etc.), the pressure waves 23 (acoustic field) and/or the subsequent acoustic cavitation may enhance the chemical reaction via convection, turbulence, agitation and/or sonochemistry. Indeed, the pressure waves 23 can enhance the chemical effects that each composition has on the unhealthy material to be removed from the tooth. For example, with a bleach-based treatment fluid, the generated pressure waves 23 can propagate so as to dissociate tissue throughout the entire tooth 10, including in the dentinal tubules and throughout tiny cracks and crevices of the tooth 10. As another example, with an EDTA-based treatment fluid, the generated pressure waves 23 can propagate so as to remove the smear layer and/or calcified deposits from the tooth 10, including in the tubules and/or in tiny cracks and crevices formed in the tooth 10. With a water-based treatment fluid, the generated pressure waves 23 can propagate so as to flush and/or irrigate undesirable materials from the tooth, including in tubules and tiny cracks and crevices. Accordingly, the generated pressure waves 23 can enhance the removal of undesirable or unhealthy materials from the tooth 10 by magnifying the chemical effects of whatever treatment fluid composition is used during a particular treatment cycle.

Furthermore, sonoporation, which is the process of using pressure waves and/or the subsequent acoustic cavitation to modify the permeability of the bacterial cell plasma membrane, may also expedite the chemical reaction that removes the microorganisms from the tooth. It should also be appreciated that generated pressure waves, and/or the subsequent acoustic cavitation of certain frequencies, may result in cellular and bacterial rupture and death (e.g., lysis) as well as removal of decayed and weakened dentin and enamel. The cellular and bacterial rupture phenomenon may kill bacteria which might otherwise reinfect the gingival pockets and/or the oral cavity.

Generated pressure waves and/or the subsequent acoustic cavitation may also loosen the bond of the structure of the unhealthy material (e.g., diseased tissue, calculus, biofilm, caries, etc.), and/or the pressure waves may dissociate the unhealthy material from the tooth 10. In some cases, pressure waves and/or acoustic cavitation may loosen the bond between the cells and the dentin and/or delaminate the tissue from the tooth. Furthermore, the pressure waves and/or the subsequent acoustic cavitation may act on decayed hard tissue (which may be relatively weak and loosely connected) through vibrations and/or shock waves, and/or the microjets created as a result of cavitation bubble implosion, to remove decayed hard tissue from other healthy portions of the tooth.

A pressure wave generator 5 can be used in various disclosed embodiments to clean a tooth 10, e.g., from interior or exterior portions of the tooth 10 and/or gums. In other embodiments, the pressure wave generator 5 can be used to fill or obturate a cleaned root canal or other treatment region of the tooth 10. In some embodiments, the pressure wave generator 5 can comprise an elongated member having an active distal end portion. The active distal end portion can be activated by a user to apply energy to the treatment tooth 10 to remove unhealthy or undesirable material from the tooth 10.

As explained herein, the disclosed pressure wave generators 5 can be configured to generate pressure waves 23 and fluid motion 24 with energy sufficient to clean undesirable material from a tooth 10. The pressure wave generator 5 can be a device that converts one form of energy into acoustic waves and bulk fluid motion (e.g., rotational motion) within the fluid 22. The pressure wave generator 5 can induce, among other phenomena, both pressure waves and bulk fluid dynamic motion in the fluid 22 (e.g., in the chamber 6), fluid circulation, turbulence, vortices and other conditions that can enable the cleaning of the tooth. The pressure wave generator 5 disclosed in each of the figures described herein may be any suitable type of pressure wave generator.

The pressure wave generator 5 can be used to clean the tooth 10 by creating pressure waves that propagate through the fluid 22, e.g., through treatment fluid at least partially retained in the chamber 6. In some implementations, the pressure wave generator 5 may also create cavitation, acoustic streaming, turbulence, etc. The pressure wave generator 5 (e.g., high-speed liquid jet, ultrasonic transducer, a laser fiber, etc.) can be placed at the desired treatment location in or on the tooth 10. The pressure wave generator 5 can create pressure waves 23 and fluid motion 24 within the fluid 22 inside a substantially-enclosed chamber 6 and/or in a tooth chamber of the tooth (e.g., the pulp cavity 11 and/or the root canal 13). In general, the pressure wave generator 5 can be sufficiently strong to remove unhealthy materials such as organic and/or inorganic tissue from teeth 10. In some embodiments, the pressure wave generator 5 can be configured to avoid substantially breaking down or harming natural dentin and/or enamel.

i. Liquid Jet Apparatus

For example, in some embodiments, the pressure wave generator 5 can comprise a liquid jet device. The liquid jet can be created by passing high pressure liquid through an orifice. The liquid jet can create pressure waves within the treatment liquid. In some embodiments, the pressure wave generator 5 comprises a coherent, collimated jet of liquid. The jet of liquid can interact with liquid in a substantially-enclosed volume (e.g., the chamber 6, the tooth chamber (e.g., pulp cavity 11 and/or root canals 13), and/or the mouth of the user) and/or an impingement member to create the acoustic waves. In addition, the interaction of the jet and the treatment fluid, as well as the interaction of the spray which results from hitting the impingement member and the treatment fluid, may assist in creating cavitation and/or other acoustic and fluid motion effects to clean the tooth.

In various embodiments, the liquid jet device can comprise a positioning member (e.g., a guide tube) having a channel or lumen along which or through which a liquid jet can propagate. The distal end portion of the positioning member can include one or more openings that permit the deflected liquid to exit the positioning member and interact with the surrounding environment in the chamber 6 and/or tooth 10. In some treatment methods, the openings disposed at or near the distal end portion of the positioning member can be submerged in liquid that can be at least partially enclosed in the tooth coupler 3 attached to or enclosing a portion of the tooth 10. In some embodiments, the liquid jet can pass through the guide tube and can impact an impingement surface. The passage of the jet through the surrounding treatment fluid and impact of the jet on the impingement surface can generate the acoustic waves in some implementations. The flow of the submerged portion of the liquid jet may generate a cavitation cloud within the treatment fluid. The creation and collapse of the cavitation cloud may, in some cases, generate a substantial hydroacoustic field in or near the tooth. Further cavitation effects may be possible, including growth, oscillation, and collapse of cavitation bubbles. In addition, as explained above, bulk fluid motion, such as rotational flow, may be induced. The induced rotational flow can enhance the cleaning process by removing detached material and replenishing reactants for the cleaning reactions. These (and/or other) effects may lead to efficient cleaning of the tooth. The rotational flow may also create sufficient shear stress onto surface which then leads to dissociation, detachment, and delamination of unhealthy materials. In some embodiments, the rotational flow may include turbulent regions working on small scale regions or small scale unhealthy materials.

Additional details of a pressure wave generator and/or pressure wave generator that includes a liquid jet device may be found at least in ¶¶ [0045]-[0050], [0054]-[0077] and various other portions of U.S. Patent Publication No. US 2011/0117517, published May 19, 2011, and in ¶¶ [0136]-[0142] and various other portions of U.S. Patent Publication No. US 2012/0237893, published Sep. 20, 2012, each of which is incorporated by reference herein in its entirety and for all purposes.

As has been described, a pressure wave generator can be any physical device or phenomenon that converts one form of energy into acoustic waves within the treatment fluid and that induces normal and shear stresses as well as small scale flows near a treatment region in the chamber 6 and/or tooth 10. The pressure wave generator 5 may also convert the energy into rotational fluid motion of various length scales in the chamber 6 and/or tooth 10. Many different types of pressure wave generators (or combinations of pressure wave generators) are usable with embodiments of the systems and methods disclosed herein.

ii. Mechanical Energy

Mechanical energy pressure wave generators can also include rotating objects, e.g. miniature propellers, eccentrically-confined rotating cylinders, a perforated rotating disk, etc. These types of pressure wave generators can also include vibrating, oscillating, or pulsating objects such as sonication devices that create pressure waves via piezoelectricity, magnetostriction, etc. In some pressure wave generators, electric energy transferred to a piezoelectric transducer can produce acoustic waves in the treatment fluid. In some cases, the piezoelectric transducer can be used to create acoustic waves having a broad band of frequencies.

iii. Electromagnetic Energy

An electromagnetic beam of radiation (e.g., a laser beam) can propagate energy into a chamber, and the electromagnetic beam energy can be transformed into acoustic waves as it enters the treatment fluid. In some embodiments, the laser beam can be directed into the chamber 6 and/or tooth coupler 3 as a collimated and coherent beam of light. The collimated laser beam can be sufficient to generate pressure waves as the laser beam delivers energy to the fluid. Furthermore, in various embodiments, the laser beam can be focused using one or more lenses or other focusing devices to concentrate the optical energy at a location in the treatment fluid. The concentrated energy can be transformed into pressure waves sufficient to clean the undesirable materials. In one embodiment, the wavelength of the laser beam or electromagnetic source can be selected to be highly absorbable by the treatment fluid in the chamber, tooth, and/or mouth (e.g., water) and/or by the additives in the treatment fluid (e.g., nanoparticles, etc.). The electromagnetic energy can be absorbed by at least one component and can turn the electromagnetic energy into either heat, vibration, or pressure waves, for example, through cavitation. For example, at least some of the electromagnetic energy may be absorbed by the fluid (e.g., water) in the chamber, which can generate localized heating and pressure waves that propagate in the fluid. The pressure waves generated by the electromagnetic beam can generate light-induced cavitation effects in the fluid. In some embodiments, the localized heating can induce rotational fluid flow in the chamber 6 and/or tooth 10 that further enhances cleaning of the tooth 10. The electromagnetic radiation from a radiation source (e.g., a laser) can be propagated to the chamber by an optical waveguide (e.g., an optical fiber), and dispersed into the fluid at a distal end of the waveguide (e.g., a shaped tip of the fiber, e.g., a conically-shaped tip). In other implementations, the radiation can be directed to the chamber by a beam scanning system.

The wavelength of the electromagnetic energy may be in a range that is strongly absorbed by water molecules. The wavelength may in a range from about 300 nm to about 3000 nm. In some embodiments, the wavelength is in a range from about 400 nm to about 700 nm, about 700 nm to about 1000 nm (e.g., 790 nm, 810 nm, 940 nm, or 980 nm), in a range from about 1 micron to about 3 microns (e.g., about 2.7 microns or 2.9 microns), or in a range from about 3 microns to about 30 microns (e.g., 9.4 microns or 10.6 microns). The electromagnetic energy can be in the ultraviolet, visible, near-infrared, mid-infrared, microwave, or longer wavelengths.

The electromagnetic energy can be pulsed or modulated (e.g., via a pulsed laser), for example with a repetition rate in a range from about 1 Hz to about 500 kHz. The pulse energy can be in a range from about 1 mJ to about 1000 mJ. The pulse width can be in a range from about 1 µs to about 500 µs, about 1 ms to about 500 ms, or some other range. In some cases, nanosecond pulsed lasers can be used with pulse rates in a range from about 100 ns to about 500 ns. The foregoing are non-limiting examples of radiation parameters, and other repetition rates, pulse widths, pulse energies, etc. can be used in other embodiments.

The laser can include one or more of a diode laser, a solid state laser, a fiber laser, an Er:YAG laser, an Er:YSGG laser, an Er, Cr:YAG laser, an Er, Cr:YSGG laser, a Ho:YAG laser, a Nd:YAG laser, a CTE:YAG laser, a $CO_2$ laser, or a Ti:Sapphire laser. In other embodiments, the source of electromagnetic radiation can include one or more light emitting diodes (LEDs). The electromagnetic radiation can be used to excite nanoparticles (e.g., light-absorbing gold nanorods or nanoshells) inside the treatment fluid, which may increase the efficiency of photo-induced cavitation in the fluid. The treatment fluid can include excitable functional groups (e.g., hydroxyl functional groups) that may be susceptible to excitation by the electromagnetic radiation and which may increase the efficiency of pressure wave generation (e.g., due to increased absorption of radiation).

During some treatments, radiation having a first wavelength can be used (e.g., a wavelength strongly absorbed by the liquid, for instance water) followed by radiation having a second wavelength not equal to the first wavelength (e.g., a wavelength less strongly absorbed by water) but strongly absorbed by another element, e.g. dentin, dyes, or nanoparticles added to solution. For example, in some such treatments, the first wavelength may help create bubbles in the fluid, and the second wavelength may help disrupt the tissue.

The electromagnetic energy can be applied to the chamber 6 for a treatment time that can be in a range from about one to a few seconds up to about one minute or longer. A treatment procedure can include one to ten (or more) cycles of applying electromagnetic energy to the tooth. A fluid can circulate or otherwise move in the chamber during the treatment process, which advantageously may inhibit heating of the tooth 10 (which may cause discomfort to the patient). The movement or circulation of treatment fluid (e.g., water with a tissue dissolving agent) in the chamber 6 can bring fresh treatment fluid to tissue and organic matter as well as flush out dissolved material from the treatment site. In some treatments using electromagnetic radiation, movement of the treatment fluid (for example small- or large scale rotational flows or turbulent flow) can increase the effectiveness of the cleaning (as compared to a treatment with little or no fluid circulation).

In some implementations, electromagnetic energy can be added to other fluid motion generation modalities. For example, electromagnetic energy can be delivered to a chamber in which another pressure wave generator (e.g., a liquid jet) is used to generate the acoustic waves.

iv. Acoustic Energy

Acoustic energy (e.g., ultrasonic, sonic, audible, and/or lower frequencies) can be generated from electric energy transferred to, e.g., an ultrasound or other transducer or an ultrasonic tip (or file or needle) that creates acoustic waves in the treatment fluid. The ultrasonic or other type of acoustic transducer can comprise a piezoelectric crystal that physically oscillates in response to an electrical signal or a magnetostrictive element that converts electromagnetic energy into mechanical energy. The transducer can be disposed in the treatment fluid, for example, in the fluid inside the chamber. As explained herein, ultrasonic or other acoustic devices used with the embodiments disclosed herein are preferably broadband and/or multi-frequency devices.

v. Further Properties of Some Pressure Wave Generators

A pressure wave generator 5 can be placed at a desired location with respect to the tooth 10. The pressure wave generator 5 creates pressure waves within the fluid 22 inside the chamber 6 and/or tooth 10 (the generation of acoustic waves may or may not create or cause cavitation). The acoustic or pressure waves 23 propagate throughout the fluid 22 inside the chamber 6 of the tooth coupler 3 and/or in a tooth chamber of the tooth 10, with the fluid 22 in the chamber 6 or tooth 10 serving as a propagation medium for the pressure waves 23. The pressure waves 23 can also propagate through tooth material (e.g., dentin). It is believed, although not required, that as a result of application of a sufficiently high-intensity acoustic wave, acoustic cavitation may occur. The collapse of cavitation bubbles may induce, cause, or be involved in a number of processes described herein such as, e.g., sonochemistry, tissue dissociation, tissue delamination, sonoporation, and/or removal of calcified structures. In some embodiments, the pressure wave generator can be configured such that the acoustic waves (and/or cavitation) do not substantially break down natural dentin in the tooth 110. The acoustic wave field by itself or in addition to cavitation may be involved in one or more of the abovementioned processes.

In some implementations, the pressure wave generator 5 generates primary cavitation, which creates acoustic waves, which may in turn lead to secondary cavitation. The secondary cavitation may be weaker than the primary cavitation and may be non-inertial cavitation. In other implementations, the pressure wave generator 5 generates acoustic waves directly, which may lead to secondary cavitation.

Additional details of pressure wave generators (e.g., which may comprise a pressure wave generator) that may be suitable for use with the embodiments disclosed herein may be found, e.g., in ¶¶[0191]-[0217], and various other portions of U.S. Patent Publication No. US 2012/0237893, published Sep. 20, 2012, which is incorporated by reference herein for all purposes.

c. Enhancement of Cleaning Using Large-Scale Fluid Motion

In some arrangements, bulk fluid motion 24 (e.g., fluid rotation, convection, planar flow, chaotic flow, etc.) can enhance the cleaning of unhealthy material from a diseased tooth. For example, the fluid motion 24 generated in the chamber 6 and/or tooth 10 can impart relatively large momentum to the tooth, which can help dissociate and irrigate unhealthy materials from the tooth. Furthermore, the fluid motion 24 can induce vortices and/or swirl in the tooth 10 that can result in negative pressures (or low positive pressures) near the apical opening 15 of the tooth 10. The resulting negative pressures at the apical opening 15 can prevent or reduce an amount of material extruded through the apical opening 15 and into the jaw of the patient. By preventing or reducing the amount of extruded material, the risk of pain and discomfort as well as infection can be lowered or eliminated, and patient outcomes and comfort can be substantially improved.

In addition, due to relatively short time scales of the chemical reaction processes between the fluid 22 and the unhealthy materials as compared to that of diffusion mechanisms, a faster mechanism of reactant delivery such as "macroscopic" liquid circulation may be advantageous in some of the embodiments disclosed herein. For example, liquid circulation with a time scale comparable to (and preferably faster than) that of chemical reaction may help replenish the reactants at the chemical reaction front and/or may help to remove the reaction byproducts from the reaction site. The relatively large convective time scale, which may relate to effectiveness of the convection process, can be adjusted and/or optimized depending on, e.g., the location and characteristics of the source of circulation. Furthermore, it should be appreciated that the introduction of liquid circulation or other fluid motion 24 generally does not eliminate the diffusion process, which may still remain effective within a thin microscopic layer at the chemical reaction front. Liquid circulation can also cause a strong irrigation effect at the treatment site (e.g. removing diseased tissue deep in the canal 13 and/or tubules and small spaces and cracks of the tooth 10) and may therefore result in loosening and/or removing large and small pieces of debris from the treatment site.

In some arrangements, various properties can be adjusted to enhance bulk fluid motion and/or fluid circulation, e.g., fluid motion in the chamber 6 of the tooth coupler 3. For example, the position of the pressure wave generator 5 relative to the location of the treatment site can be adjusted. Furthermore, in some embodiments, the pressure wave generator 5 can be disposed adjacent the access opening 18 formed in the tooth and/or adjacent an access port of the tooth coupler 3. The geometry of the space surrounding the pressure wave generator 5 and treatment site (e.g., the geometry of the tooth coupler 3) can also be varied. It should also be appreciated that circulation may be affected by the viscosity of the fluid 22 and/or the mechanism of action of the pressure wave generator 5. For example, the pressure wave generator 5, such as a jet of liquid ejected through an inlet opening, a stirrer such as a propeller or a vibrating object, etc., can be selected to enhance fluid motion of the treatment fluid. In some aspects, the input power of the source of liquid circulation can also be adjusted, such as the source of a pump that drives a liquid jet in some embodiments.

2. Enhancement of Other Dental and Endodontic Procedures

In some embodiments, the pressure wave generators 5 disclosed herein can enhance other dental and endodontic procedures. For example, after cleaning a tooth (e.g., a root canal inside the tooth, a carious region on or near an exterior surface of the tooth, etc.), the treatment region can be filled with an obturation or filler material. The clinician can also restore damaged or diseased tooth material by building up the tooth using a suitable restoration material. In some embodiments, a filler material can be supplied to the treatment region as a flowable material and can be hardened to fill the treatment region (e.g., the cleaned root canal or carious region, etc.). In some embodiments, a pressure wave generator 5 can be activated to supply the obturation material throughout the treatment region.

For example, after a root canal procedure, the pressure wave generator can supply the flowable obturation material into the tooth and root canal. The large-scale fluid movement generated by the pressure wave generator 5 can assist in propagating the obturation material throughout relatively large spaces, such as the main root canal or canals. For example, the pressure wave generator 5 may introduce sufficient momentum such that the flowable obturation material propagates throughout the canal space without introducing additional instrumentation into the tooth. For example, the bulk fluid motion of the obturation material into the canal may be such that the clinician may not need to or desire to enlarge the canals. By reducing or eliminating canal enlargement, patient outcomes and pain levels can be improved. In some arrangements, the bulk fluid motion of the flowable obturation material can be generated at relatively low frequencies produced by the pressure wave generator.

In addition to generating large-scale or bulk fluid motion of the obturation material throughout the canal, the pressure wave generators 5 disclosed herein can generate higher frequency perturbations to propagate the obturation material into smaller cracks, spaces, and crevices in the tooth. For example, higher-frequency effects, such as acoustic cavitation, can assist in propagating the filler material throughout the tooth.

Accordingly, the pressure wave generators disclosed herein can enhance the filling and/or restoration of a treatment region such as a root canal, carious region of the tooth, etc. For example, the obturation material can be propagated at a distance such that it flows into the treatment region from a remote pressure wave generator 5 (which may be disposed outside the tooth). Large-scale or bulk fluid motion of the obturation material can fill larger canal spaces or other treatment regions without further enlargening the treatment region. Smaller-scale and/or higher frequency agitation by the pressure wave generator 5 can propagate the obturation material into smaller cracks and spaces of the tooth. By filling substantially all the cleaned spaces of the tooth, the disclosed methods can improve patient outcomes relative to other methods by reducing the risk of infection in spaces unfilled by the obturation material.

3. Enhancement of Treatment Procedures with Broadband Pressure Waves

Figure 2A:
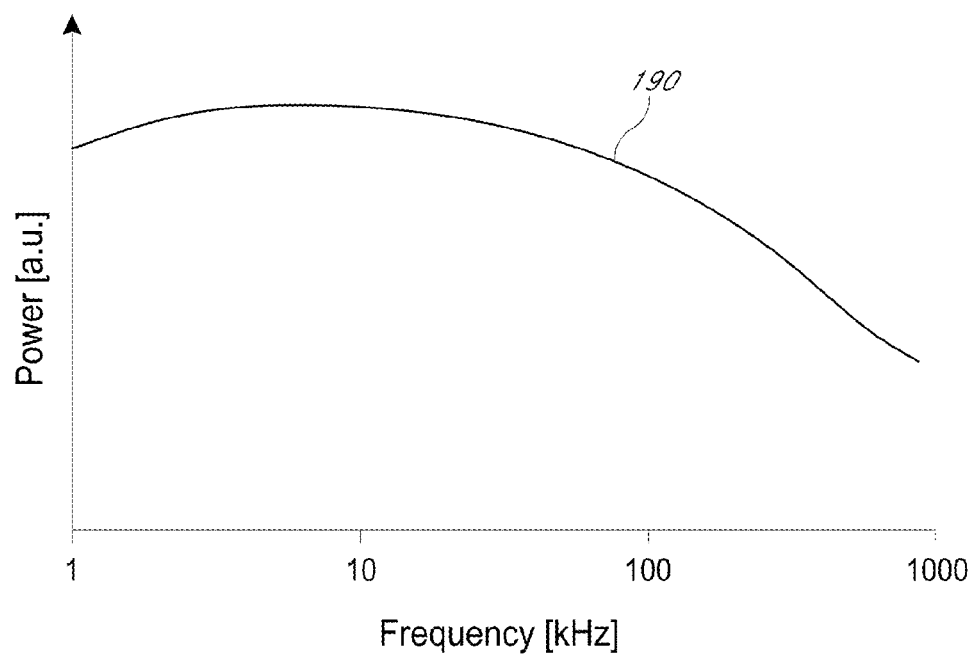
FIGS. 2A and 2B are graphs that schematically illustrate possible examples of power that can be generated by different embodiments of a pressure wave generator.
Figure 2B:
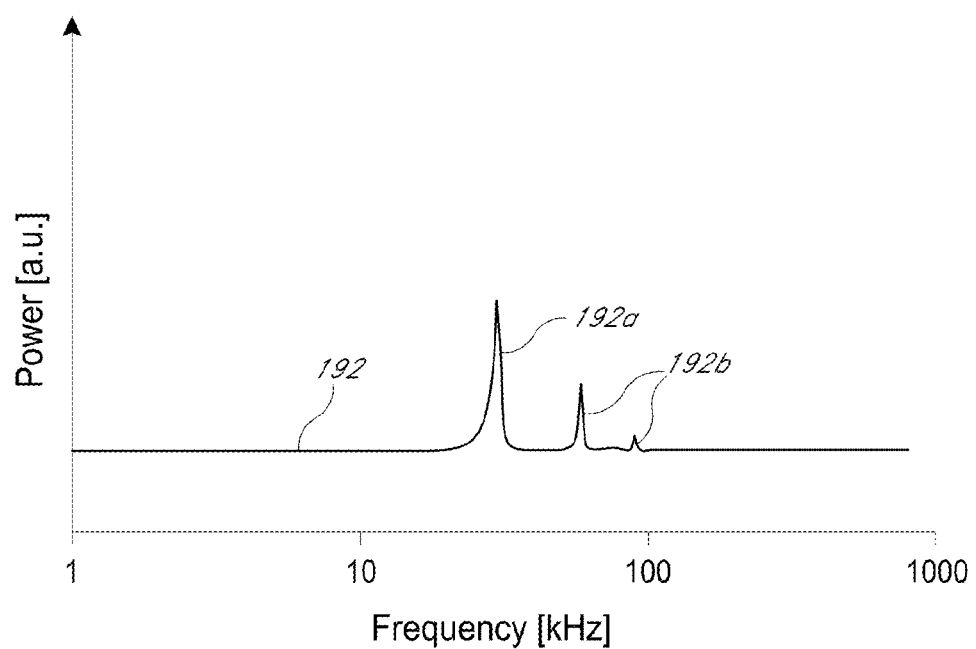

In various embodiments, disclosed herein, it can be advantageous to configure the pressure wave generator 5 to create pressure waves 23 having a broadband spectrum, e.g., including numerous or multiple frequencies of waves. FIGS. 2A and 2B are graphs that schematically illustrate possible examples of power that can be generated by different embodiments of the pressure wave generator 5. These graphs schematically show acoustic power (in arbitrary units) on the vertical axis as a function of acoustic frequency (in kHz) on the horizontal axis. The acoustic power in the tooth may influence, cause, or increase the strength of effects including, e.g., acoustic cavitation (e.g., cavitation bubble formation and collapse, normal and shear stress formation, as well as microscale flow and microjet formation), acoustic streaming, microerosion, fluid agitation, turbulence, fluid circulation and/or rotational motion, sonoporation, sonochemistry, and so forth, which may act to dissociate organic material in or on the tooth and effectively clean the undesirable materials, e.g., undesirable organic and/or inorganic materials and deposits. In some embodiments, these effects can enhance or enable the obturation or filling of treated root canals or other treatment regions of the tooth. For example, the embodiments disclosed herein can advantageously obturate or fill substantially the entire canal(s) and/or branch structures therefrom, as explained in greater detail above. In various embodiments, the pressure wave generator can produce a pressure wave including acoustic power (at least) at frequencies above: about 1 Hz, about 0.5 kHz, about 1 kHz, about 10 kHz, about 20 kHz, about 50 kHz, about 100 kHz, or greater. The pressure wave can have acoustic power at other frequencies as well (e.g., at frequencies below the aforelisted frequencies).

The graph in FIG. 2A represents a schematic example of acoustic power generated by a liquid jet impacting a surface disposed within a chamber on or around the tooth that is substantially filled with liquid and by the interaction of the liquid jet with fluid in the chamber. This schematic example shows a broadband spectrum 190 of acoustic power with significant power extending from about 1 Hz to about 1000 kHz, including, e.g., significant power in a range of about 1 kHz to about 1000 kHz (e.g., the bandwidth can be about 1000 kHz). The bandwidth of the acoustic energy spectrum may, in some cases, be measured in terms of the 3-decibel (3-dB) bandwidth (e.g., the full-width at half-maximum or FWHM of the acoustic power spectrum). In various examples, a broadband acoustic power spectrum can include significant power in a bandwidth in a range from about 1 Hz to about 500 kHz, in a range from about 1 kHz to about 500 kHz, in a range from about 10 kHz to about 100 kHz, or some other range of frequencies. In some implementations, a broadband spectrum can include acoustic power above about 1 MHz. In some embodiments, the pressure wave generator can produce broadband acoustic power with peak power at about 10 kHz and a bandwidth of about 100 kHz. In various embodiments, the bandwidth of a broadband acoustic power spectrum is greater than about 10 kHz, greater than about 50 kHz, greater than about 100 kHz, greater than about 250 kHz, greater than about 500 kHz, greater than about 1 MHz, or some other value. In some cleaning methods, acoustic power between about 1 Hz and about 200 kHz, e.g., in a range of about 20 kHz to about 200 kHz may be particularly effective at cleaning teeth. The acoustic power can have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies). In some arrangements, the broadband spectrum 190 can include one or more peaks, e.g., peaks in the audible, ultrasonic, and/or megasonic frequency ranges.

The graph in FIG. 2B represents a schematic example of acoustic power generated by an ultrasonic transducer disposed in a chamber on or around the tooth that is substantially filled with liquid. This schematic example shows a relatively narrowband spectrum 192 of acoustic power with a highest peak 192a near the fundamental frequency of about 30 kHz and also shows peaks 192b near the first few harmonic frequencies. The bandwidth of the acoustic power near the peak may be about 5 to 10 kHz, and can be seen to be much narrower than the bandwidth of the acoustic power schematically illustrated in FIG. 2A. In other embodiments, the bandwidth of the acoustic power can be about 1 kHz, about 5 kHz, about 10 kHz, about 20 kHz, about 50 kHz, about 100 kHz, or some other value. The acoustic power of the example spectrum 192 has most of its power at the fundamental frequency and first few harmonics, and therefore the ultrasonic transducer of this example may provide acoustic power at a relatively narrow range of frequencies (e.g., near the fundamental and harmonic frequencies). The acoustic power of the example spectrum 190 exhibits relatively broadband power (with a relatively high bandwidth compared to the spectrum 192), and the example liquid jet can provide acoustic power at significantly more frequencies than the example ultrasonic transducer. For example, the relatively broadband power of the example spectrum 190 illustrates that the example jet device provides acoustic power at these multiple frequencies with energy sufficient to break the bonds between the decayed and healthy material so as to substantially remove the decayed material from the carious region.

It is believed, although not required, that pressure waves having broadband acoustic power (see, e.g., the example shown in FIG. 2A) can generate acoustic cavitation or other means of cleaning and disinfection that is more effective at cleaning teeth (including cleaning, e.g., unhealthy materials in or on the tooth) than cavitation generated by pressure waves having a narrowband acoustic power spectrum (see, e.g., the example shown in FIG. 2B). One reason is that in a broadband spectrum the energy is delivered as substantially all length scales covered in the range and therefore targeting substantially all structures whose dimensions fall within that range of length scales. Further, broadband acoustic power can also generate sufficient energy at frequencies capable of obturating or filling a root canal or other treatment region (such as a treated carious region on an exterior surface of the tooth). For example, a broadband spectrum of acoustic power can produce a relatively broad range of bubble sizes in the cavitation cloud and on the surfaces on the tooth, and the implosion of these bubbles may be more effective at disrupting tissue than bubbles having a narrow size range. Relatively broadband acoustic power may also allow acoustic energy to work on a range of length scales, e.g., from the cellular scale up to the tissue scale. Accordingly, pressure wave generators that produce a broadband acoustic power spectrum (e.g., some embodiments of a liquid jet) can be more effective at tooth cleaning for some treatments than pressure wave generators that produce a narrowband acoustic power spectrum. In some embodiments, multiple narrowband pressure wave generators can be used to produce a relatively broad range of acoustic power. For example, multiple ultrasonic tips, each tuned to produce acoustic power at a different peak frequency, can be used. As used herein, broadband frequencies and broadband frequency spectrum is defined regardless of secondary effects such as harmonics of the main frequencies and regardless of any noise introduced by measurement or data processing (e.g., FFT); that is, these terms should be understood when only considering all main frequencies activated by the pressure wave generator.

Figure 2C:
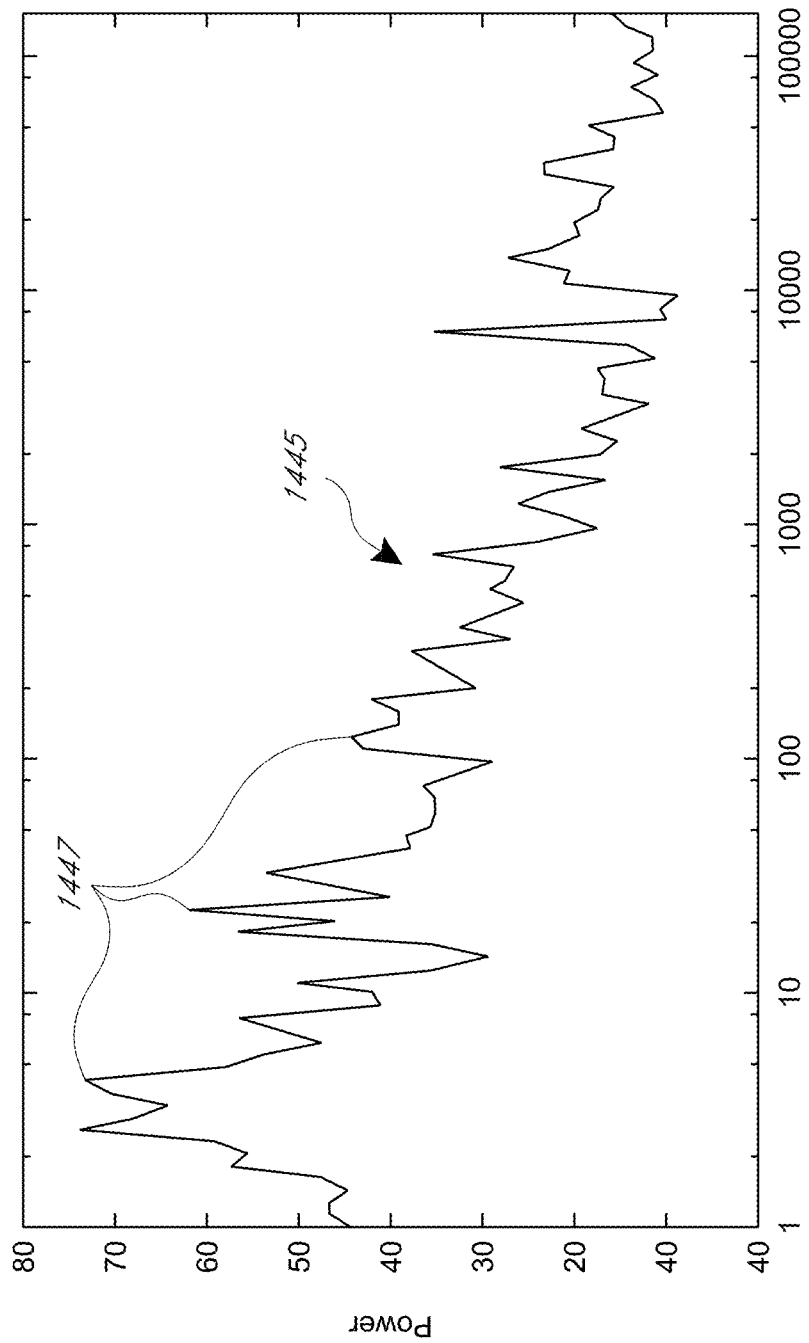
FIG. 2C is a graph of an acoustic power spectrum generated at multiple frequencies by pressure wave generators disclosed herein.

FIG. 2C is a graph of an acoustic power spectrum 1445 generated at multiple frequencies by the pressure wave generators disclosed herein. For example, the spectrum 1445 in FIG. 2C is an example of acoustic power generated by a liquid jet impacting a surface disposed within a chamber on, in, or around the tooth that is substantially filled with liquid and by the interaction of the liquid jet with fluid in the chamber. The spectrum 1445 of FIG. 2C represents acoustic power detected by a sensor spaced apart from the source of the acoustic energy, e.g., the pressure wave generator. The data was acquired inside an insulated water tank when the distance between the power wave generator and the hydrophone (e.g., sensor) being about 8 inches. The vertical axis of the plot represents a measure of acoustic power: Log $(P_{acoustic}^2)$, referred to herein as "power units". The units of $P_{acoustic}$ in the measurement were µPa (micro Pascal). Thus, it should be appreciated that the actual power at the source may be of a different magnitude because the sensor is spaced from the acoustic power generator. However, the general profile of the power spectrum at the source should be the same as the spectrum 1445 detected at the sensor and plotted in FIG. 2C. It should also be understood that, although the plot shows frequencies only up to 100 KHz, the power above 100 KHz was greater than zero (although not plotted in the figures shown herein). It should further be noted that, as would be appreciated by one skilled in the art, the plot and the values would also depend on other parameters, such as, for example, the size and shape of the tank in which data was acquired, the insulation of the inner surface of the tank, the relative distance between the source (e.g., power wave generator), and the free water surface of the tank.

As shown in FIG. 2C, the spectrum 1445 can include acoustic power at multiple frequencies 1447, e.g., multiple discrete frequencies. In particular, the spectrum 1445 illustrated in FIG. 2C includes acoustic power at frequencies in a range of about 1 Hz to about 100 KHz. The acoustic power can be in a range of about 10 power units to about 80 power units at these frequencies. In some arrangements, the acoustic power can be in a range of about 30 power units to about 75 power units at frequencies in a range of about 1 Hz to about 10 kHz. In some arrangements, the acoustic power can be in a range of about 10 power units to about 30 power units at frequencies in a range of about 1 KHz to about 100 kHz. In some embodiments, for example, the broadband frequency range of the pressure waves generated by the pressure wave generators disclosed herein can comprise a substantially white noise distribution of frequencies.

Pressure wave generators that generate acoustic power associated with the spectrum 1445 of FIG. 2C can advantageously and surprisingly clean undesirable materials from teeth. As explained above, the generation of power at multiple frequencies can help to remove various types of organic and/or inorganic materials that have different material or physical characteristics, and/or different bonding strengths at various frequencies. For example, some undesirable materials may be removed from the teeth and/or gums at relatively low acoustic frequencies, while other materials may be removed from the teeth at relatively high acoustic frequencies, while still other materials may be removed at intermediate frequencies between the relatively low and relatively high frequencies. As shown in FIG. 2C, lower frequency cleaning phases can be activated at higher powers, and higher frequency cleaning phases can be activated at lower powers. In other embodiments, low frequency cleaning phases may be activated at relatively low powers, and high frequency cleaning phases may be activated at relatively high powers. Pressure wave generators that generate acoustic power at multiple frequencies (e.g., multiple discrete frequencies) are capable of cleaning undesirable materials and decayed matter from interior and/or exterior portions of teeth.

In the embodiments disclosed herein, treatment procedures can be activated to generate acoustic power at various frequency ranges. For example, some treatment phases may be activated at lower frequencies, and other treatment phases may be activated at higher frequencies. The pressure wave generators disclosed herein can be adapted to controllably generate acoustic power at any suitable frequencies 1447 of the spectrum 1445. For example, the pressure wave generators disclosed herein can be adapted to generate power at multiple frequencies 1447 simultaneously, e.g., such that the delivered acoustic power in a particular treatment procedure can include a desired combination of individual frequencies. For example, in some procedures, power may be generated across the entire frequency spectrum 1445. In some treatment phases, the pressure wave generator can deliver acoustic power at only relatively low frequencies, and in other treatment phases, the pressure wave generator can deliver power at only relatively high frequencies, as explained herein. Further, depending on the desired treatment procedure, the pressure wave generator can automatically or manually transition between frequencies 1447 according to a desired pattern, or can transition between frequencies 1447 randomly. In some arrangements, relatively low frequencies can be associated with large-scale bulk fluid movement, and relatively high frequencies can be associated with small-scale, high-energy oscillations.

In some embodiments, the treatment procedure may include one or more treatment phases. In each treatment phase, energy can be applied at a different frequency or band of frequencies. For example, in one phase, energy (e.g., pressure or acoustic waves) propagating at a relatively low frequency (or band of frequencies) may be generated. The low frequency pressure waves can interact with the treatment fluid in the chamber and can induce removal of large-scale dental deposits or materials. Without being limited by theory, the low frequency pressure waves can remove a substantial portion of the unhealthy materials in the tooth. For example, the low frequency waves may have a sufficiently high energy at suitably low frequencies to remove large deposits or materials from the tooth. The acoustic power at the relatively low frequencies can include acoustic power at any suitable low-frequency band of the power spectrum of the pressure wave generator (see, e.g., FIG. 2A). For example, in some embodiments, the acoustic power in the first, low-frequency range can include one or more frequencies in a range of about 0.1 Hz to about 100 Hz, for example in a range of about 1 Hz to about 50 Hz in some arrangements.

In another phase, acoustic energy may be generated at relatively high frequencies. At higher frequencies, the pressure wave generator can be configured to remove smaller deposits and debris. For example, at higher frequencies, the pressure waves can propagate through the treatment fluid. The higher frequency waves can remove smaller portions from relatively small locations, such as crevices, cracks, spaces, and irregular surfaces of the tooth. In some embodiments, degassed liquid can be used to enhance the removal of matter from these small spaces. When the higher frequency cleaning is performed after the lower frequency cleaning, in some embodiments, the high frequency waves (and/or intermediate frequency waves) can clean the remainder of the unhealthy material left behind from the low frequency cleaning. In the relatively high frequency phases, acoustic energy can be generated in a range of about 10 kHz to about 1000 kHz, e.g., in a range of about 100 kHz to about 500 kHz.

In some embodiments, the treatment procedure can progress from the relatively low frequencies (or bands of frequencies) toward higher frequencies (or bands of frequencies). For example, the procedure can move from the relatively low frequency phase(s), through intermediate frequency phase(s), until the high frequency phase(s) are reached. Thus, in some embodiments, the treatment procedure can provide a gradual and/or substantially continuous transition between relatively low and relatively high frequencies. As the treatment progresses through the frequencies, unhealthy dental deposits or materials of varying size and type can be removed by the pressure wave generator. In other embodiments, however, the treatment procedure can transition or switch between frequencies (or bands of frequencies) or phases (e.g., between high, low and/or intermediate frequencies or bands of frequencies) at discrete levels. At various intermediate frequency ranges, acoustic energy can be generated in a range of about 100 Hz to about 10 kHz. For example, in some embodiments, the various phases of the treatment procedures described above may be activated by the user or clinician, or the pressure wave generator can be configured to automatically transition between the phases. In some embodiments, for example, the pressure wave generator can randomly switch between high, low, and intermediate frequencies.

Various treatment procedures may include any suitable number of treatment phases at various different frequencies. Furthermore, although various low- and high-frequency phases may be described above as occurring in a particular order, in other embodiments, the order of activating the low- and high-frequency phases, and/or any intermediate frequency phases, may be any suitable order. Furthermore, the treatment procedures and phases described herein can also be used to fill or obturate treatment regions of a tooth after cleaning. In obturation procedures, the embodiments disclosed herein can advantageously obturate or fill substantially the entire canal(s) and/or branch structures therefrom, as explained in greater detail herein.

4. Enhancing Treatment Procedures with Degassed Fluids

As described herein, the treatment fluid (and/or any of solutions added to the treatment fluid) can be degassed compared to normal liquids used in dental offices. For example, degassed distilled water can be used with or without the addition of chemical agents or solutes.

a. Examples of Possible Effects of Dissolved Gases in the Treatment Fluid

In some procedures, the treatment fluid can include dissolved gases (e.g., air). For example, the fluids used in dental offices generally have a normal dissolved gas content (e.g., determined from the temperature and pressure of the fluid based on Henry's law). During cleaning procedures using a pressure wave generator, the acoustic field of the pressure wave generator and/or the flow or circulation of fluids in the chamber can cause some of the dissolved gas to come out of solution and form bubbles.

The bubbles can block small passageways or cracks or surface irregularities in the tooth, and such blockages can act as if there were a "vapor lock" in the small passageways. In some such procedures, the presence of bubbles may at least partially block, impede, or redirect propagation of acoustic waves past the bubbles and may at least partially inhibit or prevent cleaning action from reaching, for example, unhealthy dental materials in tubules and small spaces of the tooth 10. The bubbles may block fluid flow or circulation from reaching these difficult-to-reach, or otherwise small, regions, which may prevent or inhibit a treatment solution from reaching these areas of the tooth.

In certain procedures, cavitation is believed to play a role in cleaning the tooth. Without wishing to be bound by any particular theory, the physical process of cavitation inception may be, in some ways, similar to boiling. One possible difference between cavitation and boiling is the thermodynamic paths that precede the formation of the vapor in the fluid. Boiling can occur when the local vapor pressure of the liquid rises above the local ambient pressure in the liquid, and sufficient energy is present to cause the phase change from liquid to a gas. It is believed that cavitation inception can occur when the local ambient pressure in the liquid decreases sufficiently below the saturated vapor pressure, which has a value given in part by the tensile strength of the liquid at the local temperature. Therefore, it is believed, although not required, that cavitation inception is not determined by the vapor pressure, but instead by the pressure of the largest nuclei, or by the difference between the vapor pressure and the pressure of the largest nuclei. As such, it is believed that subjecting a fluid to a pressure slightly lower than the vapor pressure generally does not cause cavitation inception. However, the solubility of a gas in a liquid is proportional to pressure; therefore lowering the pressure may tend to cause some of the dissolved gas inside the fluid to be released in the form of gas bubbles that are relatively large compared to the size of bubbles formed at cavitation inception. These relatively large gas bubbles may be misinterpreted as being vapor cavitation bubbles, and their presence in a fluid may have been mistakenly described in certain reports in the literature as being caused by cavitation, when cavitation may not have been present.

In the last stage of collapse of vapor cavitation bubbles, the velocity of the bubble wall may even exceed the speed of sound and create strong shock waves inside the fluid. The vapor cavitation bubble may also contain some amount of gas, which may act as a buffer and slow down the rate of collapse and reduce the intensity of the shockwaves. Therefore, in certain procedures that utilize cavitation bubbles for tooth cleaning, it may be advantageous to reduce the amount of the dissolved air in the fluid to prevent such losses.

The presence of bubbles that have come out of solution from the treatment fluid may lead to other disadvantages during certain procedures. For example, if the pressure wave generator produces cavitation, the agitation (e.g. pressure drop) used to induce the cavitation may cause the release of the dissolved air content before the water molecules have a chance to form a cavitation bubble. The already-formed gas bubble may act as a nucleation site for the water molecules during the phase change (which was intended to form a cavitation bubble). When the agitation is over, the cavitation bubble is expected to collapse and create pressure waves. However, cavitation bubble collapse might happen with reduced efficiency, because the gas-filled bubble may not collapse and may instead remain as a bubble. Thus, the presence of gas in the treatment fluid may reduce the effectiveness of the cavitation process as many of the cavitation bubbles may be wasted by merging with gas-filled bubbles. Additionally, bubbles in the fluid may act as a cushion to damp pressure waves propagating in the region of the fluid comprising the bubbles, which may disrupt effective propagation of the pressure waves past the bubbles. Some bubbles may either form on or between tooth surfaces, or be transferred there by the flow or circulation of fluid in the tooth. The bubbles may be hard to remove due to relatively high surface tension forces. This may result in blocking the transfer of chemicals and/or pressure waves into the irregular surfaces and small spaces in and between teeth, and therefore may disrupt or reduce the efficacy of the treatment. Existence of a very small amount of gas inside the fluid may however be beneficial as the gas may form very small volume bubbles which then act as the nucleation site for vapor cavitation to occur (and therefore facilitate vapor cavitation), and due to their small volume compared to the volume of the actual vapor cavitation, their damping and interrupting effects may be negligible.

b. Examples of Degassed Treatment Fluids

Accordingly, it may be advantageous in some systems and methods to use a degassed fluid, which can inhibit, reduce, or prevent bubbles from coming out of solution during treatments as compared to systems and methods that use normal (e.g., non-degassed) fluids. In dental procedures in which the treatment fluid has a reduced gas content (compared with the normal fluids) tooth surfaces or tiny spaces in the tooth may be free of bubbles that have come out of solution. Acoustic waves generated by the pressure wave generator can propagate through the degassed fluid to reach and clean the surfaces, cracks, and tooth spaces and cavities. In some procedures, the degassed fluid can be able to penetrate spaces as small as about 500 microns, 200 microns, 100 microns, 10 microns, 5 microns, 1 micron, or smaller, because the degassed fluid is sufficiently gas-free that bubbles are inhibited from coming out of solution and blocking these spaces (as compared to use of fluids with normal dissolved gas content).

For example, in some systems and methods, the degassed fluid can have a dissolved gas content that is reduced when compared to the "normal" gas content of water. For example, according to Henry's law, the "normal" amount of dissolved air in water (at 25 C and 1 atmosphere) is about 23 mg/L, which includes about 9 mg/L of dissolved oxygen and about 14 mg/L of dissolved nitrogen. In some embodiments, the degassed fluid has a dissolved gas content that is reduced to approximately 10%-40% of its "normal" amount as delivered from a source of fluid (e.g., before degassing). In other embodiments, the dissolved gas content of the degassed fluid can be reduced to approximately 5%-50% or 1%-70% of the normal gas content of the fluid. In some treatments, the dissolved gas content can be less than about 70%, less than about 50%, less than about 40%, less than about 30%, less than about 20%, less than about 10%, less than about 5%, or less than about 1% of the normal gas amount.

In some embodiments, the amount of dissolved gas in the degassed fluid can be measured in terms of the amount of dissolved oxygen (rather than the amount of dissolved air), because the amount of dissolved oxygen can be more readily measured (e.g., via titration or optical or electrochemical sensors) than the amount of dissolved air in the fluid. Thus, a measurement of dissolved oxygen in the fluid can serve as a proxy for the amount of dissolved air in the fluid. In some such embodiments, the amount of dissolved oxygen in the degassed fluid can be in a range from about 1 mg/L to about 3 mg/L, in a range from about 0.5 mg/L to about 7 mg/L, or some other range. The amount of dissolved oxygen in the degassed fluid can be less than about 7 mg/L, less than about 6 mg/L, less than about 5 mg/L, less than about 4 mg/L, less than about 3 mg/L, less than about 2 mg/L, or less than about 1 mg/L.

In some embodiments, the amount of dissolved gas in the degassed fluid can be in a range from about 2 mg/L to about 20 mg/L, in a range from about 1 mg/L to about 12 mg/L, or some other range. The amount of dissolved gas in the degassed fluid can be less than about 20 mg/L, less than about 18 mg/L, less than about 15 mg/L, less than about 12 mg/L, less than about 10 mg/L, less than about 8 mg/L, less than about 6 mg/L, less than about 4 mg/L, or less than about 2 mg/L.

In other embodiments, the amount of dissolved gas can be measured in terms of air or oxygen percentage per unit volume. For example, the amount of dissolved oxygen (or dissolved air) can be less than about 5% by volume, less than about 1% by volume, less than about 0.5% by volume, or less than about 0.1% by volume.

The amount of dissolved gas in a liquid can be measured in terms of a physical property such as, e.g., fluid viscosity or surface tension. For example, degassing water tends to increase its surface tension. The surface tension of non-degassed water is about 72 mN/m at 20° C. In some embodiments, the surface tension of degassed water can be about 1%, 5%, or 10% greater than non-degassed water.

In some treatment methods, one or more secondary fluids can be added to a primary degassed fluid (e.g., an antiseptic solution can be added to degassed distilled water). In some such methods, the secondary solution(s) can be degassed before being added to the primary degassed fluid. In other applications, the primary degassed fluid can be sufficiently degassed such that inclusion of the secondary fluids (which can have normal dissolved gas content) does not increase the gas content of the combined fluids above what is desired for a particular dental treatment.

In various implementations, the treatment fluid can be provided as degassed liquid inside sealed bags or containers. The fluid can be degassed in a separate setup in the operatory before being added to a fluid reservoir. In an example of an "in-line" implementation, the fluid can be degassed as it flows through the system, for example, by passing the fluid through a degassing unit attached along a fluid line (e.g., the fluid inlet). Examples of degassing units that can be used in various embodiments include: a Liqui-Cel® MiniModule® Membrane Contactor (e.g., models 1.7×5.5 or 1.7×8.75) available from Membrana—Charlotte (Charlotte, N.C.); a PermSelect® silicone membrane module (e.g., model PDM-SXA-2500) available from MedArray, Inc. (Ann Arbor, Mich.); and a FiberFlo® hollow fiber cartridge filter (0.03 micron absolute) available from Mar Cor Purification (Skippack, Pa.). The degassing can be done using any of the following degassing techniques or combinations of thereof: heating, helium sparging, vacuum degassing, filtering, freeze-pump-thawing, and sonication.

In some embodiments, degassing the fluid can include de-bubbling the fluid to remove any small gas bubbles that form or may be present in the fluid. De-bubbling can be provided by filtering the fluid. In some embodiments, the fluid may not be degassed (e.g., removing gas dissolved at the molecular level), but can be passed through a de-bubbler to remove the small gas bubbles from the fluid.

In some embodiments, a degassing system can include a dissolved gas sensor to determine whether the treatment fluid is sufficiently degassed for a particular treatment. A dissolved gas sensor can be disposed downstream of a mixing system and used to determine whether mixing of solutes has increased the dissolved gas content of the treatment fluid after addition of solutes, if any. A solute source can include a dissolved gas sensor. For example, a dissolved gas sensor can measure the amount of dissolved oxygen in the fluid as a proxy for the total amount of dissolved gas in the fluid, since dissolved oxygen can be measured more readily than dissolved gas (e.g., nitrogen or helium). Dissolved gas content can be inferred from dissolved oxygen content based at least partly on the ratio of oxygen to total gas in air (e.g., oxygen is about 21% of air by volume). Dissolved gas sensors can include electrochemical sensors, optical sensors, or sensors that perform a dissolved gas analysis. Examples of dissolved gas sensors that can be used with embodiments of various systems disclosed herein include a Pro-Oceanus GTD-Pro or HGTD dissolved gas sensor available from Pro-Oceanus Systems Inc. (Nova Scotia, Canada) and a D-Opto dissolved oxygen sensor available from Zebra-Tech Ltd. (Nelson, New Zealand). In some implementations, a sample of the treatment can be obtained and gases in the sample can be extracted using a vacuum unit. The extracted gases can be analyzed using a gas chromatograph to determine dissolved gas content of the fluid (and composition of the gases in some cases).

Accordingly, fluid delivered to the tooth from a fluid inlet and/or the fluid used to generate the jet in a liquid jet device can comprise a degassed fluid that has a dissolved gas content less than normal fluid. The degassed fluid can be used, for example, to generate the high-velocity liquid beam for generating acoustic waves, to substantially fill or irrigate a chamber, to provide a propagation medium for acoustic waves, to inhibit formation of air (or gas) bubbles in the chamber, and/or to provide flow of the degassed fluid into small spaces in the tooth (e.g., cracks, irregular surfaces, tubules, etc.). In embodiments utilizing a liquid jet, use of a degassed fluid can inhibit bubbles from forming in the jet due to the pressure drop at a nozzle orifice where the liquid jet is formed.

Thus, examples of methods for dental and/or endodontic treatment comprise flowing a degassed fluid onto a tooth or tooth surface or into a chamber. The degassed fluid can comprise a tissue dissolving agent and/or a decalcifying agent. The degassed fluid can have a dissolved oxygen content less than about 9 mg/L, less than about 7 mg/L, less than about 5 mg/L, less than about 3 mg/L, less than about 1 mg/L, or some other value. A fluid for treatment can comprise a degassed fluid with a dissolved oxygen content less than about 9 mg/L, less than about 7 mg/L, less than about 5 mg/L, less than about 3 mg/L, less than about 1 mg/L, or some other value. The fluid can comprise a tissue dissolving agent and/or a decalcifying agent. For example, the degassed fluid can comprise an aqueous solution of less than about 6% by volume of a tissue dissolving agent and/or less than about 20% by volume of a decalcifying agent.

Figure 3A:
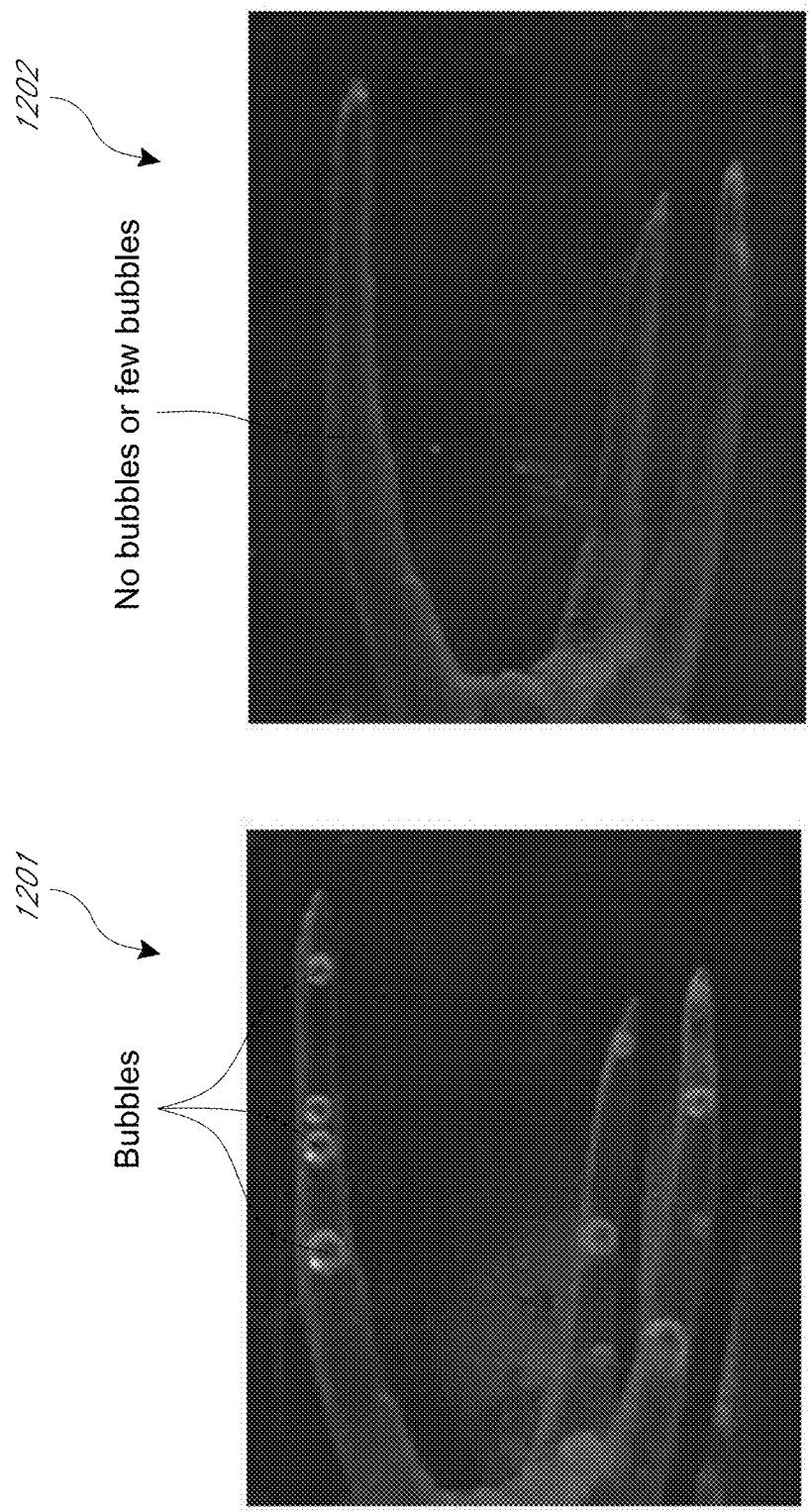
FIG. 3A illustrates images of root canals that compare the use of non-degassed liquid and degassed liquid in the disclosed pressure wave generators.
Figure 3B:
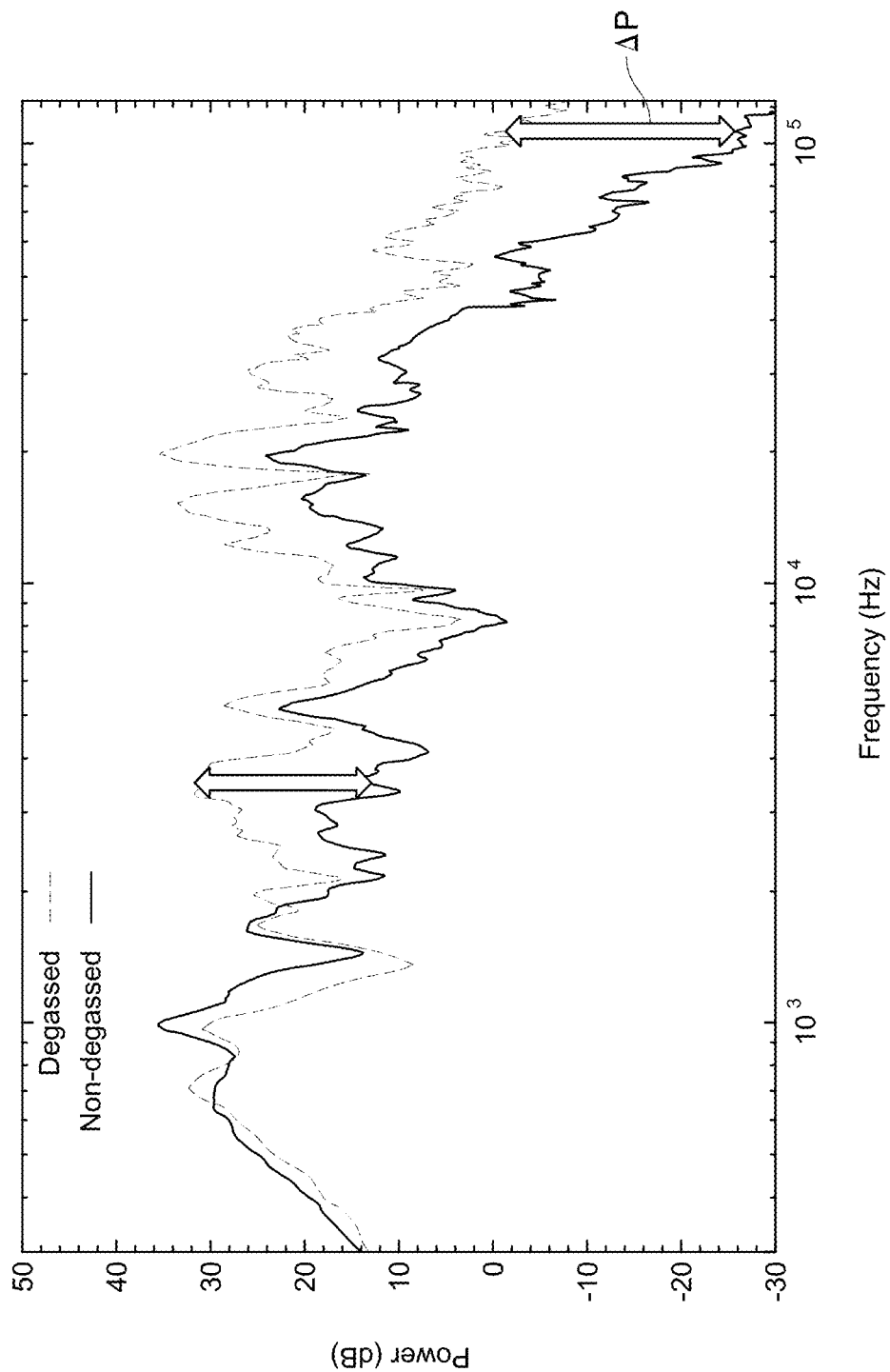
FIG. 3B is a plot comparing the power output for techniques using non-degassed and degassed liquids.

FIG. 3A illustrates images of root canals that compare the use of non-degassed liquid and degassed liquid in the disclosed pressure wave generators. As shown in image 1201 on the left side of FIG. 3A, the use of non-degassed liquid may cause bubbles to form in the canals, which may inhibit the propagation of energy in some arrangements. As shown in image 1202 on the right side of FIG. 3A, the use of degassed liquid may substantially prevent the formation of bubbles in the root canals when exposed to broadband acoustic or pressure waves. FIG. 3B is a plot comparing the power output for techniques using non-degassed and degassed liquids. The power outputs plotted in FIG. 3B are measured based on the liquid jet device described herein. As shown in FIG. 3B, at higher acoustic frequencies, the use of degassed liquid in the disclosed systems can generate significantly more power than in techniques using non-degassed liquid. As illustrated in FIG. 3B, for example, at high acoustic frequencies, the difference between power generated by degassed and non-degassed liquids can be given by ΔP, which can be in a range of about 5 dB to about 25 dB for frequencies in a range of about 20 kHz to about 200 kHz. For example, for frequencies in a range of about 70 kHz to about 200 kHz, ΔP can be in a range of about 10 dB to about 25 dB. At lower frequencies, the differences in power generated by degassed and non-degassed techniques may not be noticeable. At lower frequencies, relatively high powers may be generated even with non-degassed liquid because low frequency, large-scale fluid motion may produce substantial momentum that contributes to the cleaning of the tooth.

II. Console

FIG. 4 is a schematic perspective view of an example console 2. The console 2 may act as a central component of the system 1 that controls the operation of various treatment procedures, provides a user interface 28 for the clinician to interact with the system 1, manages data regarding the procedures performed by the system 1, and communicates with external entities regarding the treatment procedures and other aspects of the system 1. For example, the console 2 can include a housing 30 to which numerous system components are housed and/or coupled. Treatment procedure components (e.g., mechanical, fluidic, electrical, electronic, and data communication and management components) may be disposed in or on the console 2 to provide a central platform from which the clinician can perform one or more dental procedures. In some embodiments, the console 2 may include system components suitable for performing dental cleaning procedures, such as procedures for cleaning root canals of teeth, carious regions from teeth, and undesirable dental deposits (such as calculus, plaque, bacteria, etc.) from teeth. In other embodiments, the console 2 may additionally (or alternatively) include components suitable for performing other dental procedures, including obturation procedures, restoration procedures, etc.

The treatment procedure components may be disposed inside the housing 30 to enable a compact arrangement of multiple, interconnected components. One or more conduits 29 can couple the treatment procedure components in the housing 30 with the tooth coupler 3 by way of the interface member 4. For example, the conduits 29 may include or define fluid, electrical, and/or data communication pathways between the console 2 and the tooth coupler 3. The fluid pathways may include high-pressure tubing adapted to convey pressurized fluid to the tooth coupler 3. Waste lines or suction lines may convey waste fluid from the tooth coupler 3 back to the housing 30 and/or a waste reservoir. Electrical wiring may extend from the housing to the tooth coupler 3 to provide electrical power to the tooth coupler 3. Fiber optic lines or other communications pathways (which may be wired or wireless) may provide data communication between the console 2 and the tooth coupler 3.

As explained in more detail herein, the interface member 4 may be mechanically arranged such that the tooth coupler 3 and the console 2 can removably engage with one another while also accommodating different types of communication (e.g., fluidic, electrical, data, etc.) between the console 2 and the tooth coupler 3. When the tooth coupler 3 and the interface member 4 are engaged, the clinician can control the operation of the system 1 (including various treatment procedures) by interacting with the user interface 28.

FIG. 4A is a schematic perspective view of a console 2 in accordance with another embodiment. As explained above, the console 2 can include a user interface 28 and a housing 30. A handpiece 3A can removeably couple to the console 2 by way of one or more conduits 29. The handpiece 3A can rest in a cradle 633. As explained herein, the handpiece 3A can include a communications chip (see FIG. 28). The cradle 633 can comprise a reader configured to read data from the chip. A foot pedal or switch 634 can be provided in electrical communication with the console 2. The foot pedal 634 can be activated by the clinician to activate, deactivate, and/or otherwise control the operation of the handpiece 3A and liquid jet. In addition, a high pressure purge port 635 and a vacuum purge port 636 can be provided on the console 2. The purge ports 635, 636 can be part of the purge system 47 disclosed herein with respect to FIG. 5D. In particular, purge fluids can be passed through the system and through the purge ports 635, 636 before use in a treatment procedure. For example, before a treatment procedure, a high pressure tube 29a (which may supply the pressurized fluid to the jet device) may be connected to the high pressure purge port 635. Purging fluids may be run through the system 1 and through the high pressure purge port 635 to a waste reservoir and/or waste system, as described herein. In addition, before a treatment procedure, a lower pressure vacuum or suction tube 29a (which may be in communication with a suction port on the handpiece 3A to remove waste fluids from the tooth) may be connected to the vacuum purge port 636. Purging fluids may run through the system, including the evacuation system disclosed herein, and may pass through the vacuum purge port 636 and into the waste reservoir or system. Upon purging the system 1, the handpiece and tubes 29a, 29b may be coupled together for the treatment procedure.

A. Description of Console Components

Figure 5A:
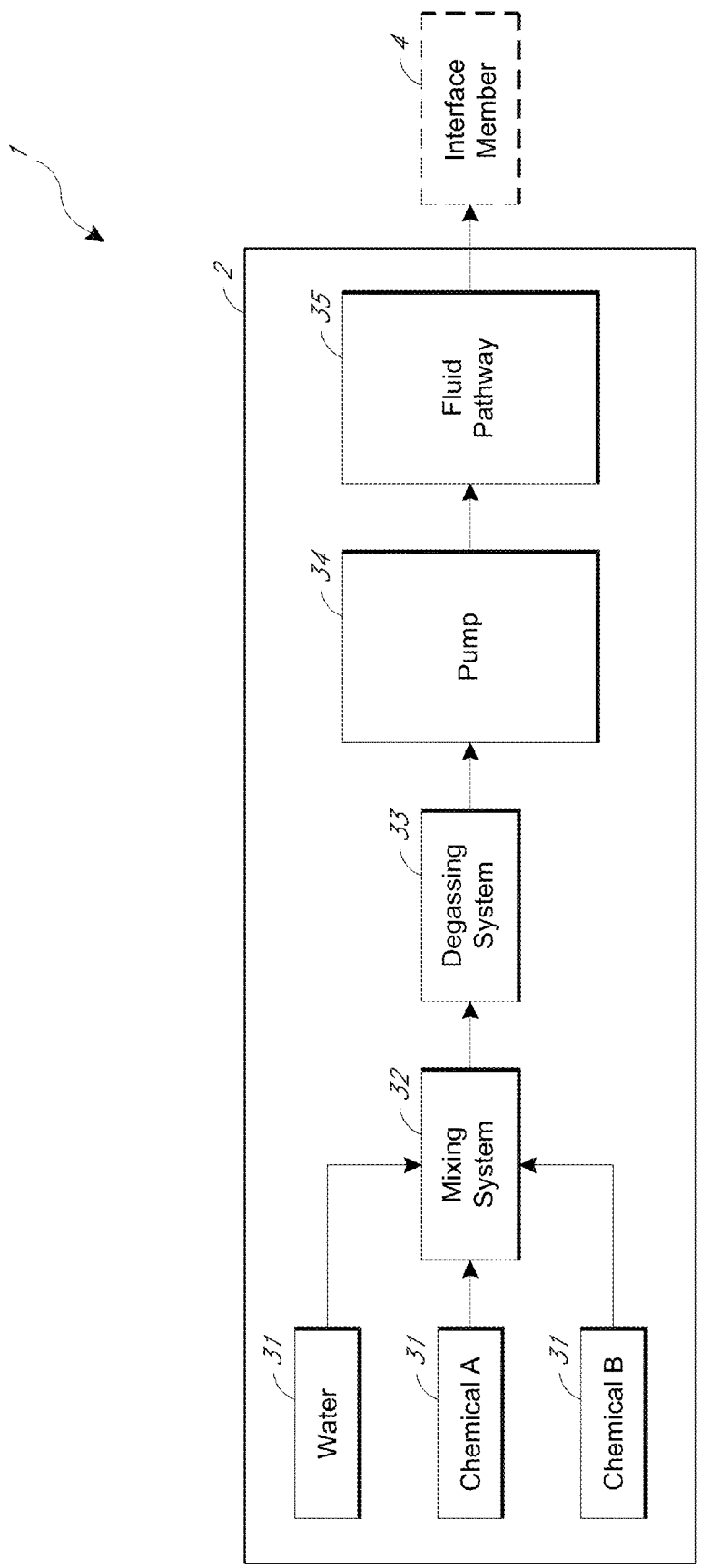
FIG. 5A is a schematic system diagram of a dental treatment system, according to some embodiments.

FIG. 5A is a schematic system diagram of a dental treatment system 1, according to some embodiments. The system 1 can include a console 2 coupled to an interface member 4. As explained herein, the interface member 4 can be configured to releasably couple to a tooth coupler 3, such as a handpiece or treatment cap. The console 2 (e.g., the housing 30) can include multiple components configured for various treatment procedures, such as tooth cleaning procedures, etc. In particular, the console 2 can include one or more fluid reservoirs 31 configured to store various types of treatment fluids. As shown in FIG. 5A, for example, the fluid reservoirs may store water and multiple chemicals, such as Chemical A and Chemical B.

In some treatments, it may be desirable to mix the one or more fluids stored in the reservoirs 31. Accordingly, a mixing system 32 can be provided to mix the fluids to a desired amount. As explained herein, in some treatment procedures, the use of degassed liquids may be desirable. For example, degassed fluids may be useful in enhancing cavitation when used in cleaning procedures. A degassing system 33 can be provided in the console to substantially remove, or reduce, the amount of dissolved gases in the fluid supplied to the tooth coupler 3. As shown in FIG. 5A, in some embodiments, the degassing system 33 may be disposed downstream of the missing system 32. In the embodiment of FIG. 5A, for example, the desired treatment fluid can be mixed, and, subsequently, dissolved gases (such as dissolved oxygen) can be removed from the mixed fluid.

A high-pressure pump 34 can be provided in the console to drive treatment fluid to the interface member 4 and the tooth coupler 3. The pump 34 may be a chemical resistant, high-pressure pump in some arrangements such that the pump 34 can accommodate both high pressure fluid flow and the chemical properties of the treatment fluid without experiencing corrosion or other deleterious effects. The pump 34 can be in fluid communication with the interface member 4 by way of a fluid pathway 35. The fluid pathway 35 may similarly be made of a material and structure such that the pathway 35 is resistant to corrosion or other negative effects caused by the treatment fluids. The fluid pathway 35 may also be configured to support high-pressure fluid flow therethrough. As explained herein, the interface member 4 can releasably or removably couple with the tooth coupler 3 to supply treatment fluid to the tooth coupler 3.

Figure 5B:
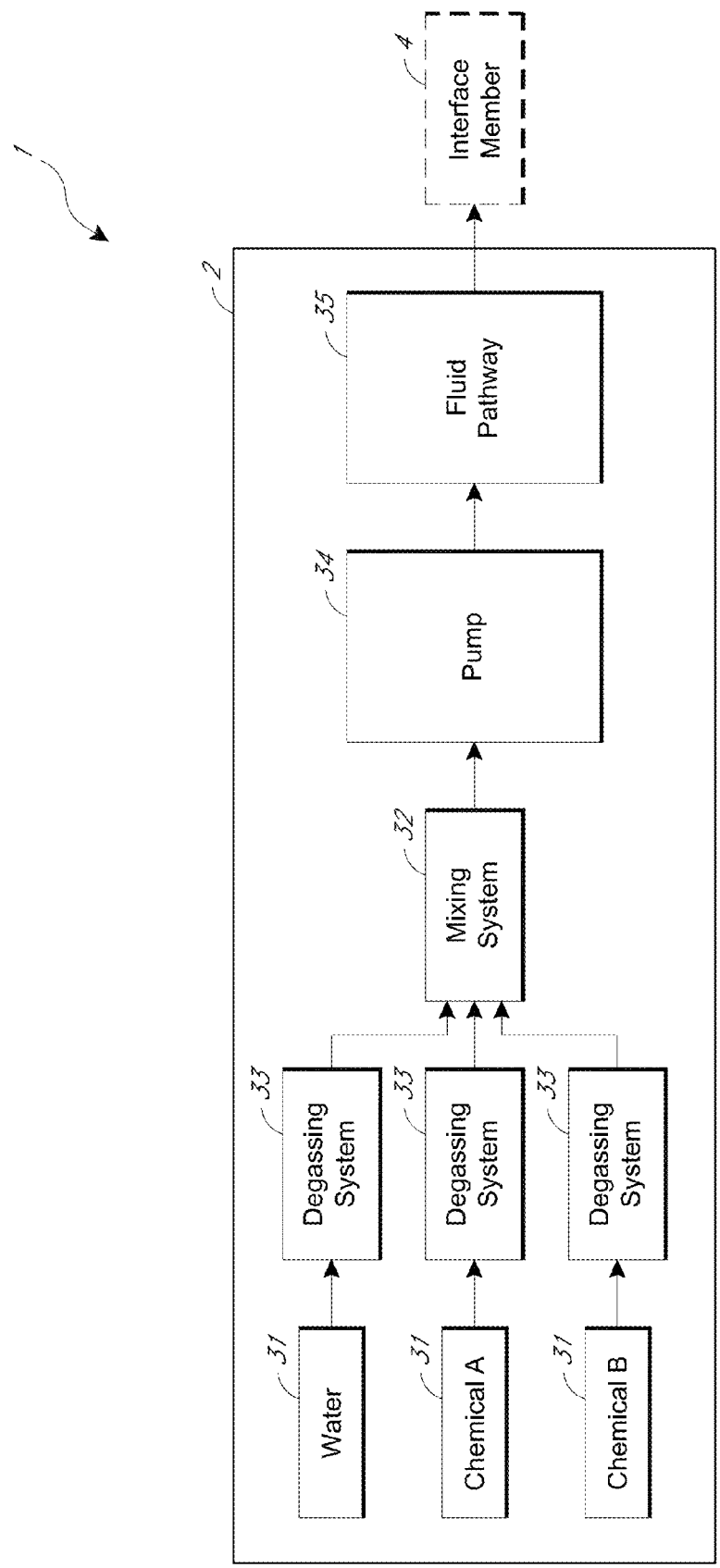
FIG. 5B is a schematic system diagram of the system, according to another embodiment.

FIG. 5B is a schematic system diagram of the system 1, according to another embodiment. As with the embodiment of FIG. 5A, the system 1 of FIG. 5B can include a console 2 having one or more fluid reservoirs 31, a mixing system 32, a pump 34, a fluid pathway 35, and an interface member 4. However, unlike the embodiment of FIG. 5A, the system 1 shown in FIG. 5B includes degassing systems 33 upstream of the mixing system 32. Indeed, the console 2 may include a degassing system 33 or apparatus for each treatment fluid or reservoir 31 in some arrangements. Thus, in the embodiment of FIG. 5B, the fluids supplied by the reservoirs 31 may be degassed before mixing the fluids together. For example, water may be degassed by a degassing system 33, Chemical A may be degassed by a separate degassing system 33, and Chemical B may be degassed by another degassing system 33. After degassing each fluid supplied by the reservoirs 31, the mixing system 32 can mix the fluids as desired and supply the mixed and degassed fluid to the pump 34 and fluid pathway 35.

Figure 5C:
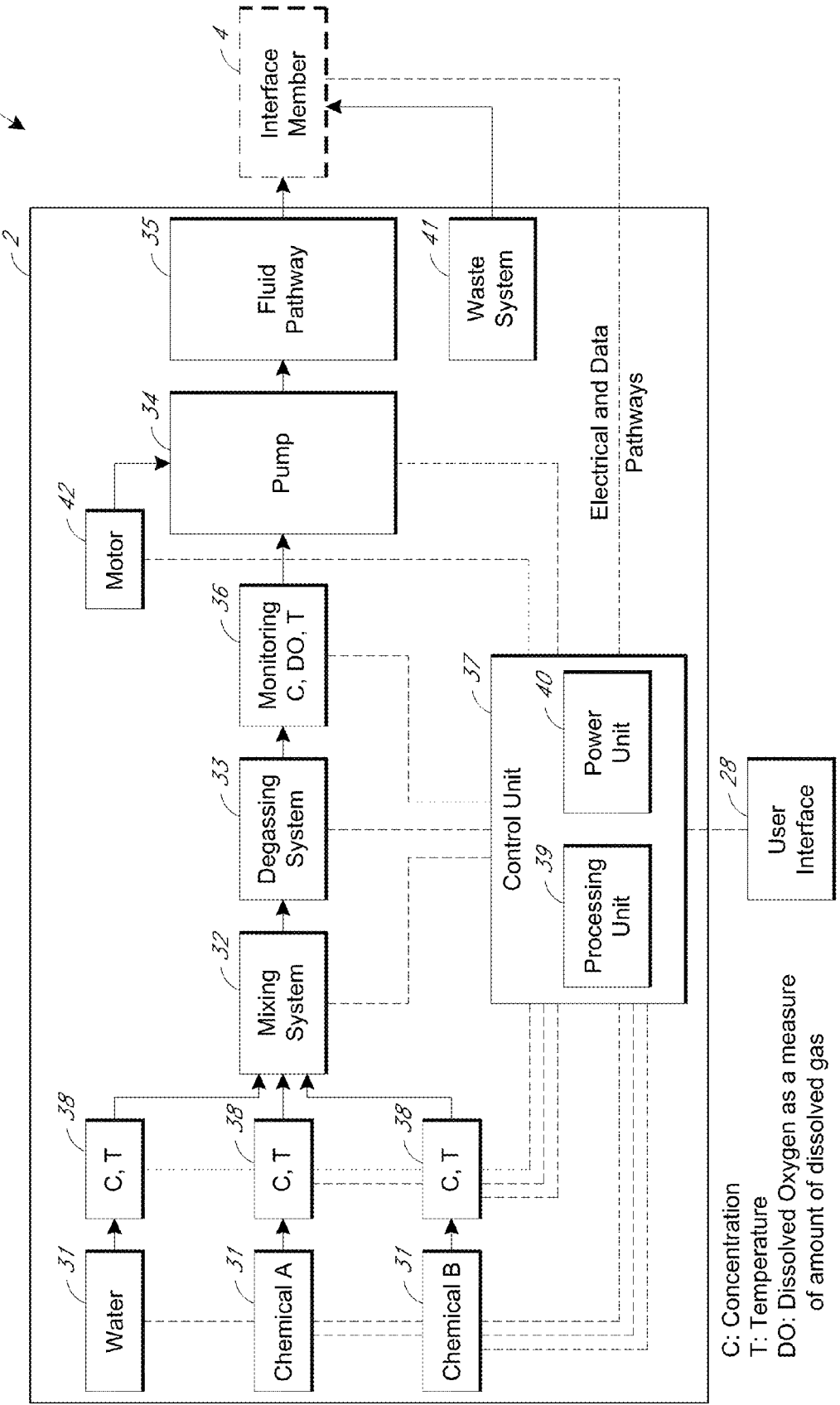
FIG. 5C is a schematic system diagram of the system according to some embodiments.

FIG. 5C is a schematic system diagram of a system 1 according to some embodiments. As with the embodiment of FIGS. 5A-5B, the console 2 can include fluid reservoirs 31, a mixing system 32, a degassing system 33, a pump 34, a motor 42 for driving the pump 34, a fluid pathway 35, and an interface member 4. As shown in FIG. 5C, the mixing system 32 may be upstream of the degassing system 33, but in some arrangements the degassing system 33 may be upstream of the mixing system 32 (see FIG. 5B). In the embodiment of FIG. 5C, the console 2 can include one or more monitoring sensors 38 disposed downstream of the fluid reservoirs 31. The monitoring sensors 38 can be part of a monitoring system and can measure various properties of the fluids before mixing and/or degassing the fluids. For example, as shown in FIG. 5C, the sensors 38 can measure at least one of concentration (C) and temperature (T) of the treatment fluids before mixing. The console 2 can further include a monitoring apparatus 36 downstream of the degassing system 33 and mixing system 32. The monitoring apparatus 36 can measure at least one of concentration (C), temperature (T), and dissolved oxygen (DO) content of the degassed and mixed solution.

Furthermore, the system 1 shown in FIG. 5C can include a control unit 37 in electrical and data communication with the components of the system 1. The control unit 37 can include various units and/or modules. For example, the control unit 37 can include a processing unit 39 and a power unit 40. The control unit 37 can be in electrical and data communication with the fluid reservoirs 31 (and/or with valves that are associated with the reservoirs 31) and the sensors 38 to control and measure the fluids supplied by the reservoirs 31. The control unit 37 can also communicate with the mixing system 32 and the degassing system 33 to control the amount of fluid mixing and degassing, respectively. Further, the control unit 37 can be in electrical and data communication with the monitoring apparatus 36 to manage the properties of the fluid supplied to the pump 34. The pump 34 can be driven by the motor 42 that can be controlled by the control unit 37. In addition, the control unit 37 of the console 2 can communicate with the interface member 4, and thus the tooth coupler 3, by way of electrical and data pathways passing through the interface member 4 and to the tooth coupler 3. The control unit 37 can couple to the user interface 28, through which the user can control the treatment procedures and/or monitor the progress of the treatment procedures and the system 1.

Figure 5D:
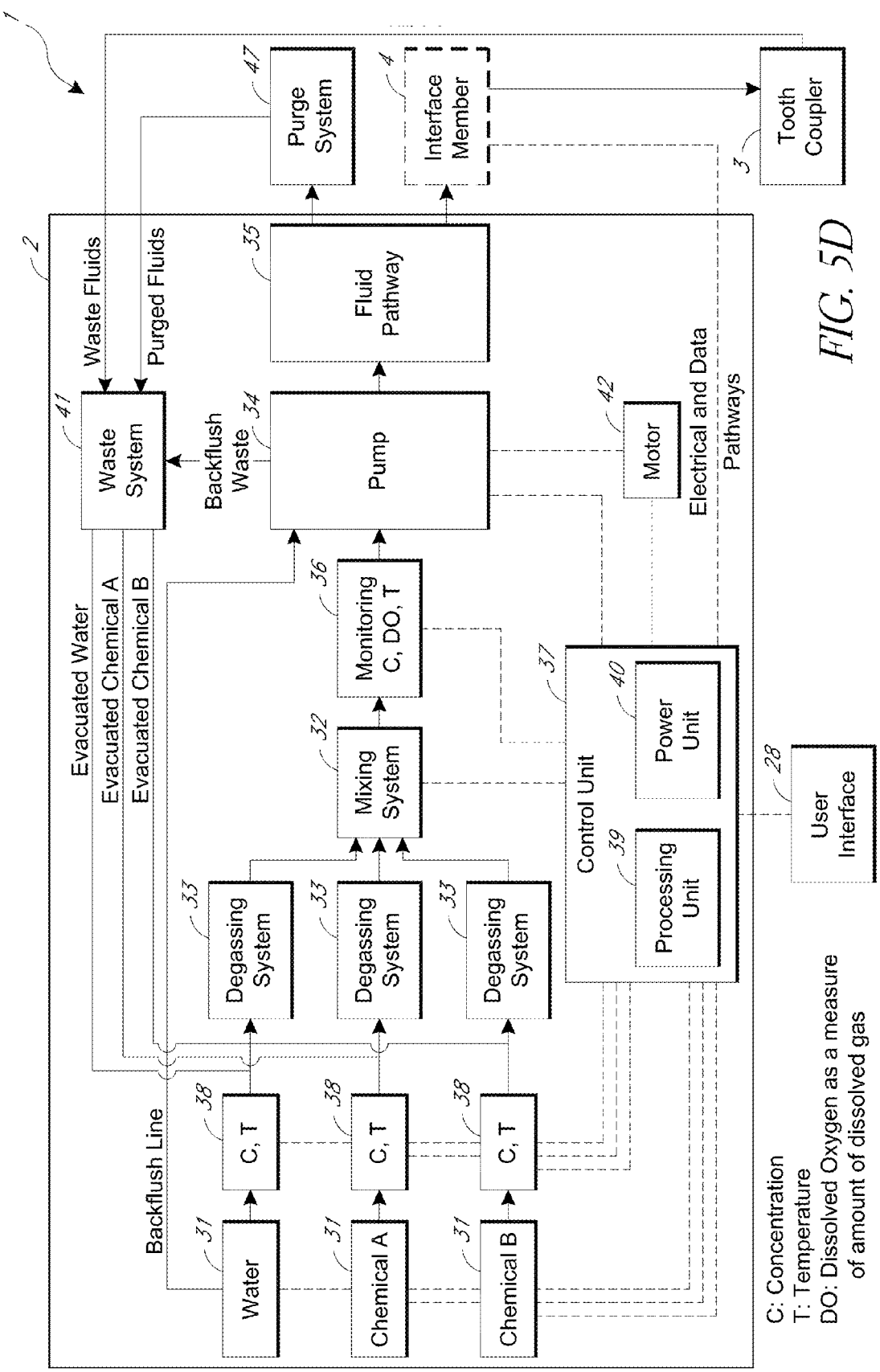
FIG. 5D is a schematic system diagram of a system, according to another embodiment.

FIG. 5D is a schematic system diagram of a system 1, according to another embodiment. As with the embodiment of FIGS. 5A-5C, the console 2 can include fluid reservoirs 31, monitoring sensors 38, a degassing system 33 associated with each fluid line, a mixing system 32, a monitoring apparatus 36, a pump 34, a motor 42 for driving the pump 34, a waste system 41, a fluid pathway 35, an interface member 4 configured to couple to a tooth coupler 3, a user interface 28, and a control unit 37. As shown in FIG. 5D, the tooth coupler 3 can be in fluid communication with the waste system 41, which can comprise a waste reservoir. For example, as explained herein, a vacuum pump can act to suction waste fluids from the tooth 10 by way of a suction port. A waste line can convey the waste fluids from the tooth 10 to the waste reservoir of the waste system 41.

In addition, in the embodiment of FIG. 5D, a purge system 47 can be provided between upstream of the interface member 4 and/or the tooth coupler 3. For example, the purge system 47 can be disposed downstream of and fluidly communicate with the fluid pathway 35. In other arrangements, the purge system 47 can be disposed between the pump 34 and fluid pathway 35. The purge system 47 can be activated by the clinician using the user interface 28 before a treatment procedure and/or for general maintenance. The purge system 47 can be configured to operate at low pressures, e.g. at pressures lower than that output from the pump 34. The purge system 47 can be activated to clean out the system 1 before a treatment procedure. For example, water can be flushed at low pressures through the system 1 before a treatment procedure to remove residual fluids and/or particulates that may have built up from prior procedures. In some embodiments, the purge system 47 can be activated to flush other fluids (such as EDTA, bleach, or any other suitable chemical) through the system 1 at relatively low pressures to ensure that those fluids' flow paths are functioning correctly and/or are unobstructed. The purging fluids can pass through the system components (for example, through the degassing system 33, mixing system 32, monitoring apparatus 36, pump 34, fluid pathway 35, etc.) and can be conveyed by an evacuation system to the waste system 41.

In some embodiments, the water reservoir 31 can also be used to supply a backflush line to the pump 34. It can be advantageous in some embodiments to clear the pump 34 of fluids and/or other materials after prior treatments or runs. Accordingly, water can be supplied by way of the backflush line to the pump 34. The water can pass through the pump 34 and substantially flush the pump 34 of undesirable materials. A backflush waste line can convey the flushed water and waste materials from the pump to the waste reservoir of the waste system 41. To supply water to the pump 34, a suitable valve may be used. For example, in some embodiments, a solenoid valve, such as Model EW-01540-01, manufactured by Cole-Parmer of Vernon Hills, Ill., may be used.

In addition, each fluid line associated with the fluid reservoirs 31 can be in fluid communication with an evacuation line upstream of the respective degassing system 33. For example, a bypass valve can be controllably actuated to pass the respective fluid (e.g., water, EDTA, bleach, etc.) through to the degasser 33 or to the waste system 41 along the evacuation line. The bypass valve can be any suitable valve, such as, e.g., Model 080T2-S2038, manufactured by Bio-Chem Fluidics Inc., of Boonton, N.J. Each fluid evacuation line can convey a respective fluid (e.g., water, Chemical A, Chemical B, etc.) to the waste system 41.

1. Fluid Reservoirs

The fluid reservoirs 31 shown in FIGS. 5A-5D can be any suitable type of reservoir or container and can contain any suitable type of treatment fluid used in the system's treatment procedures. For example, the reservoirs 31 may comprise plastic bins or containers, such as high-density polyethylene (HDPE). In various embodiments, plastic Nalgene™ bottles manufactured by Cole-Parmer, of Vernon Hills, Ill., may be used. Various sizes (such as 250 mL, 500 mL, 2 L, etc.) may be suitable. In other embodiments, the reservoirs 31 may comprise glass, a plastic bag (e.g., an IV bag), or any other suitable material. The reservoirs 31 may comprise any material that is chemically resistant to the treatment fluids stored in the reservoirs 31 such that the reservoirs 31 do not chemically degrade. The reservoirs 31 may, in some arrangements, be disposed in a drawer or other compartment that is slidably removed relative to the console 2. The reservoirs 31 may be designed to have a volume sufficient for treatment of at least one patient, e.g., for at least one treatment procedure. In other embodiments, the reservoirs 31 may have a volume sufficient to treat multiple patients. A liquid level sensor may also be provided to measure and/or monitor the volume of fluid in each container 31. For example, the liquid level sensor can comprise a capacitive sensor. In some embodiments, for example, a capacitive sensor manufactured by Sensortechnics™, a part of First Sensor AG, of Berlin, Germany (model no. CLW025F15N), may be used. Any suitable type of level sensor can be used, such as an optical sensor, a hydrostatic level sensor, etc. A quick connect coupler may be provided to couple the reservoirs 31 to outlet tubing. In some embodiments, the reservoirs 31 may be disposable such that the clinician can dispose of the reservoirs 31 after each treatment. In other arrangements, the reservoirs 31 may be re-usable for a number of treatments. In some embodiments, a valve, such as a duck-bill valve, can be provided so as to allow air in the container 31 to prevent a vacuum from forming in the container 31.

Any suitable number of reservoirs 31 may be disposed in the console 2. As shown in FIGS. 5A-5C, for example, three reservoirs 31 may be used. One reservoir 31 may contain water (e.g., distilled water, purified water, etc.). Another reservoir 31 may contain a Chemical A. In some embodiments, Chemical A may include a cleaning treatment fluid, such as bleach, for dissociating diseased tissue from the tooth 10. Another reservoir 31 may contain a Chemical B. Chemical B may comprise another cleaning treatment fluid, such as EDTA, for removing calcified deposits and/or a smear layer from the tooth 10. Indeed, any suitable treatment fluid may be stored in the reservoirs 31, including, e.g., bleach, EDTA, water, a medical-grade saline solution, an antiseptic or antibiotic solution (e.g., sodium hypochlorite), a solution with chemicals or medications, medicaments, surfactants, nanoparticles, etc.

In some embodiments, as explained above, the system 1 can be configured for obturation and/or restoration procedures. In such embodiments, the reservoirs 31 can contain a suitable obturation and/or restoration material. For example, the reservoirs 31 may contain a root canal filling resin, a gutta percha-based material, a calcium hydroxide-based material, a dental cement material, a dental cement comprising zinc oxide, a filing material comprising particles responsive to a non-contacting force field, a filling material comprising nanoparticles, a flowable filling material, a syringable filling material, a liner, a sealer, a cement, a paste, and a gel. The obturation material may be disposed in the container 31 in a flowable state, which may be hardened to a solid or semisolid state.

The fluids in the containers 31 may be in fluid communication with the other components of the console 2 by way of tubes coupled to outlets of the containers 31. Valves may be provided downstream of the containers to selectively open and close fluid pathways between the containers 31 and the remainder of the system. The valves may be controllably actuated using the control unit 37 in some embodiments.

2. Degassing System

As explained herein, it can be advantageous in some treatment procedures to supply a fluid (e.g., a liquid) that is substantially free of dissolved gases. For example, dental cleaning treatments can be enhanced by using treatment fluids that are degassed so that small passageways in or through the tooth are not blocked by bubbles and/or so that cavitation can be enhanced, as explained herein. Accordingly, the degassing system 33 may be configured to remove dissolved gases (such as oxygen) from each treatment fluid to a desired amount.

The degassing system 33 can comprise any suitable degassing apparatus, such as the PermSelect® silicone membrane module (e.g., model PDMSXA-2500) available from MedArray, Inc. (Ann Arbor, Mich.). Other examples of degassing units that can be used in various embodiments include: a Liqui-Cel® MiniModule® Membrane Contactor (e.g., models 1.7×5.5 or 1.7×8.75) available from Membrana—Charlotte (Charlotte, N.C.); and a FiberFlo® hollow fiber cartridge filter (0.03 micron absolute) available from Mar Cor Purification (Skippack, Pa.). The degassing can be done using any of the following degassing techniques or combinations of thereof: heating, helium sparging, vacuum degassing, filtering, freeze-pump-thawing, and sonication. In some embodiments, degassing the fluid can include de-bubbling the fluid to remove any small gas bubbles that form or may be present in the fluid. De-bubbling can be provided by filtering the fluid. In some embodiments, the fluid may not be degassed (e.g., removing gas dissolved at the molecular level), but can be passed through a de-bubbler to remove the small gas bubbles from the fluid.

As explained herein, the degassing system 33 can be provided upstream or downstream of the mixing system 32. In some arrangements, the degassing system 33 is disposed upstream of the mixing system 32, and each treatment fluid may pass through a separate degassing apparatus. One advantage of disposing the degassing system upstream of the mixing system 32 is that solutes may be added after degassing such that the solutes do not pass through (and possibly degrade) the degassing system 33. In some arrangements, the degassing system 33 may be configured to be chemically compatible with the chemicals used in the treatment solutions. The degassing system 33 can be disposed downstream of the mixing system 32 such that the mixed fluid is degassed in a single degasser. In still other embodiments, the degassing system 33 and the mixing system 32 may be combined into a single unit that both mixes and degasses the treatment fluid.

In some embodiments, the degassed fluid has a dissolved gas content that is reduced to approximately 10%-40% of its "normal" amount as delivered from a source of fluid (e.g., before degassing). In other embodiments, the dissolved gas content of the degassed fluid can be reduced to approximately 5%-50% or 1%-70% of the normal gas content of the fluid. In some treatments, the dissolved gas content can be less than about 70%, less than about 50%, less than about 40%, less than about 30%, less than about 20%, less than about 10%, less than about 5%, or less than about 1% of the normal gas amount. In some implementations, it may be desired that the fluid entering the tooth coupler 3 be degassed to a certain degree (e.g., about 40% of normal dissolved gas amount in one example). In some such implementations, the degassing system 33 may "over-degas" the solvent so that the solvent's dissolved gas content is below the desired degree (e.g., about 35% in this example) so that when solute(s) are added by the mixing system 32, the resulting fluid (solvent plus solute) is degassed to less than the desired degree (e.g., adding un-degassed antiseptic solution may raise the dissolved gas content to 38% in this example).

3. Mixing System

In different treatment procedures, it may be desirable to mix the treatment fluids supplied by the reservoirs 31 to a desired concentration, e.g., drawing and mixing a proper volume ratio of treatment chemicals. For example, in some cleaning treatments, it may be desirable to mix bleach or EDTA with water to a desired concentration, to enhance the cleaning effects for the particular procedure, whether a root canal cleaning procedure, a caries removal procedure, or a hygiene procedure (e.g., removing undesirable dental deposits such as plaque, calculus, etc.). The mixing system may adjust a multiple-way valve that is electronically or mechanically controlled to draw the correct amount of chemicals to prepare the prescribed concentration of the treatment solution. For example, different amounts of different chemicals can be mixed by activating a valve to selectively alternate between the different chemicals. As one example, if the system 1 is to mix water and Chemical A by a particular amount, then the valve can be activated to alternate selection of water and Chemical A. Accordingly, if the desired mixture is to include more Chemical A than water by a particular concentration, then the valve can be activated longer for Chemical A than for the water by a particular amount. For example, a flow selection valve, such as Model No. 080T3-S2039 manufactured by Bio-Chem Fluidics Inc., of Boonton, N.J., may be used in some embodiments.

The mixing system may include a fluid flow control system. The fluid flow control system may be passive in some arrangements, and the mixing ratio may be adjusted by using proportional valves. The proportional valve may be a multiple inlet port solenoid valve. The proportional flow may be achieved by, for example, adjusting cross-sections or pulsating valve openings. The fluid flow control system may be active and the mixing ratio may be adjusted using positive displacement metering pumps. The active configuration may include a holding chamber to adjust for the overall system flow rate.

Accordingly, the mixing system 32 can be configured to mix the appropriate volumes of each fluid together in a mixing chamber. The control unit 37 can be programmed to operate the mixing system 32 such that the inputs to the mixing system 32 comprise the appropriate amounts or volumes of each treatment fluid. The control unit 37 can also be programmed to selectively output the mixed fluid to the downstream components.

4. Pump

The pump 34 can be any suitable high-pressure pump that is configured to pressurize the treatment fluid to a desired pressure. In some embodiments, the pump 34 can be driven by the motor 42 or other suitable mechanism. For example, one or more pistons can be activated by the motor 42 to generate positive pressure flow through the pump 34. The pump 34 may be a constant pressure or a constant flow rate pump in various arrangements. The pump 34 can drive the pressurized fluid to the interface member 4 by way of the fluid pathway 35. A pressure sensor may be used to sense the pressure of the liquid and communicate pressure information to the control unit 37. The control unit 37 can use the pressure information to make adjustments to the motor 42 and/or the pump 34 to provide a target pressure for the fluid delivered to the interface 4 and tooth coupler 3. For example, in embodiments in which the pump 34 comprises a piston pump, the control unit 37 may signal the motor 42 to drive the piston more rapidly or more slowly, depending on the pressure information from the pressure sensor. The pump 34 may be actuated continuously or cyclically in various arrangements. The pump 34 can be any suitable type of pump, including Model 170240 manufactured by Scientific Systems, Inc., of State College, Pa. The motor 42 can be any suitable type of motor.

The pump 34 can deliver pressurized fluid to the interface member 4 and tooth coupler 3 sufficient to create a fluid jet, in some embodiments. For example, in some embodiments utilizing a fluid jet, the pressure of the liquid that can be delivered to the interface member 4 and/or tooth coupler 3 can be adjusted within a range from about 500 psi to about 50,000 psi. In certain embodiments, it has been found that a pressure range from about 2,000 psi to about 15,000 psi produces jets that are particularly effective for cleaning treatments. In some embodiments, the pressure can be between about 8,000 psi and about 11,000 psi, for example, about 9,200 psi in one arrangement. In another arrangement, the pressure can be about 10,000 psi.

5. Fluid Pathway

The fluid pathway 35 can convey the pressurized fluid from the pump 34 to the interface member 4. The fluid pathway 35 can be configured to accommodate the high-pressure fluid delivered by the pump 34 and the various chemistries of the treatment fluids passing through the pathway 35. The fluid pathway 35 can also be flexible such that the clinician can manipulate the fluid pathway 35 before, during, or after treatment. For example, in some embodiments, the fluid pathway 35 can comprise one or more tubes disposed between the pump 34 and the interface member 4. The tubes can comprise any suitable high-pressure, chemical-resistant material, such as a polymer or a chemical-resistant metal such as titanium.

6. Waste System

The console 2 can also include a waste system 41 configured to convey waste fluids or materials from the tooth coupler 3 back to a waste reservoir. The waste reservoir may be positioned with or near the reservoirs 31 discussed above, or it may be positioned separately in the console 2. For example, during some dental treatment procedures, such as cleaning procedures, the tooth coupler 3 (such as a handpiece) may include a suction port and/or vents that are configured to transport waste fluids or particles from the treatment tooth 10 back to the console 2 to the waste system 41. The waste system 41 can couple to the tooth coupler 3 by way of one or more waste lines. The waste lines may comprise tubes that extend from the tooth coupler 3 back to the console 2. Although the waste system 41 is shown as coupling to the interface member 4 in FIG. 5C, in some embodiments, the waste system 41 may have a separate interface or connector that couples to the tooth coupler 3. For example, the waste line or tubes may be threaded, snapped, or otherwise engaged with the tooth coupler 3. In some embodiments, the waste lines are disposed on or through the interface member 4 to connect to the tooth coupler 3. Additional details of the waste system 41 are discussed below with respect to the evacuation system 75 shown in FIG. 5E.

A vacuum pump can be provided to provide suction between the tooth coupler 3 and the console 2 by way of the waste lines. One example of a suitable vacuum pump is Model DBM30B-201 manufactured by Brenner-Fiedler & Associates, Inc., of Riverside, Calif. For example, the suction port may be similar to evacuation units found in dental offices. For example, some dental evacuation units are designed to operate at about −6 in-Hg to about −8 in-Hg and have an airflow rate of about 7 standard cubic feet per minute (SCFM) per chairside high-volume inlet. Independent vacuum systems can be used. In one embodiment, the operating pressure of the evacuation unit is about −4 to −10 in-Hg. In other embodiments, the operating pressure is in a range of about −0.1 to −5 in-Hg or −5 to −10 in-Hg or −10 to −20 in-Hg, or other values. In some embodiments, the flow provided by the evacuation unit can be pulsating. In another embodiment, the evacuation unit flow can be intermittent. In one embodiment, the evacuation unit flow can be substantially uniform. The air flow rate of the evacuation unit can be 5 to 9 SCFM or 2 to 13 SCFM or 0.1 to 7 SCFM or 7 to 15 SCFM or 15 to 30 SCFM or 30 to 50 SCFM, or other values.

7. Console Monitoring System

The console monitoring systems disclosed herein can include monitoring sensors 38 and/or the monitoring apparatus 36 illustrated in FIG. 5C. For example, the monitoring sensors 38 may be disposed downstream of the fluid reservoirs 31 before the mixing system 32 and degassing system 33. The monitoring sensors 38 can measure various properties of the treatment fluids before mixing and degassing to ensure that the fluids are adequately mixed and/or degassed. For example, concentration sensors can be provided to measure the concentration of each fluid. The control unit 37 can utilize information about the concentration of each treatment fluid to determine how much of each fluid to add in the mixing system 32 to achieve the desired mixtures.

The concentration sensors can be any suitable type of sensor capable of measuring the concentration of the fluids. The concentration sensor may directly measure concentration in some embodiments. The concentration sensor may also indirectly measure concentration by measuring pH, oxidation reduction potential (ORP), optical density, electrical conductivity, etc. A concentration sensor may check the prepared treatment fluid concentration and send feedback to the mixing valves if adjustments are desired to bring the prepared treatment solutions concentration to the prescribed value. Some concentration sensors may measure the conductivity of the solution to determine the concentration. One example of such a concentration sensor is the Digital C/R Sen, ISM 3/4 NPT 0.1 C Ti 2" manufactured by Mettler-Toledo, of Greifensee, Switzerland.

In addition, the sensors 38 may comprise temperature sensors to measure the temperature of the solution. It may be desirable to maintain the treatment fluid at a temperature that is not too hot or not too cold for the mixing and degassing procedures. Accordingly, temperature sensors (e.g., thermocouples or any other suitable temperature sensor) may be disposed in contact or proximate the fluid along fluid lines leading from the reservoirs 31 to the mixing and degassing systems. The control unit 37 can receive the temperature data from the temperature sensors to monitor the temperature at various locations in the console 2.

Other sensors, such as pressure sensors, dissolved oxygen sensors, etc. may be provided downstream of the fluid reservoirs 31 before the mixing and degassing systems.

The monitoring apparatus 36 disposed downstream the degassing system 33 and mixing system 32 in FIG. 5C may be provided to measure various properties of the treatment fluid after mixing and degassing. The monitoring apparatus 36 may include any suitable sensors, such as concentration sensors, temperature sensors, dissolved oxygen sensors, pressure sensors, etc. The concentration sensors may be similar to those described above and can measure the resulting concentration of the fluid after mixing. Similarly, the temperature sensors can be configured to measure the temperature of the mixed, degassed fluid before delivery to the tooth coupler 3 and patient. It can be important to ensure that the temperature is not too hot and not too cold so as to avoid harming the patient and/or tooth 10.

In addition, a dissolved oxygen (DO) sensor can be provided to measure the amount of dissolved gases remaining in the mixed, degassed fluid, which may be representative of the amount of air dissolved in the liquid. The dissolved oxygen sensor may check the level of dissolved oxygen in the treatment fluid, and, if the dissolved oxygen level is not sufficient, the system may be disabled in some arrangements, or the control unit 37 can instruct the console 2 to engage in further degassing. Any suitable dissolved oxygen sensor can be used, including, e.g., optical sensors. One example of such a dissolved oxygen sensor is the Model EOM-O2-mini-90-PHB1.511-v1 manufactured by PreSens Precision Sensing GmbH of Regensburg, Germany.

In addition, one or more pressure sensors may be disposed upstream or downstream of the pump 34 to measure the pressure of liquid output from the pump 34, as explained above. Furthermore, as above, the control unit 37 can receive and process the data output from the monitoring apparatus 36, including data from sensors, such as concentration sensors, temperature sensors, pressure sensors, dissolved oxygen sensors, etc. The feedback received from the control unit 37 can be used to adjust the various processes performed in the console until the desired concentrations, temperatures, pressures, and amounts of dissolved oxygen are suitable for a particular treatment procedure.

8. User Interface

The user interface 28 can be configured to receive instructions from the clinician and/or to display data to the clinician regarding a treatment procedure and/or a status of the system. The user interface 28 can include a display configured to display data regarding a procedure to the clinician. The display may comprise a touch-screen display, in which the clinician can also send instructions to the system 1 by way of the display. In other arrangements, the user interface 28 can include a separate keyboard, keypad, joy stick, etc. to enable the clinician to send instructions to the console 2 and system 1. In some embodiments, the user interface 28 may include controls for a dental practitioner to operate the liquid jet apparatus. For example, the controls can include a foot switch to actuate or deactuate the jet (e.g., which may be coupled to the tooth coupler 3).

The clinician can interact with the user interface 28 to select a treatment procedure, e.g., to select whether a particular procedure is a cleaning procedure (e.g., of root canals, caries, undesirable deposits, etc.), an obturation procedure, a restoration procedure, etc. Once the procedure type is selected, the clinician can activate the procedure and can monitor the status of the procedure on the display. For example, the clinician may set a desired pressure for the pump, or other desired parameters for the jet. The clinician can set when the procedure is to begin and end by way of the interface 28. Furthermore, the clinician can use the user interface 28 to communicate various data about the procedure to other entities, as explained in more detail herein with respect to the various communications aspects of the system 1. In some arrangements, the clinician can interact with the user interface 28 to access patient medical records or other data about the patient. In some embodiments, the display of the user interface 28 can display images or video of the progress of a procedure, e.g., how much of a root canal has been cleaned, filled, etc. The clinician can interact with the user interface 28 in some aspects to determine how much supply of various materials is on hand, and can access patient scheduling systems. The user interface 28 may also have emergency systems by which the clinician can shut down the system 1 in case of emergency. In some arrangements, the system 1 may automatically contact emergency responders, or the user interface 28 can include a button or other interface by which the clinician can actively seek emergency responders.

9. Control Unit

The control unit 37 can receive data from and send instructions to the various components of the console 2, the interface member 4, and the tooth coupler 3. For example, as shown in FIG. 5C, the control unit 37 can be in electrical and/or data communication with the fluid reservoirs 31, the monitoring sensors 38 and apparatus 36, the mixing system 32, the degassing system 33, the pump 34, the interface member 4, the user interface 28, and any other suitable components of the system 1. The control unit 37 may comprise a microprocessor, a special or general purpose computer, a floating point gate array, and/or a programmable logic device. Programmable instructions for carrying out the various processes disclosed herein may be stored on any suitable computer readable medium, such as a non-transitory computer readable medium (e.g., a RAM, ROM, or any other suitable memory device). In some embodiments, the control unit 37 may include a power unit 40 configured to supply electrical power to the various system components.

The control unit 37 can include a processing unit 39 configured to receive, send, and/or process data regarding the system components. For example, the processing unit 39 can receive signals from the sensors 38 and monitoring apparatus 36, and can process and store those signals for later use. The processing unit 39 can send instructions to valves that control the flow of fluid from the reservoirs 31 to selectively actuate the valves in a desired manner, e.g., to selectively cause fluid to flow from the reservoirs 31. The processing unit 39 can similarly control the operation of the mixing system 32 to ensure that the proper proportions of fluids are mixed together. The processing unit 39 can control the operation of the degassing system 33 to accurately and precisely degas the treatment fluids.

The processing unit 39 can send and receive instructions from the pump 34 (or a motor coupled to the pump 34). As explained above, the processing unit 39 can process the pressure of the fluid at the output of the pump 34, and can send instructions to the motor and pump 34 to adjust the pressure output at the pump 34 to the desired level. As explained above, various control algorithms (such as PID control) may be implemented to achieve the desired pump output. In some arrangements, the console 2 and processing unit 39 can be programmed to deliver the treatment fluid at prescribed pressure oscillations. For example, the processing unit 39 can be programmed to control the shear thinning properties of the fluid and/or to produce the desired pressure waves for propagating at the treatment region of the tooth 10. The pressure oscillations may be generated by the delivery mechanism (e.g., by way of the pump 34 and the control unit 37), or by way of a secondary mechanism or process (e.g., ultrasonic agitation), or a combination of both.

The processing unit 39 can also communicate with the user interface 28 to receive inputs from the clinician and to send data about the procedure to be displayed to the clinician. The processing unit 39 can communicate with the tooth coupler 3 and the working end of the system by passing through or along the interface member 4 in some embodiments. In other embodiments, the electrical and data pathways (which may include optical fibers or wireless data transmission devices) may connect to the tooth coupler 3 separate from the interface member 4.

As explained in more detail herein, the control unit 37 can also communicate with external entities regarding the status of a procedure or about the history of procedures performed on the system 1. The control unit 37 can be configured to access patient medical records and/or patient scheduling systems. The control unit 37 can also monitor office inventory, including the amounts of fluids and other materials used for procedures, as explained herein. As explained herein, the control unit 37 can therefore include any suitable communications modules to enable the system 1 to communicate with external entities (such as suppliers, emergency responders, patients, etc.).

10. Evacuation System

Figure 5E:
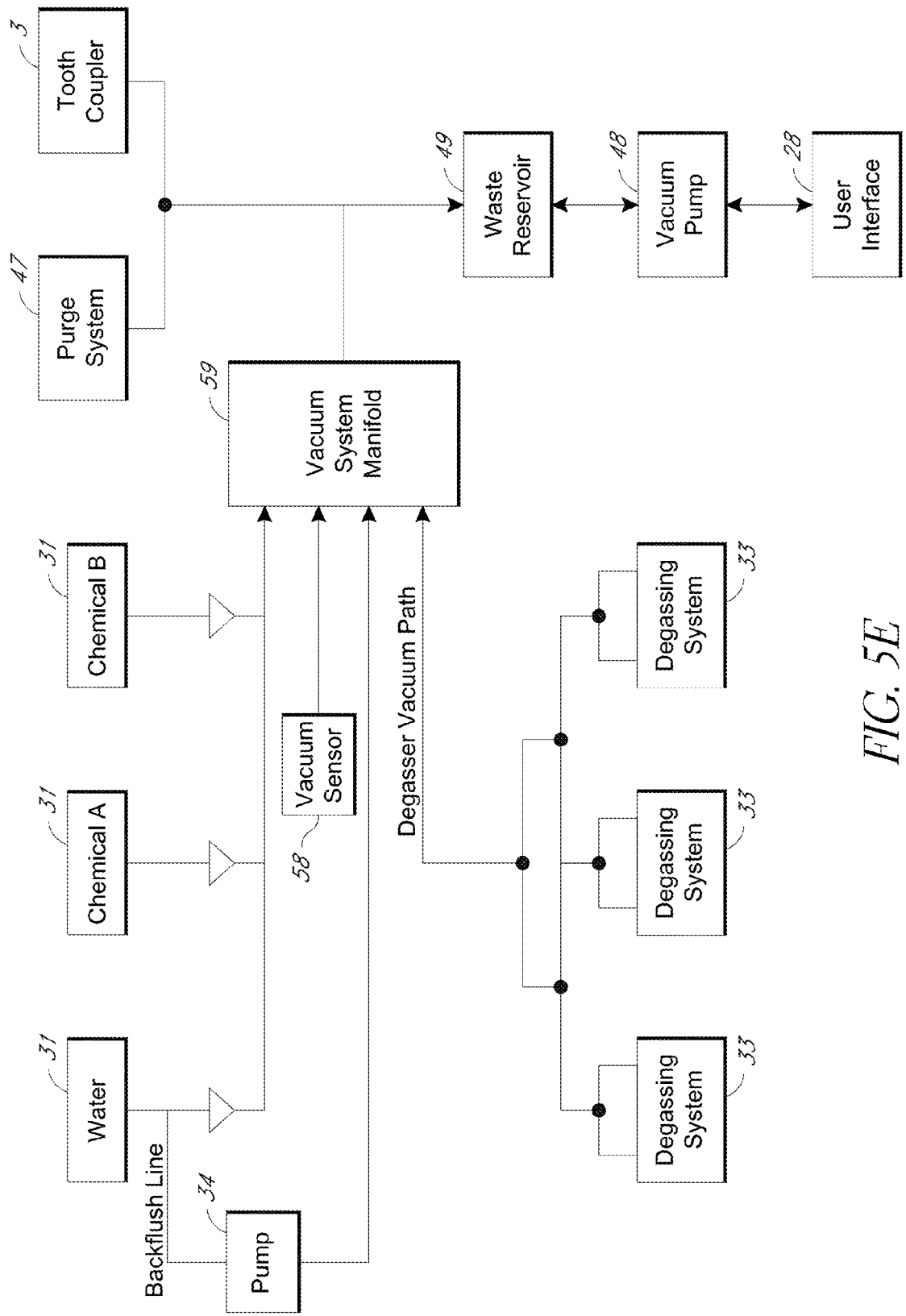
FIG. 5E is a schematic system diagram of an evacuation system configured to apply vacuum pressure to various components of the system.

FIG. 5E is a schematic system diagram of an evacuation system 57 configured to apply a vacuum pressure to various components of the system 1. The user interface 28 can communicate with a vacuum pump 48, which can be any suitable vacuum pump, such as the Model DBM30B-201 manufactured by Brenner-Fiedler & Associates, Inc., of Riverside, Calif. The vacuum pump 48 can be configured to apply a vacuum or negative pressure throughout the evacuation system 57. In particular, the vacuum pump 48 can draw fluids from the system 1 to a waste reservoir 49, which can be any suitable container.

As explained above, the tooth coupler 3 can include a suction port that is in fluid communication with the waste reservoir 49 and vacuum pump 48. When the vacuum pump 48 is activated, waste fluids and/or materials can be drawn out through the suction port in the tooth coupler 3 and can be conveyed to the waste reservoir 49. Similarly, during a purging operation, the waste line (which may be the same waste line coupled to the tooth coupler 3 in some arrangements) may be coupled to the purge system 47. Purge fluids passing through the purge system 47 can likewise be drawn to the waste reservoir 49.

The vacuum pump 48 can apply negative pressure to other system components by way of a vacuum system manifold 59. Although the purge system 47 and tooth coupler 3 are not illustrated as being inputs to the manifold 59, in some embodiments, the purge system 47 and/or the tooth coupler 3 may pass through the manifold 59. The manifold 59 can include several inputs. For example, the evacuation lines passing between the reservoirs 31 of treatment fluids (e.g., water, Chemical A, Chemical B, etc.) may convey the respective fluids to the manifold 59. A vacuum sensor 58 can communicate with the manifold 59 to measure the pressure provided by the vacuum pump 48 and manifold 59. The control unit 37 can monitor and/or activate the manifold to ensure that an adequate vacuum is provided.

Further, as explained above, the backflush line can supply water from the reservoir 31 to the pump 34. After passing through the pump 34, the flushed fluid can enter the manifold 59. In addition, the vacuum system manifold 59 can apply vacuum pressures to the degassing system(s) 33. As explained herein, in some embodiments, the degassing systems 33 may be activated by applying a vacuum across the inlet and outlets to draw dissolved gases out through a semipermeable membrane. The vacuum provided by the manifold 59 can apply suction across the degasser inlets and outlets to activate the degassing systems 33 and to degas the respective treatment fluids.

B. Dental Office Management Systems and Networks

The system 1 disclosed herein can advantageously act as a core component of the dental office. The console 2 can act as a gateway to the system 1 by way of the user interface 28 illustrated herein, or by way of remote access using wireless or wired network communications. Indeed, in some embodiments, the clinician can access and/or manage many of the typical day-to-day aspects of the dental office, including treatment procedures, dental devices and apparatus, diagnostic, evaluation and imaging procedures and systems, patient health and billing records, scheduling systems, inventory systems, emergency systems, and various other systems that are used by dentists, endodontists, and other clinicians.

Figure 5F:
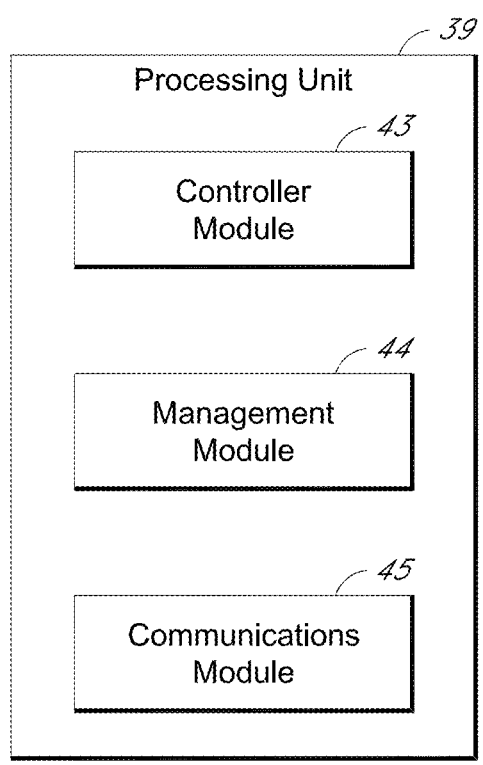
FIG. 5F is a schematic diagram of a processing unit, according to some embodiments.

FIG. 5F is a schematic diagram of the processing unit 39, according to some embodiments. The processing unit 39 can include or communicate with various software modules that, when executed by a processor, perform the various methods and procedures disclosed herein. The software modules can be stored on a non-transitory computer readable medium, such as a memory device (e.g., RAM, ROM, flash, or any other suitable memory known to those of skill in the art). For example, the processing unit can comprise a controller module 43. The controller module 43 may be configured or programmed to control the operation of the treatment procedure components in the system 1. As explained above with respect to FIG. 5C, for example, the controller module 43 may be configured to control the operation of at least one of the reservoirs 31, the monitoring sensors 38 and apparatus 36, the mixing system 32, the degassing system 33, the motor 42, the pump 34, valves, various components of the tooth coupler 3, other sensors (e.g., pressure sensors, etc.), and other mechanical, electrical, or fluidic components. The controller module 43 may also be configured to receive data from and send instructions to these components to monitor and manage the operation of the system 1. For example, the controller module 43 may be programmed to receive and process instructions input to the user interface 28 by the clinician, and may be programmed to display or notify the clinician about the status of the system 1 or procedures by way of the user interface 28. The controller module 43 may be programmed to communicate with the manufacturer, the distributor and/or the service provider, and to report status of the system and receive updates, e.g. software updates for the console 2.

The processing unit 39 can also include a management module 44 configured to store, organize, and/or manage data about the system 1 and about the procedures performed by the system 1. For example, the management module 44 can be programmed to monitor the number and type of procedures performed by the system 1, and can log the history of the system 1 (e.g., the date, time and length of the procedure, the clinician who performed the procedure, etc.). The management module 44 can associate each procedure with a particular patient and can store events recorded by the system 1 and/or by the clinician (by way of the user interface 28). For example, if a particular event occurs during a cleaning procedure (e.g., the patient requires a second visit due to uncontrollable pain or drainage), then the clinician may record such an event using the user interface 28, or various sensors of the system 1 may automatically store such events to the system 1. As explained herein, the system 1 can include various verification devices to ensure that the tooth coupler 3 (e.g., a handpiece) is a valid, sterile handpiece. The management module 44 can store such verification data for the system 1.

Moreover, the management module 44 can track the amount of treatment materials and disposable devices that are associated with the system 1. For example, the management module 44 can track each procedure and can receive information from the system sensors to determine how much of each type of treatment fluid remains in the fluid reservoirs 31. The management module may make the determination based on the number of treatment procedures that drew from the reservoirs 31, or the fluid level sensors disposed on or near the reservoirs may send a signal to the control unit 37 indicating that additional fluid is needed at the system 1. The control unit 37 and/or management module 44 can send a signal to the clinician (e.g., by way of the user interface 28) that additional fluids should be added to the system 1 and/or console 2. Furthermore, the management module 44 may indicate that additional tooth couplers 3 (e.g., handpieces) should be ordered based on the number of procedures performed by the system 1 and the initial number of couplers 3 supplied to the system 1. Likewise, the management module can track the amount of obturation and/or restoration materials available and can notify the clinician that additional materials should be supplied.

The management module 44 may also track the number of procedures that each system component has been active. For example, the management module 44 can track how many procedures have been performed by the mixing system 32, the degassing system 33, the monitoring sensors or apparatus, the pump 34, the motor 42, the fluid pathway 35, the interface 4, etc. If the number of procedures exceeds desired safety levels for the particular component, then the management module 44 can send a signal to the clinician (e.g., by way of the user interface 28) that replacement components should be installed. Furthermore, if one of the sensors signals that a particular component is damaged, then the management module 44 can also notify the clinician that the damaged component should be replaced or fixed. The management module 44 can also be configured to notify the manufacturer, distributor and/or the service provider and can report the matter requesting maintenance or repair. The management module 44 can also determine when the waste system 41 is full of waste fluids and particles, and can signal the clinician that the waste system 41 should be emptied or replaced.

The processing unit 39 can also include a communications module 45 configured to provide data communication with external systems (e.g., external systems in the dental office, external supplier systems, etc.) and/or external entities (e.g., persons, businesses, or organizations). The communications module 45 can be configured to communicate with the external systems and/or entities by way of any suitable communications system, such as wireless (e.g. 802.11 networking protocols), Bluetooth, wired networks (e.g., fiber optic lines), mobile telephone networks (e.g., 3G, 4G, etc.), etc. The communications module 45 can also communicate with other system components, by way of direct wire communications, wireless networking, radio frequency identification (RFID), etc.

Figure 5G:
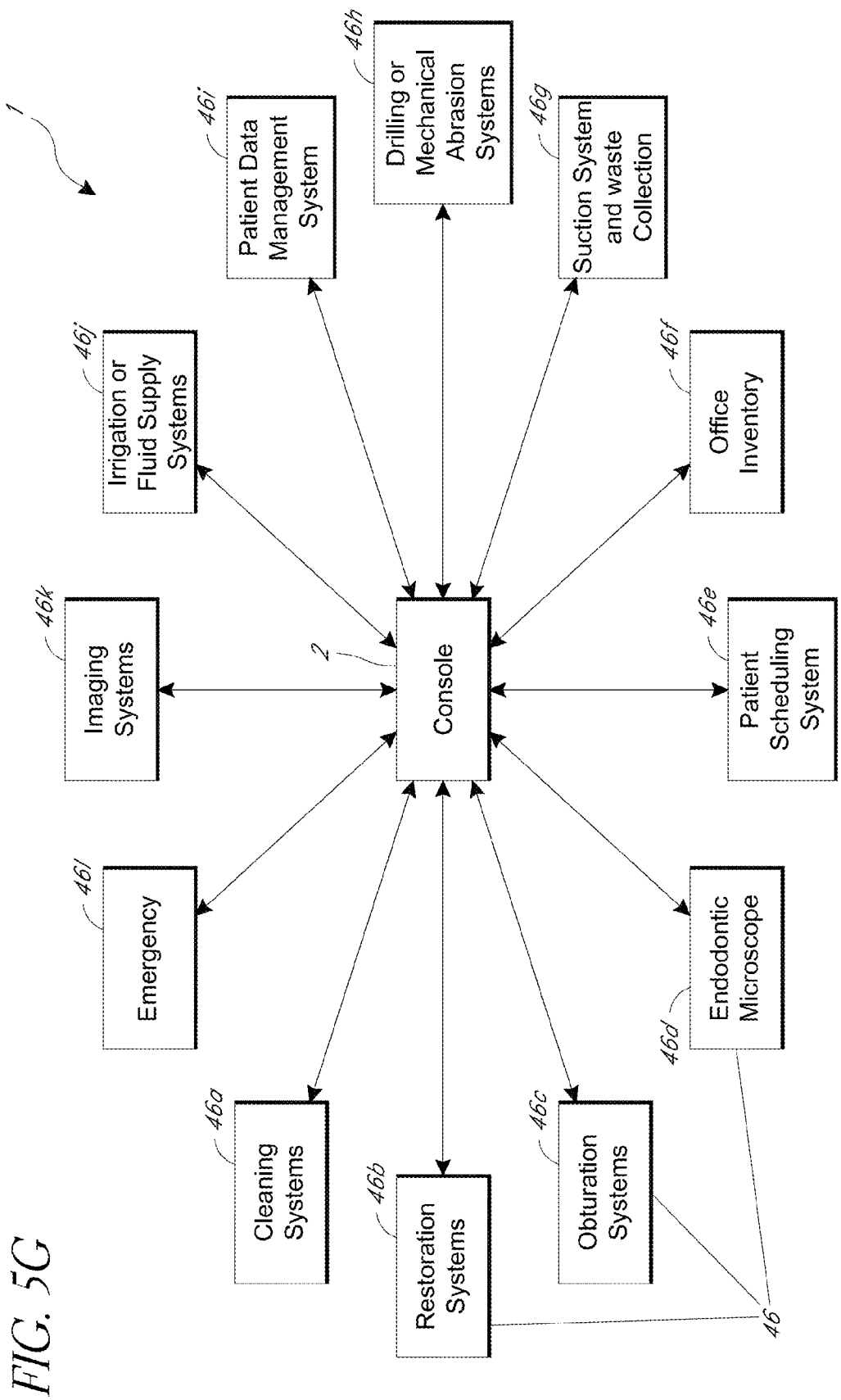
FIG. 5G is a schematic diagram of the system and various network relationships the system may have with external systems.

FIG. 5G is a schematic diagram of the system 1 and various network relationships the system 1 may have with external systems 46. For example, the console 2 (for example, by way of the communications module 45) may communicate with other cleaning systems 46a to initiate a particular cleaning procedure and/or to communicate the status of the procedure performed by the system 1. For example, pre- or post-treatment cleaning may be performed by the external cleaning system 46a. The console 2 can communicate with restoration systems 46b and/or obturation systems 46c to indicate the status of any procedures being performed by the system 1, and can also send instructions for the restoration systems 46b or the obturations systems 46c to initiate their respective procedures. For example, after the system 1 and console 2 complete a cleaning procedure, the console 2 may indicate to the obturation system 46c that the cleaning procedure is complete and may initiate an obturation procedure. The obturation system 46c and the restoration system 46b may be external systems in some embodiments. In other embodiments, the obturation system 46c and the restoration system 46b may be located on or near, or coupled to, the system 1.

The console 2 can communicate with an endodontic microscope 46d in the dental office (which may be integrated with or separate from the console 2) to initiate imaging of a tooth and/or to retrieve microscopic images of the tooth. The system 1 (e.g., the control unit 37) can process the image and display it for the clinician on the user interface 28. Software may analyze the image to automatically detect unhealthy areas of the tooth, the status of a cleaning procedure, and/or can identify areas that may be difficult to treat (e.g., narrow or curved canals).

The console 2 can also communicate with a patient scheduling system 46e. The patient scheduling system 46e may be a component of the clinician's office management systems and can manage the schedule of appointments. The console 2 can retrieve scheduling data from the scheduling system 46e to identify when a patient is scheduled to arrive in some embodiments. The console 2 can also enable the clinician to communicate with the patient at the dental chair about availability for a future appointment. In addition, the console 2 can be configured to send reminders to patients regarding appointments or cancellations (e.g., by e-mail, telephone, etc.). If a particular treatment procedure is taking longer than expected, then the console 2 can also notify the patient scheduling system 46e that the clinician may be late for his or her next appointment.

The console 2 can also communicate with an office inventory system 46f. As explained herein, the management module 44 can track the inventory of materials and system components (both disposable and re-usable). The communications module 45 can be configured to send requests to the office inventory system 46f notifying the system 46f that a particular material (e.g., a treatment fluid, obturation material, etc.) or component (e.g., a handpiece, fluid pathway, etc.) should be replaced. The clinician or the clinician's staff can then order the materials or components that should be replaced. Alternatively, the communications module 45 can be configured to automatically notify the clinician's suppliers that additional materials or components should be shipped to the clinician's office. For example, if the management module 44 determines that additional handpieces should be ordered, then the communications module 45 can communicate with the handpiece manufacturer or supplier requesting additional handpieces.

The console 2 can also communicate with a suction and waste collection system 46g, which may be integrated with or may be separate from the system 1. For example, the console 2 can control the activation of a vacuum pump associated with the suction system to activate and deactivate the suction and removal of waste materials from the treatment site. The console 2 can also track the amount of waste fluid that fills a waste reservoir. When the waste reservoir is filled, the console 2 can indicate that the waste materials should be disposed of.

The console 2 can also communicate with a drilling or mechanical abrasion system 46h. For example, in some treatments, a conventional drill may be used to remove portions of the tooth, e.g., to form an access opening. The console 2 can be in electrical and/or data communication with the drilling system 46h and can instruct the drilling system 46h to activate and deactivate based on the clinician's instructions.

In addition, the console 2 can communicate with a patient data management system 46i. The patient data management system 46i may be a component of the clinician's office management system, or it may be part of the system 1 in some arrangements. The console 2 can receive information about a particular patient, such as a patient's biographical information (e.g., address, phone number, occupation, etc.) and health information (e.g., health problems, past dental procedures, x-rays, etc.). The console 2 can display selected information about the patient to the clinician by way of the user interface 28 in real-time. In addition, the console 2 can send information about a particular treatment procedure to the patient data management system 46i to record information about the treatment in the patient's medical files. For example, the console 2 can store information about the treatment, including any complications or other follow-up treatments (such as restoration procedures), in the patient's medical records. In some arrangements, the clinician can interact with the user interface 28 to make specific notes about the procedure, which can be transmitted to the patient data management system 46i. Advantageously, such automatic recording of treatment information can improve the efficiency of recording patient medical data.

Irrigation or other fluid supply systems 46j can also communicate with the console 2. For example, the console 2 may instruct the irrigation system 46j that water or another treatment solution should be supplied to the tooth 10. The clinician can operate the irrigation system 46j by way of the user interface 28. The irrigation system 46j may be integrated with or separate from the system 1. In addition, imaging systems 46k may communicate with the console 2. For example, the console 2 can communicate with x-ray imaging systems, cone beam computed tomography (CBCT), or other imaging systems to provide real-time imaging data to the clinician, for example, by way of the user interface 28. The clinician can activate the imaging systems 46k by way of the user interface 28, and the desired images can be displayed on the display. The images can also be recorded, associated with the patient, and stored in the patient's medical files by way of the patient data management system 46i.

The console 2 can also communicate with various emergency systems 46l. For example, if an emergency arises (e.g., excessive bleeding or other complications), then the clinician may activate an emergency button or other emergency interface to notify emergency responders of the emergency and to request an ambulance. In some arrangements, sensors in the system 1 may detect an emergency event and can similarly request emergency assistance.

Thus, in various arrangements, the system 1 can track the progression of a procedure and communicate such a progression to any desirable external entity and/or system 1. Furthermore, the system 1 can recognize which type of treatment handpiece is attached to the console 2 (by way of, e.g., the conduits 29). The system 1 can switch to the settings that are required or desired to run that specific treatment. For example, the system 1 may recognize that the handpiece 3A coupled to the console 2 is a molar handpiece for cleaning a root canal. The system 1 can accordingly select a molar root canal procedure. As another example, the system 1 may recognize that the handpiece 3A coupled to the console 2 is a handpiece for treating caries, and can accordingly select the appropriate treatment.

In some embodiments, the console 2 can be incorporated into a dental chair. In such embodiments, the console 2 can be formed with the chair and can provide easy access for the clinician conducting the treatment. In other embodiments, such as those disclosed herein, the console 2 can be a separate, stand-alone unit.

C. Housing for Console

Figure 5H:
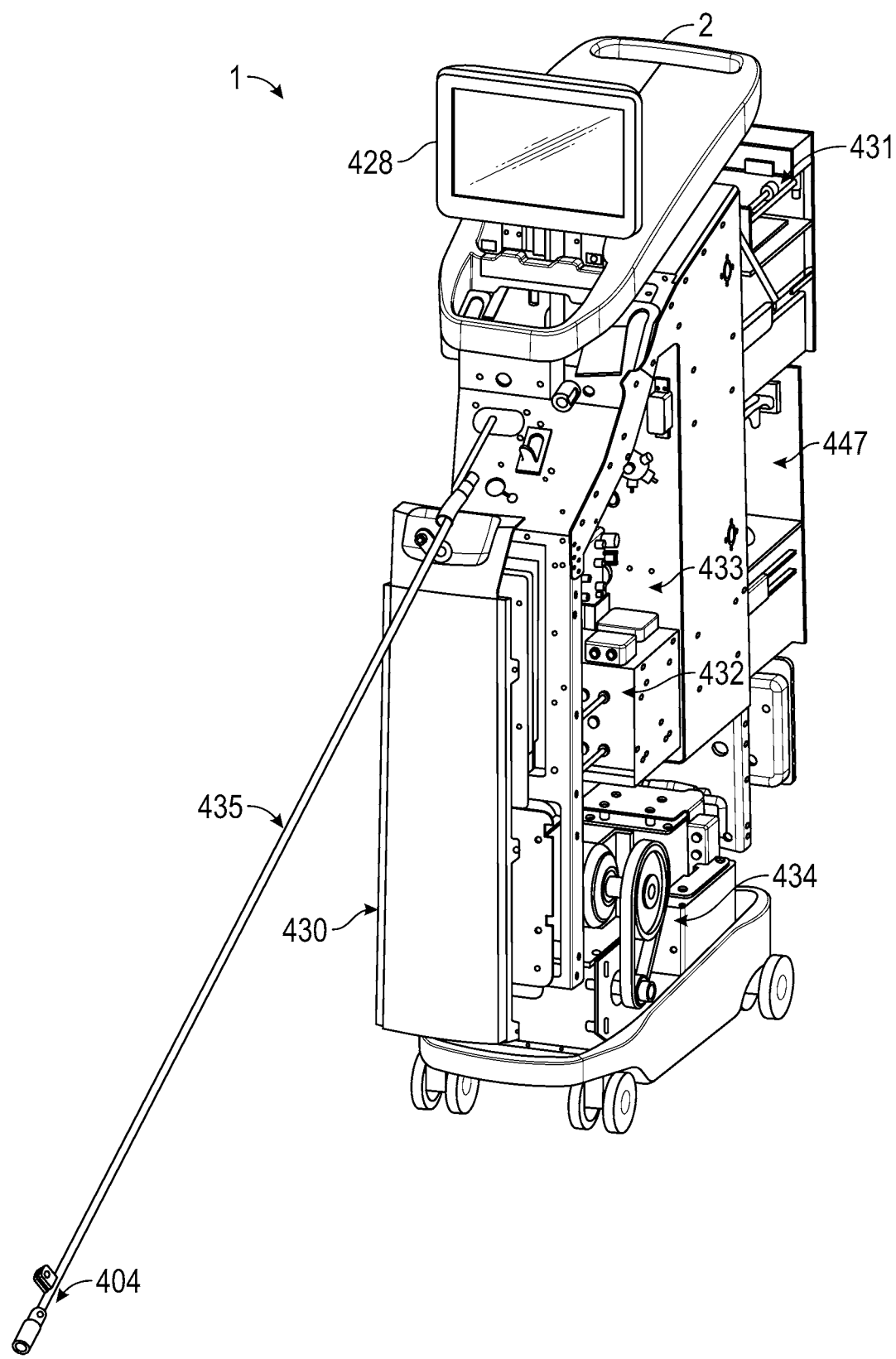
FIG. 5H is a front perspective view of a system having a console comprising a housing, according to one embodiment.
Figure 5I:
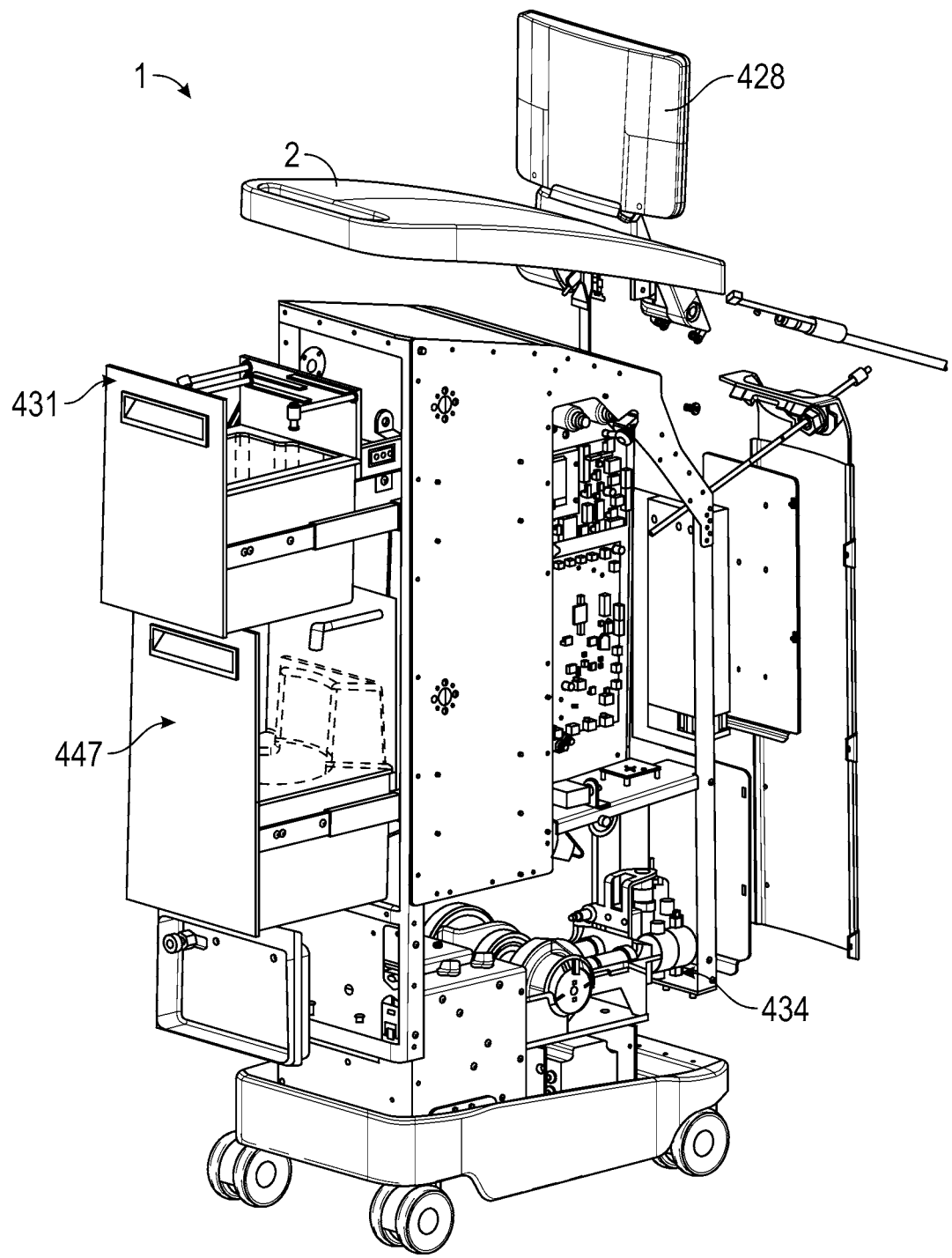
FIG. 5I is a rear perspective view of the system shown in FIG. 5H.

FIG. 5H is a front perspective view of a system 1 having a console 2 comprising a housing 430, according to one embodiment. FIG. 5I is a rear perspective view of the system 1 of FIG. 5H. As explained herein, the system components can be coupled to and/or housed in the housing 430. As above, the console 2 can include a user interface 428. A fluid reservoir drawer 431 can be provided to house the fluid reservoir(s) 31. Similarly, a waste reservoir drawer 447 can be provided to house the waste reservoir 47. The degassing system(s) 33 can be housed in a degassing apparatus region 433 of the housing 430, and the mixing system 32 can be housed in a mixing apparatus region 432 of the housing 430. The pump 34 can be housed in a pump housing region 434. As explained herein, a fluid pathway 435 can connect the console 2 to an interface member 404. It should be appreciated that the housing 430 shown in FIGS. 5H and 5I are only one example of a housing; any other suitable housing may be suitable for housing the components of the disclosed system 1.

III. Tooth Couplers

As explained herein, the tooth coupler 3 can be any suitable mechanism configured to be coupled to the tooth 10 and to perform a treatment procedure. In some embodiments, the pressure wave generator 5 can be coupled to, formed with, and/or disposed at least partially within the tooth coupler 3. The clinician can couple a portion of the tooth coupler 3 to the tooth 10 to be treated. In some procedures, a chamber 6 of the tooth coupler 3 or a chamber of the tooth 10 can be at least partially or substantially filled with a treatment fluid. The clinician can initiate and control the procedure using the console 2, e.g., to activate the pressure wave generator 5 to perform the desired treatment procedure. As explained herein, the pressure wave generator 5 can comprise a liquid jet device in some embodiments. The tooth coupler 3 can comprise a handpiece 3A, a treatment cap 3B, etc.

A. Examples of Liquid Jet Devices

Figure 6:
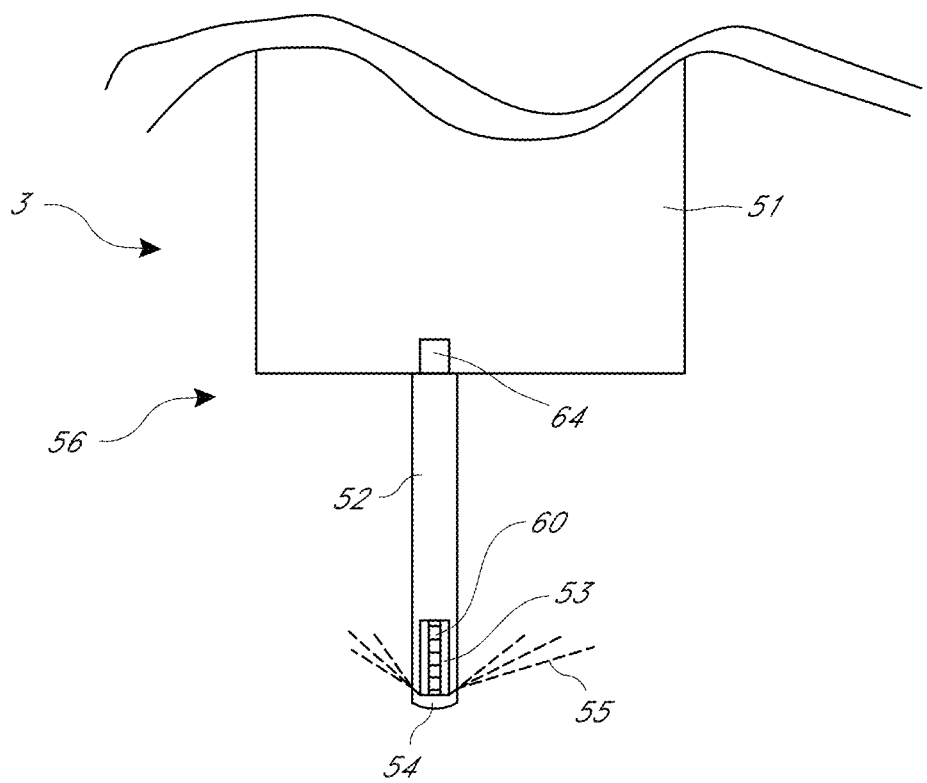
FIG. 6 is a schematic side view of a tooth coupler comprising a liquid jet device.

One example of a pressure wave generator 5 is a liquid jet device, e.g., a device configured to generate a coherent, collimated jet of liquid. FIG. 6 is a schematic side view of a tooth coupler 3 comprising a liquid jet device 56. The liquid jet device 56 can include a proximal portion 51, which may include or be coupled to a nozzle 64 configured to form a liquid jet 60. The nozzle 64 may be formed at or coupled to any suitable portion of the tooth coupler 3 and/or guide tube 52. The liquid jet device 56 can further comprise a guide tube 52 sized and shaped to form a channel, along which the liquid jet 60 can propagate. A distal portion of the guide tube 52 can comprise one or more openings 53. The openings 53 can enable the liquid jet 60 to interact with fluid in the chamber 6 of the tooth coupler 3 and/or a chamber of the tooth 10 (e.g., pulp cavity and/or canal spaces of the tooth 10). The liquid jet 60 can impact upon an impingement member 54 at the distal portion of the guide tube 52 to generate a spray 55 of liquid that passes through the one or more openings 53. As explained herein, the interaction of the liquid jet 60 with surrounding fluid can generate pressure waves and/or fluid motion sufficient to clean the tooth 10.

Figure 7A:
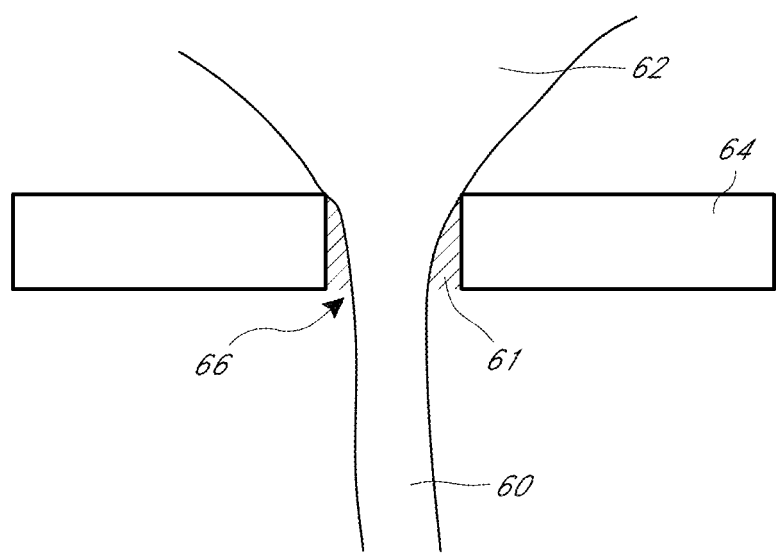
FIGS. 7A-7C are schematic, side cross-sectional views of a nozzle, in accordance with various embodiments.

In certain embodiments, the system 1 may be configured to produce a liquid jet 60 that forms a substantially parallel beam (e.g., is "collimated") over distances ranging from about 0.01 cm to about 10 cm. In some embodiments, the velocity profile transverse to the propagation axis of the jet is substantially constant (e.g., is "coherent"). For example, in some implementations, away from narrow boundary layers near the outer surface of the jet 60 (if any), the jet velocity is substantially constant across the width of the jet. Therefore, in certain advantageous embodiments, the liquid jet 60 delivered by the tooth coupler 3 may comprise a coherent, collimated jet (a "CC jet"). In some implementations, the CC jet may have velocities in a range from about 100 m/s to about 300 m/s, for example, about 190 m/s in some embodiments. In some implementations, the CC jet can have a diameter in a range from about 5 microns to about 1000 microns, in a range from about 10 microns to about 100 microns, in a range from about 100 microns to about 500 microns, or in a range from about 500 microns to about 1000 microns. Further details with respect to CC jets that can be produced by embodiments of the system and apparatus described herein can be found in U.S. Patent Publication No. 2007/0248932, U.S. Patent Publication No. 2011/0117517, and/or U.S. Patent Publication No. 2012/0237893, each of which is hereby incorporated by reference herein in its entirety for all that it discloses or teaches FIG. 7A is a schematic, side cross-sectional view of the nozzle 64, in accordance with one embodiment. As explained above, the proximal portion 51 of the tooth coupler 3 may comprise or be coupled to the nozzle 64. The nozzle 64 can be sized and shaped such that when a pressurized stream of liquid 62 passes through an orifice 66 of the nozzle 64, a liquid jet 60 is formed. The nozzle 64 can comprise a circular, cylinder- or disc-like element having an orifice 66 formed therein. The nozzle 64 may be fabricated from a suitably rigid material that resists deformation under high pressure such as, for example, metal, ceramic, or synthetic sapphire or ruby. Embodiments of the nozzle 64 can be manufactured by a variety of processes including, e.g., electroforming (including nickel-cobalt electroforms), micro-plunge electrical discharge machining (EDM), laser cutting, liquid jet cutting, chemical etching, etc. The orifice 66 may have any desired shape such as, e.g., circular, oval, rectangular, polygonal, etc. The orifice 66 may, but need not be, substantially centered in the nozzle 64. In some embodiments, the nozzle 64 may have two or more orifices 66, with each orifice configured to emit a liquid jet. In some embodiments, the tooth coupler 3 may include additional components, for example, to assist guiding or directing the jet 60 and/or to provide aspiration.

In various embodiments, it can be advantageous for the nozzle 64 to abruptly change the direction of the pressurized stream of liquid 62 delivered to the orifice 66. For example, abrupt changes in velocity of the stream of liquid 62 may lead to a more confined jet, e.g., a coherent, collimated jet having energy sufficient to clean a tooth (and/or to perform other procedures discussed herein). Furthermore, as shown schematically in FIG. 7A, it can be advantageous to increase a separation space 61 between walls of the orifice 66 and the jet 60. Increasing the space 61 can reduce the likelihood that the orifice 66 or other portions of the nozzle 64 interfere with or otherwise obstruct the jet 60, or that the jet 60 reattaches to the wall of the orifice 66, which may result in the disruption of the coherent, collimated jet 60. Interference from wall of the orifice 66 or other portions of the nozzle 64 may act to reduce the energy of the jet 60, and thereby, the effectiveness of the treatment procedure.

Figure 7B:
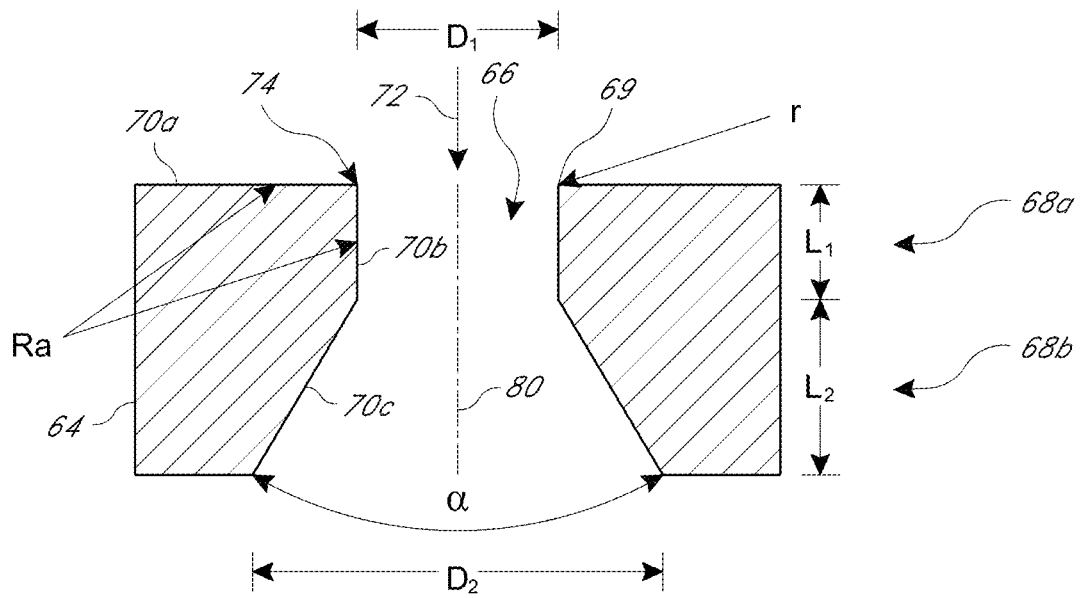
Figure 7C:
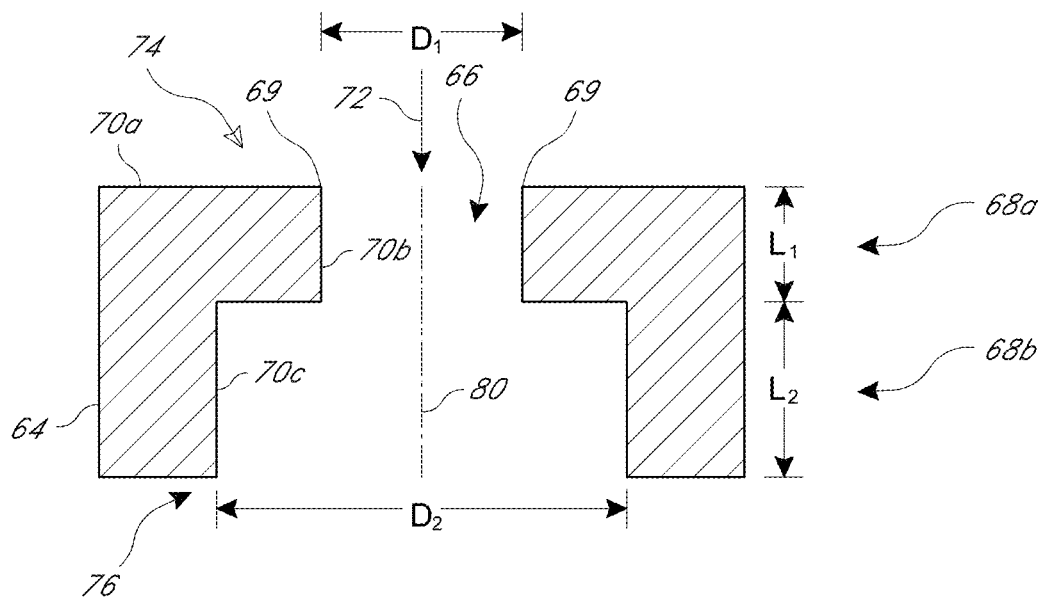

Different types of fluid streams (e.g., a jet or a spray) can be generated by the nozzle 64 and/or orifice 66 based at least in part on flow parameters, nozzle geometry, surface quality of the orifice 66 (or other surfaces in the nozzle 64), and so forth. FIGS. 7B and 7C are cross-section views that schematically illustrate embodiments of a nozzle 64 having an orifice 66. Nozzles and/or orifices can be configured in a number of ways to provide a CC jet. For example, as schematically illustrated in FIG. 7B, in some embodiments a relatively sharp-edged, cone-down orifice 66 can be used. In other embodiments, other shapes can be used, e.g., conical orifices, capillary orifices, cone-capillary orifices, etc. Arrow 72 shows the direction of fluid flow through the orifice 66 during operation of the liquid jet apparatus.

In the illustrated embodiments, the orifice 66 is substantially circularly symmetric, although this is not a requirement. The orifice 66 may, but need not, be formed at an angle to a proximal surface 70a of the nozzle 64. The angle may be about 0 degrees (e.g., the orifice is substantially perpendicular to the proximal surface 70a), about 10 degrees, about 20 degrees, about 30 degrees, about 40 degrees, about 50 degrees, about 60 degrees, or some other angle. The orifice 66 shown in FIGS. 7B and 7C comprises a proximal portion 68a that can be substantially cylindrical with a length $L_1$ and a diameter $D_1$. The orifice 66 can comprise a distal portion 68b that can be substantially conical with a cone angle $\alpha$ and can have a length $L_2$ and a diameter $D_2$. As schematically illustrated in FIG. 7C, the cone angle $\alpha$ can be about 180 degrees, so that the distal portion 68b is substantially cylindrical. The diameter $D_2$ can, but need not be, different from the diameter $D_1$. For example, in various embodiments, $D_2$ can be approximately the same as $D_1$, $D_2$ can be larger than $D_1$, or $D_2$ can be smaller than $D_1$. The length $L_2$ can, but need not be, different from the length $L_1$. For example, in various embodiments, $L_2$ can be approximately the same as $L_1$, $L_2$ can be larger than $L_1$, or $L_2$ can be smaller than $L_1$. The orifice geometry schematically illustrated in FIGS. 7B and 7C may cause a relatively abrupt change in velocity of the liquid flowing through the orifice 66.

For length-to-diameter ratios $L_1/D_1$ in a range from about 0 to about 1.2, about 0 to about 0.9, or about 0 to about 0.8, the flow may be constricted, may not reattach to the walls of the orifice, and may form a CC-Jet with a relatively long break-up length. In some embodiments, for example, the length-to-diameter ratios $L_1/D_1$ may be about 1. For lengthto-diameter ratios $L_1/D_1$ in a range from about 0.7 to about 4, or about 0.7 to about 1.2, cavitation may be induced. Initially, the flow out of the nozzle 64 may reattach to the walls of the orifice 66, and the fluid stream may not be a CC jet. For sufficiently high pressures (near the inlet 74 to the nozzle 64), cavitation may occur near the inlet 74. The cavitation region can grow and may form an air entrainment region sufficiently large to induce air from downstream to flow up to the nozzle's outlet 76 and separate liquid from the walls of the orifice 66, which may help create a CC jet. In other embodiments, length-to-diameter ratios $L_1/D_1$ above 4 can be used.

A possible advantage of using length-to-diameter ratios $L_1/D_1$ in the range from about 0 to about 0.7 is that cavitation may cause damage to the nozzle. Accordingly, in such ranges of $L_1/D_1$ it may be important to select a material strong enough for the nozzle. A possible disadvantage is that a sufficiently hard material able to withstand relatively high pressure may be used for the nozzle 64, which may limit the variety of materials used for the nozzle. In some arrangements, a suitably strong material for the nozzle may not be available to avoid failure. A possible advantage of using length-to-diameter ratios $L_1/D_1$ in the range from about 0.7 to about 4 is that the larger $L_1/D_1$ ratio allows the nozzle's geometry to be adapted for a wider range of materials. A possible disadvantage of higher $L_1/D_1$ ratios is that cavitation may cause damage to the nozzle 64 and lead to a shorter working life for the nozzle.

It is believed, although not required, that for $L_1/D_1$ ratios at least in the range from about 0 to about 4, the nozzle design may be relatively insensitive to the cone angle α. Accordingly, cone angles near about 0 degrees can be used (e.g., the orifice 64 is approximately a cylinder over the length $L_1$ and $L_2$). In this case, the orifice 66 may be thought of as comprising just the proximal portion 68a and not the distal portion 68b. In other embodiments, only the distal portion 68b is used, and the orifice 66 is substantially conical. Many possible configurations of the orifice 66 can be used, and the examples in FIGS. 7B and 7C are intended to be illustrative and not to be limiting.

For example, as schematically illustrated in FIG. 7C, cone angles of about 180 degrees can be used. In this example, both the proximal portion 68a and the distal portion 68b are substantially cylindrical, with the diameter $D_2$ of the distal portion 68b larger than the diameter $D_1$ of the proximal portion 68a. In other embodiments, the diameter $D_2$ of the distal portion 68b may be smaller than the diameter $D_1$ of the proximal portion 68a. Shaping the proximal portion 68a or the distal portion 68b substantially as cylinders may advantageously make manufacturing the orifice simpler. In other embodiments, cone angles in a range from about 0 degrees to about 20 degrees, about 20 degrees to about 45 degrees, about 45 degrees to about 90 degrees, about 90 degrees to about 120 degrees, or some other range can be used.

In various embodiments of the nozzle 64, the orifice 66 may have a diameter $D_1$ at the inlet 74 or a diameter $D_2$ at the outlet 76 that may be in a range from about 5 microns to about 1000 microns. Other diameter ranges are possible. In various embodiments, one or both of the diameters $D_1$ or $D_2$ may be in a range from about 10 microns to about 100 microns, a range from about 100 microns to about 500 microns, or range from about 500 microns to about 1000 microns. In various other embodiments, one or both of the orifice diameters $D_1$ or $D_2$ may be in a range of about 40-80 microns, a range of about 45-70 microns, or a range of about 45-65 microns. In one embodiment, the orifice diameter $D_1$ is about 60 microns. The ratio of axial length $L_1$ to diameter $D_1$, the ratio of axial length $L_2$ to diameter D2, or the ratio of total axial length $L_1+L_2$ to diameter $D_1$, $D_2$, or average diameter $(D_1+D_2)/2$ may, in various embodiments, be about 50:1, about 20:1, about 10:1, about 5:1, about 1:1, or less. In one embodiment, the axial length $L_1$ is about 500 microns. In some cases, the axial length $L_2$ (or the ratio $L_2/D_2$) can be selected so that the flow through the orifice 66 does not reattach to surface 70c. The axial length $L_2$, the diameter $D_2$, or other parameters shown in FIGS. 7B and 7C may be selected so that the nozzle 64 has sufficient structural rigidity to withstand load from pressurized fluid.

With reference to the example nozzle 64 schematically illustrated in FIG. 7B, the curvature of corner or edge 69 is denoted by r, and the surface roughness of surfaces 70a, 70b, and 70c is denoted by Ra. Relatively abrupt geometry changes in the nozzle 64 may induce a relatively large velocity change, which may lead to a relatively constricted jet. For example, the ratio of surface roughness Ra to orifice diameter $D_1$, $Ra/D_1$, for some or all of the surfaces 70a-70c may be less than about 0.01, less than about 0.005, or less than about 0.001 in various embodiments. The ratio of corner curvature radius r to orifice diameter $D_1$, $r/D_1$, may be less than about 0.1, less than about 0.05, less than about 0.04, less than about 0.02, less than about 0.01, or less than about 0.004 in various embodiments. The surface roughness Ra of the surfaces 70a, 70b, or 70c can have a root-mean-square (rms) surface roughness less than about 10 microns, less than about 1 micron, or less than about 0.1 microns.

In certain embodiments, the nozzle 64 (or surface portions adjacent the liquid) can be formed from a hydrophobic material. In certain such embodiments, the contact angle (e.g., the angle formed between a solid surface and a liquid) of the hydrophobic material may be smaller than about π/2 radians. In some implementations, the nozzle 64 may comprise stainless steel or a plastic such as, e.g., acrylic. Other materials may be used such as, e.g., aluminum, copper, or polycarbonate, but in some cases, nozzles formed from such materials may not produce a substantially constricted jet.

The behavior and characteristics of liquid streams ejected through an orifice 66 can be dependent upon the design and quality of the orifice 66. For instance, a specific orifice design may produce different streams of liquid ranging from a coherent, collimated jet to a spray, depending at least in part on the edge sharpness of the orifice 66 and the surface roughness of the orifice 66, as explained above with respect to FIGS. 7B-7C. Accordingly, it can be important to identify suitable dimensions, design and surface properties of the desired orifice 66 (as described above with respect to FIGS. 7B-7C, for example), and to develop suitable methods of making the orifice 66 with such properties. The present disclosure describes methods of making orifices 66 of various designs to produce liquid streams of desired properties, in particular, orifices 66 capable of producing coherent collimated jets 60 (or any jet of liquid with reduced or minimal loss of momentum over the length of travel) which can be used as a source of acoustics, fluid circulation and/or irrigation in dental and endodontic procedures.

Figure 8A:
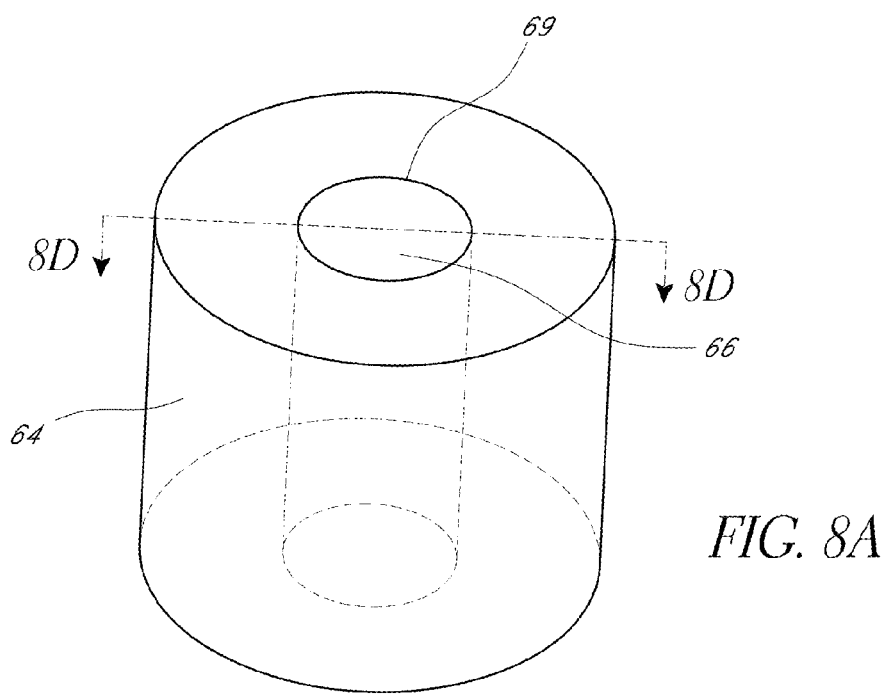
FIG. 8A is a perspective view of a nozzle with a substantially cylindrical orifice.
Figure 8B:
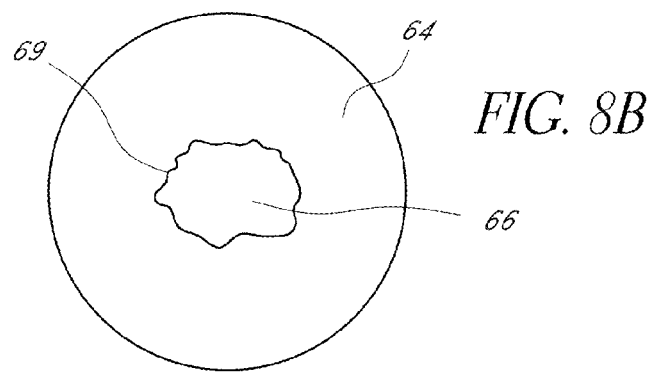
FIG. 8B is a top plan view of the nozzle in which edges of the orifice are relatively rough.
Figures 8C, 8D:
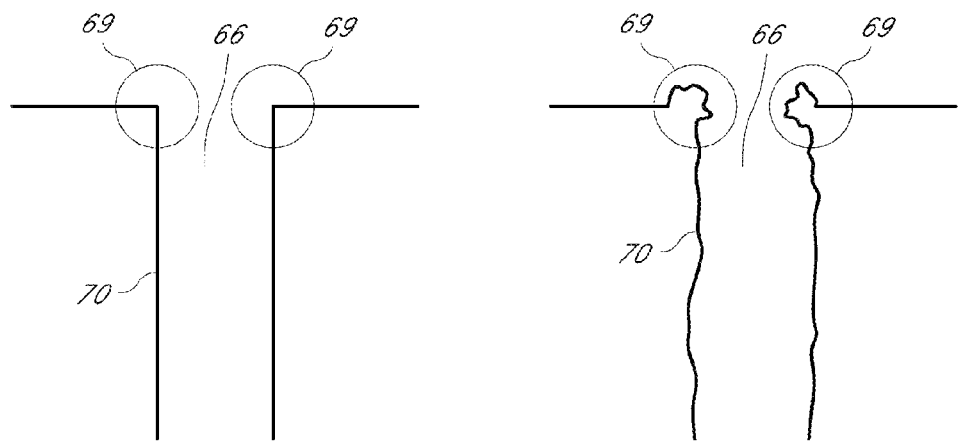
FIG. 8C is a side cross-sectional view of a nozzle in which edges of the orifice are relatively sharp and the walls of the orifice are relatively smooth.
FIG. 8D is a side cross-sectional view of the nozzle of FIG. 8B with rough edges.
Figure 8E:
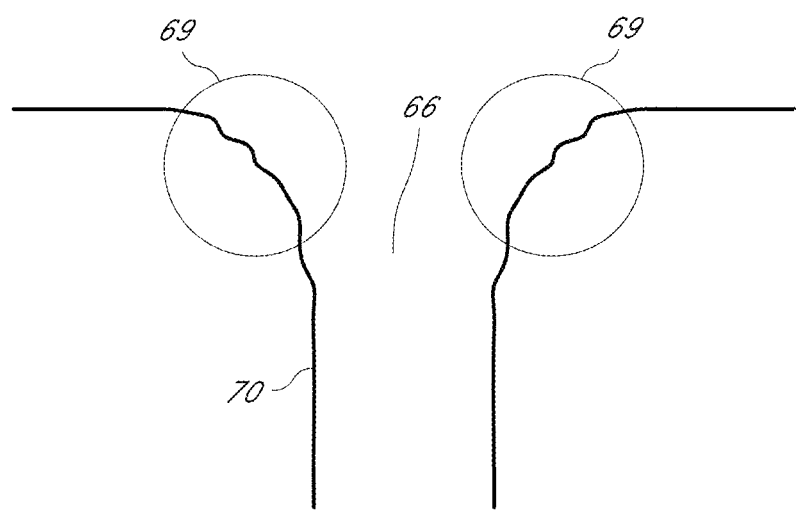
FIG. 8E is a side cross-sectional view of the nozzle, in which the edges of the nozzle are removed and/or rounded.

As explained herein, it can be advantageous to form the nozzle 64 having an orifice 66 defined by sufficiently smooth walls 70 and edges 69. However, many manufacturing methods may not be able to form the orifice 66 with sufficiently smooth walls 70 and/or edges 69. FIG. 8A is a perspective view of a nozzle 64 with a substantially cylindrical orifice 66. FIG. 8B is a top plan view of the nozzle 64 in which edges 69 of the orifice 66 are relatively rough. FIG. 8D is a side cross-sectional view of the nozzle 64 of FIG. 8B with rough edges 69. The nozzles 64 with relatively rough or jagged edges 69 and walls 70 shown in FIGS. 8B and 8D may be undesirable for forming a liquid jet 60 in accordance with the embodiments disclosed herein. For example, the burrs or other non-uniformities that define the jagged edges 69 and walls 70 may reduce the energy of the pressurized liquid entering and passing through the orifice 66. Indeed, in some arrangements, rough or jagged edges 69 can spread the pressurized stream of liquid 62 out and/or induce spray, which can reduce the degree of collimation and momentum of the liquid jet 60. Similarly, FIG. 8E is a side cross-sectional view of the nozzle 64, in which the edges 69 of the nozzle 64 are removed and/or rounded. As with the rough edges 69 of FIGS. 8B and 8D, a nozzle 64 having rounded edges 69 may likewise spread the pressurized beam of liquid and/or otherwise reduce the energy of the jet 60, which can reduce the effectiveness of the jet 60 in various treatment procedures (e.g., by reducing the momentum of the jet 60).

By contrast, FIG. 8C is a side cross-sectional view of a nozzle 64 in which edges 69 of the orifice 66 are relatively sharp and the walls 70 of the orifice 66 are relatively smooth. The sharp, smooth edges 69 of the orifice 66 of FIG. 8C may help to cause an abrupt transition in the stream 62 such that the velocity rapidly changes to form a coherent collimated jet 60. The smooth walls 70 of the orifice 66 in FIG. 8C may be sufficiently smooth such that the walls 70 do not inhibit the momentum of the jet 66. Accordingly, it can be important to manufacture the nozzle 64 such that the edges 69 are relatively sharp and the walls 70 are relatively sharp, as explained in more detail above with respect to FIGS. 7B-7C.

Various processes may be used to form orifices 66 having sufficiently smooth walls and/or sharp edges 69. For example, in various embodiments, the orifice 66 can be manufactured using at least one of a laser cutting apparatus, electrical discharge machining (EDM), mechanical drilling or machining, injection molding, stereolithography, punching, three-dimensional printing, plastic extrusion, chemical etching, or other suitable techniques. Various types of laser cutting systems may be employed. For example, in various embodiments a femto-second laser or a pico-second laser may be used. The laser can comprise a Ytterbium laser in some arrangements, which can operate at about a 1070 nm wavelength. The laser used to form the orifice 66 may be pulsed or continuous wave (CW). In some embodiments, the laser used to form the orifice 66 can be coupled with or formed in a stream of water. The stream of water can comprise a coherent and collimated jet in some embodiments. Such processes can advantageously form orifices having smooth walls 70 and sharp edges 69 sufficient to form a liquid jet 60 for use in the treatments disclosed herein, as described with respect to the parameters shown and described in FIGS. 7B-7C.

Figure 9A:
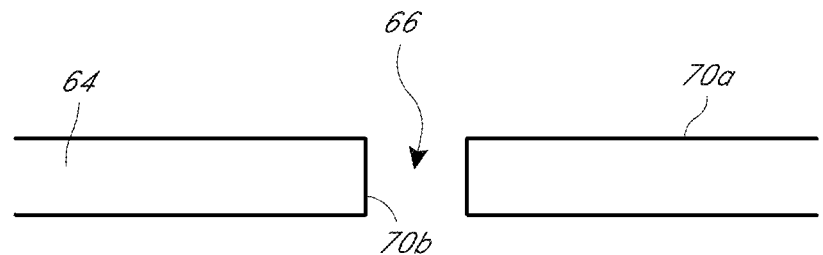
Figure 9B:
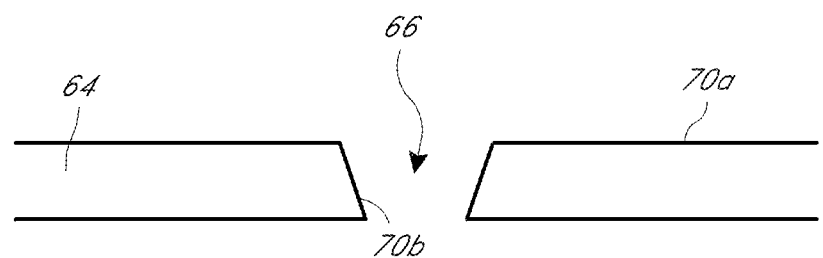
Figure 9C:
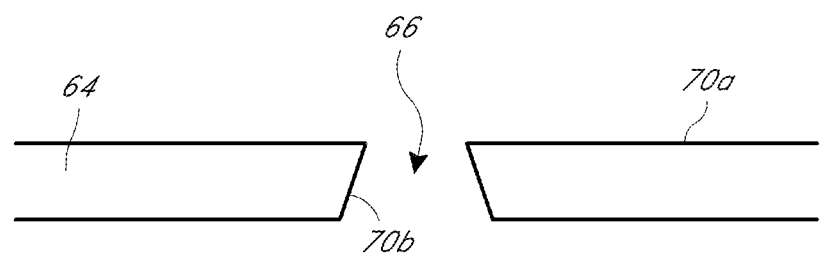
Figure 9D:
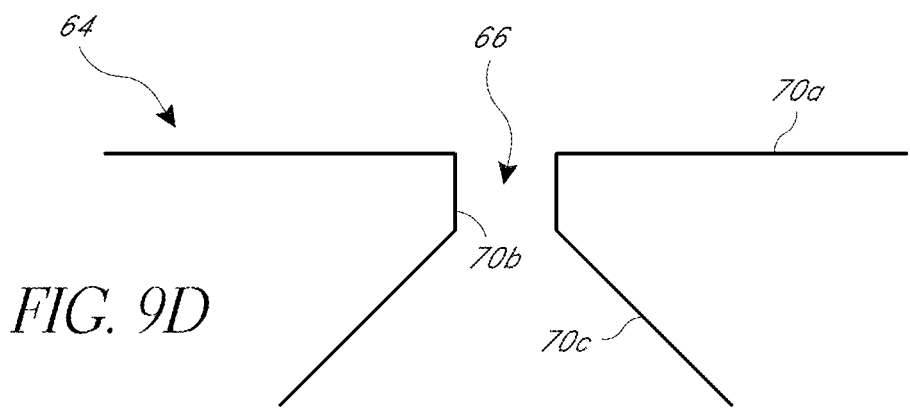
Figure 9E:
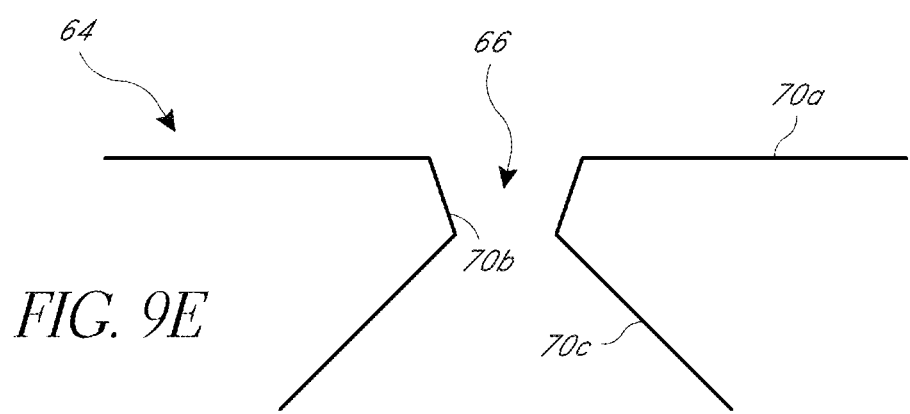
Figure 9F:
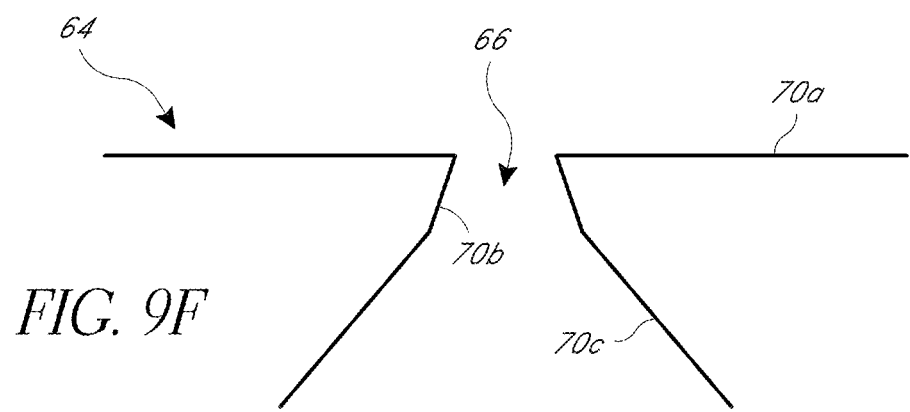

FIGS. 9A-9I are side cross-sectional views of example nozzle profiles, according to various embodiments. In FIGS. 9A-9C, the nozzle 64 includes an orifice 66, a proximal wall 70a and a second wall 70b. The orientation of the second wall 70b shown in FIGS. 9A-9C can be selected to form a suitable stream of liquid, such as a coherent collimated jet 60. In the embodiment of FIG. 9A, for example, the second wall 70b is substantially parallel to a direction of fluid flow through the orifice 66. By contract, the second wall 70b of FIG. 9B is transverse to the direction of fluid flow and tapers inwardly towards the jet 60 along the direction of flow. The second wall 70b of FIG. 9C is transverse to the direction of fluid flow and tapers outwardly away from the jet 60 along the direction of flow.

In FIGS. 9D-9I, the nozzle 64 includes an orifice 66, a proximal wall 70a, a second wall 70b, and a third wall 70c. In various arrangements, the nozzles 64 shown in FIGS. 9D-9I can comprise a counterbore. The respective orientations of the second and third walls 70b, 70c can be selected to form a suitable stream of liquid, such as a coherent collimated jet 60. For example, the nozzle 64 of FIG. 9D includes a second wall 70b that is oriented substantially parallel to a direction of flow and a third wall 70c that tapers away from the jet 60 along the direction of flow. The nozzle 64 of FIG. 9E includes an inwardly-tapering second wall 70b and an outwardly-tapering third wall 70c. By contrast, the nozzle 64 of FIG. 9F includes an outwardly-tapering second wall 70b and an outwardly-tapering third wall 70c.

The nozzle 64 shown in FIG. 9G may be generally similar to the nozzle 64 shown in FIG. 7C, e.g., the nozzle 64 can include a second wall 70b substantially parallel to a direction of flow and a third wall 70c spaced apart radially from the second wall 70b. The third wall 70c can also be substantially parallel to the direction of flow. By contrast, the nozzle 64 shown in FIG. 9H can include an inwardly-tapering second wall 70b, e.g., that tapers towards the jet 60 along the direction of flow. The nozzle 64 shown in FIG. 9I can include an outwardly-tapering second wall 70b, e.g., that tapers away from the jet 60 along the direction of flow. The nozzles 64 disclosed in FIGS. 9A-9I may be selected according to the stream of liquid desired for a particular treatment procedure. Furthermore, although the direction of flow is illustrated as going from top to bottom in FIGS. 9A-9I, it should be appreciated that, in some arrangements, the direction of fluid flow may be reversed. For example, in some arrangements, lower pressures and/or larger diameter nozzles may allow flow to be reversed relative to that shown in FIGS. 9A-9I.

FIGS. 10A-10C are side cross-sectional views of a nozzle 64 at various stages of an example manufacturing process. In particular, FIG. 10A illustrates a partially-fabricated nozzle 64' in which a plate 73 of a suitable nozzle material (described above) can be selected. As shown in FIG. 10B, a first trench 75 can be formed partially through a thickness of the plate 73. The first trench 75 may define the orifice 66 when complete. Accordingly, it can be advantageous to define a smooth second wall 70b of the first trench 75 so that the orifice 66 will be sufficiently smooth so as to form a liquid jet 60. As explained herein, the first trench 75 can be formed using a process that will result in a sufficiently smooth second wall 70b. For example, in various embodiments, the first trench 75 can be formed using at least one of a laser cutting apparatus, electrical discharge machining (EDM), stereolithography, or other suitable techniques.

Turning to FIG. 10C, a second trench 77 can be formed partially through the thickness of the plate 73 to define the third wall 70c and the larger diameter distal portion of the nozzle 64. In some embodiments, the second trench 77 can be formed using a mechanical technique, such as drilling or end milling a back side of the plate 73. However, in some arrangements, using mechanical techniques to form the second trench 77 may yield a bottom wall 70d that is uneven, rough, and/or jagged. A rough bottom wall 70d may be undesirable because the portion of the bottom wall 70d that joins with the second wall 70b at least in part defines the length of the orifice 66. If the bottom wall 70d is rough about the perimeter of the orifice 66, then the length of the orifice 66 may be different along different portions of the perimeter, which can create an uneven jet or a stream having reduced momentum. Accordingly, in some embodiments, it can be desirable to define the second trench 77 using a high precision process, such as a laser cutting apparatus, EDM, stereolithography, etc. By defining a more uniform or smooth bottom wall 70d, the length of the orifice 66 may be maintained substantially constant, which can advantageously improve the jet-forming characteristics of the nozzle 64.

Although FIGS. 10A-10C illustrated the first trench 75 as being formed before the secon trench 77, it should be appreciated that the larger second trench 77 may be formed before forming the first trench 75. The second trench 77 may be formed using a precision method, such as laser cutting. In other arrangements, the second trench 77 may be formed as a counter bore with an endmill, EDM, chemical etch, etc.

Figure 11:
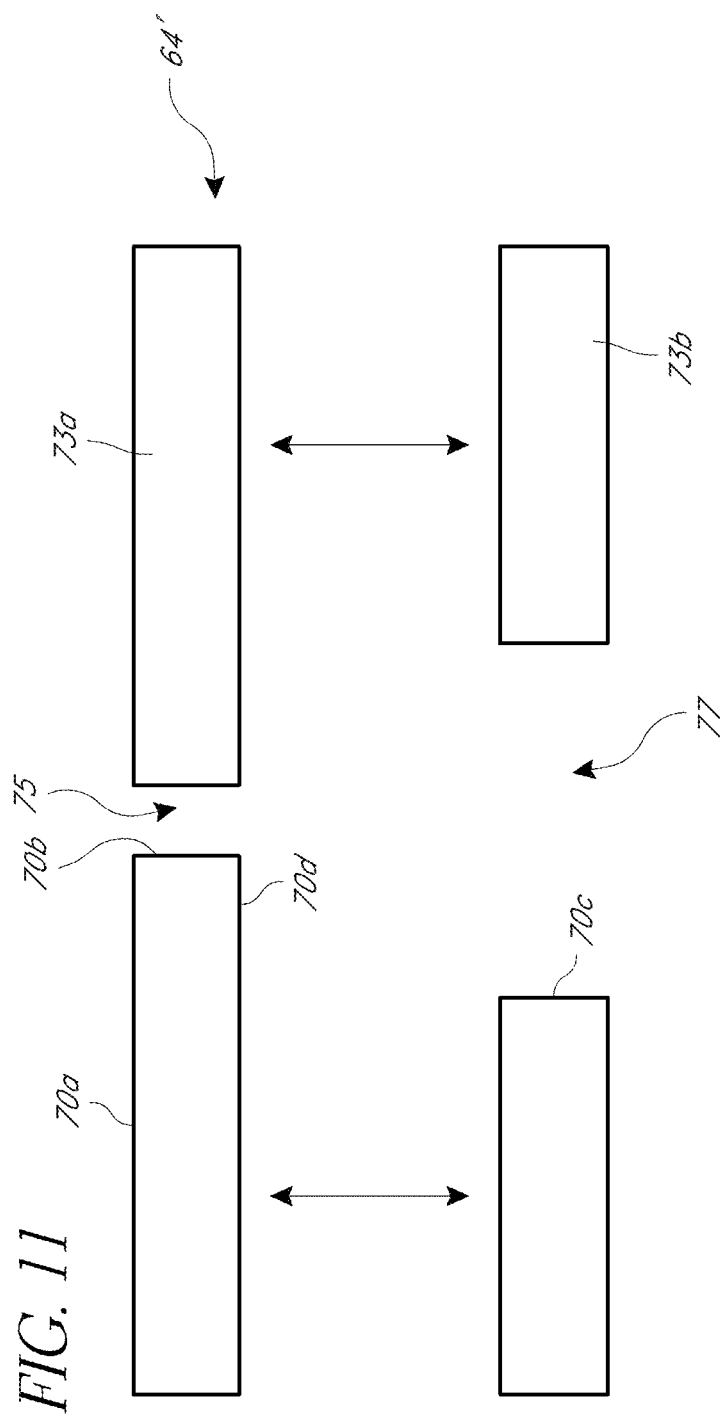
FIG. 11 is a schematic side cross-sectional view of a partially fabricated nozzle, according to another embodiment.

FIG. 11 is a schematic side cross-sectional view of a partially fabricated nozzle 64', according to another embodiment. In the embodiment of FIG. 11, a first plate 73a and a second plate 73b can be selected. The plates 73a, 73b may comprise any suitable material for forming the nozzle 64, as explained above. The plates 73a, 73b may comprise the same material or a different material. A first trench 75 can be formed through the first plate 73a. As shown in FIG. 11, the first trench 75 may be formed through the entire thickness of the first plate 73a. As with the embodiment of FIGS. 10A-10C, the second wall 10b of the first trench 75 may define the second wall 70b of the orifice 66 when the nozzle 64 is completed. Accordingly, it can be advantageous to form a smooth wall 70b such that the nozzle 64 can form a coherent collimated jet 60. In some embodiments, the trench 75 can be formed through the first plate 73a using any suitable process, such as a laser cutting apparatus, electrical discharge machining (EDM), stereolithography, or other suitable techniques. Still other techniques may be suitable.

A second trench 77 can be formed through the second plate 73b, e.g., through the entire thickness of the second plate 73b as shown in FIG. 11. The first plate 73a and the second plate 73b can be attached together, e.g., by a thermal pressing operation, diffusion bonding, an adhesive, or any other suitable mechanism for attaching the plates 73a, 73b together. Once joined, the first and second plates 73a, 73b can define a completed nozzle 64, such as that shown in FIG. 10C.

The second trench 77 can be formed using any suitable technique, including techniques that may yield relatively rough surface profiles. For example, the second trench 77 can be formed mechanically by drilling, punching, milling, etc. In the embodiment of FIG. 11, the surface roughness of the bottom wall 70d may be defined at least in part by the roughness of the back side of the first plate 73a. Accordingly, the first plate 73 may be selected to be sufficiently smooth such that the length of the orifice 66 defined in the nozzle 64 is substantially constant. Thus, the method of forming the second trench 77 may not affect the length of the bottom wall 70d, and hence, the length of the orifice 66. Although the description of the process shown in FIG. 11 discussed an example sequence, it should be appreciated that the orders may be reversed or switched. For example, the second trench 77 may be formed before or simultaneously with the first trench 75. Other orders of manufacturing the nozzle 64 may be suitable.

B. Examples of Handpieces

As explained herein, one example of the tooth coupler 3 is a handpiece 3A. FIG. 12A is a schematic side view of a handpiece 3A, in accordance with one embodiment. FIG. 12B is a side cross-sectional view of the handpiece 3A. The handpiece 3A can be configured to receive the high pressure liquid and can be adapted at a distal end 94 to generate a high-velocity beam or jet 60 of liquid for use in dental procedures. In some embodiments, the system 1 may produce a coherent, collimated jet of liquid. The handpiece 3A may be sized and shaped to be maneuverable in the mouth of a patient by the clinician so that the guide tube 52 and jet 60 may be directed toward or away from various portions of the tooth 10. In some embodiments, the handpiece 3A comprises a housing or sealing cap 170 that can be coupled to the tooth 10, e.g., that can couple the handpiece 3A to the tooth 10.

The handpiece 3A can comprise an elongated tubular body 80 having a proximal end 93 that is adapted to engage one or more conduits 29 from the console 2 and a distal end 94 adapted to be coupled or attached to the tooth 10. As explained above, the one or more conduits 29 can provide fluidic and/or electrical communication between the console 2 and the handpiece 3A. The conduit 29 can comprise high-pressure, chemical resistant tubing configured to convey high pressure liquid from the console 2 to the handpiece 3A, e.g., high pressure treatment liquids that the nozzle 64 can form into a liquid jet 60. In addition, the handpiece 3A can comprise tubing configured to convey other suitable fluids, such as irrigation fluids, compressed air (for example, for driving a drilling device), etc. As explained in more detail herein, the conduit 29 can mechanically couple to the proximal end 93 of the handpiece 3A by way of the interface member 4.

The distal end 94 of the handpiece 3A can comprise a pressure wave generator 5, for example, a liquid jet device 56 comprising a guide tube 52 and nozzle 64, as explained above. A housing or sealing cap at a distal portion of the handpiece 3A can be coupled to the tooth 10 in some embodiments. The cap may be a detachable member that can be sized/shaped to fit on the patient's tooth and/or to position the distal end of the guide tube 56 at a desired location in the pulp cavity or chamber 6. A kit of caps may be provided such that a dental practitioner can select an appropriately-sized cap and attach it to the handpiece 3A (see, e.g., description of tooth sizing herein) and/or tooth. The distal end 94 of the handpiece 3A can also include a suction port 83 configured to remove material from the tooth 10 or treatment site. The suction port 83 can be in fluid communication with a waste line 81. The waste line 81 can comprise tubing in communication with the waste system 41 described above. For example, a vacuum pump can be activated to provide suction to the waste line 81 and suction port 83 to enable the removal of waste materials from the tooth 10 or treatment site. The handpiece 3A may include various other features, including a fluid inlet for delivering treatment fluid to the tooth 10 or treatment site, a power line (e.g., to provide energy to a pressure wave generator), a fluid outlet, an irrigation source for irrigating the treatment area, a light source to illuminate the treatment area, or a combination of some or all of the foregoing. Moreover, as explained in more detail herein, a communications chip 92 (e.g., a radio frequency identification, or RFID, chip) can be coupled to the handpiece 3A to provide wireless communication between the handpiece 3A and other system components.

The handpiece 3A can be used to apply the pressure wave generator 5 relative to the tooth 10. The body 80 may include features or textures that enhance grasping the handpiece 3A with the fingers and thumb of the clinician. The handpiece 3A can be configured to be handheld and maneuvered as desired by the clinician during a treatment procedure. In some cases, the handpiece 3A can be configured to be portable, movable, orientable, or maneuverable with respect to the patient. In some implementations, the handpiece 3A can be configured to be coupled to a positioning device (e.g., a maneuverable or adjustable arm). The handpiece 3A can be disposable (e.g., single-use) or reusable. In some embodiments, the distal end 94 of the handpiece 3A can include additional components such as, for example, a sealer or gasket (which may be an elastomeric material or a closed-cell foam), spacers (e.g., to position the distal end of the guide tube 52 at a desired location in the tooth 10 and/or chamber 6), vents, etc. In embodiments in which the pressure wave generator 5 comprises a liquid jet, the jet 60 may supply any suitable treatment fluid, such as, e.g., water, EDTA, bleach, or other chemicals. In other embodiments, the jet 60 may be formed of and may supply one fluid and a separate irrigation inlet can supply additional fluids. For example, in some embodiments, the jet 60 can comprise water (e.g., degassed water), and other treatment fluids (e.g., chemicals such as EDTA, bleach, etc.) may be flowed into the treatment region or tooth by a separate conduit at lower pressures. The fluids supplied at lower pressures relative to the jet 60 can mix with the pressurized degassed water in the tooth 10 or treatment region to assist in cleaning the tooth 10.

The handpiece 3A can be applied to the tooth 10 so as to create a substantially closed fluid circuit as the distal end 94 of the handpiece 3A engages the tooth 10, thereby enabling fluid to be delivered into and out of the chamber 6 and/or pulp cavity 11 without substantial spillage or leakage into the patient's mouth. The handpiece 3A may include a fluid retention member (e.g., sponge, seal, gasket, and/or vent) to reduce the likelihood of fluid leakage and/or to allow fluid to flow from the tooth 10 and/or chamber 6 (e.g., to inhibit overpressurization or under-pressurization). Leakage can have various negative effects depending on entry type, fluid type, direction, etc. The fluid retention member can be configured to inhibit air from entering the tooth 10 and/or chamber 6 (which may reduce the effectiveness of cavitation) while permitting air to enter the suction port 83.

With reference to FIG. 12B, an internal high pressure fluid supply line 82 can provide fluid communication between the liquid jet device 56 and the proximal end 93 of the handpiece 3A. As with the conduits 29, the supply line 82 can be adapted to reliably convey high pressure liquid to the distal end 94 of the handpiece 3A and the liquid jet device 56, in addition to being resistant to the chemicals included in the treatment fluids passing through the supply line 82. As explained herein, the liquid jet device 56 can convert the pressurized liquid supplied by the supply line 82 into a liquid jet 60 suitable for use in various treatment procedures.

The handpiece 3A can be connected to the conduit 29 and system 1 by the clinician before treatment, and can be disconnected from the conduit 29 and the rest of the system 1 by the clinician after treatment. However, it can be challenging to provide a removable connection between the high pressure supply line 82 and the conduit 29, at least because it can be difficult to form a sealed connection between the supply line 82 and the conduit 29 that can also be engaged and disengaged by the user. The high pressures of the fluid flowing through the conduit 29 can make it particularly, difficult to provide sealed connections between removable components.

Accordingly, the handpiece 3A can include a connector 84 at or near the proximal end 93 of the handpiece body 80. The connector 84 can be configured to be connected to and disconnected from the interface member 4, which can couple the connector 84 to the conduit(s) 29 and the rest of the system 1. Thus, the clinician can connect the handpiece 3A to the interface member 4 and conduits 29 by way of the connector 84 to enable fluid, electrical, and/or data communication between the handpiece 3A and the console 2. The clinician can perform the desired treatment procedure. After the procedure, the clinician can disconnect the handpiece 3A from the interface member 4 and conduits 29.

The connector 84 can include an inner tubular body 85 and an outer tubular body 86 disposed about the inner tubular body 85. As shown in FIG. 12B, in some embodiments, the inner tubular body 85 and the outer tubular body 86 can be threaded together. An outer surface of the connector 84 (e.g., the outer surface of the outer tubular body 86) can include an engagement feature configured to removably engage with the interface member 4. For example, as shown in the FIG. 12B, a recess 90 can be formed in the outer surface of the connector 84. In some arrangements, the recess 90 can comprise a groove disposed circumferentially about the outer surface of the connector 84. In other embodiments, the recess 90 can comprise one or more discrete recessed regions in the outer surface of the connector 84. As explained in more detail herein, the recess 90 can receive a projection of the interface member 4 to releasably secure the interface member 4 to the connector 84 and handpiece 3A.

The connector 84 can comprise a fluid line coupling portion 87 disposed proximal a proximal end of the high pressure fluid supply line 82. The coupling portion 87 can be sized and shaped to receive a corresponding high pressure line from the interface member 4, as explained herein. The fluid line coupling portion 87 can thereby provide fluid communication between the high pressure line(s) of the interface member 4 and the high pressure fluid supply line 82 of the handpiece 3A. In some arrangements, the coupling portion 87 can comprise a filter configured to remove particulates or other debris before the debris reaches the orifice 66. The connector 84 can also include a first opening 88 and a second opening 89 proximal the first opening 88. As shown in FIG. 12B, the second opening 89 can have a diameter larger than a diameter of the first opening 88. As explained herein, a distal portion of the interface member 4 can be inserted into the second opening 89, and the distal end of the supply line of the interface member 4 can be inserted through the first opening 88 and into the fluid line coupling portion 87. A first gasket 91 (e.g., an o-ring) can be disposed near the second opening 89 so as to provide friction between the handpiece 3A and interface member 4. In some arrangements, the first gasket 92 can assist in providing a fluid seal. A second gasket 95 (e.g., an o-ring) can provide a fluid seal between the first opening 88 and the coupling portion 87. The connector 84 can thereby provide substantially sealed fluid communication between fluid line(s) in the interface member 4 and the high pressure fluid supply line 82, while also enabling the engagement and disengagement between the connector 84 and interface member 4. In the handpiece 3A shown in FIG. 12B, the connector 84 is configured to be inserted into the interface member 4, e.g., the connector 84 may act as a male connector and the interface member 4 may act as a female connector. Thus, in the embodiment of FIG. 12B, the connector 84 may be inserted into an aperture of the interface member 4. In other embodiments, however, it should be appreciated that male and female components may be interchangeable. For example, in other embodiments, the connector 84 may act as a female connector, and the interface member 4 may act as a male connector. In such other embodiments, the interface member 4 may be inserted into the connector 84. A filter may be disposed in the connector 84 or inside the handpiece 3A to prevent the nozzle from being clogged by particles or debris.

Figure 12C:
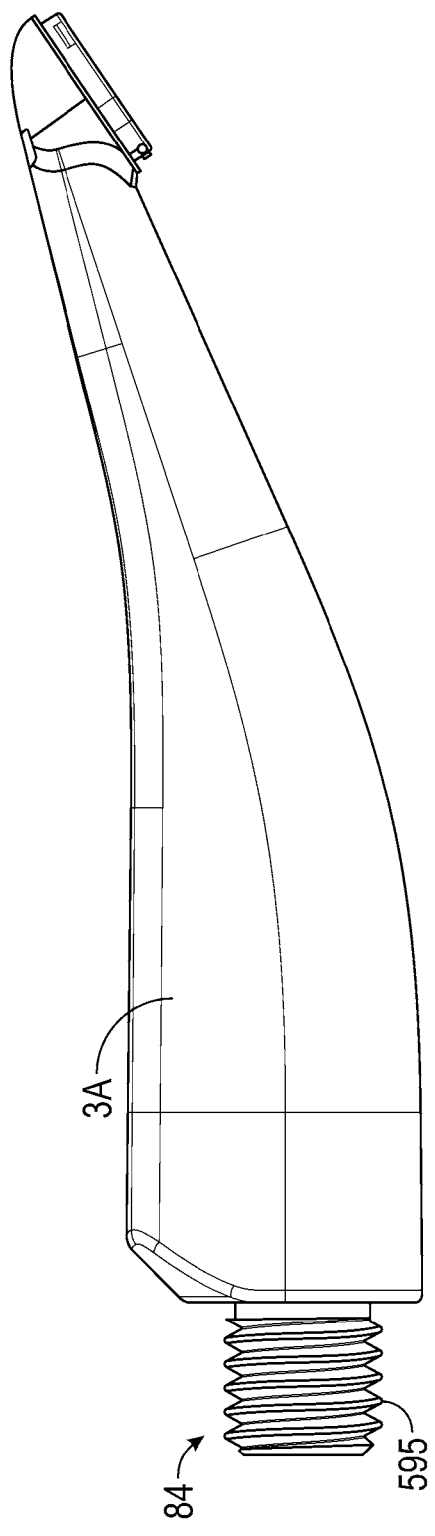
FIG. 12C is a side cross-sectional view of a handpiece, in accordance with another embodiment.
Figure 12D:
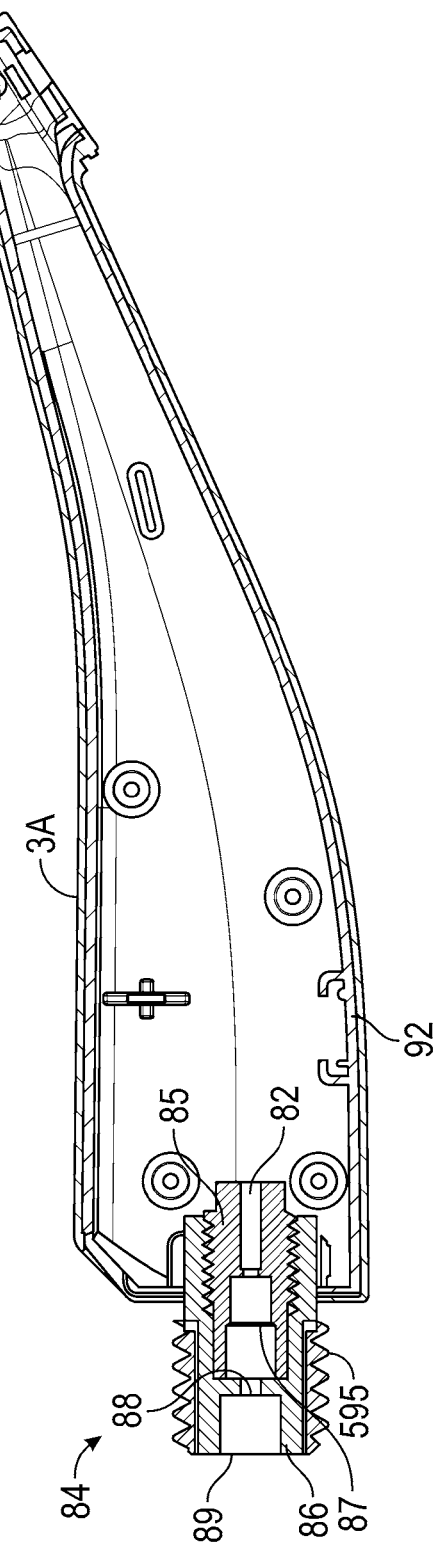
FIG. 12D is a side cross-sectional view of the handpiece shown in FIG. 12C.

FIG. 12C is a schematic side view of a handpiece 3A, in accordance with another embodiment. FIG. 12D is a side cross-sectional view of the handpiece 3A shown in FIG. 12C. The handpiece 3A shown in FIGS. 12C-12D may be generally similar to the handpiece 3A shown in FIGS. 12A-12B. However, unlike the embodiment of FIGS. 12A-12B, the handpiece shown in FIGS. 12C-12D may include a connector 84 having a shank and an engagement structure. The engagement structure can comprise a threaded engagement features 595. For example, the threaded engagement features 595 can comprise external threads disposed on an outer surface of the connector 84. As explained below, the connector 84 can be inserted into an interface member 4, and the connector 84 and interface member 4 can be rotated relative to one another to threadably secure the connector 84 and interface member 4. In the embodiment of FIGS. 12C-12D, therefore, the connector 84 can act as a male connector and the interface member 4 can act as the female connector. In other embodiments, however, the connector 84 can act as a female connector, and the interface member 4 can act as a male connector.

With reference to FIG. 12D, as explained above, the handpiece 3A can include a communications chip 92 and a high pressure fluid supply line 82 configured to convey pressurized fluid to a liquid jet assembly at a distal portion of the handpiece 3A. The connector 84 can include an inner tubular body 85 and an outer tubular body 86. As shown in FIG. 12D, the inner tubular body 85 can threadably couple to the outer tubular body 86. In addition, the threaded engagement feature 595 can be disposed on an outer surface of the outer tubular body 86. In arrangements where the connector is a female connector, the threaded engagement features 595 can be disposed on an inner surface of the connector so as to engage an outer surface (and threads formed thereon) of the interface member 4. Further, as explained above with respect to FIGS. 12A-12B, the connector 84 can include a first opening 88 and a second opening 89 proximal the first opening 88. The second opening 89 can be larger than the first opening 88.

A fluid line coupling portion 87 can be disposed proximal a proximal end of the high pressure fluid supply line 82. The coupling portion 87 can be configured to provide a transitional or coupling region between the high pressure tubing in the interface member 4 and the fluid supply line 82. In some embodiments, the coupling portion 87 can include a filter and one or more gaskets disposed therein. The gasket(s) can provide a substantial fluid seal for the high pressure fluid lines and/or friction between the handpiece 3A and interface member 4. The filter can act to filter particulates and debris from the treatment fluid before the treatment fluid reaches the orifice 66. Accordingly, as shown in FIG. 12D, the first opening 88 can define a necked portion between the second opening 89 and the coupling portion 87. The first opening 88 can be sized and shaped to closely conform to an outer surface of high pressure tubing extending from the interface member (e.g. tubing 518 shown in FIG. 26C). The first opening 88 can act, at least in part, to provide a high pressure fluid coupling between the tubing 518 of the interface member and the fluid supply line 82 of the tooth coupler 3.

C. Examples of Treatment Caps

Figure 13:
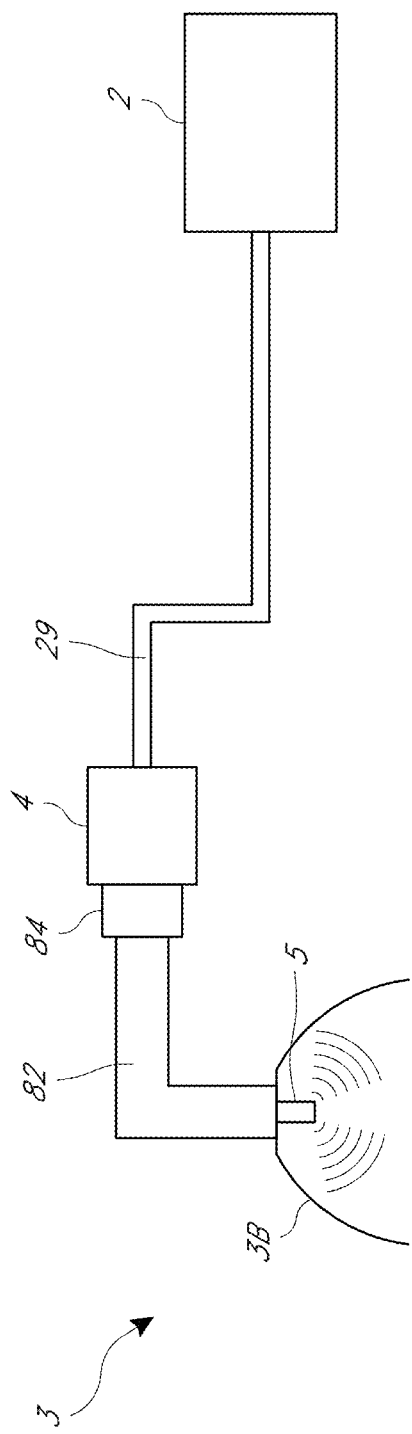
FIG. 13 is a schematic side view of a system in which the tooth coupler comprises a treatment cap 3B.

FIG. 13 is a schematic side view of a system 1 in which the tooth coupler 3 comprises a treatment cap 3B. As with the embodiment of FIGS. 12A-12D, a pressure wave generator 5 can be coupled to or formed with the treatment cap 3B. A high pressure fluid supply line 82 can supply pressurized fluid to the treatment cap 3B and/or pressure wave generator 5. As explained above, in some embodiments, a sealing cap may be coupled to the distal end 94 of the handpiece 3A to couple the handpiece 3A to the tooth 10. In other embodiments, a dental handpiece may not be used, and a dental practitioner may maneuver a sealing cap into a desired location in the patient's mouth. The patient may bite down on the treatment cap 3B to hold the treatment cap 3B in place during a treatment. In other embodiments, the treatment cap 3B can be clamped or attached to the tooth 10 (e.g., via a rubber dam clamp commonly used in endodontic procedures) such that the device doesn't require substantial user intervention during the procedure. In some embodiments, the clinician can adhere the treatment cap 3B to the tooth 10 using a tooth seal material.

The treatment cap 3B can couple to the interface member 4 using a connector 84 at or near a proximal end of the sealing sap 3B and/or at a proximal end of the supply line 82. The interface member 4 can be the same as (or similar to) the interface member 4 used to couple the handpiece 3A to the rest of the system 1. The connector 84 can also be the same as or similar to the connectors 84 shown in FIGS. 12A-12D with respect to the handpiece 3A. The use of a common interface member 4 and/or connector 84 can advantageously enable the use of any suitable working end with the console 2 and conduit 29. For example, if a particular treatment procedure is to be performed with a handpiece 3A, then the connector 84 on the handpiece 3A can engage the interface member 4 that is coupled to the console 2. If a particular procedure is to be performed with a treatment cap 3B, then the connector 84 on the treatment cap 3B (or coupled to the treatment cap 3B), which may have the same or similar structure as the connector 84 on the handpiece 3A, can engage the same interface member 4 as the handpiece 3A. In other embodiments, the working end of the system 1 (e.g., a portion of the system 1 that comprises the pressure wave generator 5) may couple to the tooth 10 and/or mouth of the patient in a different manner. For example, in some embodiments, a mouthpiece may be used to couple to the patient's mouth. In such embodiments, the common connector 84 can be coupled to the working end and can engage with the interface member 4, just as the handpiece 3A and treatment cap 3B engage with the interface member 4.

Thus, providing a common connector 84 and interface member 4 can advantageously enable the use of different working ends with the system 1 and console 2. For example, in some embodiments, a handpiece 3A can couple to the interface member 4, and a treatment cap 3B can couple to the same interface member 4. Still other working ends of the system may similarly couple to the same interface member 4.

D. Examples of a Tooth Sizer

In some embodiments, it can be important to measure a depth of a tooth chamber 128, e.g., a chamber exposed by way of an access opening 18 in the tooth 10. In some methods, a distal end of a pressure generator 5 can be positioned inside the tooth chamber 128, (e.g., a portion of the pulp cavity 11) with the distal end at a desired distance from a root canal orifice. By positioning the distal end of the pressure wave generator 5 at a suitable location in the tooth chamber 128, patient safety may be improved by, e.g., not over-pressurizing root canal spaces 13. By positioning the distal end of the pressure wave generator 5 at a suitable location in the pulp cavity 11, effectiveness of the acoustic waves 23 at generating cavitation and cleaning effects may be increased. Other treatment procedures, such as obturation procedures, may also be enhanced, as explained herein. Further, fluid circulation in portions of the tooth chamber 128 (e.g., circulation in a root canal space 13) may be enhanced. In various methods, the vertical distance between the distal end of the fluid dispenser and/or the pressure wave generator 5 and the highest point of the pulpal floor may be in a range from about 0 to 1 mm, 0 to 5 mm, 5 to 10 mm, 10 to 15 mm, 15 to 30 mm, 0 to 30 mm, or some other range.

Figure 14A:
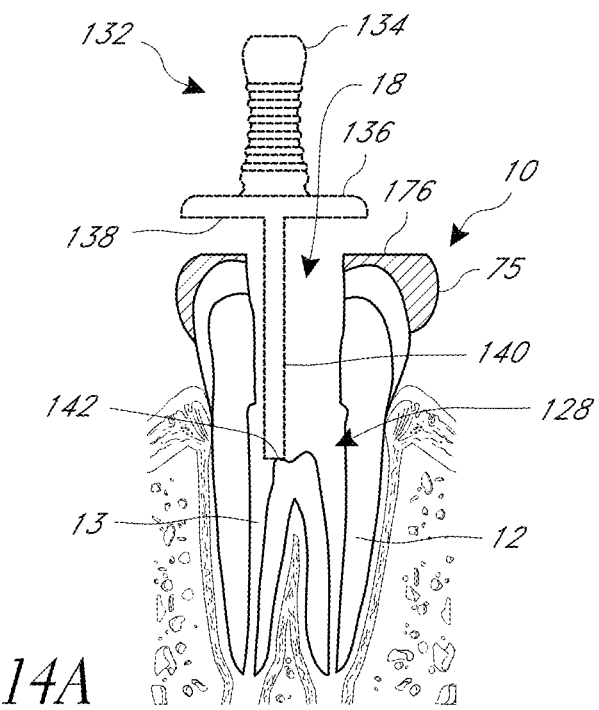
FIG. 14A schematically illustrates an example of a sizer inserted into a tooth chamber of an example tooth.
Figure 14B:
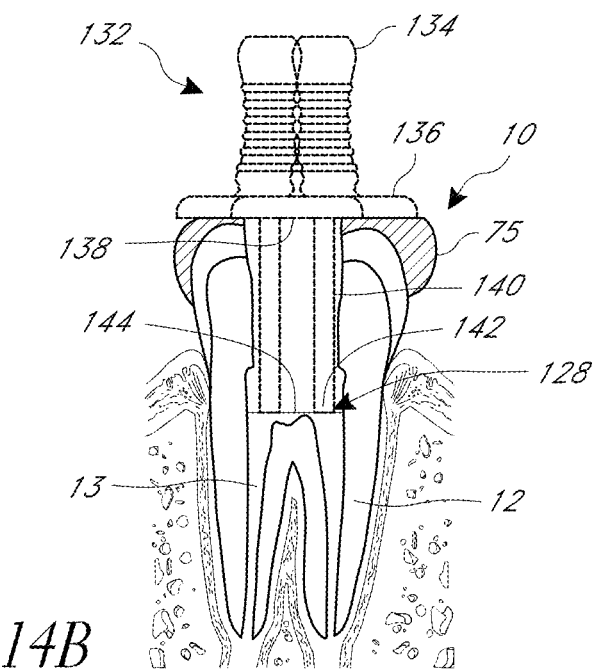
FIG. 14B schematically illustrates another example of a sizer inserted into the tooth chamber of a tooth.

With reference to the examples shown in FIGS. 14A and 14B, a set or kit of sizers can be used to measure the distance between a substantially flat surface 176 created by the tooth seal material 75 on the occlusal surface and the highest point on the pulpal floor.

FIG. 14A schematically illustrates an example of a sizer 132 inserted into a tooth chamber 128 of an example tooth 10. In this example, the sizer 132 is too large for the tooth chamber 128. FIG. 14B schematically illustrates another example of a sizer 132 inserted into the tooth chamber 128 of a tooth 10. In this example, the sizer 132 is the desired size for the tooth chamber 128. The sizer 132 can be moved laterally across the width of the chamber 128, with the solid lines showing the sizer 132 in a first position and the dashed lines showing the sizer 132 in a different position in the tooth chamber 128.

In the example shown in FIGS. 14A and 14B, the sizer 132 has a handle 134 (which may be similar to that of endodontic files), a pin 140 whose length varies among sizers of different sizes, and a disk 136 separating the handle 134 from the pin 140. The handle 134 can be grasped in the fingers or by dental pliers. The distal surface 138 of the disk 136 can be substantially flat. The sizer pin 140 can be inserted into the tooth chamber 128 of the tooth 10. The dental practitioner may determine the depth or size of the tooth chamber 128 by inserting sizers 132 with different pin lengths into the tooth chamber 128. In FIG. 14A, the sizer pin 140 is too long for the tooth chamber 128, because the sizer disk 136 extends above the flat surface 176 of the tooth seal 75 when a distal end 142 of the pin 140 touches the tooth chamber floor. A shorter sizer pin 140 can be selected and moved laterally around the tooth chamber 128. This process can be repeated until a sizer pin 140 is found that does not contact the pulp floor as it is moved around the tooth chamber 128. The sizer 132 having the correct or desired length may have the longest pin 140 that does not come in contact with the chamber floor when the sizer disk 136 is placed over and slid laterally (schematically shown by solid double-headed arrow 146 in FIG. 14B) on the flat surface 176 of the tooth seal 75. FIG. 14B shows a sizer 132 with an appropriate pin length for the illustrated tooth 10, because the distal end 142 of the pin 140 is positioned an appropriate height above the pulp or chamber floor (as indicated by the horizontal dashed line 144). This sizer 132 can be used to establish the depth of the tooth chamber 128.

In another implementation, a single sizer 132 can be used. The sizer pin 140 can be marked or scaled with measurement indicia, and the sizer disk 136 can be adjustable and configured to move up or down relative to the pin 140. The dental practitioner can insert the sizer 132 into the tooth chamber 128 and move the sizer disk 136 until it contacts the upper surface 176 of the tooth seal 75. The sizer 132 is then removed from the tooth chamber 128, and the position of the disk 136 relative to the measurement indicia provides a measurement of the depth of the tooth chamber 128. The distal end of the pressure wave generator 5 (or fluid inlet) may be positioned at a depth slightly less than the measured depth of the tooth chamber 128 so that the distal end is at a desired height above the pulp chamber or tooth chamber floor (e.g., from about 1 mm to about 5 mm above the floor).

In other embodiments, a ruler or depth gauge graduated with suitable indicia can be inserted into the tooth chamber 128 to measure the distance from an upper surface (e.g., the flat surface 176 of a tooth seal 75, if used) to a lower surface (e.g., the floor of the pulp chamber or tooth chamber 128).

In other embodiments, a radiograph (e.g., X-ray) of the tooth 10 may be taken, and the size or depth of the tooth chamber 128 determined from the radiograph.

An example method of determining a depth of a tooth chamber 128 comprises providing a kit comprising a set of sizers, where each sizer in the set is configured to measure a different tooth chamber depth. The method includes repeatedly inserting different sizers into the tooth chamber 128 to determine the depth. In some embodiments of the method, the depth is determined as the longest sizer that does not contact the pulpal floor. In some embodiments, the method includes moving a sizer laterally around the tooth chamber 128.

E. Examples of a Cap and Sealer

Figure 15A:
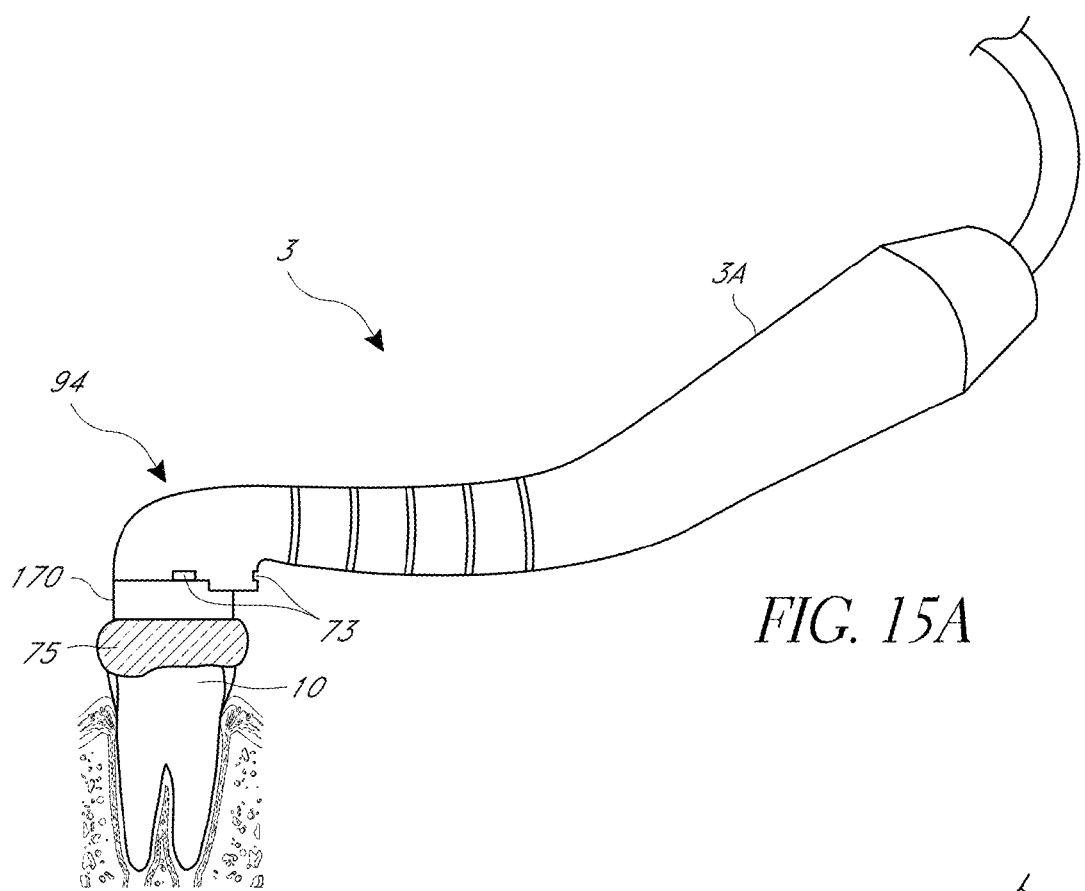
FIG. 15A is a schematic side view of a tooth coupler comprising a handpiece coupled to a tooth for a root canal treatment procedure.
Figure 15B:
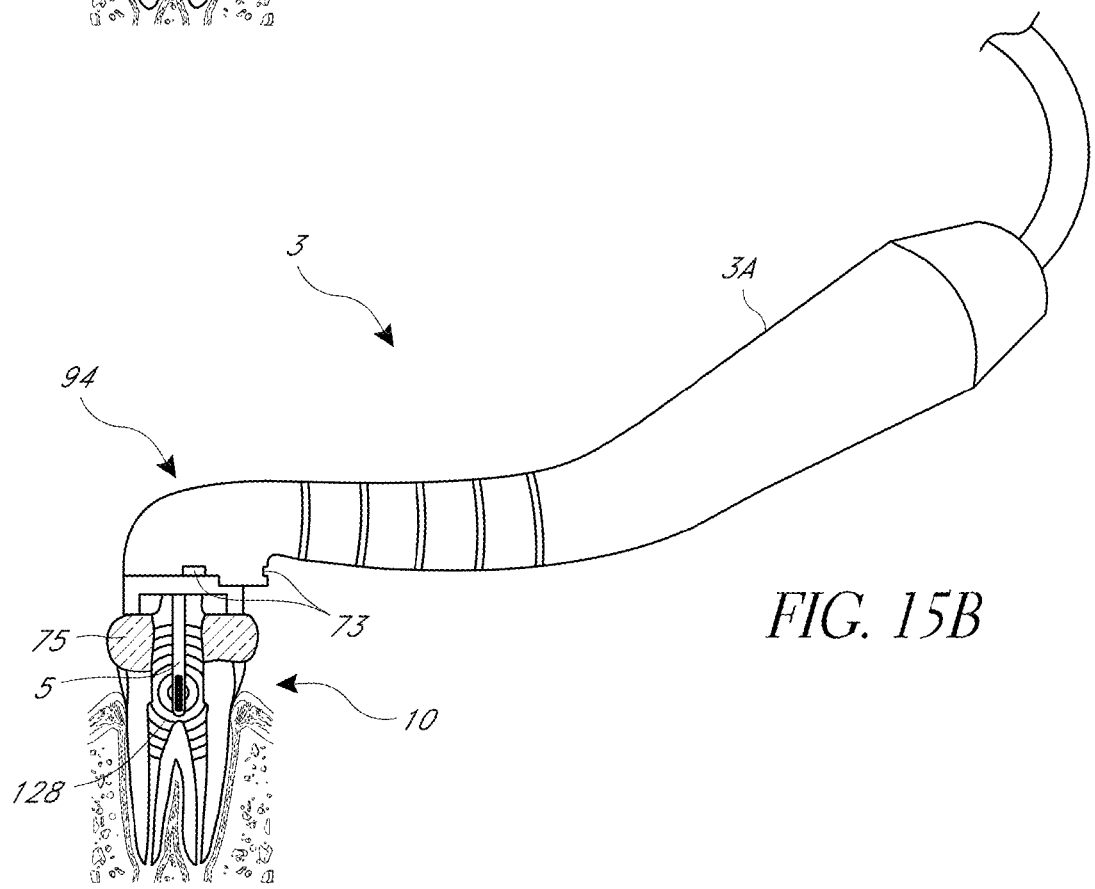
FIG. 15B is a schematic side cross-sectional view of a distal end of the handpiece illustrated in FIG. 15A.
Figure 15C:
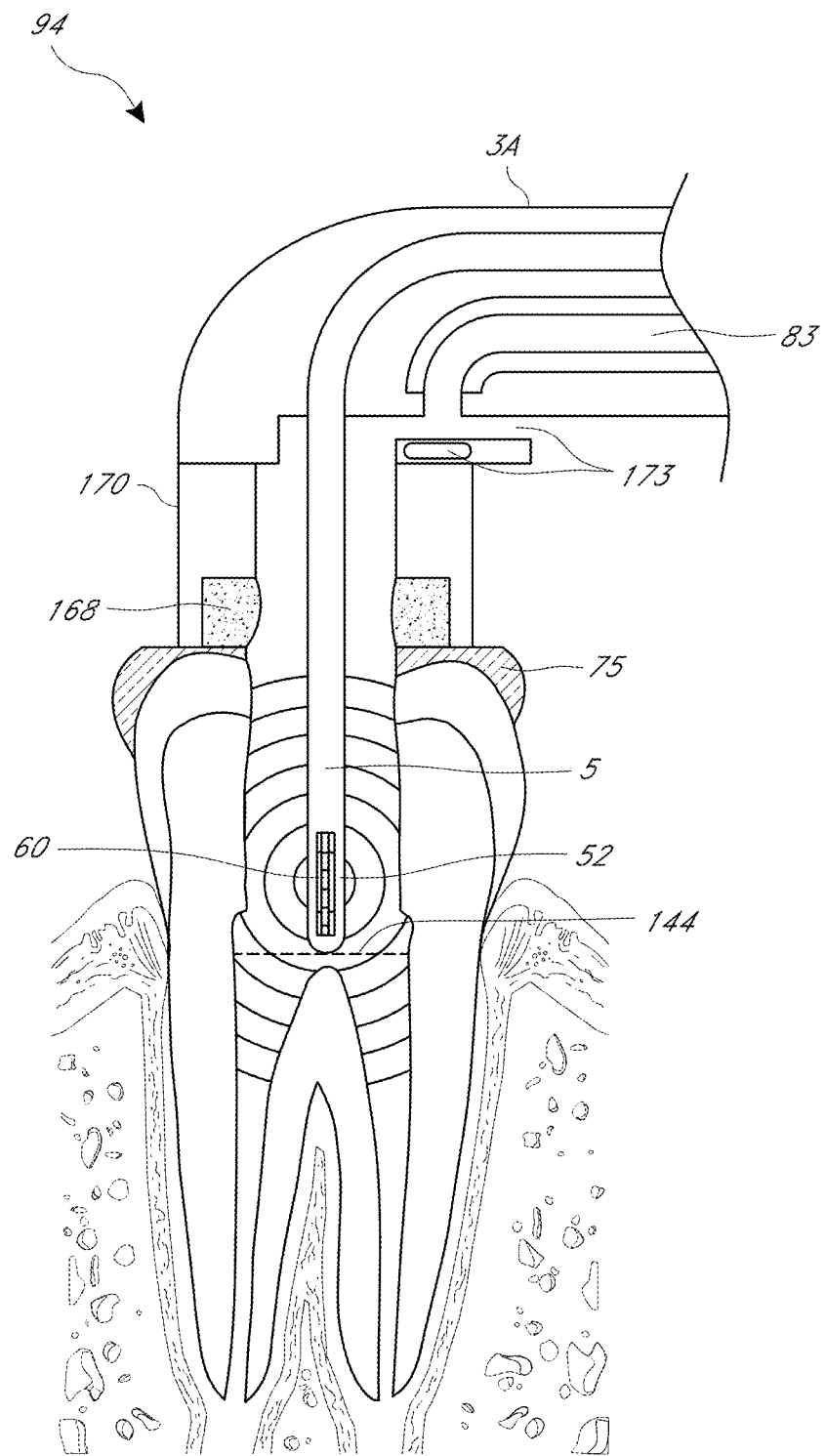
FIG. 15C is an enlarged cross-sectional view of the distal end of the handpiece shown in FIG. 15B.

As explained herein, the tooth coupler 3 can attach to a tooth 10 to enable the clinician to perform a suitable treatment procedure. FIG. 15A is a schematic side view of a tooth coupler 3 comprising a handpiece 3A coupled to a tooth 10 for a root canal treatment procedure. FIG. 15B is a schematic side cross-sectional view of a distal end 94 of the handpiece 3A illustrated in FIG. 15A. FIG. 15C is an enlarged cross-sectional view of the distal end 94 of the handpiece 3A shown in FIG. 15B. The handpiece 3A (or other tooth coupler 3) may include a sealing cap 170, or cap, (and an optional sealer 168 for providing a fluid seal) at or near the distal end 94 that can be sized so that a distal end of a pressure wave generator 5 is at a desired location in the tooth chamber 128. In some systems, each sizer 132 can be associated with a cap 170 that can be applied to the tooth 10. As described, the sealing cap 170 can, in some cases, be attached to the distal end 94 of the handpiece 3A or manually applied to the tooth 10 (e.g., without using the handle of a handpiece as explained above with respect to the treatment cap 3B). The cap 170 can be used so that the distal end of the fluid inlet or pressure wave generator 5 is located at the desired height above the chamber floor (indicated by the horizontal dashed line 144 in FIG. 15C) when the handpiece 3A is applied to the tooth seal 75. The size increments of the caps may be substantially equal to the size increments of the pins 140 on the sizers 132 illustrated in FIGS. 14A-14B. After the depth of the tooth chamber 128 is determined using the sizers 132, an appropriately-sized cap 170 can be selected and (optionally) mounted on the handpiece 3A. In other embodiments, the treatment cap 3B can comprise the sealing cap 170 and can be attached to the tooth 10 by the clinician, as explained herein. The cap 170 can be attached to the handpiece 3A chemically (e.g. glued, using an adhesive), mechanically (e.g., snapped or screwed), magnetically (e.g., by making the cap 170 and the distal end 94 of the handpiece 3A of opposite magnetic polarities), or by a combination of the foregoing. Alternatively, the cap 170 can be attached (e.g., glued) onto tooth 10.

The fluid connection created between the cap 170 and the tooth 10 (or tooth seal 75) may be flexible in nature such that the connection can accommodate movements in the handpiece 3A relative to the tooth 10 while maintaining the fluid connection. In some embodiments, the cap 170 is formed from a durable, biocompatible material, and the optional sealer 168 is used to accommodate movements and provide a good fluid connection. In other embodiments, the cap 170 may be made from one or more materials with different elasticities, permeabilities, and/or degrees of firmness. For example, a softer, more permeable material can be used to engage with the tooth 10, reducing (or potentially eliminating) the need for a separate sealer 168. Caps can have different shapes depending on which tooth 10 is being treated (e.g., molar, incisor, canine, etc.).

In some cases, a relatively small amount of force is used to create a positive seal between the tooth 10 (or tooth seal 75) and the cap 170. For example, in the case of a handpiece 3A, the pressure applied to the handpiece 3A to form the seal can be low enough for the operator to comfortably apply during the procedure. In case where the handpiece is not handheld, e.g., such as the embodiment of the treatment cap 3B shown in FIG. 13, the sealing cap 170 can be applied to the tooth 10 (or tooth seal 75) without excessive clamping/holding force (e.g., by the patient biting down, by the cap 170 being adhered to the tooth 10, etc.). The sealing cap 170 can be used throughout the procedure and can be configured to withstand chemical exposure (such as irrigants introduced during the procedure).

Accordingly, the distal end 94 of the handpiece 3A (or other tooth coupler 3) can include a cap 170 selected as described above so as to position the distal end of the pressure wave generator 5 at a desired distance above the chamber floor (shown by the horizontal dashed line 144 in FIG. 15C). In this example, the cap 170 includes a sealer 168 to assist in providing a substantially water-tight connection between the cap 170 and the upper surface 176 of the tooth seal 75 (see, e.g., FIGS. 15B and 15C). FIG. 15C shows that, in this example, the handpiece 3A includes the pressure wave generator 5 (e.g., a liquid jet device capable of forming a liquid jet 60), the suction port 83, and one or more vents 173. In this example, treatment fluid enters the chamber 128 via the liquid jet 60 and is removed by the suction port 83.

F. Examples of Magnetic Sealing Assemblies

In some embodiments, the tooth coupler 3 (e.g., handpiece 3A) can be coupled to and/or fluidly sealed with the tooth 10 by way of a magnetic sealing assembly 200. The use of the magnetic seal assembly 200 can provide a mechanical engagement between the tooth 10 and coupler 3, and can provide a seal such that fluids do not leak through the assembly 200. In addition, the magnetic seal assembly 200 can act as a safety mechanism. For example, if the clinician makes an abrupt movement relative to the tooth 10, the magnetic forces may be arranged such that the tooth coupler 3 breaks away from the tooth 10 without damaging the tooth 10. Moreover, the use of the magnetic sealing assembly 200 can act to align the distal portion of the handpiece 3A to the tooth 10. Advantageously, the magnetic sealing assembly 200 can substantially align and/or center the guide tube 52 with respect to the access opening 18 and tooth 10.

Accordingly, the magnetic forces provided by the magnetic seal assembly 200 may be sufficiently strong so as to provide secure mechanical engagement and a substantially sealed fluid connection. For example, the magnetic forces normal to the major surfaces of the magnets (e.g., the forces acting generally along a direction extending from the distal portion of the handpiece 3A towards the tooth 10) may be relatively strong so as to provide a fluid seal and to resist forces that tend to pull the magnets upwardly away from the tooth 10. However, the magnetic forces parallel to the major surfaces of the magnets (e.g., forces acting generally parallel to the tooth seal 75 and/or transverse to the pressure wave generator 5) may be sufficiently weak such that, if the clinician inadvertently moves the handpiece transversely, the magnets can break away to avoid harming the patient.

Figure 16A:
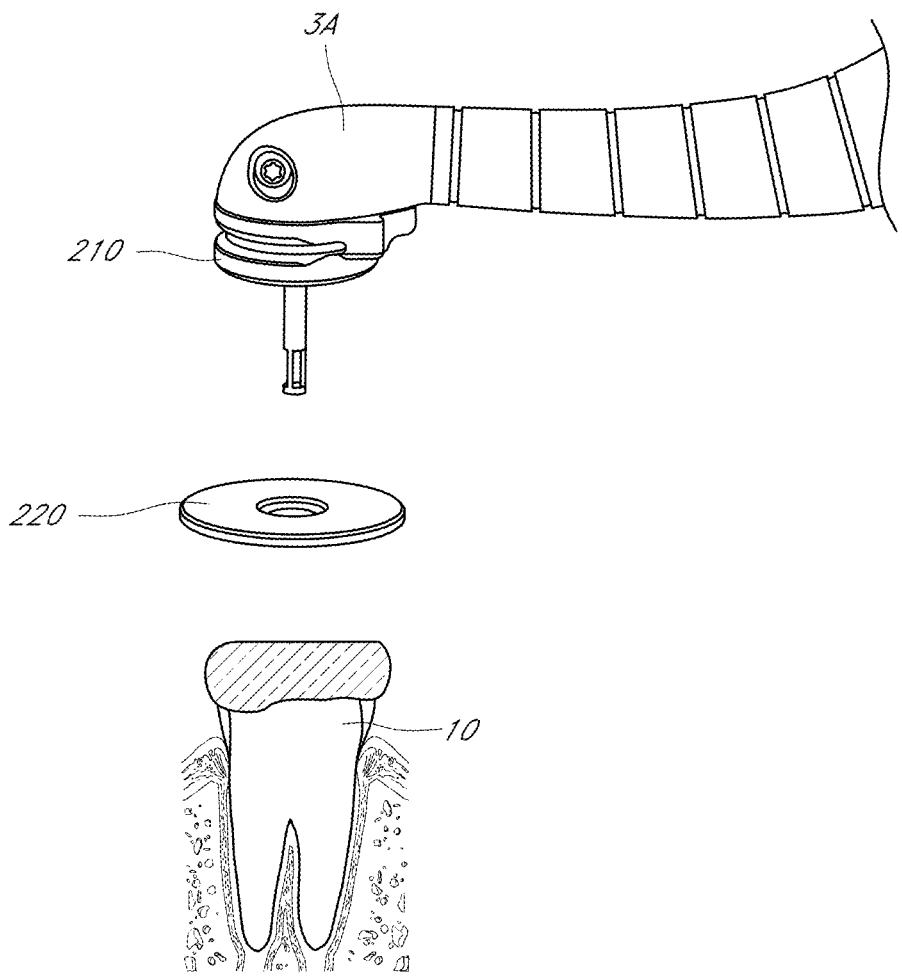
FIG. 16A is a perspective, exploded view of one embodiment of a handpiece configured to couple to a treatment tooth by way of a magnetic seal assembly.
Figure 16B:
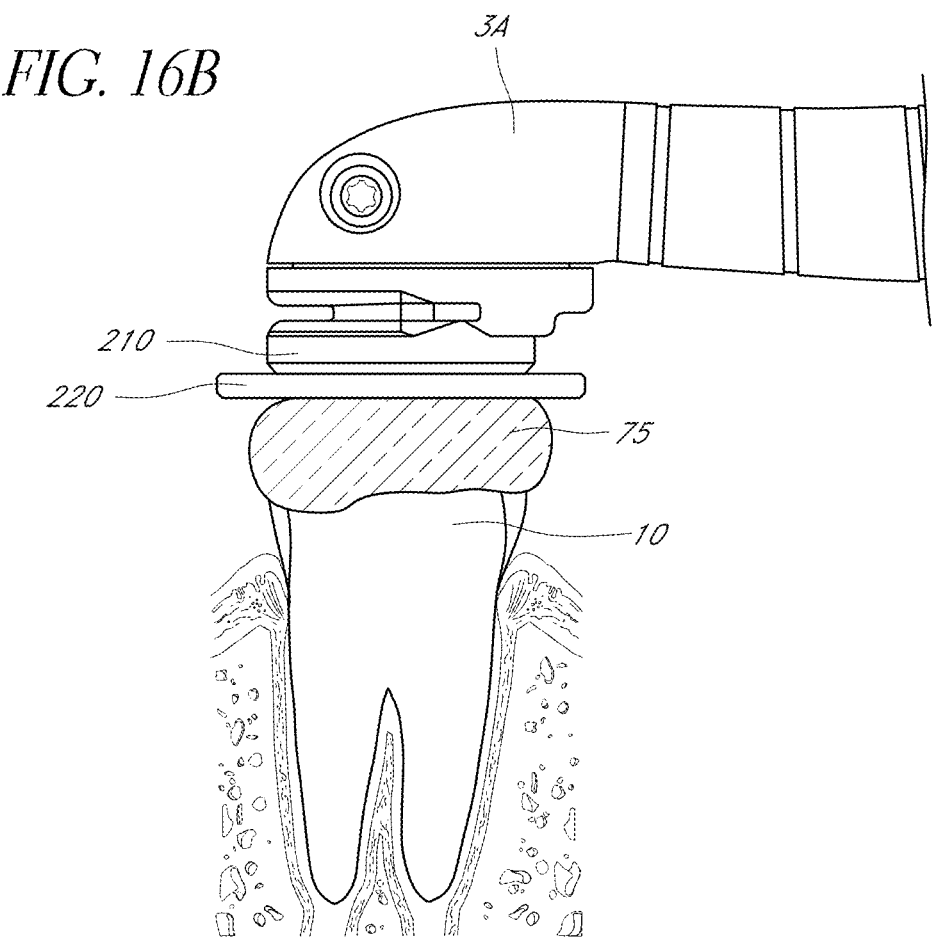
FIG. 16B is a schematic side view of the handpiece coupled to the tooth with the magnetic seal assembly.
Figure 16C:
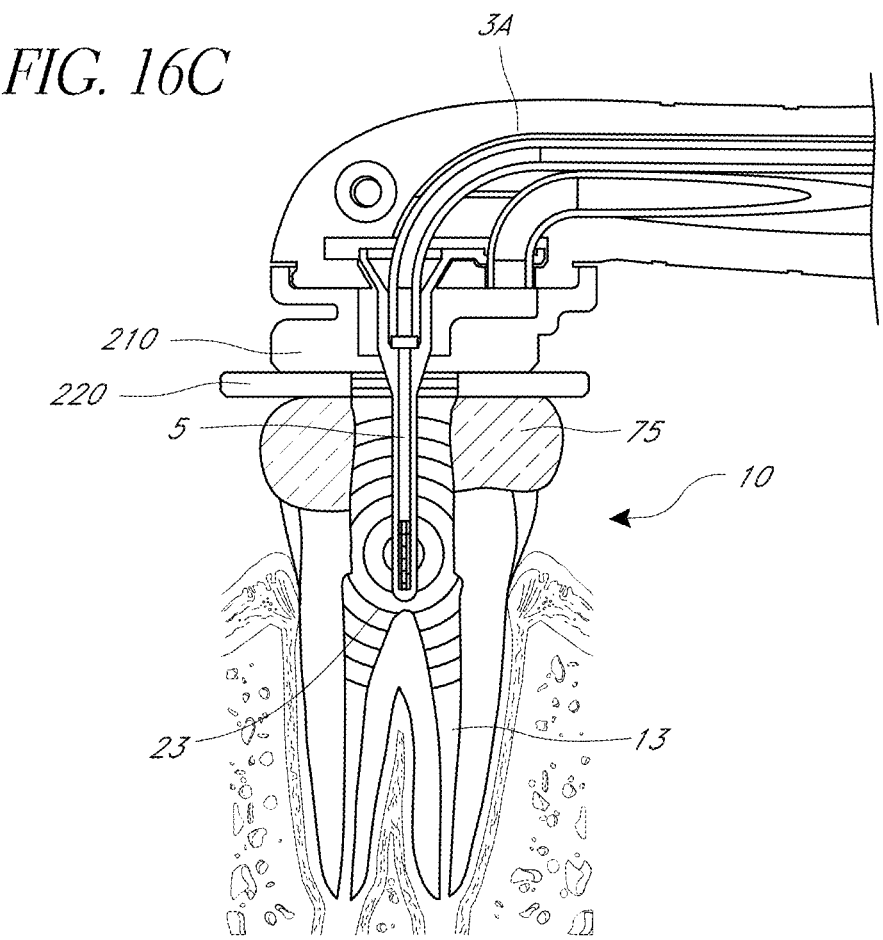
FIG. 16C is a side cross-sectional view of the handpiece and magnetic seal assembly shown in FIG. 16B.

In some embodiments, the magnetic sealing assembly 200 may include a handpiece magnet 210 and an occlusal magnet 220, as shown in FIGS. 16A-16C. In some embodiments, a magnetic sealing assembly 200 may also include a plurality of spacer magnets 230 (alternatively referred to herein as magnetic spacers), as shown in FIGS. 17A-17C and 18. The spacer magnets 230 can be arranged to provide the desired spacing between the distal end of a pressure wave generator 5 and a floor of the tooth chamber 128, as explained above. Although the handpiece 3A is shown in FIGS. 16A-18, it should be appreciated that any other tooth coupler 3 may be used, such as a treatment cap 3B.

1. Examples of Magnetic Assemblies with Occlusal and Handpiece Magnets

FIG. 16A is a perspective, exploded view of one embodiment of a handpiece 3A configured to couple to a treatment tooth 10 by way of a magnetic seal assembly 200. FIG. 16B is a schematic side view of the handpiece 3A coupled to the tooth 10 with the magnetic seal assembly 200. FIG. 16C is a side cross-sectional view of the handpiece 3A and magnetic seal assembly 200 shown in FIG. 16B. The magnetic assembly 200 may be used to provide a seal on the occlusal surface of the tooth 10. The magnetic assembly may also be configured to adjust the position of the handpiece tip (e.g. pressure wave generator 5) with respect to the pulp chamber floor. As shown in FIGS. 16A-C, for example, the magnetic assembly 200 can include a handpiece magnet 210 coupled to or formed with the handpiece 3A. An occlusal magnet 220 can be attached or coupled to the tooth 10 by way of, e.g., various types of attachment media, such as the tooth seal 75. The disclosed assembly can seal and/or attach the handpiece 3A to the tooth 10 and can enable the user to adjust the handpiece tip relative to a chamber in the tooth 128 or another position on the tooth 10. For example, the handpiece magnet 210 and occlusal magnets 220 can have opposite polarities such that the occlusal magnet 210 is attracted to the occlusal magnet 220. In some embodiments, the occlusal magnet 220 may not be a magnet; rather, the occlusal magnet 220 may comprise a ferrous material that is attracted to the handpiece magnet 210. Alternatively, the handpiece magnet 210 may comprise a ferrous metal attracted to the occlusal magnet 220. In some embodiments, a user can rotate the handpiece 3A to a desired location, and the magnetic assembly can rotate with the handpiece 3A while maintaining a fluidic and/or mechanical seal between the handpiece 3A and the tooth 10. In addition, the handpiece magnet 210 and occlusal magnet 220 can cooperate to substantially align and/or center the guide tube 52 with respect to the access opening 18 and tooth 10.

Handpiece Magnet

The handpiece 3A may include a fixed ring magnet on the face of the handpiece 3A. The handpiece magnet 210 may be integrally formed with the handpiece 3A, may be mechanically coupled to the handpiece 3A, and/or may be removable engaged with the handpiece 3A. In some arrangements, the handpiece magnet 210 may be separate from the handpiece 3A and can be attached to the handpiece 3A by the user. In other arrangements, the handpiece 3A can be manufactured to include the handpiece magnet 210. The handpiece magnet 210 can act as a magnetic interface for the handpiece 3A. For example, the handpiece magnet 210 can be configured to interact with other magnets to orient the handpiece 3A relative to the anatomy (and/or components) associated with the other magnets, e.g., the tooth 10. In some embodiments, different polarities can be used for handpiece magnets 210 used in different types of tooth couplers 3. For example, in some embodiments, a positive polarity can be used with a handpiece magnet 210 for a molar handpiece 3A, and a negative polarity can be used with a handpiece magnet 210 for a pre-molar handpiece 3A, or vice versa. Having different polarities in different types of tooth couplers 3 can act as a safety measure such that the correct tooth couplers 3 couple to the appropriate types of teeth and occlusal magnets 220.

Occlusal Magnet

The occlusal magnet 220 may be adhered to the occlusal surface of a built-up tooth 10 with, e.g., a UV-cure adhesive, a tooth seal material, a bite-registration material, etc. The occlusal magnet 220 can act as a base magnet to which other magnets can be coupled. For example, the occlusal magnet 220 can be secured to the tooth 10, and any suitable number or type of magnets can be coupled to the occlusal magnet 220. The inner diameter of the occlusal magnet 220 may be the same as or substantially the same as the inner diameter of the spacer magnet(s) 230. The outer diameter of the occlusal magnet 220 may be in a range of between about 10 mm and about 17 mm. The outer diameter of the occlusal magnet 220 may be larger than the magnetic spacers 230. The upper limit of the outer diameter may be constrained by interference with adjacent teeth. The thickness of the occlusal magnet 220 may be approximately 1 mm thick depending on durability of the magnet, e.g., in a range of about 0.5 mm thick and about 1.5 mm thick.

Figure 17A:
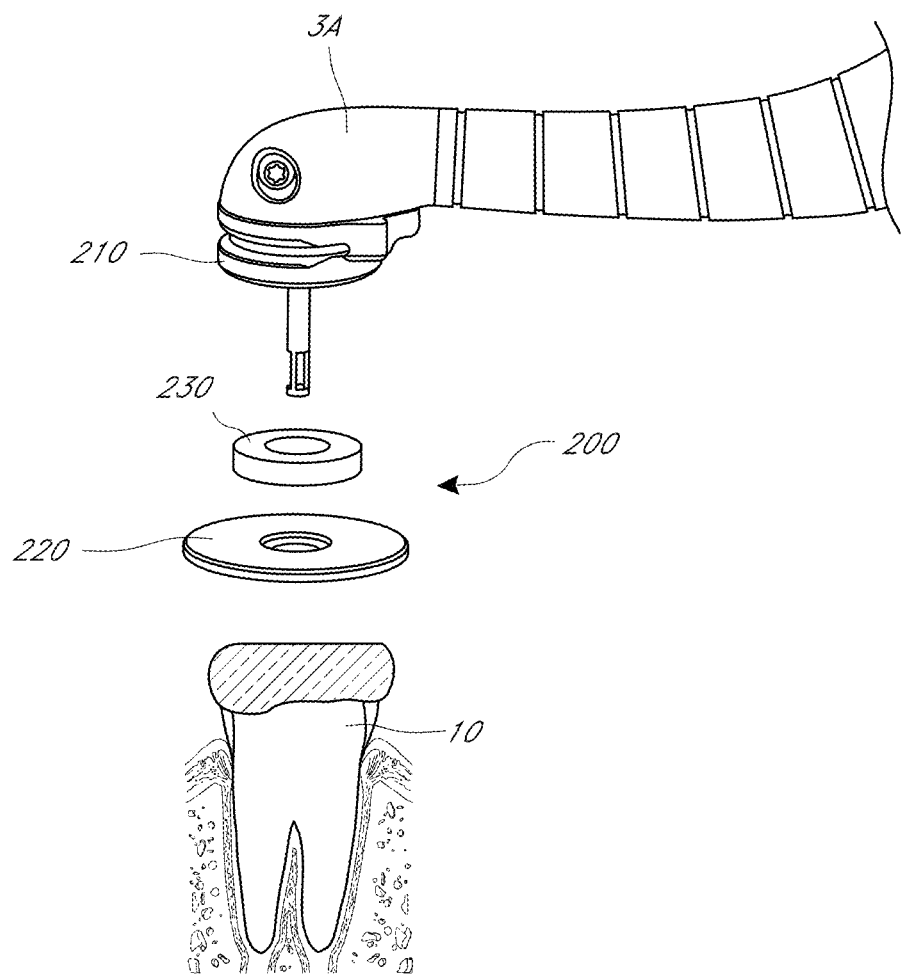
FIG. 17A is a perspective, exploded view of one embodiment of a handpiece configured to couple to a treatment tooth by way of a magnetic seal assembly.
Figure 17B:
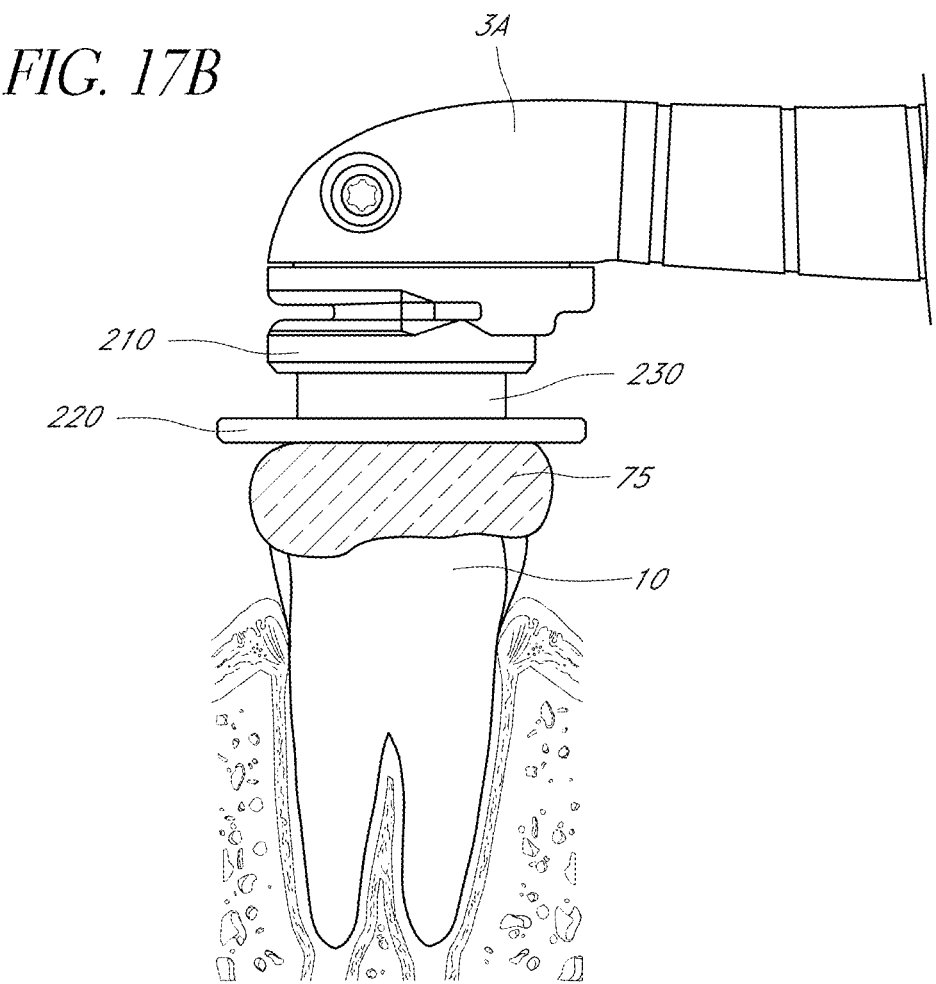
FIG. 17B is a schematic side view of the handpiece coupled to the tooth with the magnetic seal assembly.

2. Examples of a Handpiece and Magnetic Assembly Applied to a Tooth Seal with Spacer Magnets FIGS. 17A-C illustrate many of the components shown in FIGS. 16A-C. However, in the embodiment illustrated in FIGS. 17A-C, a magnetic spacer 230 is included. FIG. 17A is a perspective, exploded view of one embodiment of a handpiece 3A configured to couple to a treatment tooth 10 by way of a magnetic seal assembly 200. FIG. 17B is a schematic side view of the handpiece 3A coupled to the tooth 10 with the magnetic seal assembly 200. FIG. 17C is a side cross-sectional view of the magnetic sealing assembly 200 disclosed in FIG. 17B. For example, a magnetic assembly 200 may be used to seal and/or couple the handpiece 3A to the tooth 10. As shown in FIGS. 17A-C, for example, the magnetic assembly can include a handpiece magnet 210 coupled to or formed with the handpiece 3A. In various procedures, such as a root canal procedure, an access opening can be formed in the tooth 10. A sealing and adhesion material (e.g., tooth seal 75) can be applied to the tooth 10 around the access opening. In some arrangements, the sealing and adhesion material can be planarized or otherwise shaped to support a portion of the magnetic seal assembly 200. For example, the magnetic seal assembly 200 can include an occlusal magnet 220. The occlusal magnet 220 can be attached or coupled to the sealing and adhesion material (e.g., attachment media). One or more magnetic spacers (or spacer magnets) 230 can couple the handpiece magnet 210 to the occlusal magnet 220. The magnetic spacers 230 can be configured to provide a separation distance between the handpiece 3A (and/or pressure wave generator 5) and a portion of the tooth 10 (e.g., a floor or bottom surface of the pulp chamber).

For example, as explained herein with reference to FIGS. 14A-14B, the clinician can use the sizers 132 to determine a suitable separation distance between the floor of the tooth chamber 128 and the distal end portion of the pressure wave generator 5 (e.g., component 144 in FIG. 15C). Once the clinician determines the desired separation distance, a suitable spacer magnet 230 can be selected. In the embodiment of FIGS. 17A-17C, the system can include a kit of spacer magnets 230, each spacer magnet 230 having a different size, e.g., a different thickness corresponding to a desired separation distance. For example, if the clinician determines that the separation distance is about X, then the clinician can select one or more spacer magnets 230 that corresponds approximately to the separation distance X. The clinician can insert the selected spacer magnet(s) 230 between the occlusal magnet 220 and the handpiece magnet 210 to provide the desired spacing between the distal portion of the pressure wave generator 5 and the floor of the tooth chamber 128.

Figure 18:
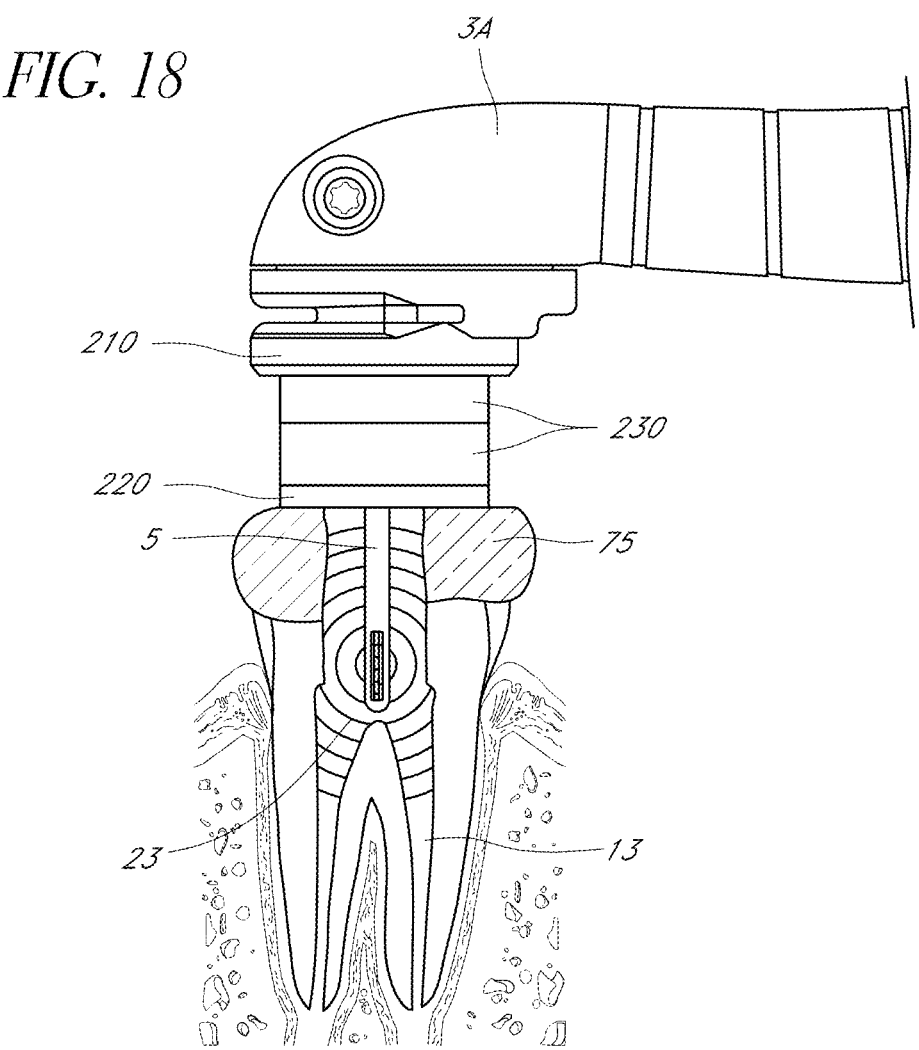
FIG. 18 is a schematic side view of a handpiece coupled to a treatment tooth.

FIG. 18 is a schematic side view of a handpiece 3A coupled to a treatment tooth 10. FIG. 18 illustrates many of the components shown in FIGS. 17A-C. In FIG. 18, the handpiece 3A can be applied to the tooth 10 and substantially sealed onto the tooth 10. A pressure wave generator 5 can be coupled to or formed with the handpiece 3A and can be disposed in a prescribed location in the tooth 10 by way of a combination of magnets. However, in the embodiment illustrated in FIG. 18, a plurality of magnetic spacers 230 is coupled between the handpiece magnet 210 and the occlusal magnet 220. In particular, FIG. 18 illustrates two magnetic spacers 230 between a handpiece magnet 210 and an occlusal magnet 220. Although two magnetic spacers are shown, it should be appreciated that any suitable number of magnetic spacers may be used. For example, a kit of magnetic spacers 230 can be provided to the clinician. The kit of spacers 230 can include a plurality of spacer magnets 230. Each of the plurality of spacer magnets 230 may have substantially the same size or thickness in some embodiments. In other embodiments, each of the plurality of spacer magnets 230 may have a different size or thickness. The handpiece magnet 210, the spacer magnets 230 and the occlusal magnet 220 can act to seal and/or mechanically couple the handpiece 3A to the tooth 10 (e.g., to provide a substantially sealed liquid pathway between the handpiece 3A and the tooth 10).

Accordingly, as explained herein with respect to FIGS. 17A-17C, the clinician may determine a desired separation distance X between the distal portion of the pressure wave generator 5 and the floor of the tooth chamber 128. The clinician can select from the kit of spacer magnets 230a set of magnets that will provide the desired separation distance X, and can couple the selected set of magnets 230 between the occlusal magnet 220 and the handpiece magnet 210.

As shown in FIG. 18, a pressure wave generator 5 (such as a liquid jet device) can be activated. Pressure waves 23 can propagate in a tooth chamber 128 (e.g., in treatment fluid in the tooth chamber 128 in some embodiments) to clean the tooth 10. For example, the pressure waves 23 can propagate through the tooth chamber 128 or tooth 10 and can have energy sufficient to substantially remove organic material and unhealthy tissue from the tooth 10 and/or root canals. In FIG. 18, for example, the pressure wave generator 5 can include a proximal portion coupled to or formed with the handpiece 3A and a distal portion configured to be disposed in the tooth chamber 128. As shown in the exploded view in FIG. 17A, for example, the distal portion of the pressure wave generator 5 can pass through an opening or aperture formed through the handpiece magnet 210, the spacer magnet(s) 230, and the occlusal magnet 220.

Thus, each of the handpiece magnet 210, the spacer magnet(s) 230, and the occlusal magnet 220 can include or define an inner diameter (defined by the opening or aperture) and an outer diameter. In some embodiments, the inner diameters of the occlusal magnet 220 and an adjacent spacer magnet 230 can be the same or substantially the same. By having the same or substantially the same inner diameters, the occlusal magnet 220 and the adjacent spacer magnet 230 can be accurately aligned by the attractive magnetic forces. In some embodiments, the inner diameters of all the magnets (e.g., the handpiece magnet 210, the spacer magnet(s) 230, and the occlusal magnet 220) can be the same or substantially the same to improve alignment.

In various embodiments, the magnetic strength (e.g., the attractive force) between the occlusal magnet 220 and one or more spacer magnets 230 can be less than the magnetic strength between the one or more spacer magnets 230 and the handpiece magnet 210, and/or can be less than the magnetic strength between adjacent spacer magnets 230. In such embodiments, for example, the clinician can break the seal between the one or more spacer magnet(s) 230 and the occlusal magnet 220 by applying a force to the handpiece 3A in a direction opposite to or away from the occlusal magnet 220 with a magnitude that exceeds the attractive force between the occlusal magnet 220 and the one or more spacer magnet(s) 230, e.g., the attractive magnetic force between the occlusal magnet 220 and an adjacent spacer magnet 230. The clinician can thereby remove the handpiece 3A, handpiece magnet 210, and the spacer magnet(s) 230 from the treatment site while leaving the occlusal magnet 220 coupled to the tooth 10 (for later removal).

In other embodiments, the magnetic interfaces (e.g., the interfaces between the magnets in the magnetic assembly) can be designed to have attractive magnetic forces such that the clinician can separate the handpiece 3A from the occlusal magnet 220 at any other suitable interface. For example, in some embodiments, the handpiece 3A can be separated from the occlusal magnet 220 at an interface between two adjacent spacer magnets 230, and/or between a spacer magnet 230 and the handpiece magnet 210. In such embodiments, the magnetic strength at the separation interface (e.g., the interface at which the magnetic assembly is to be separated) is less than the magnetic strength at other magnetic interfaces.

Figure 19:
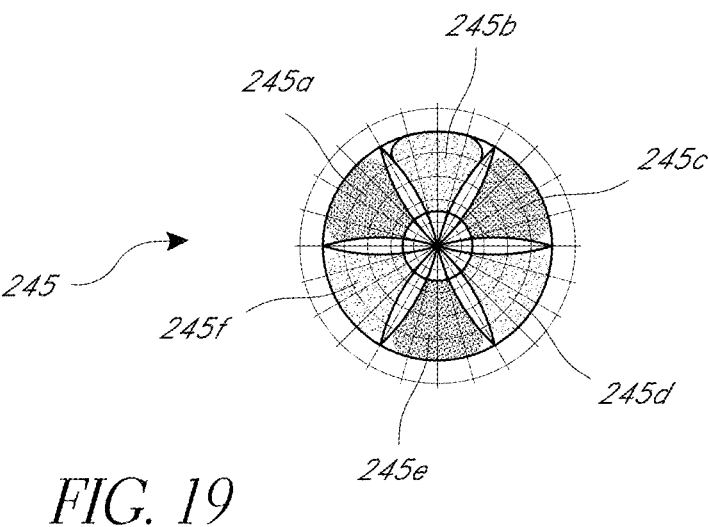
FIG. 19 is a schematic illustration of a multipoled magnet configured for use in various magnets of the disclosed magnetic assemblies.

FIG. 19 is a schematic illustration of a multipoled magnet 245 configured for use in various magnets of the disclosed magnetic assemblies. For example, the multipoled magnet 245 can be configured for use in a handpiece magnet 210, an occlusal magnet 220, and a magnetic spacer 230. As shown in FIG. 19, for example, the multipoled magnet 245 can included alternating polarities (e.g., north and south) at different circumferential positions of the magnet. For example, a multipoled magnet 245 can include north regions 245a, 245c and 245e, and south regions 245b, 245d and 245f. As shown in FIG. 19, the north and south regions can alternate such that one half of the magnet (e.g., the top half) includes two north regions 245a and 245c and one south region 245b and such that the other half of the magnet (e.g., the bottom half) includes two south regions 245d and 245f and one north region 245e. Although six polarities are shown, it should be appreciated that any suitable number of north and south regions may be used. For example, in some embodiments, four alternating polarities (e.g., north and south) can be used at different circumferential positions of the magnet. In other embodiments, eight alternating polarities (e.g., north and south) can be used at different circumferential positions of the magnet. Any suitable number of poles can be used.

In various embodiments of the magnetic assemblies disclosed herein, the use of a multi-poled magnet 245 magnetized through its thickness can be used to allow for separation of the magnets by rotation of the handpiece 3A. For example, to secure two adjacent magnets, the two magnets can be aligned such that regions of opposite polarity (e.g., a north region and a south region) are proximate one another, which results in an attractive force between the two adjacent magnets. In some embodiments, the clinician can separate two adjacent, coupled magnets (e.g., a spacer magnet 230 and the occlusal magnet 220, two adjacent spacer magnets 230, and/or a spacer magnet 230 and the handpiece magnet 210) by applying a torque to the handpiece 3A sufficient to cause the polarities to become aligned, e.g., sufficient to cause a north region of one magnet to align with a north region of the other magnet and/or to cause a south region of one magnet to align with a south region of the other magnet. Thus, in some embodiments, two adjacent magnets can be separated by rotating the handpiece 3A at a sufficient applied torque.

Spacer Magnets

A plurality of spacer magnets 230 with various thicknesses may also be provided, e.g., between the handpiece magnet 210 and the occlusal magnet 220. In the disclosed embodiment, there are 3 magnetic spacers 230 having approximate thicknesses of about 1 mm, 2 mm, and 3 mm, respectively. These three spacers can be connected to the handpiece magnet 210 to offset the handpiece 3A from the tooth 10 by a separation distance in a range of about 0 mm to about 5 mm. The spacer magnets 230 may have about the same inner diameters and outer diameters to maintain alignment and strength while stacking. The spacer magnets 230 may have an inner diameter in a range of between about 0.01 mm to about 10 mm and may have an outer diameter in a range of between about 1 mm and about 17 mm. The surface area and strength of the magnet may be important factors in determining the magnets' ability to maintain a fluid seal between the inner and outer diameter of the magnets.

General Properties

In some embodiments, the magnets described herein may be made from neodymium. The grade of each magnet can be selected for the magnetic strength desired. Each magnet may be coated to protect against chemicals. Each magnet may also be coated to be biocompatible. The coating may also provide mechanical strength and durability to counteract the brittleness of neodymium. The coatings and magnets may be sterilizable, for example, with gamma radiation. The coating and magnets may also be able to withstand manufacturing and operating temperatures.

The inner diameter of the disclosed magnets may be in the range of about 0.5 mm to about 10 mm. In some arrangements, the inner diameter of each of the magnets is about the same. For example, the magnetic spacer(s) 230 and the occlusal magnet 220 may have the same or substantially the same inner diameter. Advantageously, the magnetic spacer(s) 230 can be accurately aligned with the occlusal magnet 220 by designing the spacer magnet(s) 230 and the occlusal magnets 220 to have the same or about the same inner diameter. In some embodiments, all the magnets of the magnetic assembly (including, e.g., the handpiece magnet 210, the spacer magnet(s) 230 and the occlusal magnet 220) may have the same or substantially the same inner diameters. In other embodiments, the inner diameters of each magnet may differ.

The outer diameters of the magnets may be in a range of about 1 mm to about 17 mm. The outer diameters for each magnet may be dissimilar between the three magnetic sections. The thickness of the magnetic plates may range from about 0.01 mm to about 10 mm. The outer diameter of the occlusal magnet 220 may be larger than the magnetic spacers 230.

Any of the magnets disclosed herein (e.g., the occlusal 220, spacer 230, and/or handpiece magnets 210) may be ferromagnetic, paramagnetic, diamagnetic, etc. The magnets disclosed herein can include magnetic metallic elements, composites, rare-earth magnets (e.g. samarium-cobalt, neodymium-iron-boron), single-molecule magnets, single-chain magnets, nano-structured magnets, or electromagnets. In embodiments using electromagnets, for example, a power supply may be provided in the console 2, and power lines can couple to the handpiece 3A by way of electrical conduits.

One or more of the magnets may be made from neodymium. One or more of the magnets may be thoroughly or partially coated with another material to, for example, reduce brittleness. This may, therefore, reduce the shattering or chipping of the magnets. The coating can also provide a food-grade or biocompatible interface to allow color-coding, to avoid corrosion, to improve mechanical strength, to improve sealing on the surface of the magnets, etc.

For example, one or more of the disclosed magnets (e.g., the occlusal 220, spacer 230, and/or handpiece magnets 210) may be coated in Parylene C or Parylene N for mechanical strength and durability to counteract the brittleness of neodymium. In one embodiment, for example, a thin conformal coat of silicone may provide the coloration of the magnet, the sealability to fluids in between the magnets (e.g., to provide a liquid seal between the various magnets), and the spacing between the magnets to reduce magnetic strength when stacked. In some embodiments, the coating can be applied between adjacent magnets to reduce the magnetic strength between the adjacent magnets.

The magnets can be color-coded to assist the operator with identification of a suitable spacer magnet 230 to use and/or to guide the operator to use the proper combination of the spacers. For example, in some embodiments, it can be important to space the distal portion of the pressure wave generator 5 from the floor of the pulp chamber (or other surface of the tooth 10) by a desired amount, such that the pressure wave generator 5 is sufficiently spaced from the tooth 10. To assist the clinician or operator in providing sufficient separation between the pressure wave generator 5 and the tooth 10, thicknesses of the spacer magnets 230 can be selected to provide adequate separation.

The spacer magnets 230 can be color-coded such that the colors correspond to a measure of the tooth 10. In some embodiments, the measure of the tooth 10 can be a depth of the pulp chamber. Further, in some embodiments, for example, a kit can be provided in which each spacer magnet 230 corresponds to a corresponding measuring tool (and that may have the same color as the corresponding spacer magnet 230). The measuring tool can be used to measure or estimate a depth of the pulp chamber, or any other appropriate dimension of the tooth 10. When the clinician determines that a particular measuring tool corresponds to a suitable separation distance between the tooth 10 (e.g., floor of pulp chamber) and pressure wave generator 5 (and/or handpiece 3A), the clinician can select one or more spacer magnets 230 that corresponds to the particular selected measuring tool and that will provide the suitable separation distance. Thus, in some embodiments, a particular spacer magnet 230 may correspond to a corresponding measuring tool, and may be color-coded or otherwise identified with the corresponding measuring tool. Although color-coding is one way to identify a spacer magnet 230 with a corresponding measuring tool, it should be appreciated that any other suitable way to identify a particular spacer with a corresponding measuring tool may be used.

In various embodiments, spacers may be sized, for example, to have a thickness in a range of about 1 mm to about 6 mm, in increments of about 1 mm. A corresponding measuring tool (e.g., a gauge with the same color) may also be provided for each spacer. In another embodiment, the spacers can have thicknesses of about 1 mm, 2 mm, and 3 mm, and other separation distance values can be provided by combining these 3 spacers. For example, a 4 mm spacer can be made by attaching a 1 mm spacer and a 3 mm spacer. The measuring tool (gauge) for this 4 mm spacer, for example, may have the colors of the respective 1 mm and 3 mm spacers. Such a color coding (or other way of identifying the combination of spacers) would tell the operator to combine a 1 mm spacer and a 3 mm spacer to make a 4 mm spacer.

The spacers may be color-coded only on one side to avoid an attempt to attach them together on same-polarity surfaces, which would make them repel each other. The spacer magnets 230 can thus be color-coded to guide the operator as to what surfaces should be attached together (e.g., opposite polarities). Colors may be chosen to be easily identified even by users who have impaired vision or color-blindness.

The coatings on the various magnets may be soft to improve sealing. The coatings and magnets may be sterilizable with gamma radiation, steam-autoclave, chemical sterilization, or other methods. The magnets and their coatings may be made in such a way to withstand one or various methods of sterilization. In addition, the magnets and their coatings may be made to withstand manufacturing and operating temperatures. The coating may also be made in such a way to tolerate exposure to various chemicals; in particular, those chemicals that may be used during the procedure, e.g. NaOCl, EDTA, etc.

The inner diameter of all the magnets in the magnetic assembly (e.g., the handpiece magnet 210, the spacer magnet(s) 230, and the occlusal magnet 220) can vary or can be the same. In one embodiment, the inner diameter of each of the magnets is the same, or substantially the same, to enhance the automatic alignment of the magnets. The outer diameters of all the magnets also may or may not be the same, or substantially the same. In one embodiment for instance, the outer diameters are substantially the same, e.g., about 10 mm in some arrangements. Each magnet and item in the kit may be configured to be multiple-use (e.g., reusable) or one-use only (e.g., disposable).

The magnetic forces and strength of the spacers may be chosen to allow the assembly to detach from a preferred location, e.g., from a desired magnetic interface. For instance, in one embodiment, the strength of the magnets are chosen such that the magnetic sealing assembly 200 detaches at the surface of the occlusal magnet 220, e.g., such that the magnetic strength between the occlusal magnet 220 and the spacer magnet(s) 230 is less than the magnet strength between the other magnets.

For example, the magnets may be designed with different grades and coating thicknesses to ensure that the separation force between the stack of magnets applied to the handpiece 3A acts at the occlusal-to-spacer magnet interface. Thus, the force that causes the handpiece 3A to separate from the treatment site may cause separation between the occlusal magnet 220 and the spacer magnet 230 (e.g., the spacer magnet 230 adjacent to the occlusal magnet 220 in some embodiments). The magnets may also be designed to have the same separation force of about 2.4 lbs at the occlusal-to-spacer magnet interface in each stacking configuration. The force required to separate the magnets can vary between about 0.1 lbf to about 50 lbf depending on the design. In some embodiments, the required force to separate the magnets can be in a range of about 1 lbf to about 10 lbf. For example, in various embodiments, the separation force between two magnets can be in a range of about 1 lbf to about 5 lbf.

In some embodiment, the magnetic assembly is designed to not interfere with implants, body piercings, or electronic/ medical, dental devices and tools. Many dental tools are of the 3xx series and, thus, are mildly magnetic. In most cases of the 3xx series stainless steel, the magnetism is not strong enough to affect dental tools in an unpredictable way.

In certain configurations, magnets can be used as a binary switch to alert the dentist or console of a partial separation of two magnets. This configuration can also be used to alert the dentist or console of correct alignment and placement of the handpiece 3A.

In some embodiments, an oval-shaped occlusal magnet 220 can be used. An oval shaped occlusal magnet 220 can reduce the separation force between the spacer and occlusal magnet 220 due to an indirect force between them. An oval shaped occlusal magnet 220 also can be oriented to accommodate different diameters of teeth.

In some embodiments, the handpiece magnet 210 can orient itself in a position that would prevent the dentist from using the handpiece 3A more than once for single-use handpieces.

3. Example Handpiece Magnets

The following specifications represent one non-limiting example of a handpiece magnet 210. In this example embodiment, the handpiece magnet 210 includes a fixed N52 Neodymium ring magnet on the face of the handpiece 3A. The handpiece magnet 210 can be attached (e.g. glued) to the handpiece 3A using, e.g., a medical grade cyanoacrylate. The handpiece magnet 210 can be incorporated into the handpiece 3A in such a way that the handpiece shell or body holds the handpiece magnet 210 permanently. In some embodiments, the inner diameter of the handpiece magnet 210 can be in a range of about 1 mm to about 10 mm., and the outer diameter can be in a range of about 5 mm to about 17 mm. In this example embodiment, the inner diameter of the handpiece magnet 210 is about 5 mm and the outer diameter is about 10 mm. The overall thickness of the handpiece magnet 210 in this example embodiment is about 2 mm. The handpiece magnet 210 can be silicone-dipped to a thickness of 0.05 mm. Thus, accounting for the coating, the actual magnet material thickness can be about 1.9 mm. The silicone on this magnet can be colored (e.g. white) and can have a shore A hardness of 70. The white color can correspond to a specific height of the chamber, or prescribed location of the pressure wave generator 5 with respect to the tooth 10, or both, or can correspond to another measured value which would assist in locating and placing the handpiece 3A properly. In one example, the handpiece magnet 210 can be formed of Neodymium (N52 (52 MGOe)). The handpiece magnet 210 can have an outer diameter of about 0.394"+/−0.001" (10 mm, +/−0.025 mm). The handpiece magnet 210 of this example can have an inner diameter of about 0.197"+/−0.001" (5 mm, +/−0.025 mm). The thickness of the Neodymium, including the Parylene coating, can be about 0.075"+/−0.001" (1.9 mm+/−0.025 mm). The thickness of the silicone coating can be about 0.002" (0.05 mm).

4. Examples of Magnetic Spacers

The following specifications represent one non-limiting example of a set of magnetic spacers 230. In this example embodiment, there can be three N32 Neodymium (32 MGOe) ring spacers of overall thicknesses of 1 mm, 2 mm, and 3 mm, respectively. Of course, the dimensions disclosed above are merely examples; any suitably dimensioned spacer magnets 230 may be appropriate. The 1 mm, 2 mm, 3 mm magnets can contain a neodymium core having thicknesses of roughly 0.9 mm (e.g., 0.035"+/−0.001", or about 0.9 mm+/−0.25 mm), 1.9 mm (e.g., 0.075"+/−0.001", or about 1.9 mm+/−0.25 mm), and 2.9 mm (e.g., 0.114"+/−0.001", or about 2.9 mm+/−0.25 mm), respectively. Each side of the spacer magnets 230 can be coated with silicone to a thickness of, for example, about 0.05 mm (e.g., 0.002"). As one non-limiting example, the silicone on the 1 mm, 2 mm, and 3 mm spacer can be colored, for example, Yellow, Red, and Blue, respectively. The silicone can have a shore A hardness of 70. The spacer magnets 230 can have the same or substantially the same inner diameters and outer diameters to maintain alignment and strength while stacking. The spacer magnets 230 can have an inner diameter in a range of between about 0.01 mm to about 10 mm, or more particularly, in a range of about 1 mm to about 10 mm, and can have an outer diameter in a range of between about 5 mm and about 17 mm. For example, in this example, the spacer magnets 230 can have an inner diameter of about 5 mm (e.g., 0.197"+/−0.001", or about 5 mm, +/−0.025 mm) and can have an outer diameter of about 10 mm (e.g., 0.394"+/−0.001", or about 10 mm, +/−0.025 mm). The surface area, the coating, and strength of the magnet, among other parameters, can determine the magnets' ability to maintain a fluid seal between the inner and outer diameter of the magnet.

The three different spacers (e.g., Blue—3 mm, Red—2 mm, Yellow—1 mm) can be coupled to the handpiece magnet 210 to offset the handpiece 3A from the tooth 10 and occlusal magnet 220 by a suitable separation distance, e.g., about 0 mm to about 5 mm. A summary of the specifications for the non-limiting example embodiment is provided below.

As explained herein, various combinations of spacer magnets 230 can be used to provide the appropriate separation between the tooth 10 and the handpiece 3A or pressure wave generator 5. Table 1 lists various example combinations of spacers for particular tooth depths. In the non-limiting example of Table 1, for example, it may be desirable to provide a total separation between the tooth chamber floor and the handpiece magnet of about 10 mm. It should be appreciated that in other arrangements, other separations may be suitable. Accordingly, if the tooth depth is 5 mm in this example, then the clinician may apply spacer magnets 230 in a combination suitable to provide an additional 5 mm spacing, for a total of 10 mm separation. Similarly, if the tooth depth is 6 mm, spacers 230 can provided in a combination to provide an additional 4 mm, and so on.

TABLE 1

Example spacer magnet combinations based on tooth depth

| Tooth Depth | Spacers Used | Sizer Colors | Spacer Colors |
| --- | --- | --- | --- |
| 5 mm | 3 mm + 2 mm | Blue + Red | Blue + Red |
| 6 mm | 3 mm + 1 mm | Blue + Yellow | Blue + Yellow |
| 7 mm | 3 mm | Blue | Blue |
| 8 mm | 2 mm | Red | Red |
| 9 mm | 1 mm | Yellow | Yellow |
| 10 mm | None | White | None (White Handpiece Magnet) |

5. Examples of Occlusal Magnets

The following specifications represent one non-limiting example of an occlusal magnet 220. In this example embodiment, the occlusal magnet 220 can include a Neodymium N32 (32 MGOe) magnet placed onto a tooth 10. The occlusal magnet 220 can contain a neodymium core having a thickness of about 0.9 mm (e.g., 0.035"+/−0.001", or about 0.9 mm+/−0.25 mm), which can include a Parylene coating. Each side of the magnet 220 can be coated with silicone to a thickness of 0.05 mm (e.g., about 0.002"). The occlusal magnet 220 can have an inner diameter in a range of between about 0.01 mm to about 10 mm, or more particularly, in a range of about 1 mm to about 10 mm, and can have an outer diameter in a range of between about 5 mm and about 17 mm. In this example, the outer diameter of the occlusal magnet 220 can be about 10 mm (e.g., 0.394"+/−0.001", or about 10 mm+/−0.025 mm). The dimension of the outer diameter may be constrained by interference with adjacent teeth, e.g., such that the outer diameter may be small enough such that it does not interfere with or contact adjacent teeth. The inner diameter of the occlusal magnet 220 can be about 5 mm (e.g., 0.197"+/−0.001", or about 5 mm+10.025 mm) in this example. The silicone on the occlusal magnet 220 can be colored grey and can have a shore A hardness of 70. The occlusal magnet 220 can be adhered to the occlusal surface of a built-up tooth 10 with Light-cure GC TION Gingival Protectant. An occlusal magnet tool can be used to ensure that the dentist places the occlusal magnet 220 on the tooth 10 in the correct orientation and centered on the tooth 10. The occlusal magnet tool can also serve as a light-post to direct the light from a light-cure gun to the light-curing GC TION.

IV. Interface Members

As explained above, it can be advantageous to provide an interface member 4 configured to be connected to, and disconnected from, a tooth coupler 3. A proximal end of the interface member 4 can couple to the conduit 29 which provides fluid, electrical, and/or data communication with the console 2. A distal end of the interface member 4 can engage with a connector 84 coupled to or formed with a proximal portion of the tooth coupler 3. The interface member 4 and connector 84 can be configured such that the clinician can easily connect and disconnect the connector 84 from the interface member 4. Moreover, as explained herein, it can be challenging to provide adequate sealing for removable couplers when high pressure fluid passes through the system components. In the disclosed embodiments, adequate sealing can be provided in the interface member 4 and/or connector 84 to reduce or eliminate leakage of treatment fluids at the point of connection.

Figure 20A:
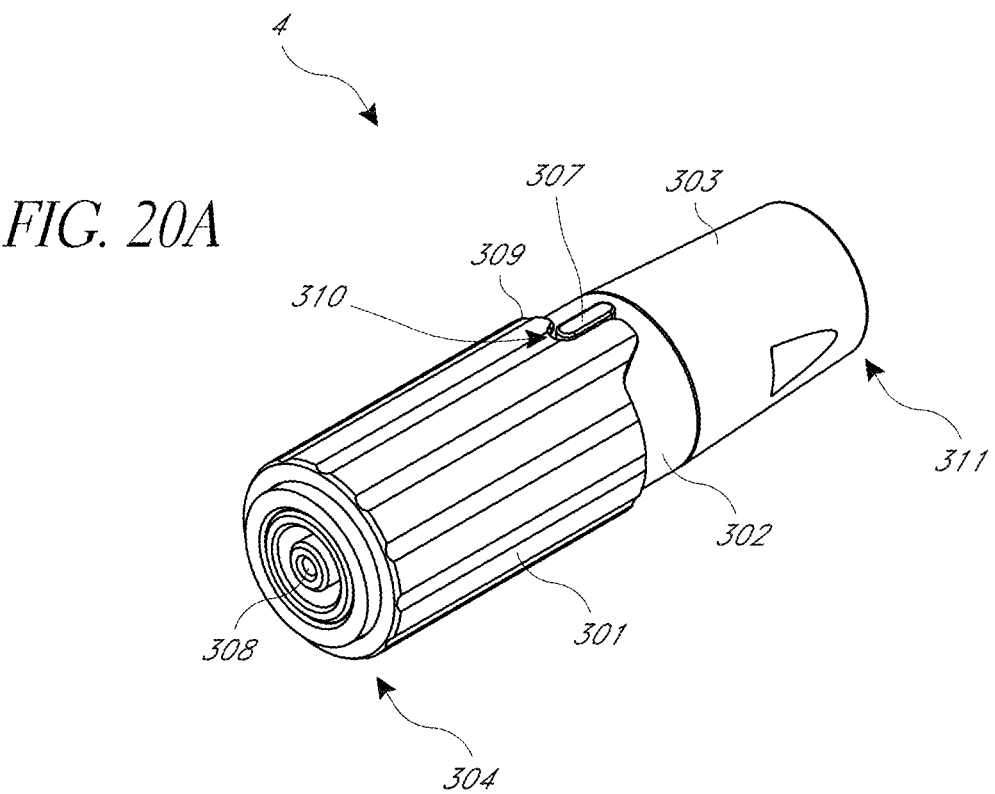
FIG. 20A is a three-dimensional perspective view of an interface member, according to one embodiment.

FIG. 20A is a three-dimensional perspective view of an interface member 4, according to one embodiment. The interface member 4 can have a proximal portion 311 adapted to couple to the conduit(s) 29 that are connected to the console 2. As explained herein, the conduit(s) 29 can provide fluid, electrical, data, and/or other types of communication with the console 2. The interface member can have a distal portion 304 configured to engage with the connector 84 of the tooth coupler 3 (e.g., the handpiece 3A). The interface member 4 can comprise an outer shell 301 and an inner shell 302. As shown in FIG. 20A, the inner shell 302 can be disposed inside the outer shell 301. As explained herein, the inner shell 302 and outer shell 301 can be rotationally coupled together by a spring, such that the inner shell 302 and outer shell 301 are rotationally biased relative to one another.

A conduit coupler 303 can be mechanically coupled to the inner shell 302. The conduit coupler 303 can be coupled to or formed with the conduit(s) 29, and can provide fluid communication between the conduit 29 and the inner shell 302 when engaged with the inner shell 302. As illustrated below, the conduit coupler 303 can threadably couple to the inner shell 302 in some arrangements.

The inner shell 302 can include a latch 307 on an outer surface of the inner shell 302. As shown in FIG. 20A, the latch 307 may be positioned proximal the outer shell 301. As explained in more detail below, the interface member 4 shown in FIG. 20A is in a disengaged configuration, in which the interface member 4 is disconnected and/or disengaged with the tooth coupler 3 (e.g., handpiece 3A, treatment cap 3B, etc.). In some embodiments, in the disengaged configuration, the latch 307 is urged into a notch 310 formed in the outer shell 301. In an engaged configuration (illustrated and explained below with respect to FIGS. 24A-24C), the latch 307 may be rotated relative to the disengaged configuration and may bear against an edge 309 of the outer shell 301. The edge 309 of the outer shell 301 can prevent the latch 307 from translating distally, which can ensure that the outer shell 301 and inner shell 302 remain in the engaged configuration, as explained in detail below.

Figure 20B:
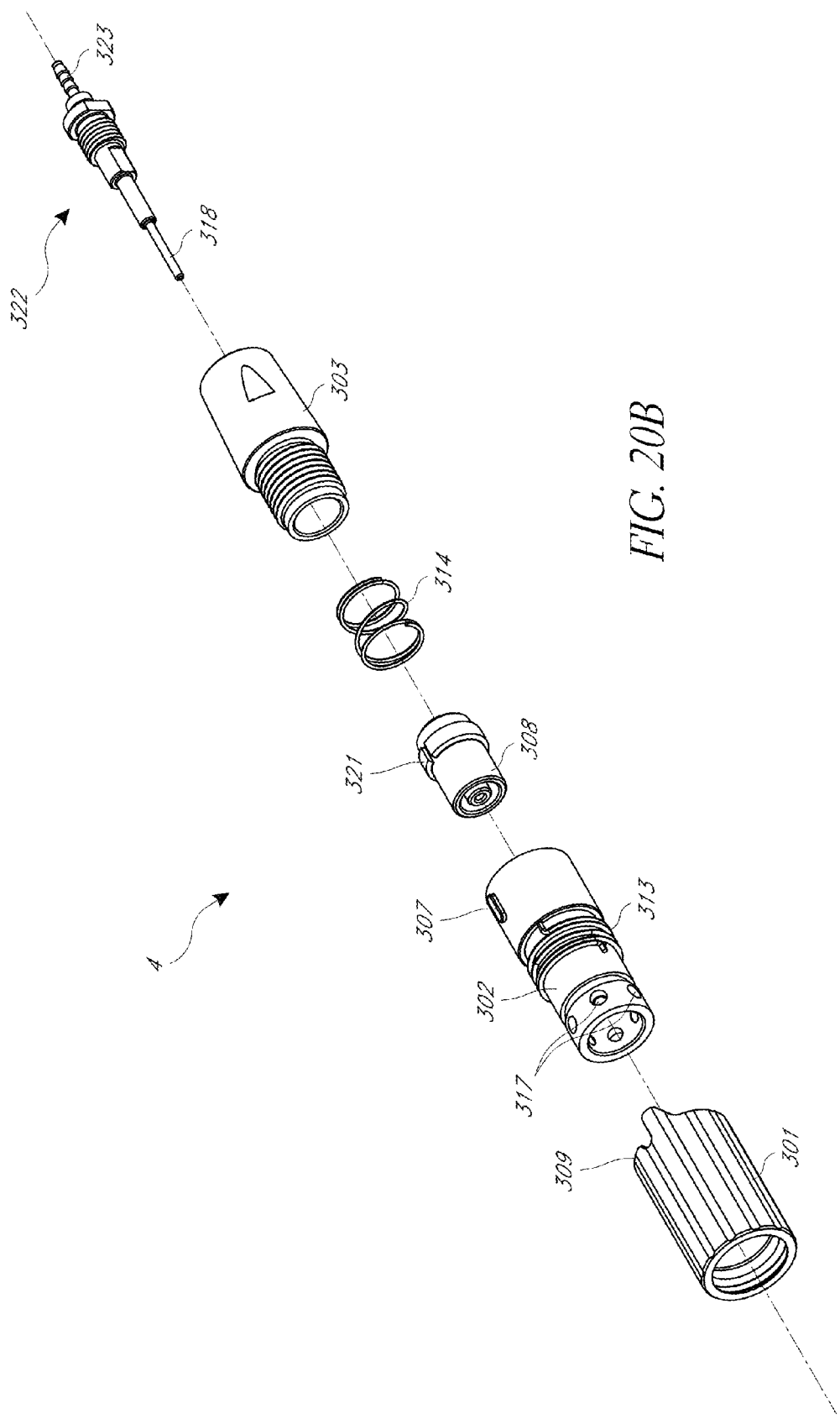
FIG. 20B is a three-dimensional perspective, exploded view of the interface member shown in FIG. 20A.

FIG. 20B is a three-dimensional perspective, exploded view of the interface member 4 shown in FIG. 20A. As in FIG. 20A, the interface member 4 shown in the exploded view of FIG. 20B can include the outer shell 301, the inner shell 302, the slider 308, and the conduit coupler 303. As shown in FIG. 20B, the slider 308 can be disposed within the inner shell 302, and the distal portion of the inner shell 302 can be disposed within the outer shell 301, e.g., such that the latch 307 remains proximal the edge 309 of the outer shell 301 when engaged. The slider 308 can be disposed near the distal end 304 of the interface member 4, as illustrated in FIG. 20A. Further, the slider 308 can include a rib 321 extending radially outward from the slider 308. The inner shell 302 can include a plurality of apertures 317. As explained below, one or more projections (e.g., ball bearings) can be disposed through the apertures 317 to engage with the recess 90 of the connector 84 when in the engaged configuration.

The conduit coupler 303 can be threadably coupled to the inner shell 302. A high pressure interconnect 322 can threadably engage within the conduit coupler 303. The interconnect 322 can include a distal high pressure tube 318 configured to convey a high pressure fluid or liquid between the conduit 29 and the handpiece 3A. A sealing joint 323 can be formed near the proximal end of the interconnect 322 and can couple to the conduit(s) 29 to form a sealed interface between the interconnect 322 and the conduit(s) 29.

The interface member 4 can also include an inner spring 314 and an outer spring 313. The inner spring 314 can be disposed within the inner shell 302 between the rib 321 of the slider 308 and the conduit coupler 303. When the slider 308 is translated proximally, the rib 321 can bear against the inner spring 314 to compress the inner spring 314 proximally between the rib 321 and the conduit coupler 303.

The outer spring 313 can have a distal end coupled to an inner wall of the outer shell 301 and a proximal end coupled to an outer wall of the inner shell 302. The outer spring 313 can be disposed in a space between the outer shell 301 and the inner shell 302, and can traverse a helical path about the inner shell 302. Indeed, the helical path can traverse a helical angle between the proximal and distal ends of the outer spring 313. The outer spring 313 can have a relaxed state and a compressed state. For example, if the outer spring 313 traverses N turns (including fractional turns) about the inner shell 302 in the relaxed state, where N is a positive real number, then the helical angle in the relaxed state is about 360*N degrees.

In the compressed state, the outer spring 313 can be compressed axially (e.g., proximally) and circumferentially (e.g., about a circumference of the inner shell 302). In the compressed state, a helical angle between the distal and proximal ends of the spring 313 can be less than that when in the relaxed state. For example, in the compressed state, the outer spring 313 can be compressed circumferentially by an amount d turns, where d is a real number of turns about the inner shell 302 (and indeed may be a fractional number of turns). Accordingly, in the compressed state, the helical angle of the outer spring 313 can be about 360*(N−d) degrees. Thus, when in the compressed state, the ends of the outer spring 313 are rotationally displaced relative to when in the relaxed state.

Figure 21:
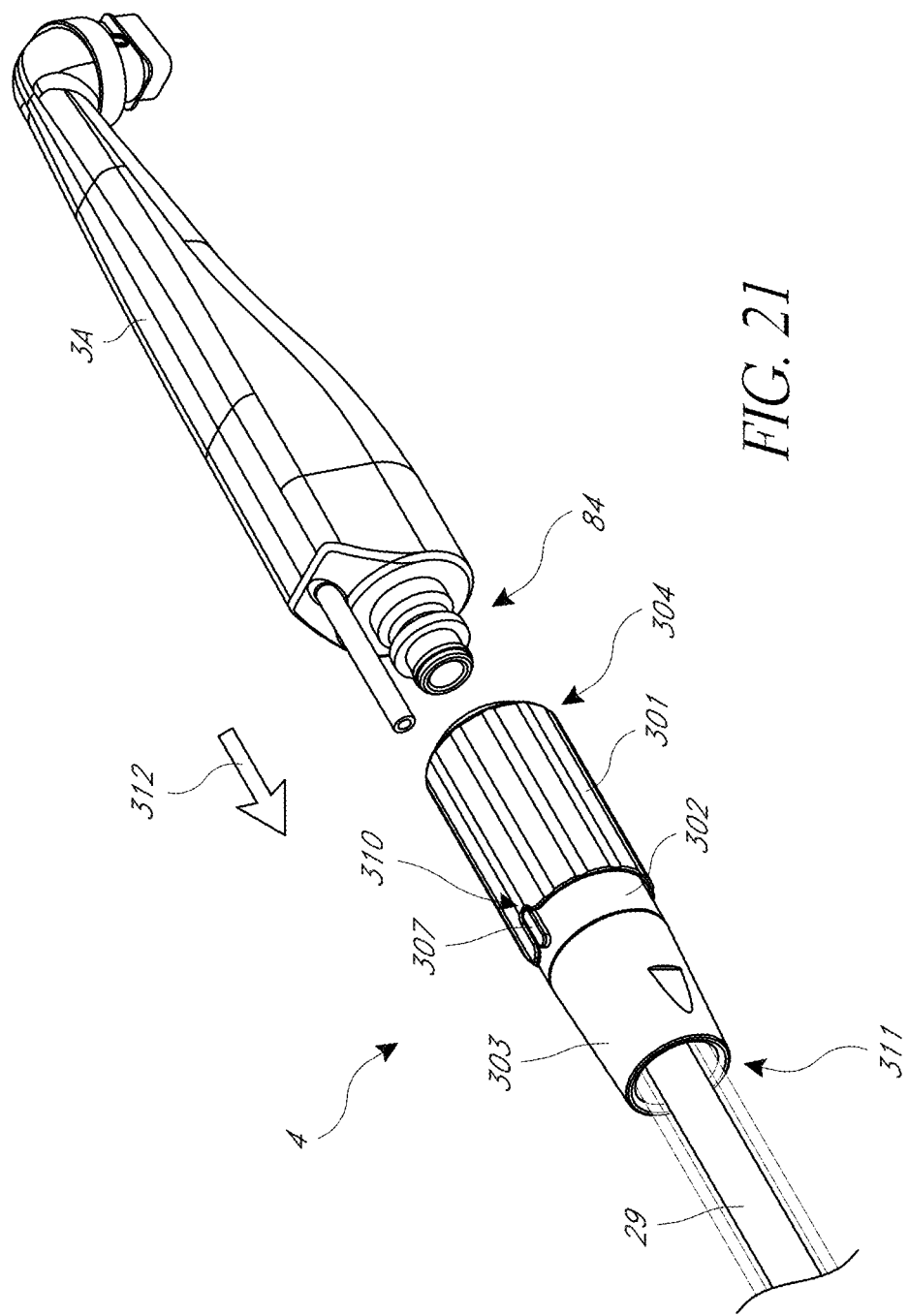
FIG. 21 is a three-dimensional perspective view of a handpiece and interface member prior to engagement.

FIG. 21 is a three-dimensional perspective view of a handpiece 3A and interface member 4 prior to engagement. Prior to a treatment procedure, the clinician can select a suitable tooth coupler 3, which in the embodiment of FIG. 21 comprises a handpiece 3A. As explained herein, the handpiece 3A can be configured for any suitable treatment procedure, e.g., a tooth cleaning procedure, an obturation procedure, etc. The interface member 4 can be coupled with a distal end of the one or more conduits 29, which may provide at least one of fluidic, electrical, and/or data communication with the console 2. For example, the conduit 29 can comprise a high pressure fluid pathway configured to convey pressurized treatment fluid to the handpiece 3A. As shown in FIG. 21, the interface member 4 is in the disengaged configuration such that the latch 307 is disposed in the notch 310 of the outer shell 301.

To connect the handpiece 3A with the interface member 4, the clinician can insert the connector 84 of the handpiece 3A into the distal portion 304 of the interface member 4. The clinician can urge the connector 84 and handpiece 3A proximally (e.g., along a proximal direction 312) until the connector 84 engages with the interface member 4 to secure the interface member 4 and the handpiece 3A together. Of course, it should be appreciated that the clinician could likewise urge the interface member 4 distally towards the connector 84 until the connector 84 and interface member 4 engage. Once secured in the engaged configuration, the handpiece 3A and interface member 4 may be fixed relative to one another along a longitudinal direction, e.g., fixed relative to the proximal direction 312. However, the handpiece 3A may rotate relative to the interface member 4 when engaged. Allowing the handpiece 3A to rotate relative to the interface member 4 can enable the clinician to better manipulate the handpiece 3A during the procedure. In addition, once engaged, the interface member 4 and connector 84 provide a substantially sealed fluid pathway between the conduit 29 and the handpiece 3A.

Figure 22A:
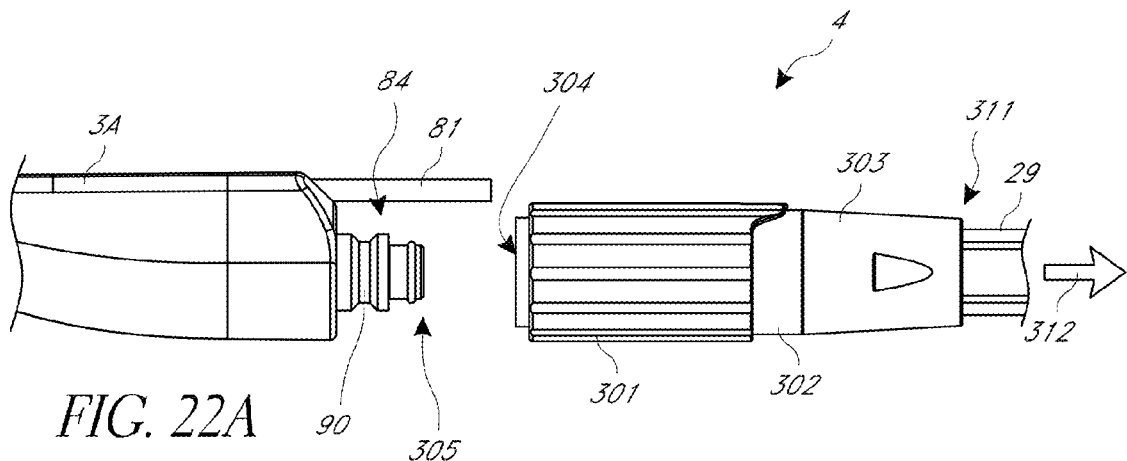
FIG. 22A is a side view of the handpiece and the interface member before inserting the connector into the interface member.
Figure 23A:
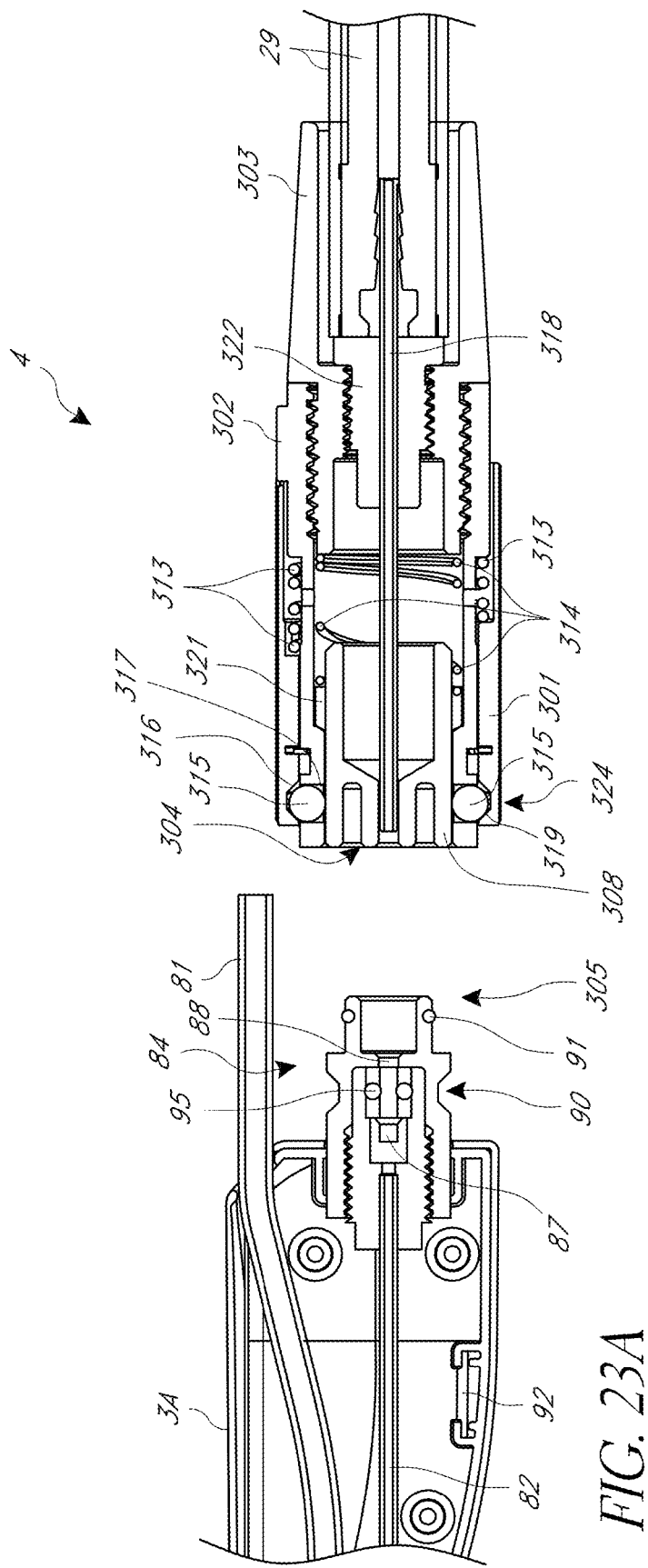
FIG. 23A is a side cross-sectional view of the arrangement shown in FIG. 22A.

FIG. 22A is a side view of the handpiece 3A and the interface member 4 before inserting the connector 84 into the interface member 4, for example, when the interface member 4 is in the disengaged configuration. FIG. 23A is a side cross-sectional view of the arrangement shown in FIG. 22A. As shown in FIGS. 22A and 23A, a proximal portion 305 of the connector 84 of the handpiece 3A can be positioned near the distal portion 304 of the interface member 4. As explained above with respect to FIGS. 12A-12B, the connector 84 can include the first opening 88, the second opening 89 proximal the first opening 88, the first gasket 91, the second gasket 95, the fluid line coupling portion 87, and the recess 90. A proximal end of the high pressure supply line 82 can be disposed near and/or distal to the fluid line coupling portion 87. The waste line 81 can extend from the handpiece 3A proximally to the console 2 and the waste system 41.

With reference to FIG. 23A, the slider 308 can be disposed within the inner shell 302, and the inner spring 314 can be disposed within the inner shell 302 distal the conduit coupler 303. A distal portion of the inner spring 314 can be disposed about a proximal portion of the slider 308. The rib 321 of the slider 308 can bear against the inner spring 314.

Accordingly, the slider 308 can be linearly biased relative to the conduit coupler 303 by way of the inner spring 314.

The outer shell 301 and the inner shell 302 can be rotatably coupled to one another by the outer spring 313. The outer spring 313 can be disposed in a space between the inner shell 302 and the outer shell 301, and can be disposed about a circumference of the inner shell 302. For example, a distal end of the outer spring 313 can connect to an inner wall or surface of the outer shell 301, and a proximal end of the outer spring 313 can connect to an outer wall or surface of the inner shell 302.

One or more projections 315, which may be ball bearings, can be disposed in a cavity 324 formed in an inner surface of the outer shell 301. Indeed, as shown in FIG. 23A, the projection 315 can be positioned in the cavity 324 through the aperture 317 in the inner shell 302. In particular, the projection 315 can be disposed in the cavity 324 between a proximal-facing shoulder 319 of the outer shell 301 and a distal-facing shoulder 316 of the outer shell 301.

In the disengaged configuration shown in FIG. 23A, the outer spring 313 is in the compressed state, such that the spring 313 applies a distally-directed force against the outer shell 301 (e.g., to the left as shown in FIG. 23A). In particular, the outer spring 313 can apply a longitudinal force that presses the distal-facing shoulder 316 against the projection 315. However, in the disengaged configuration, the slider 308 is linearly biased distally such that outer walls of the slider 308 force the projections 315 radially outward into the cavity 324 of the outer shell 301. Accordingly, in the disengaged configuration, the position of the slider 308 (biased distally by the inner spring 314) maintains the projections 315 within a space defined by the cavity 324 of the outer shell 301 and the apertures 317 of the inner shell 302.

Figure 22B:
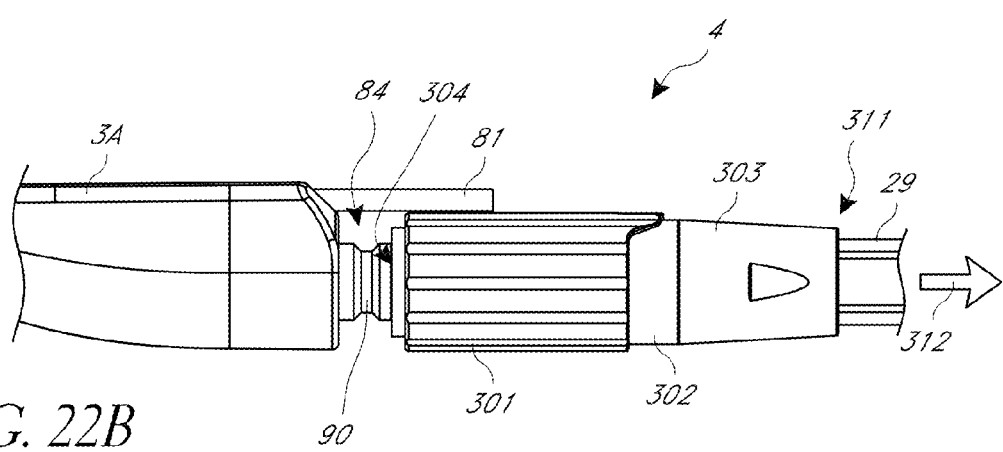
FIG. 22B is a side view of the handpiece and the interface member after aligning the connector with the interface member.
Figure 23B:
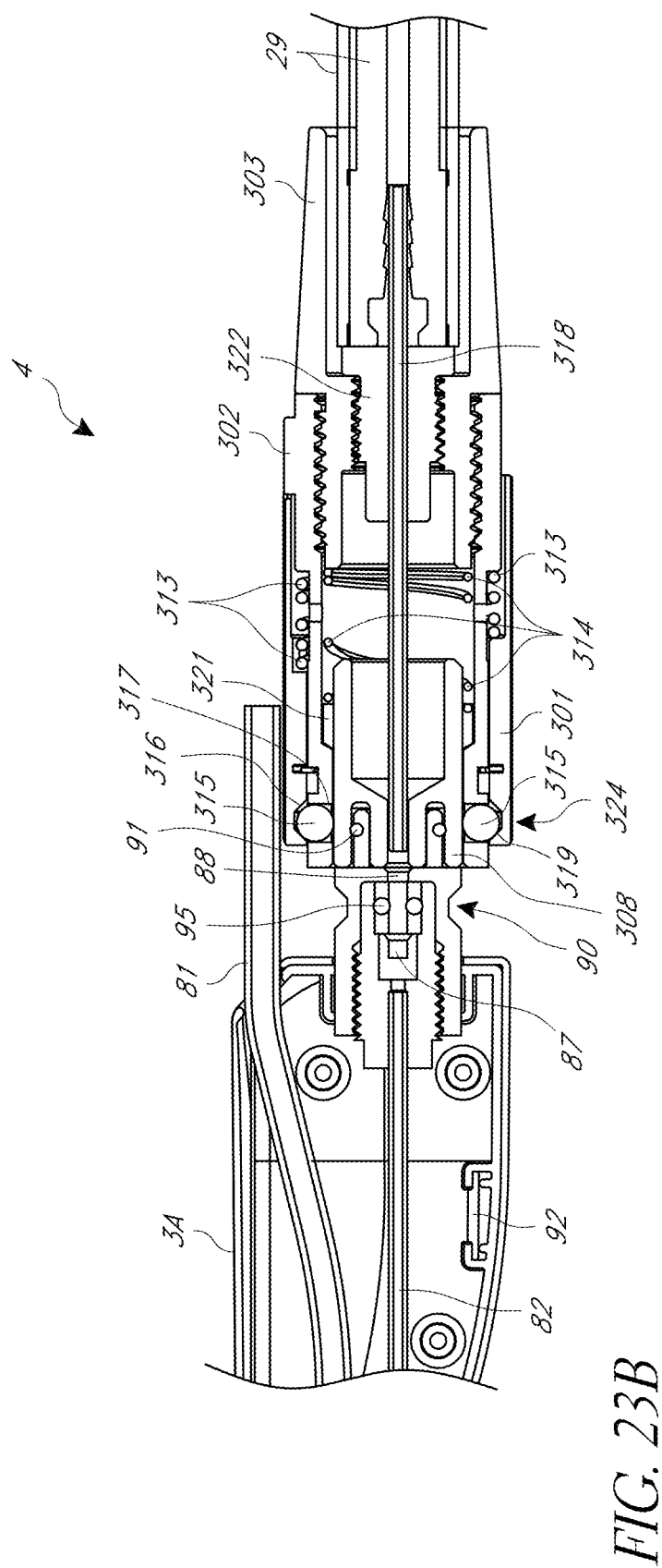
FIG. 23B is a side cross-sectional view of the arrangement shown in FIG. 22B.

FIG. 22B is a side view of the handpiece 3A and the interface member 4 after aligning the connector 84 with the interface member 4. FIG. 23B is a side cross-sectional view of the arrangement shown in FIG. 22B. In FIGS. 22B and 23B, the interface member 4 is still in the disengaged configuration, in which the handpiece 3A and interface member 4 are not yet secured together. For example, before securing the handpiece 3A and interface member 4, the clinician can align and insert the proximal portion 305 of the connector 84 into receptors formed in the distal portion of the slider 308.

Figure 22C:
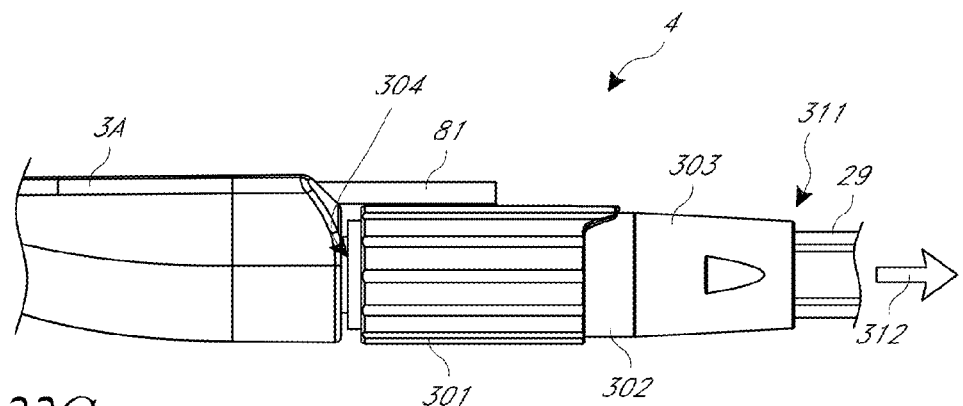
FIG. 22C is a side view of the handpiece and the interface member in the engaged configuration.
Figure 23C:
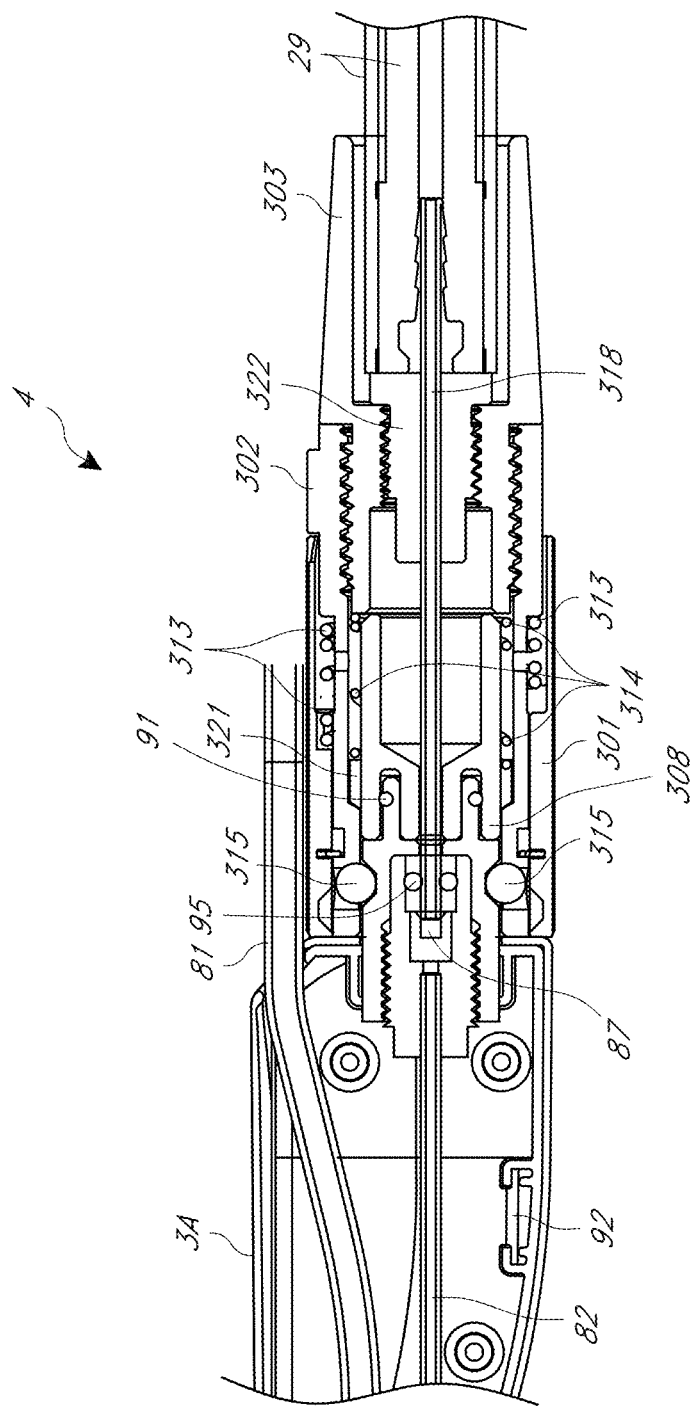
FIG. 23C is a side cross-sectional view of the engaged configuration illustrated in FIG. 22C.

Turning to FIGS. 22C and 23C, the clinician can apply additional force to further advance the connector 84 and handpiece 3A proximally relative to the interface member 4 until the connector 84 and interface member 4 are secured together. Thus, FIG. 22C is a side view of the handpiece 3A and the interface member 4 in the engaged configuration. FIG. 23C is a side cross-sectional view of the engaged configuration illustrated in FIG. 22C.

In the engaged configuration, the proximal portion 305 of the connector 84 bears against the slider 308 to advance the slider 308 proximally relative to the inner shell 302. As explained above, in the disengaged configuration, the outer spring 313 is biased such that it applies a distally-directed force against the outer shell 301 to cause the distal-facing shoulder 316 against the projection 315. When the recess 90 (which may comprise a circumferential groove) is positioned adjacent the projection 315, the distal-facing shoulder 316 (which is biased distally by the outer spring 313) can urge the projection 315 radially inward into the recess 90 to secure the connector 84 and handpiece 3A to the interface member 4.

In addition, when the connector 84 and interface member 4 are thereby engaged, the outer shell 301 can extend distally to cause the outer spring 313 to be in the relaxed state. Accordingly, as explained above, in the relaxed state, the outer spring 313 can extend longitudinally such that the ends of the spring 313 are longitudinally elongated, and can also extend circumferentially such that the ends of the outer spring 313 are rotationally displaced relative to the compressed state. In the relaxed state, therefore, the helical angle of the spring 313 can be larger than when in the compressed state.

When in the engaged configuration, the projection(s) 315 can prevent the handpiece 3A from translating longitudinally relative to the interface member 4. The methods and apparatus disclosed herein can therefore provide a relatively simple mechanism for connecting a tooth coupler 3 with the interface member 4. In addition, as shown in FIG. 23C, the interface member 4 and connector 84 can provide a sealed fluid pathway between the handpiece 3A and conduit(s) 29 through which the high pressure treatment fluids can pass. For example, when engaged, the high pressure tube 318 of the interconnect 322 can extend distal of the slider 308 and can be received through the first opening 88 of the connector 84. The tube 318 can pass within the second gasket 95 and to the coupling portion 87 of the connector 84. The coupling portion 87 can provide sealed fluid communication between the high pressure supply line 82 of the handpiece 82A and the high pressure tube 318 of the interconnect 322. The gaskets 91, 95 can assist in sealing the pressurized fluid passing through the tube 318 and supply line 82 to prevent or mitigate liquid from leaking during operation of the system 1.

Accordingly, the interface member 4 and connector 84 can provide secure mechanical engagement and sealed fluid communication between the handpiece 3A and the conduits 29 during a treatment procedure. The clinician can initiate and conduct the treatment procedure using the console 2. When the procedure is completed, the clinician can remove the handpiece 3A from the interface member 4. In some arrangements, as explained herein, the clinician can dispose the handpiece 3A after the procedure.

Figure 24A:
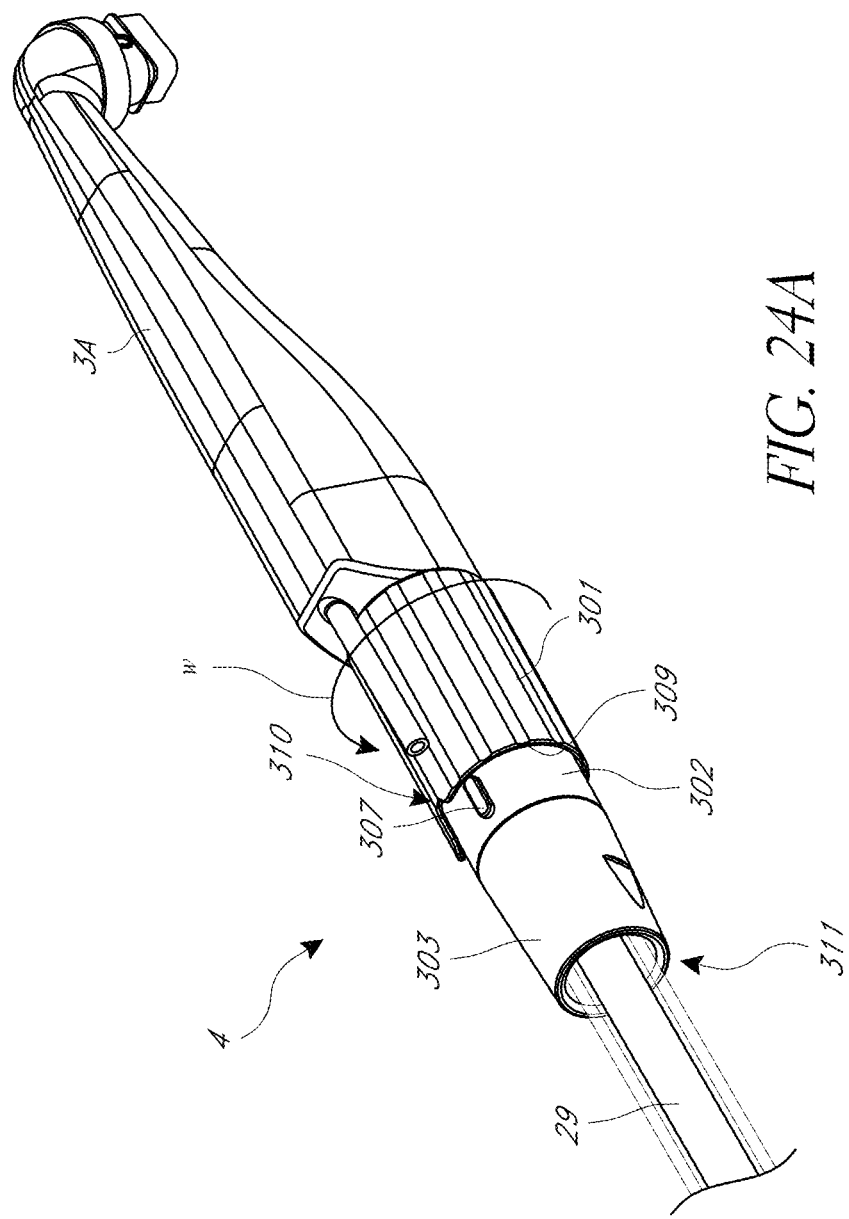
FIG. 24A is a three-dimensional perspective view of the handpiece coupled to the interface member prior to disengagement.

FIG. 24A is a three-dimensional perspective view of the handpiece 3A coupled to the interface member 4 prior to disengagement. For example, in the engaged configuration shown in FIG. 24A, the latch 307 is rotated relative to the notch 310. As explained above, when the projection 315 is urged into the recess 90 of the connector 84, the outer spring 303 becomes relaxed and elongates both longitudinally and circumferentially. Accordingly, in the engaged configuration of FIG. 24A, the outer spring 313 is relaxed and the latch 307 is rotated circumferentially relative to the notch 310. In the engaged configuration, the edge 309 of the outer shell 301 bears against the latch 307 to prevent the latch from translating distally and disconnecting the handpiece 3A from the interface member 4.

To disengage and/or disconnect the handpiece 3A from the interface member 4, the inner shell 302 can be rotated in a direction w to substantially align the latch 307 with the notch 310. FIG. 24B is a three-dimensional perspective view of the handpiece 3A when the latch 307 is substantially aligned with the notch 310. Aligning the notch 310 with the latch 307 can permit the inner shell 302 and outer shell 301 to translate towards one another. To disengage the handpiece 3A from the interface member 4, the clinician can move the outer shell 301 towards the inner shell 302, or vice versa. For example, the clinician can translate the outer shell 301 proximally (e.g., in the proximal direction 312) relative to the inner shell 302, or can translate the inner shell 302 distally relative to the outer shell 301. Translating the outer shell 301 and inner shell 302 towards one another can cause the distal end of the slider 308 to bear against the projections 315 to force the projections 315 radially outward into the cavity 324 and into the disengaged configuration.

Figure 24C:
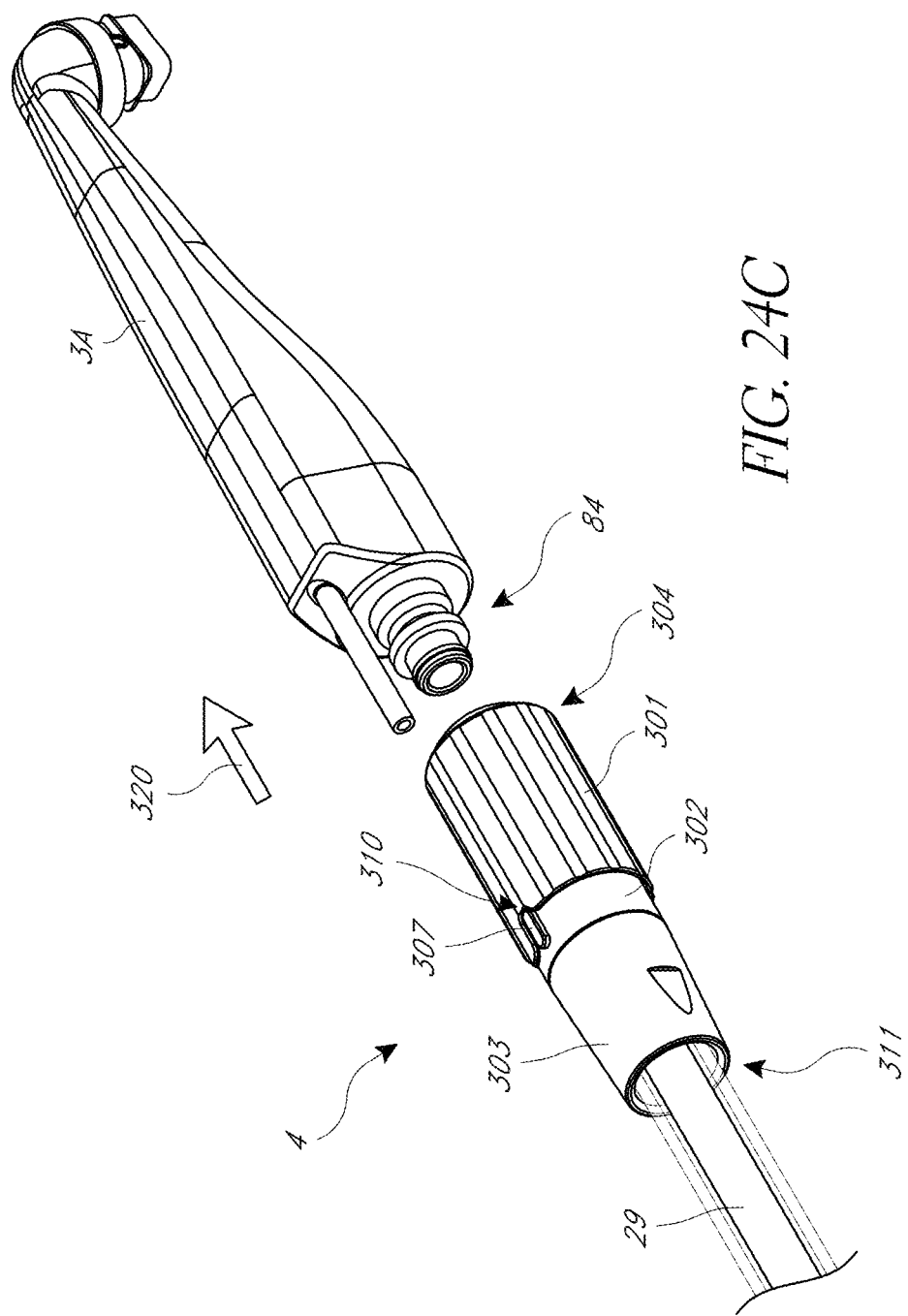
FIG. 24C is a three-dimensional perspective view of the handpiece and interface member after disconnection.

Once the interface member 4 and connector 84 are disengaged, the handpiece 3A can be moved distally relative to the interface member 4, e.g., along a distal direction 320. FIG. 24C is a three-dimensional perspective view of the handpiece 3A and interface member 4 after disconnection. When disengaged, the latch 307 can be urged into the notch 310. The interface member 4 may be configured to couple to another tooth coupler 3 for a subsequent treatment procedure.

Figure 25A:
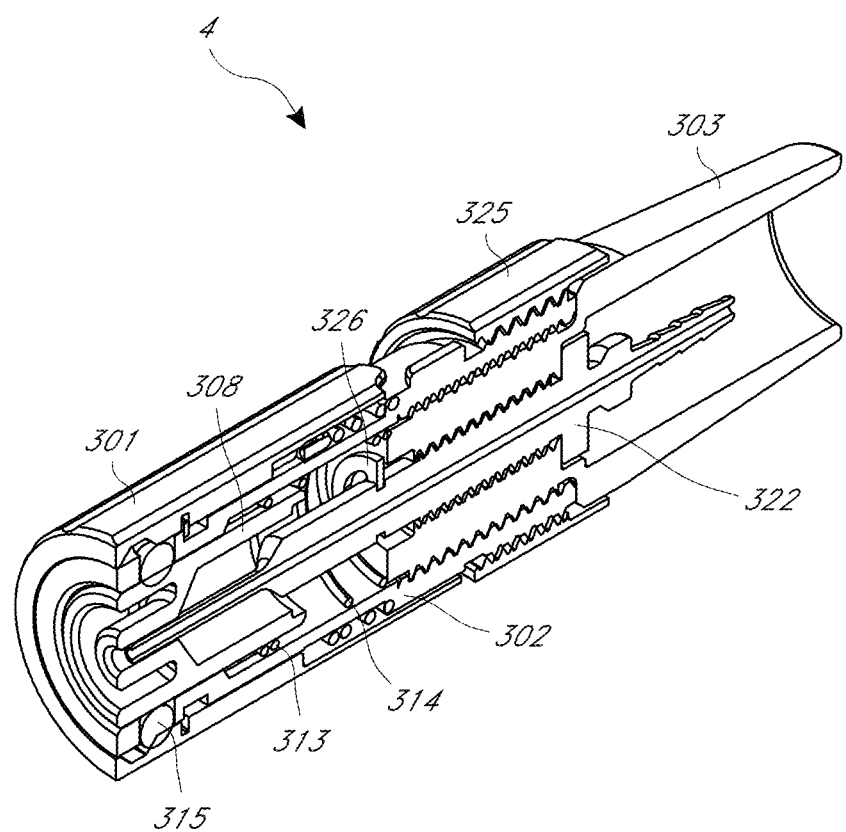
FIG. 25A is a three-dimensional perspective, cross-sectional view of an interface member according to another embodiment.

FIG. 25A is a three-dimensional perspective, cross-sectional view of an interface member 4 according to another embodiment. In some arrangements, the handpiece 3A and interface member 4 may be accidentally disengaged. For example, the clinician may inadvertently rotate the outer shell 301 relative to the inner shell 302, risking disconnection of the handpiece 3A. It can be important to ensure that inadvertent disconnections are avoided, particularly during a treatment procedure. Accordingly, the interface member 4 of FIG. 25A includes a locking collar 325 adapted to prevent accidental disengagement of the handpiece 3A.

Like the embodiments presented above with respect to FIGS. 20A-24C, the interface member 4 of FIG. 25A can include an outer shell 301, an inner shell 302, a slider 308, a conduit coupler 303, an interconnect 322, an inner spring 314, an outer spring 313, and one or more projections 315. In addition, the locking collar 325 can be threadably mounted relative to the outside surface of the inner shell 302. A retaining ring 326 can also be provided on the interconnect 322. As shown in FIG. 25A, for example, the retaining ring 326 can be inserted into dimples in outer surfaces of the interconnect 322. In some embodiments, the retaining ring 326 can act to prevent translation of other components (e.g., the conduit coupler 303) relative to the ring 326 and/or interconnect 322.

Figure 25B:
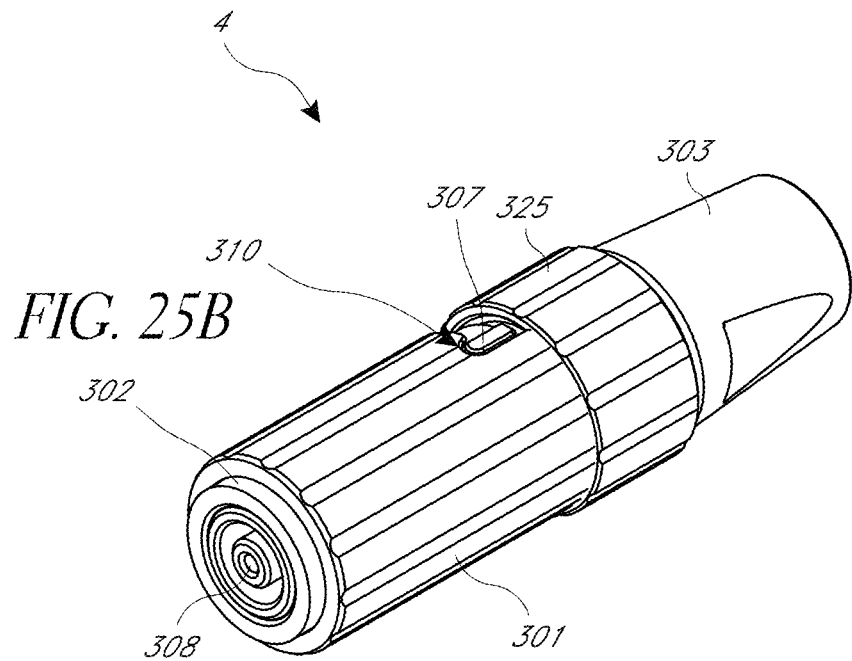
FIG. 25B is a three-dimensional perspective view of the interface member of FIG. 25A in the disengaged configuration.
Figure 25C:
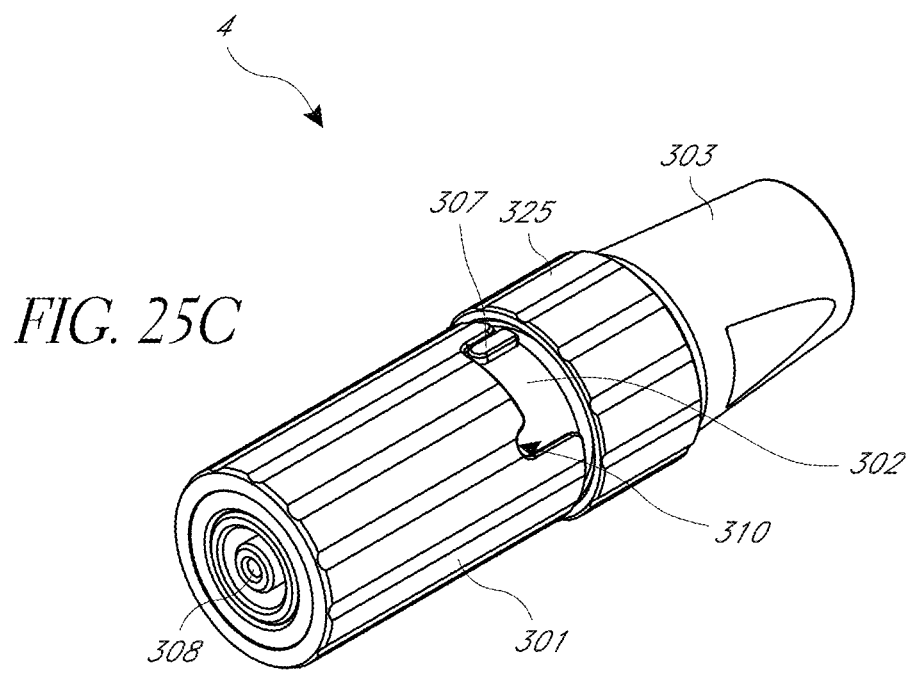
FIG. 25C is a three-dimensional perspective view of the interface member of FIG. 25A in the engaged configuration.

FIG. 25B is a three-dimensional perspective view of the interface member 4 of FIG. 25A in the disengaged configuration. By contrast, FIG. 25C is a three-dimensional perspective view of the interface member 4 of FIG. 25A in the engaged configuration. In the disengaged configuration of FIG. 25B, as explained above, the latch 307 can be disposed in the notch 310 of the outer shell 301. The outer spring 313 can be in a compressed configuration. In the engaged configuration of FIG. 25C, the latch 307 can be rotationally offset from the notch 310, for example, because the outer spring 313 is relaxed relative to the disengaged configuration. In the engaged configuration of FIG. 25C, the edge 309 of the outer shell 301 can prevent the latch 307 and inner shell 302 from translating distally relative to the outer shell 301.

During use, however, the clinician may accidentally cause the latch 307 to rotate relative to the outer shell 301. If the latch 307 and notch 310 substantially align, the handpiece 3A (or other tooth coupler 3) may become inadvertently disengaged. The locking collar 325 can act to rotationally secure the inner shell 302 relative to the outer shell 301. For example, as shown in FIG. 25C, the locking collar 325 can be threaded or otherwise coupled to the inner shell 302. The distal end of the locking collar 325 can engage with a proximal-most edge of the outer shell 301. The resulting mechanical interference between the locking collar 325 and the outer shell 301 can prevent accidental disengagement between the handpiece 3A and the interface member 4.

Figure 26A:
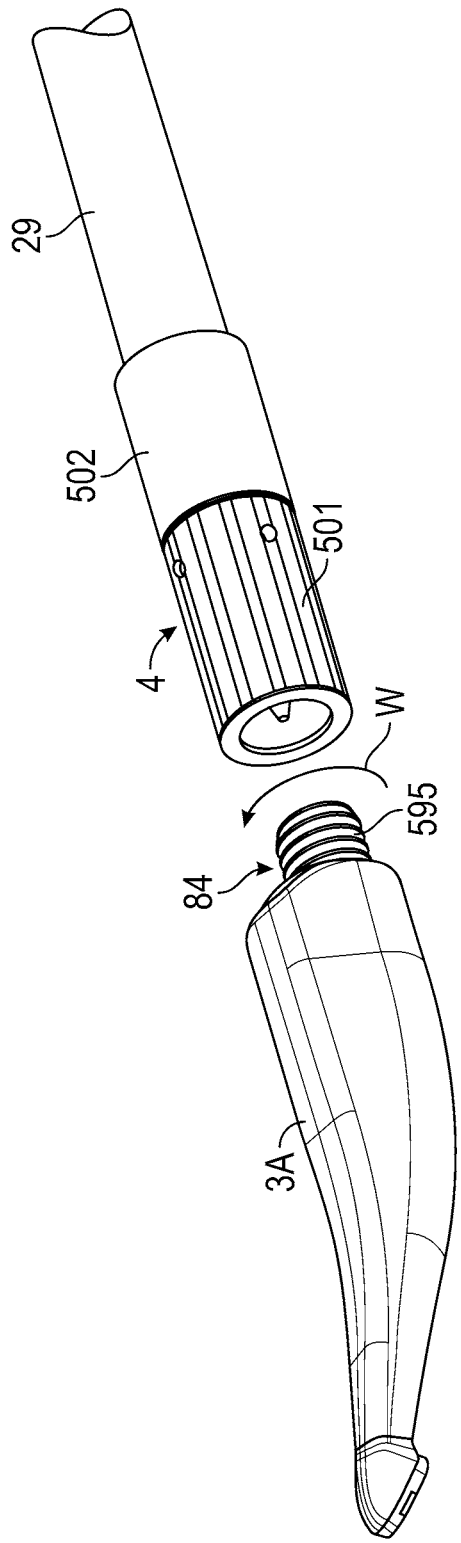
FIG. 26A is a perspective exploded view of a handpiece and interface member before engagement, in accordance with another embodiment.
Figure 26B:
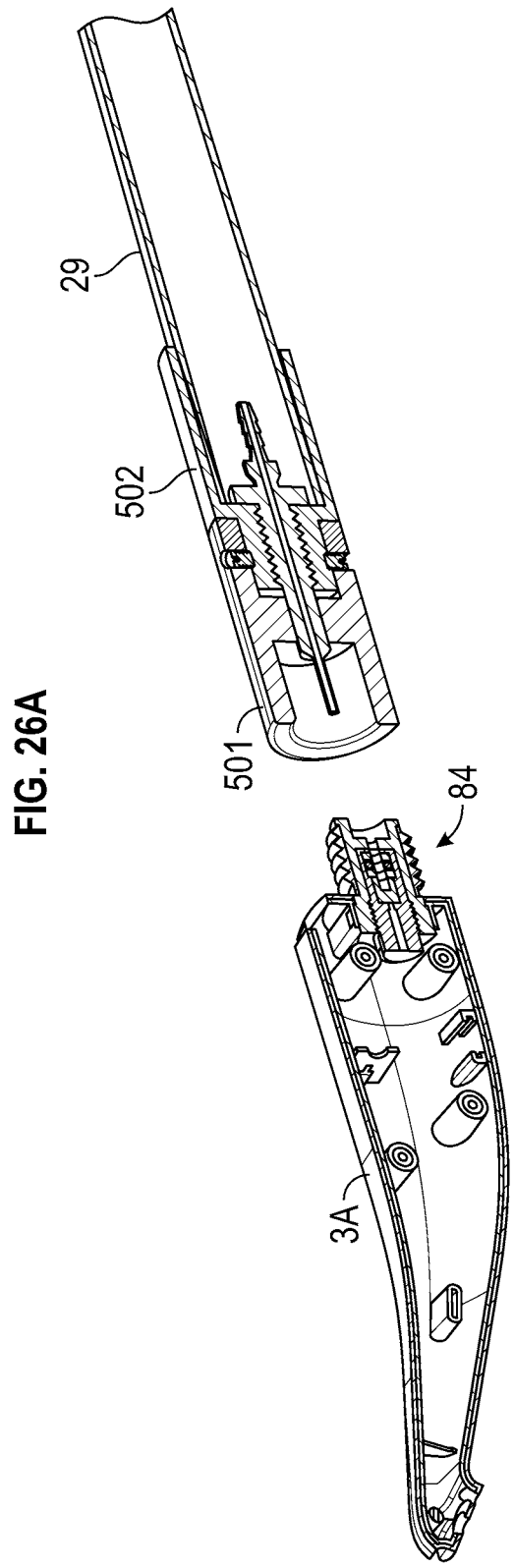
FIG. 26B is a perspective, cross-sectional view of the handpiece and interface member illustrated in FIG. 26A.

FIG. 26A is a perspective exploded view of a handpiece 3A and interface member 4 before engagement, in accordance with another embodiment. FIG. 26B is a perspective, cross-sectional view of the handpiece 3A and interface member 4 illustrated in FIG. 26A. For example, as explained above with respect to FIGS. 12C-12D, the handpiece 3A can include a connector 84 having a threaded engagement feature 595, which can comprise external threads on an outer surface of the connector 84. The interface member 4 can comprise an outer shell 501 and an inner shell 502 disposed at least partially within the outer shell 501. The inner shell 502 can mechanically and fluidly engage the conduit 29. In the embodiment of FIGS. 26A-26B, the connector 84 of the handpiece 3A can be inserted into the interface member 4. The connector 84 can be rotated relative to the interface member 4 about an axis w extending along a longitudinal axis of the system 1, or vice versa, to removably secure the connector 84 to the interface member 4. For example, the threaded engagement feature 595 can engage with an inner surface of the outer shell 501 in some embodiments. In other embodiments, the interface member 4 can act as the male connector and can be inserted into and rotated relative to the connector 84.

Figure 26C:
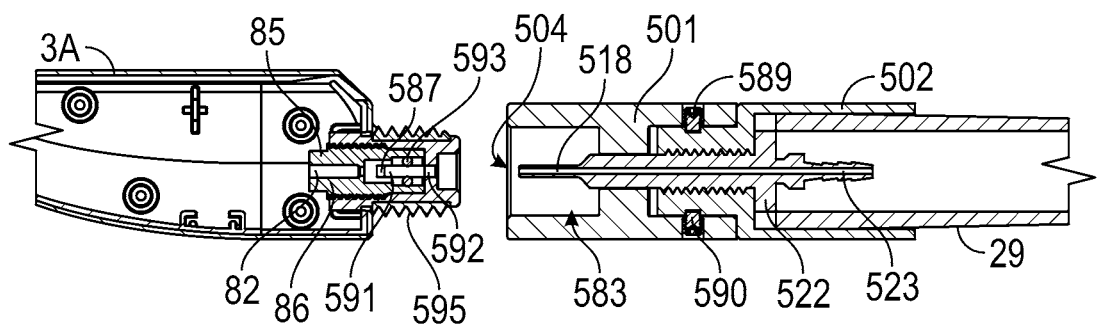
FIG. 26C is a side cross-sectional view of the handpiece of FIGS. 26A-26B before engagement with the interface member.
Figure 26D:
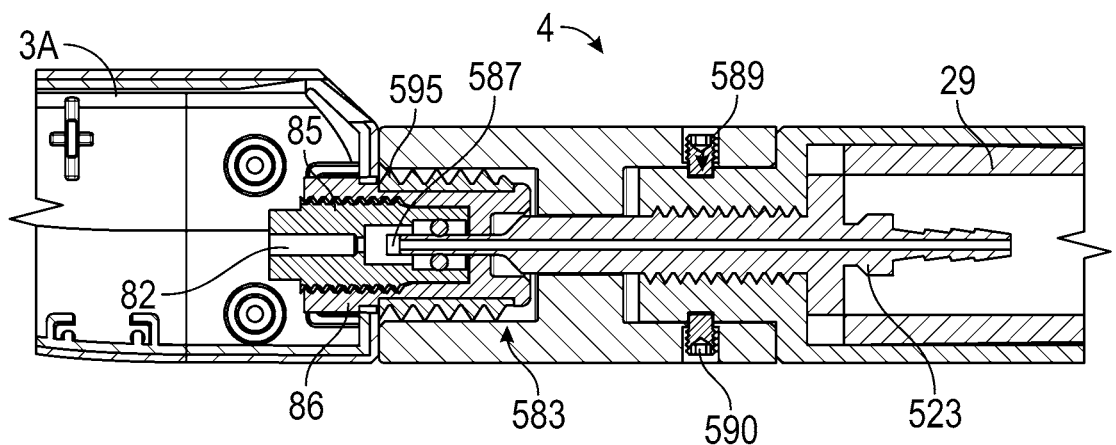
FIG. 26D is a side cross-sectional view of the handpiece of FIGS. 26A-26B after engagement with the interface member.

FIG. 26C is a side cross-sectional view of the handpiece 3A before engagement with the interface member 4. FIG. 26D is a side cross-sectional view of the handpiece 3A after engagement with the interface member 4. As shown in FIGS. 26C-26D, the high pressure fluid supply line 82 can be disposed distal of and can fluidly communicate with a filter 587 disposed in the coupling portion 87 of the connector 84. The filter 587 can act to filter undesirable particulates and debris from the fluid before the fluid passes through the orifice 66 and jet assembly. A proximal gasket 592 and a distal gasket 591 can be disposed in a cavity of the connector 84. An intermediate gasket 593 can be disposed between the proximal gasket 592 and the distal gasket 591. The gaskets 591, 592, 593 can act to provide a substantial fluid seal to prevent fluids from leaking from the high pressure fluid path. In some arrangements, the proximal gasket 592 and the distal gasket 591 can each comprise polyether ether ketone (PEEK) rings. The intermediate gasket 593 can comprise an ethylene propylene diene monomer (EPDM) rubber o-ring.

The interface member 4 can further include a high pressure interconnect 522 that can threadably engage within the inner shell 502. The interconnect 522 can include a distal high pressure tube 518 configured to convey a high pressure fluid or liquid between the conduit 29 and the handpiece 3A. A sealing joint 523 can be formed near the proximal end of the interconnect 522 and can couple to the conduit(s) 29 to form a sealed interface between the interconnect 522 and the conduit(s) 29.

The outer shell 501 can include threads 583 on an inner surface of an aperture 504 formed in the shell 501. The threads 583 can threadable engage with the threaded engagement feature 595 of the connector 84 to releasably secure the interface member 4 and the connector 84 of the handpiece 3A. Accordingly, the connector 84 and handpiece 3A can be rotated relative to the interface member 4, or vice versa, to couple the interface member 4 to the handpiece 3A. The high pressure tube 518 of the interconnect 522 can be received through the openings 588, 589 of the connector 84 such that the distal end of the high pressure tube 518 extends inside a portion of the filter 587. Thus, high pressure treatment fluids passing through the interconnect 522 and through the high pressure tube 518 can be filtered by the filter 587 before passing through the fluid supply line 82 to the jet assembly.

The embodiment shown in FIGS. 26A-26D can advantageously provide a simpler and more secure removable connection between the interface member 4 and the handpiece 3A (or other tooth coupler 3). For example, the interface member 4 of FIGS. 26A-26D can include only two components in some arrangements, enabling simpler and more cost effective manufacturing procedures. Furthermore, as explained above, some interfaces may be configured such that the clinician may accidentally disengage the handpiece 3A from the interface member 4. The embodiment shown in FIGS. 26A-26D can provide a safer connection because it may be more difficult for the clinician to accidentally disengage the connector 84 from the interface member 4. Indeed, to disengage the connector 84 and handpiece 3A, the clinician may thread the connector 84 about a direction opposite to that used for connecting the connector 84 and interface member 4. Threadably disengaging the handpiece 3A and interface member 4 may enable the clinician controllably disconnect the handpiece 3A and interface member 4, while preventing accidental disengagement. Furthermore, in some arrangements, disconnection of the handpiece 3A may be unsafe for the clinician and patient, as the high-pressure jet or fluid stream may cause injury. If the threaded connection between the handpiece 3A and interface member 4 shown in FIGS. 26A-26D becomes slightly unscrewed, then pressure within the lines 518, 82 may slowly release such that if complete disconnection occurs, the high pressure built up in the system 1 may be released before it can injure the patient and/or clinician.

Moreover, as explained herein, it can be advantageous for the clinician to be able to rotate the handpiece 3A relative to the conduit(s) 29 and/or console 2, e.g., to improve maneuverability during a treatment procedure. Accordingly, the arrangement shown in FIGS. 26A-26D can include a swiveling mechanism to enable the clinician to rotate the handpiece 3A without disengaging the handpiece 3A from the interface member 4. For example, as shown in FIGS. 26C-26D, the interface member 4 can include one or more projections 590 inserted into corresponding recesses 589 (which may comprise a circumferential groove) in the interface member. As shown in FIGS. 26C-26D, for example, the projections 590 can be formed in or through the outer shell 501, and the recesses 589 can be formed in an outer surface of the inner shell 502. In some embodiments, the projections 590 can comprise a set screw, a spring-loaded pin, etc. that can engage the recesses 589. The projections 590 and recesses 589 can cooperate to prevent lateral (e.g., longitudinal movement in proximal and/or distal directions) translations, while permitting relative rotation or swiveling between the interface member 4 and the connector 84.

Figure 27A:
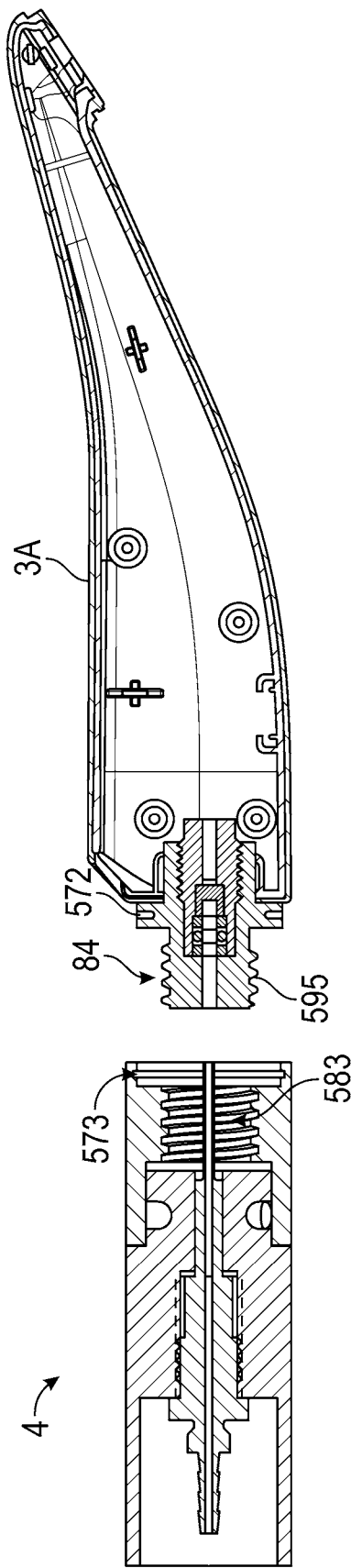
FIG. 27A is a side cross-sectional view of a handpiece and interface member prior to engagement, according to yet another embodiment.
Figure 27B:
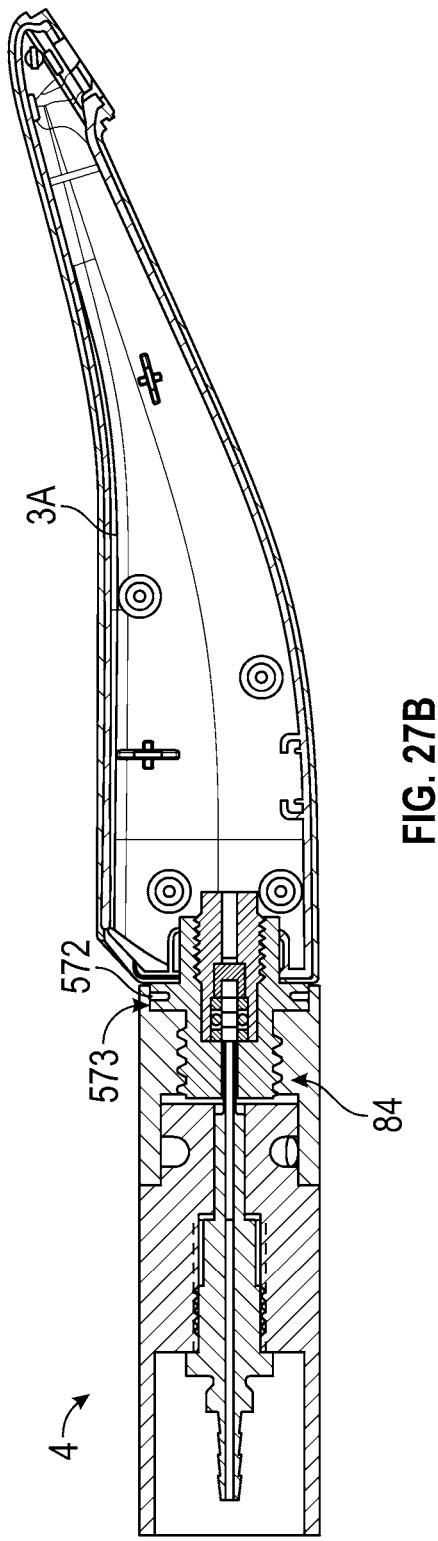
FIG. 27B is a side cross-sectional view of the handpiece and interface member shown in FIG. 27A after engagement.

FIG. 27A is a side cross-sectional view of a handpiece 3A and interface member 4 prior to engagement, according to yet another embodiment. FIG. 27B is a side cross-sectional view of the handpiece 3A and interface member 4 shown in FIG. 27A after engagement. The embodiment shown in FIGS. 27A-27B may be generally similar to the embodiment shown in FIGS. 26A-26D. For example, the interface member 4 can include threads 583 that rotatably couple to corresponding threadable engagement features 595 of a connector 84. In addition, the connector 84 and interface member 4 can be configured to couple to one another by snap-fit engagement. For example, in some embodiments, the connector 84 can include a flange 572 extending radially outward from the connector 84. The interface member 4 can include a recess 573 at a distal end. When the interface member 4 is threaded onto the connector 84, the recess 573 can snap onto the flange 572 to further secure the interface member 4 and connector 84. Moreover, the snap-fit engagement can signal to the clinician that there is secure engagement between the handpiece 3A and interface member 4.

V. Recording Data about Various System Components

As explained herein with respect to FIGS. 5F-5G, the console 2 can organize and manage information about the various system components and treatment procedures performed by the system 1. In some embodiments, suitable system components can transmit data regarding to the console 2 (e.g., the processing unit 39) regarding the status or disposition of the component itself or about treatment procedures associated with the component. For example, as explained herein, various system components may be disposable. For disposable components (such as the handpiece 3A, treatment cap 3B, etc.), it can be important to verify that the component has not been used in a procedure before to assist in determining whether or not the component is unsanitary. Furthermore, it can be important to ensure that the disposable component is a valid component that is legally and/or clinically suitable for use with the system 1. Additional data regarding the system components may be desirable.

Figure 28:
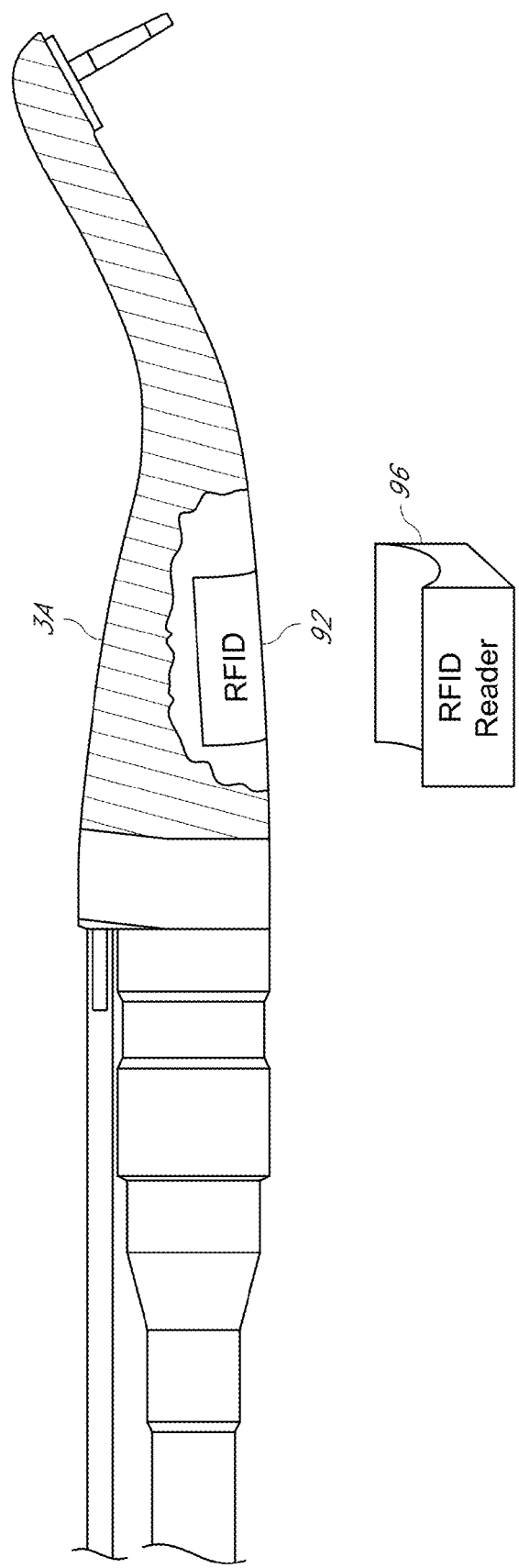
FIG. 28 is a schematic perspective view of a handpiece having a communications chip coupled thereto and configured to communicate with a wireless reader.

In some embodiments, the handpiece 3A can include a memory device configured to store and/or communicate information about at least one of a treatment procedure and the handpiece 3A. The memory device may be a passive system or an active system. FIG. 28 is a schematic perspective view of a handpiece 3A having a memory device comprising a communications chip 92 (e.g., a wireless or wired communications chip) coupled thereto and configured to communicate with a wireless reader 96. In some embodiments, the communications chip 92 can comprise a radio frequency identification (RFID) chip, and the reader 96 can comprise a RFID reader. For example, in one embodiment, the RFID chip can be a GammaTag® manufactured by Verigenics™ of Southampton, Pa. The wireless reader 96 can communicate with the chip 92 on the handpiece 3A when the handpiece 3A is brought within range of the reader 96. The communications chip 92 can be programmed with information about the particular handpiece 3A to which the chip 92 is coupled. For example, the communications chip 92 can be programmed to store information regarding at least one of the type of tooth coupler 3 or handpiece 3A (e.g., a molar handpiece, pre-molar handpiece, etc.), whether or not the handpiece 3A has been used in a treatment procedure, information concerning any treatment procedures performed by the handpiece 3A (e.g., at least one of date and time of procedure, name of clinician, name of patient, location of treatment, type of procedure, etc.), whether or not the handpiece 3A is a genuine product by way of, for example, a unique identifier associated with the particular handpiece 3A (e.g., whether the handpiece 3A is supplied by or manufactured by an authorized entity), date of manufacture, lot or serial number, etc. As explained herein, the handpiece 3A can comprise a suitable dental treatment assembly, such as, e.g., a fluid jet device.

When the handpiece 3A is brought into range of the reader 96 (such as when the handpiece 3A is placed in a cradle containing the reader 96), the reader 96 can read the data stored on the communications chip 92. As explained herein, it can be important to reduce the risk of infection or contamination by disposing the handpiece 3A after a single treatment procedure. In some embodiments, the communications chip 92 of the handpiece 3A can be specially configured to have memory space for storing data indicating that the handpiece 3A has never been used in a treatment procedure. When the handpiece 3A is proximate the reader 96, the reader 96 and chip 92 can communicate over an encrypted data link in some arrangements. Before, during, or after the initial treatment procedure, the reader 96 can write to the chip 92 data indicating that the handpiece 3A has been used in a treatment procedure. For example, in some embodiments, the reader 96 can physically erase the data stored or allotted to a particular location on the chip 92, or can otherwise permanently indicate on the chip 92 that the handpiece 3A has been used before. The reader 96 can be in data communication with the console 2 (whether wireless or wired communication), and the console 2 can identify that the handpiece 3A has been used previously. If it is determined that a particular handpiece 3A has been used previously, then the system 1 can prevent the clinician from performing another procedure using that particular handpiece 3A. The system 1 can thereby assist in ensuring that the handpiece 3A is sanitary or sterile before use in a treatment procedure.

In addition, the chip 92 can store information relating to the serial number or other unique identifying information related to the particular handpiece 3A. Thus, the manufacturer, owner, or supplier can ensure that the system 1 is used only with authorized handpieces 3A (or other types of tooth couplers 3). For example, the reader 96 can read a unique identifier (such as serial number, etc.) from the chip 92 and can determine whether or not the particular handpiece 3A is an authorized handpiece. If the handpiece 3A is not authorized for use with the system 1, then the system 1 can prevent the clinician from using the unauthorized handpiece 3A or other tooth coupler 3.

The chip 92 can store and transmit any suitable information regarding the handpiece 3A and/or a treatment procedure performed by the handpiece 3A. For example, in some embodiments, the chip 92 on board the handpiece 3A can record information about the procedure, such as treatment type, treatment duration, patient name, treatment outcome, etc. Information related to the treatment can be sent to the console 2 by way of the reader 96. For example, in some embodiments, if a treatment is ended prematurely, then the chip 92 can store and transmit to the reader 96 that the treatment was incomplete. In some embodiments, the chip 92 on the handpiece 3A can identify whether there were any malfunctions or other defects in the handpiece and can transmit such information to the console 2. The manufacturer can utilize information regarding such defects to apply refunds to the customer and/or to improve system design. Any other suitable information about the handpiece 3A and/or treatment procedures can be stored on the chip 92.

Although the chip 92 and reader 96 of FIG. 28 are described as communicating by way of RFID, any suitable communications protocol may be suitable. For example, in some embodiments, wireless internet connections (e.g., under the 802.11 standards), Bluetooth, etc. may be used. In still other embodiments, wired data connections may be used to communicate between the handpiece 3A and the reader 96 or console 2.

Furthermore, although FIG. 28 relates to communication between the handpiece 3A and a reader 96, it should be appreciated that any other suitable system component can communicate information regarding the component's status, or a status of a treatment procedure, to the console 2. For example, the high pressure conduit 29 can include information regarding the number of treatment procedures performed and/or the amount of time the conduit 29 (or any other component) has been in service in the system 1. When the number of procedures and/or time of service exceeds a desirable threshold, the console 2 can indicate to the clinician that the particular component should be replaced.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and subcombinations are intended to fall within the scope of this disclosure.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

What is claimed is:

1. A dental treatment system comprising:
    a console including at least one fluid reservoir and at least one electrical component;
    a treatment instrument sized to be disposed in a mouth of a patient at a treatment location for one or more teeth, the treatment instrument including:
        a pressure wave generator producing pressure waves across a broad spectrum of frequencies;
        at least one inlet through which fluid from the fluid reservoir enters the treatment instrument;
        at least one outlet through which said fluid is directed at the treatment location; and
        a communications chip storing data about one or more operational characteristics of the treatment instrument or a treatment procedure, wherein the communications chip stores a unique identifier associated with the particular treatment instrument; and
    a reader communicating with the console and being capable of obtaining data from the communications chip,
    wherein, in response to receiving a communication from the console indicating use of the treatment instrument in the treatment procedure, the reader is configured to send a signal to the treatment instrument, and processing electronics of the treatment instrument are configured to write data to a memory accessible by the communications chip that, in response to receiving the signal, prevents the treatment instrument from being used in another treatment procedure.

2. The dental treatment system of claim 1, wherein the communications chip comprises a wireless chip, the wireless chip being configured to wirelessly transmit the data to the reader.

3. The dental treatment system of claim 1, wherein the communications chip comprises a radio frequency identification (RFID) chip, and wherein the reader comprises a RFID reader.

4. The dental treatment system of claim 1, wherein the communications chip is configured to communicate data related to a status of a tooth cleaning procedure.

5. The dental treatment system of claim 1, wherein the communications chip is configured to communicate identifying data related to properties of the treatment procedure or of the fluid.

6. The dental treatment system of claim 1, wherein the treatment instrument comprises a handpiece.

7. The dental treatment system of claim 1, wherein the reader comprises a cradle for the treatment instrument.

8. The dental treatment system of claim 1, further comprising a hose in fluid communication with the console, the treatment instrument configured to couple with a distal portion of the hose.

9. The dental treatment system of claim 8, further comprising an interface, the interface configured to couple the treatment instrument to the distal portion of the hose.

10. The dental treatment system of claim 1, wherein the pressure wave generator comprises a liquid jet device.

11. The dental treatment system of claim 1, wherein the electrical component comprises a motor to drive a pump to pressurize a treatment fluid.

12. The dental treatment system of claim 1, wherein the console comprises a degassing system for reducing dissolved gas content of a treatment fluid.

13. The dental treatment system of claim 1, wherein the console comprises a mixing system for mixing a treatment fluid.

14. The dental treatment system of claim 1, wherein the console comprises a sensor to characterize a treatment fluid.

15. The dental treatment system of claim 14, wherein the sensor comprises a concentration sensor, a temperature sensor, a dissolved oxygen sensor, or a pressure sensor.

16. The dental treatment system of claim 1, wherein the console further comprises a user interface to provide information to a user.

17. The dental treatment system of claim 1, wherein the pressure wave generator comprises the at least one outlet.

18. The dental treatment system of claim 1, wherein the reader is configured to receive data transmitted from the communications chip.

19. The dental treatment system of claim 1, wherein the communications chip stores information identifying the treatment instrument as being supplied by or manufactured by an authorized entity.

20. The dental treatment system of claim 19, wherein the reader is configured to read information from the communications chip identifying the treatment instrument as being supplied by or manufactured by an authorized entity, wherein the treatment system is configured to prevent use of the treatment instrument if the reader does not read information from the communications chip identifying the treatment instrument as being supplied by or manufactured by an authorized entity.

21. The dental treatment system of claim 1, wherein the communications chip is configured to record data about a location of the treatment procedure.

22. The dental treatment system of claim 1, wherein the communications chip is configured to record data about a type of the treatment procedure.

23. The dental treatment system of claim 1, wherein the communications chip stores data about a type of the treatment instrument.

24. The dental treatment system of claim 1, wherein the communications chip is configured to communicate with the reader over an encrypted data link.

25. The dental treatment system of claim 1, wherein the communications chip is configured to record data about an outcome of the treatment procedure.

26. The dental treatment system of claim 1, wherein the communications chip is configured to record data indicating that the treatment procedure is incomplete, wherein the communications chip is configured to transmit data indicating that the treatment procedure is incomplete to the reader.

27. The dental treatment system of claim 1, wherein the communications chip is configured to identify malfunctions or defects in the treatment instrument, wherein the communications chip is configured to transmit data about malfunctions or defects to the reader.

28. The dental treatment system of claim 1, wherein the communications chip comprises the processing electronics.

29. The dental treatment system of claim 1, wherein the reader is configured to identify whether the treatment instrument has been used in a previous treatment procedure when the treatment instrument is brought into close proximity with the reader.

30. The dental treatment system of claim 29, wherein if the reader determines that the treatment instrument has been used in the previous treatment procedure, the reader transmits to the console an indication that the treatment instrument has been previously used.

31. The dental treatment system of claim 30, wherein, in response to receiving the indication, a processing unit of the console is configured to prevent the treatment instrument from being used in a subsequent treatment procedure.

32. The dental treatment system of claim 1, wherein the processing electronics are configured to erase data from the memory to permanently indicate that the treatment instrument has been previously used.

33. A dental treatment apparatus for treating a tooth, the apparatus comprising:
a treatment instrument sized to be disposed in a mouth of a patient at a treatment location for one or more teeth, the treatment instrument including:
a pressure wave generator to produce pressure waves across a broad spectrum of frequencies;
at least one inlet through which fluid enters the treatment instrument;
at least one outlet through which said fluid is directed at the treatment location; and
a communications chip storing data about one or more operational characteristics of the treatment instrument or a treatment procedure, wherein the communications chip stores a unique identifier associated with the particular treatment instrument,
wherein the communications chip is configured to communicate the data to a reader,
wherein, in response to receiving a signal indicating use of the treatment instrument in the treatment procedure, processing electronics of the treatment instrument are configured to write data to a memory accessible by the communications chip that prevents the treatment instrument from being used in another treatment procedure.

34. The dental treatment apparatus of claim 33, wherein the treatment instrument comprises a treatment handpiece configured to removably couple to a console.

35. The dental treatment apparatus of claim 33, wherein the communications chip comprises a wireless chip, the wireless chip configured to wirelessly transmit the information to the reader.

36. The dental treatment apparatus of claim 35, wherein the wireless chip comprises a radio frequency identification (RFID) chip, and wherein the reader comprises a RFID reader.

37. The dental treatment apparatus of claim 33, wherein the communications chip is configured to communicate information related to a status of a tooth cleaning procedure.

38. The dental treatment apparatus of claim 33, wherein the communications chip is configured to communicate identifying information related to properties of the cleaning procedure or of the treatment fluid.

39. The dental treatment apparatus of claim 33, wherein the treatment instrument comprises a pressure wave generator.

40. The dental treatment apparatus of claim 39, wherein the pressure wave generator comprises a liquid jet device.

41. The dental treatment apparatus of claim 33, wherein the communications chip stores information identifying the treatment instrument as being supplied by or manufactured by an authorized entity.

42. The dental treatment apparatus of claim 33, wherein the communications chip is configured to record data about a location of the treatment procedure.

43. The dental treatment apparatus of claim 33, wherein the communications chip is configured to record data about a type of the treatment procedure.

44. The dental treatment apparatus of claim 33, wherein the communications chip stores data about a type of the treatment instrument.

45. The dental treatment apparatus of claim 33, wherein the communications chip is configured to communicate with the reader over an encrypted data link.

46. The dental treatment apparatus of claim 33, wherein the communications chip has a memory space for permanently storing data indicating that the treatment instrument has never been used in any treatment procedure.

47. The dental treatment apparatus of claim 33, wherein the communications chip is configured to record data about an outcome of the treatment procedure.

48. The dental treatment apparatus of claim 33, wherein the communications chip is configured to record data indicating that the treatment procedure is incomplete, wherein the communications chip is configured to transmit data indicating that the treatment procedure is incomplete to the reader.

49. The dental treatment apparatus of claim 33, wherein the communications chip is configured to identify malfunctions or defects in the treatment instrument, wherein the communications chip is configured to transmit data about malfunctions or defects to the reader.

50. The dental treatment apparatus of claim 33, wherein the processing electronics are configured to erase data from the memory to permanently indicate that the treatment instrument has been previously used.

* * * * *